US012668640B2

(12) United States Patent
Lee et al.

(10) Patent No.: US 12,668,640 B2
(45) Date of Patent: Jun. 30, 2026

(54) ANTI-CD30 ANTIBODY AND CHIMERIC ANTIGEN RECEPTOR COMPRISING THEREOF

(71) Applicants: ABCLON INC., Seoul (KR); The Trustees of the University of Pennsylvania, Philadelphia, PA (US)

(72) Inventors: Jong-Seo Lee, Gyeonggi-do (KR); Jong-Hoon Kim, Gyeonggi-Do (KR); Ki Hyun Kim, Seoul (KR); Hyun-Jong Lee, Incheon (KR); Marco Ruella, Ardmore, PA (US); Puneeth Guruprasad, Philadelphia, PA (US)

(73) Assignees: ABCLON INC., Seoul (KR); The Trustees of the University of Pennsylvania, Philadelphia, PA (US)

( * ) Notice: Subject to any disclaimer, the term of this patent is extended or adjusted under 35 U.S.C. 154(b) by 517 days.

(21) Appl. No.: 18/198,937

(22) Filed: May 18, 2023

(65) Prior Publication Data

US 2024/0392023 A1     Nov. 28, 2024

(51) Int. Cl.
| | |
|---|---|
| *C07K 16/28* | (2006.01) |
| *A61K 39/00* | (2006.01) |
| *A61K 40/31* | (2025.01) |
| *C07K 14/705* | (2006.01) |
| *C07K 14/725* | (2006.01) |

(52) U.S. Cl.
CPC .......... *C07K 16/2878* (2013.01); *A61K 40/31* (2025.01); *C07K 14/7051* (2013.01); *C07K 14/70517* (2013.01); *C07K 14/70578* (2013.01); *A61K 2039/505* (2013.01); *A61K 2239/13* (2023.05); *A61K 2239/21* (2023.05); *A61K 2239/22* (2023.05); *C07K 2317/622* (2013.01); *C07K 2317/73* (2013.01); *C07K 2317/92* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 10,808,035 B2 | 10/2020 | Chmielewski et al. | |
| 2019/0233528 A1 | 8/2019 | Srivatsa Srinivasan et al. | |
| 2020/0095329 A1* | 3/2020 | Medin .................. | C07K 16/462 |

FOREIGN PATENT DOCUMENTS

| | | |
|---|---|---|
| CN | 113227147 B | 7/2022 |
| KR | 10-1815265 B1 | 1/2018 |
| KR | 10-2290335 B1 | 8/2021 |

OTHER PUBLICATIONS

International Search Report from corresponding PCT Application No. PCT/KR2024/005653, dated Aug. 16, 2024.
1030—Immunotherapy: The BTLA-HVEM Axis is a Crucial Immune Checkpoint of T Cell Immunotherapies for Cancer, Immunotherapy| vol. 25, Issue 6, Supplement , S226-S227, May 2023.

* cited by examiner

*Primary Examiner* — Samira J Jean-Louis
*Assistant Examiner* — Maureen Varina Driscoll
(74) *Attorney, Agent, or Firm* — Harness, Dickey & Pierce, P.L.C.

(57) ABSTRACT

Disclosed herein are a novel antibody and an antigen binding fragment thereof that targets CD30 to treat cancer, a chimeric antigen receptor, and a use thereof. The antibody, which binds specifically to CD30 that is highly expressed in cancer cells (specifically blood cancer), is very low in sequence homology with the CDR sequences of conventional CD30 targeting antibodies and thus has a unique sequence. Cells that express the chimeric antigen receptor including the anti-CD30 antibody or the antigen binding fragment responds to CD30-expressing positive cells to induce immune cell activity, thus finding advantageous applications as a CAR-immune cell product.

18 Claims, 12 Drawing Sheets

Specification includes a Sequence Listing.

SEQUENCE LISTING

Sequence total quantity: 226
SEQ ID NO: 1          moltype = AA   length = 5
FEATURE               Location/Qualifiers
source                1..5
                      mol_type = protein
                      organism = synthetic construct
SEQUENCE: 1
GYGMS                                                            5

SEQ ID NO: 2          moltype = AA   length = 17
FEATURE               Location/Qualifiers
source                1..17
                      mol_type = protein
                      organism = synthetic construct
SEQUENCE: 2
YISGYSYYTY YADSVKG                                               17

SEQ ID NO: 3          moltype = AA   length = 8
FEATURE               Location/Qualifiers
source                1..8
                      mol_type = protein
                      organism = synthetic construct
SEQUENCE: 3
YDGNGFDY                                                         8

SEQ ID NO: 4          moltype = AA   length = 13
FEATURE               Location/Qualifiers
source                1..13
                      mol_type = protein
                      organism = synthetic construct
SEQUENCE: 4
SGSSSNIGSN YVY                                                   13

SEQ ID NO: 5          moltype = AA   length = 7
FEATURE               Location/Qualifiers
source                1..7
                      mol_type = protein
                      organism = synthetic construct
SEQUENCE: 5
RNNQRPS                                                          7

SEQ ID NO: 6          moltype = AA   length = 8
FEATURE               Location/Qualifiers
source                1..8
                      mol_type = protein
                      organism = synthetic construct
SEQUENCE: 6
AADSSDDS                                                         8

SEQ ID NO: 7          moltype = AA   length = 117
FEATURE               Location/Qualifiers
source                1..117
                      mol_type = protein
                      organism = synthetic construct
SEQUENCE: 7
EVQLLESGGG LVQPGGSLRL SCAASGFTFS GYGMSWVRQA PGKGLEWVSY ISGYSYYTYY 60
ADSVKGRFTF SRDNSKNTLY LQMNSLRAED TAVYYCARYD GNGFDYWGQG TLVTVSS    117

SEQ ID NO: 8          moltype = AA   length = 110
FEATURE               Location/Qualifiers
source                1..110
                      mol_type = protein
                      organism = synthetic construct
SEQUENCE: 8
QSVLTQPPSA SGTPGQRVTI SCSGSSSNIG SNYVYWYQQL PGTAPKLLIY RNNQRPSGVP 60
DRFSGSKSGT SASLAISGLR SEDEADYYCA ADSSDDSYVF GGGTKLTVLG           110

SEQ ID NO: 9          moltype = AA   length = 242
FEATURE               Location/Qualifiers
source                1..242
                      mol_type = protein
                      organism = synthetic construct
SEQUENCE: 9
EVQLLESGGG LVQPGGSLRL SCAASGFTFS GYGMSWVRQA PGKGLEWVSY ISGYSYYTYY 60
ADSVKGRFTF SRDNSKNTLY LQMNSLRAED TAVYYCARYD GNGFDYWGQG TLVTVSSGGG 120
GSGGGGSGGG GSQSVLTQPP SASGTPGQRV TISCSGSSSN IGSNYVYWYQ QLPGTAPKLL 180
IYRNNQRPSG VPDRFSGSKS GTSASLAISG LRSEDEADYY CAADSSDDSY VFGGGTKLTV 240
LG                                                              242

-continued

```
SEQ ID NO: 10              moltype = AA   length = 470
FEATURE                    Location/Qualifiers
source                     1..470
                           mol_type = protein
                           organism = synthetic construct
SEQUENCE: 10
EVQLLESGGG LVQPGGSLRL SCAASGFTFS GYGMSWVRQA PGKGLEWVSY ISGYSYYTYY   60
ADSVKGRFTF SRDNSKNTLY LQMNSLRAED TAVYYCARYD GNGFDYWGQG TLVTVSSGGG  120
GSGGGGSGGG GSQSVLTQPP SASGTPGQRV TISCSGSSSN IGSNYVYWYQ QLPGTAPKLL  180
IYRNNQRPSG VPDRFSGSKS GTSASLAISG LRSEDEADYY CAADSSDDSY VFGGGTKLTV  240
LGGQAGQTTT PAPRPPTPAP TIASQPLSLR PEACRPAAGG AVHTRGLDFA CDIYIWAPLA  300
GTCGVLLLSL VITLYCKRGR KKLLYIFKQP FMRPVQTTQE EDGCSCRFPE EEEGGCELRV  360
KFSRSADAPA YQQGQNQLYN ELNLGRREEY DVLDKRRGRD PEMGGKPRRK NPQEGLYNEL  420
QKDKMAEAYS EIGMKGERRR GKGHDGLYQG LSTATKDTYD ALHMQALPPR           470

SEQ ID NO: 11              moltype = DNA   length = 15
FEATURE                    Location/Qualifiers
source                     1..15
                           mol_type = other DNA
                           organism = synthetic construct
SEQUENCE: 11
ggttatggta tgagc                                                   15

SEQ ID NO: 12              moltype = DNA   length = 51
FEATURE                    Location/Qualifiers
source                     1..51
                           mol_type = other DNA
                           organism = synthetic construct
SEQUENCE: 12
tacatctctg gttactctta ctacacgtat tacgctgatt ctgtaaaagg t           51

SEQ ID NO: 13              moltype = DNA   length = 24
FEATURE                    Location/Qualifiers
source                     1..24
                           mol_type = other DNA
                           organism = synthetic construct
SEQUENCE: 13
tacgacggta acggtttcga ctac                                         24

SEQ ID NO: 14              moltype = DNA   length = 39
FEATURE                    Location/Qualifiers
source                     1..39
                           mol_type = other DNA
                           organism = synthetic construct
SEQUENCE: 14
agtggctctt catctaatat tggctctaat tatgtctac                         39

SEQ ID NO: 15              moltype = DNA   length = 21
FEATURE                    Location/Qualifiers
source                     1..21
                           mol_type = other DNA
                           organism = synthetic construct
SEQUENCE: 15
agaaataacc agcggccaag c                                            21

SEQ ID NO: 16              moltype = DNA   length = 24
FEATURE                    Location/Qualifiers
source                     1..24
                           mol_type = other DNA
                           organism = synthetic construct
SEQUENCE: 16
gctgctgact cttctgacga ctct                                         24

SEQ ID NO: 17              moltype = DNA   length = 351
FEATURE                    Location/Qualifiers
source                     1..351
                           mol_type = other DNA
                           organism = synthetic construct
SEQUENCE: 17
gaggtgcagc tgttggagtc tgggggaggc ttggtacagc ctggggggtc cctgagactc   60
tcctgtgcag cctctggatt cacctttagc ggttatggta tgagctgggt ccgccaggct  120
ccagggaagg ggctggagtg ggtctcatac atctctggtt actcttacta cacgtattac  180
gctgattctg taaaaggtcg gttcaccttc tccagagaca attccaagaa cacgctgtat  240
ctgcaaatga acagcctgag agccgaggac acggccgtgt attactgtgc gcgttacgac  300
ggtaacggtt tcgactactg gggccagggt acactggtca ccgtgagctc a          351

SEQ ID NO: 18              moltype = DNA   length = 330
FEATURE                    Location/Qualifiers
```

```
source                  1..330
                        mol_type = other DNA
                        organism = synthetic construct
SEQUENCE: 18
cagtctgtgc tgactcagcc accctcagcg tctgggaccc ccgggcagag ggtcaccatc   60
tcttgtagtg gctcttcatc taatattggc tctaattatg tctactggta ccagcagctc  120
ccaggaacgg cccccaaact cctcatctat agaaataacc agcggccaag cggggtccct  180
gaccgattct ctggctccaa gtctggcacc tcagcctccc tggccatcag tgggctccgg  240
tccgaggatg aggccgatta ttactgtgct gctgactctt ctgacgactc ttatgtcttc  300
ggcggaggca ccaagctgac ggtcctaggt                                    330

SEQ ID NO: 19            moltype = DNA   length = 726
FEATURE                 Location/Qualifiers
source                  1..726
                        mol_type = other DNA
                        organism = synthetic construct
SEQUENCE: 19
gaggtgcagc tgttggagtc tggggggggc ttggtacagc ctggggggtc cctgagactc   60
tcctgtgcag cctctggatt cacctttagc ggttatggta tgagctgggt ccgccaggct  120
ccagggaagg ggctggagtg ggtctcatac atctctggtt actcttacta cacgtattac  180
gctgattctg taaaaggtcg gttcaccttc tccagagaca attccaagaa cacgctgtat  240
ctgcaaatga acagcctgag agccgaggac acggccgtgt attactgtgc gcgttacgac  300
ggtaacggtt tcgactactg gggccagggg acactggtca ccgtgagctc aggtggaggc  360
ggttcaggcg gaggtggatc cggcggtggc ggatcgcagt ctgtgctgac tcagccaccc  420
tcagcgtctg gaccccccgg gcagagggtc accatctctt gtagtggctc ttcatctaat  480
attggctcta attatgtcta ctggtaccag cagctcccag gaacggcccc caaactcctc  540
atctatagaa ataaccagcg gccaagcggg gtccctgacc gattctctgg ctccaagtct  600
ggcacctcag cctccctggc catcagtggg ctccggtccg aggatgaggc cgattattac  660
tgtgctgctg actcttctga cgactcttat gtcttcggcg gaggcaccaa gctgacggtc  720
ctaggt                                                              726

SEQ ID NO: 20            moltype = DNA   length = 1410
FEATURE                 Location/Qualifiers
source                  1..1410
                        mol_type = other DNA
                        organism = synthetic construct
SEQUENCE: 20
gaggtgcagc tgttggagtc tggggggggc ttggtacagc ctggggggtc cctgagactc   60
tcctgtgcag cctctggatt cacctttagc ggttatggta tgagctgggt ccgccaggct  120
ccagggaagg ggctggagtg ggtctcatac atctctggtt actcttacta cacgtattac  180
gctgattctg taaaaggtcg gttcaccttc tccagagaca attccaagaa cacgctgtat  240
ctgcaaatga acagcctgag agccgaggac acggccgtgt attactgtgc gcgttacgac  300
ggtaacggtt tcgactactg gggccagggg acactggtca ccgtgagctc aggtggaggc  360
ggttcaggcg gaggtggatc cggcggtggc ggatcgcagt ctgtgctgac tcagccaccc  420
tcagcgtctg gaccccccgg gcagagggtc accatctctt gtagtggctc ttcatctaat  480
attggctcta attatgtcta ctggtaccag cagctcccag gaacggcccc caaactcctc  540
atctatagaa ataaccagcg gccaagcggg gtccctgacc gattctctgg ctccaagtct  600
ggcacctcag cctccctggc catcagtggg ctccggtccg aggatgaggc cgattattac  660
tgtgctgctg actcttctga cgactcttat gtcttcggcg gaggcaccaa gctgacggtc  720
ctaggtggcc aggccggcca gacaacgaca cctgctccca gaccgcctac tcccgcccca  780
accattgcat ctcagccact ctctctgaga cccgaagcgt gtagacctgc ggccggggagc  840
gctgtccaca caagaggctt agacttcgcc tgcgatatct atatctgggc cccactcgca  900
ggcacttgtg gagtgctgct gctttcactc gtgataaccc tgtactgcaa aagggggaga  960
aagaagctgc tgtatatttt taaacaacca tttatgagac ctgttcagac tacccaggaa 1020
gaaagacggt gtagttgcag attccccgag gaggaagaag gaggttgcga gttgagagta 1080
aagttcagca gatccgcaga tgcccctgct taccagcagg gtcaaaacca gctttacaac 1140
gagctgaatt taggtagaag agaggaatat gacgtgttgg ataaaagaag aggaagagac 1200
ccggaaatgg gcggcaagcc tcgaagaaaa aatccccaag agggactcta caatgagctg 1260
cagaaggaca aaatggctga gcctacagc gagatcggca tgaagggaga agacgcagga 1320
gggaaagggc atgatgggct ttatcagggc ttgtccaccg ctacaaagga tacttatgac 1380
gcactacaca tgcaggccct gccacccgt                                    1410

SEQ ID NO: 21            moltype = AA   length = 5
FEATURE                 Location/Qualifiers
source                  1..5
                        mol_type = protein
                        organism = synthetic construct
SEQUENCE: 21
GYGMS                                                                 5

SEQ ID NO: 22            moltype = AA   length = 17
FEATURE                 Location/Qualifiers
source                  1..17
                        mol_type = protein
                        organism = synthetic construct
SEQUENCE: 22
YISSGSYYTY YADSVKG                                                   17

SEQ ID NO: 23            moltype = AA   length = 13
```

```
FEATURE               Location/Qualifiers
source                1..13
                      mol_type = protein
                      organism = synthetic construct
SEQUENCE: 23
YRGDNDYYGY FDY                                                         13

SEQ ID NO: 24         moltype = AA  length = 13
FEATURE               Location/Qualifiers
source                1..13
                      mol_type = protein
                      organism = synthetic construct
SEQUENCE: 24
SCSSSNIGNN AVS                                                         13

SEQ ID NO: 25         moltype = AA  length = 7
FEATURE               Location/Qualifiers
source                1..7
                      mol_type = protein
                      organism = synthetic construct
SEQUENCE: 25
RNNQRPS                                                                7

SEQ ID NO: 26         moltype = AA  length = 7
FEATURE               Location/Qualifiers
source                1..7
                      mol_type = protein
                      organism = synthetic construct
SEQUENCE: 26
AADYGSD                                                                7

SEQ ID NO: 27         moltype = AA  length = 122
FEATURE               Location/Qualifiers
source                1..122
                      mol_type = protein
                      organism = synthetic construct
SEQUENCE: 27
EVQLLESGGG LVQPGGSLRL SCAASGFTFS GYGMSWVRQA PGKGLEWVSY ISSGSYYTYY      60
ADSVKGRFTI SRDNSKNTLY LQMNSLRAED TAVYYCARYR GDNDYYGYFD YWGQGTLVTV      120
SS                                                                    122

SEQ ID NO: 28         moltype = AA  length = 109
FEATURE               Location/Qualifiers
source                1..109
                      mol_type = protein
                      organism = synthetic construct
SEQUENCE: 28
QSVLTQPPSA SGTPGQRVTI SCSCSSSNIG NNAVSWYQQL PGTAPKLLIY RNNQRPSGVP      60
DRFSGSKSGT SASLAISGLR SEDEADYYCA ADYGSDYVFG GGTKLTVLG                  109

SEQ ID NO: 29         moltype = AA  length = 246
FEATURE               Location/Qualifiers
source                1..246
                      mol_type = protein
                      organism = synthetic construct
SEQUENCE: 29
EVQLLESGGG LVQPGGSLRL SCAASGFTFS GYGMSWVRQA PGKGLEWVSY ISSGSYYTYY      60
ADSVKGRFTI SRDNSKNTLY LQMNSLRAED TAVYYCARYR GDNDYYGYFD YWGQGTLVTV      120
SSGGGGSGGG GSGGGGSQSV LTQPPSASGT PGQRVTISCS CSSSNIGNNA VSWYQQLPGT      180
APKLLIYRNN QRPSGVPDRF SGSKSGTSAS LAISGLRSED EADYYCAADY GSDYVFGGGT      240
KLTVLG                                                                246

SEQ ID NO: 30         moltype = AA  length = 474
FEATURE               Location/Qualifiers
source                1..474
                      mol_type = protein
                      organism = synthetic construct
SEQUENCE: 30
EVQLLESGGG LVQPGGSLRL SCAASGFTFS GYGMSWVRQA PGKGLEWVSY ISSGSYYTYY      60
ADSVKGRFTI SRDNSKNTLY LQMNSLRAED TAVYYCARYR GDNDYYGYFD YWGQGTLVTV      120
SSGGGGSGGG GSGGGGSQSV LTQPPSASGT PGQRVTISCS CSSSNIGNNA VSWYQQLPGT      180
APKLLIYRNN QRPSGVPDRF SGSKSGTSAS LAISGLRSED EADYYCAADY GSDYVFGGGT      240
KLTVLGGQAG QTTTPAPRPP TPAPTIASQP LSLRPEACRP AAGGAVHTRG LDFACDIYIW      300
APLAGTCGVL LLSLVITLYC KRGRKKLLYI FKQPFMRPVQ TTQEEDGCSC RFPEEEEGGC      360
ELRVKFSRSA DAPAYQQGQN QLYNELNLGR REEYDVLDKR RGRDPEMGGK PRRKNPQEGL      420
YNELQKDKMA EAYSEIGMKG ERRRGKGHDG LYQGLSTATK DTYDALHMQA LPPR            474

SEQ ID NO: 31         moltype = DNA  length = 15
FEATURE               Location/Qualifiers
```

-continued

```
source                  1..15
                        mol_type = other DNA
                        organism = synthetic construct
SEQUENCE: 31
ggttatggta tgagc                                                     15

SEQ ID NO: 32           moltype = DNA   length = 51
FEATURE                 Location/Qualifiers
source                  1..51
                        mol_type = other DNA
                        organism = synthetic construct
SEQUENCE: 32
tacatctctt ctggttctta ctacacgtat tacgctgatt ctgtaaaagg t            51

SEQ ID NO: 33           moltype = DNA   length = 39
FEATURE                 Location/Qualifiers
source                  1..39
                        mol_type = other DNA
                        organism = synthetic construct
SEQUENCE: 33
taccgtggtg acaacgatta ctacggttac ttcgactac                          39

SEQ ID NO: 34           moltype = DNA   length = 39
FEATURE                 Location/Qualifiers
source                  1..39
                        mol_type = other DNA
                        organism = synthetic construct
SEQUENCE: 34
agttgctctt catctaatat tggcaataat gctgtctcc                          39

SEQ ID NO: 35           moltype = DNA   length = 21
FEATURE                 Location/Qualifiers
source                  1..21
                        mol_type = other DNA
                        organism = synthetic construct
SEQUENCE: 35
agaaataacc agcggccaag c                                              21

SEQ ID NO: 36           moltype = DNA   length = 21
FEATURE                 Location/Qualifiers
source                  1..21
                        mol_type = other DNA
                        organism = synthetic construct
SEQUENCE: 36
gctgctgact acggttctga c                                              21

SEQ ID NO: 37           moltype = DNA   length = 366
FEATURE                 Location/Qualifiers
source                  1..366
                        mol_type = other DNA
                        organism = synthetic construct
SEQUENCE: 37
gaggtgcagc tgttggagtc tgggggaggc ttggtacagc ctggggggtc cctgagactc   60
tcctgtgcag cctctggatt caccttTagc ggttatggta tgagctgggt ccgccaggct   120
ccagggaagg ggctggagtg ggtctcatac atctcttctg gttcttacta cacgtattac   180
gctgattctg taaaaggtcg gttcaccatc tccagagaca attccaagaa cacgctgtat   240
ctgcaaatga acagcctgag agccgaggac acggccgtgt attactgtgc gcgttaccgt   300
ggtgacaacg attactacgg ttacttcgac tactggggcc agggtacact ggtcaccgtg   360
agctca                                                               366

SEQ ID NO: 38           moltype = DNA   length = 327
FEATURE                 Location/Qualifiers
source                  1..327
                        mol_type = other DNA
                        organism = synthetic construct
SEQUENCE: 38
cagtctgtgc tgactcagcc accctcagcg tctgggaccc ccgggcagag ggtcaccatc   60
tcttgtagtt gctcttcatc taatattggc aataatgctg tctcctggta ccagcagctc   120
ccaggaacgg cccccaaact cctcatctat agaaataacc agcggccaag cggggtccct   180
gaccgattct ctggctccaa gtctggcacc tcagcctccc tggccatcag tgggctccgg   240
tccgaggatg aggccgatta ttactgtgct gctgactacg ttctgacta tgtcttcggc   300
ggaggcacca agctgacggt cctaggt                                        327

SEQ ID NO: 39           moltype = DNA   length = 738
FEATURE                 Location/Qualifiers
source                  1..738
                        mol_type = other DNA
                        organism = synthetic construct
SEQUENCE: 39
```

```
gaggtgcagc tgttggagtc tggggggaggc ttggtacagc ctggggggtc cctgagactc    60
tcctgtgcag cctctggatt cacctttagc ggttatggta tgagctgggt ccgccaggct   120
ccagggaagg ggctggagtg ggtctcatac atctcttctg gttcttacta cacgtattac   180
gctgattctg taaaaggtcg gttcaccatc tccagagaca attccaagaa cacgctgtat   240
ctgcaaatga acagcctgag agccgaggac acggccgtgt attactgtgc gcgttaccgt   300
ggtgacaacg attactacgg ttacttcgac tactggggcc agggtacact ggtcaccgtg   360
agctcaggtg gaggcggttc aggcggaggt ggatccggcg gtggcggatc gcagtctgtg   420
ctgactcagc caccctcagc gtctgggacc cccgggcaga gggtcaccat ctcttgtagt   480
tgctcttcat ctaatattgg caataatgct gtctcctggt accagcagct cccaggaacg   540
gcccccaaac tcctcatcta tagaaataac cagcggccaa gcggggtccc tgaccgattc   600
tctggctcca agtctggcac ctcagcctcc ctggccatca gtgggctccg gtccgaggat   660
gaggccgatt attactgtgc tgctgactac ggttctgact atgtcttcgg cggaggcacc   720
aagctgacgg tcctaggt                                                 738

SEQ ID NO: 40         moltype = DNA  length = 1422
FEATURE               Location/Qualifiers
source                1..1422
                      mol_type = other DNA
                      organism = synthetic construct SEQUENCE: 40
gaggtgcagc tgttggagtc tggggggaggc ttggtacagc ctggggggtc cctgagactc    60
tcctgtgcag cctctggatt cacctttagc ggttatggta tgagctgggt ccgccaggct   120
ccagggaagg ggctggagtg ggtctcatac atctcttctg gttcttacta cacgtattac   180
gctgattctg taaaaggtcg gttcaccatc tccagagaca attccaagaa cacgctgtat   240
ctgcaaatga acagcctgag agccgaggac acggccgtgt attactgtgc gcgttaccgt   300
ggtgacaacg attactacgg ttacttcgac tactggggcc agggtacact ggtcaccgtg   360
agctcaggtg gaggcggttc aggcggaggt ggatccggcg gtggcggatc gcagtctgtg   420
ctgactcagc caccctcagc gtctgggacc cccgggcaga gggtcaccat ctcttgtagt   480
tgctcttcat ctaatattgg caataatgct gtctcctggt accagcagct cccaggaacg   540
gcccccaaac tcctcatcta tagaaataac cagcggccaa gcggggtccc tgaccgattc   600
tctggctcca agtctggcac ctcagcctcc ctggccatca gtgggctccg gtccgaggat   660
gaggccgatt attactgtgc tgctgactac ggttctgact atgtcttcgg cggaggcacc   720
aagctgacgg tcctaggtgg ccaggccggc cagacaacga cacctgctcc cagaccgcct   780
actcccgccc caaccattgc atctcagcca ctctctctga gacccgaagc gtgtagaccn   840
gcggccgggg gcgctgtcca cacaagaggc ttagacttcg cctgcgatat ctatatctgc   900
gccccactcg caggcacttg tggagtgctg ctgctttcac tcgtgataac cctgtactgc   960
aaaaggggga gaaagaagct gctgtatatt tttaaacaac catttatgag acctgttcag  1020
actacccagg aagaagacgg ttgtagttgc agattccccg aggaggaaga aggaggttgc  1080
gagttgagag taaagttcag cagatccgca gatgcccctg cttaccagca gggtcaaaac  1140
cagctttaca acgagctgaa tttaggtaga agagaggaat atgacgtgtt ggataaaaga  1200
agaggaagag acccggaaat gggcggcaag cctcgaagaa aaaatcccca agagggactc  1260
tacaatgagc tgcagaagga caaaatggct gaagcctaca gcgagatcgg catgaaggga  1320
gaaagacgca gagggaaagg gcatgatggg cttttatcagg gcttgtccac cgctacaaag  1380
gatacttatg acgcactaca catgcaggcc ctgccacccc gt                     1422

SEQ ID NO: 41         moltype = AA  length = 4
FEATURE               Location/Qualifiers
source                1..4
                      mol_type = protein
                      organism = synthetic construct SEQUENCE: 41
SYMS                                                                  4

SEQ ID NO: 42         moltype = AA  length = 17
FEATURE               Location/Qualifiers
source                1..17
                      mol_type = protein
                      organism = synthetic construct SEQUENCE: 42
SIGSGYYSTY YADSVKG                                                   17

SEQ ID NO: 43         moltype = AA  length = 8
FEATURE               Location/Qualifiers
source                1..8
                      mol_type = protein
                      organism = synthetic construct SEQUENCE: 43
DYYGGFDY                                                              8

SEQ ID NO: 44         moltype = AA  length = 13
FEATURE               Location/Qualifiers
source                1..13
                      mol_type = protein
                      organism = synthetic construct SEQUENCE: 44
SGSSSNIGSN YVY                                                       13

SEQ ID NO: 45         moltype = AA  length = 7
FEATURE               Location/Qualifiers
```

-continued

```
source                   1..7
                         mol_type = protein
                         organism = synthetic construct
SEQUENCE: 45
RNNQRPS                                                                        7

SEQ ID NO: 46            moltype = AA   length = 7
FEATURE                  Location/Qualifiers
source                   1..7
                         mol_type = protein
                         organism = synthetic construct
SEQUENCE: 46
AAYDSYS                                                                        7

SEQ ID NO: 47            moltype = AA   length = 116
FEATURE                  Location/Qualifiers
source                   1..116
                         mol_type = protein
                         organism = synthetic construct
SEQUENCE: 47
EVQLLESGGG LVQPGGSLRL SCAASGFTFS SYMSWVRQAP GKGLEWVSSI GSGYYSTYYA    60
DSVKGRFTIS RDNSKNTLYL QMNSLRAEDT AVYYCARDYY GGFDYWGQGT LVTVSS       116

SEQ ID NO: 48            moltype = AA   length = 109
FEATURE                  Location/Qualifiers
source                   1..109
                         mol_type = protein
                         organism = synthetic construct
SEQUENCE: 48
QSVLTQPPSA SGTPGQRVTI SCSGSSSNIG SNYVYWYQQL PGTAPKLLIY RNNQRPSGVP    60
DRFSGSKSGT SASLAISGLR SEDEADYYCA AYDSYSYVFG GGTKLTVLG              109

SEQ ID NO: 49            moltype = AA   length = 240
FEATURE                  Location/Qualifiers
source                   1..240
                         mol_type = protein
                         organism = synthetic construct
SEQUENCE: 49
EVQLLESGGG LVQPGGSLRL SCAASGFTFS SYMSWVRQAP GKGLEWVSSI GSGYYSTYYA    60
DSVKGRFTIS RDNSKNTLYL QMNSLRAEDT AVYYCARDYY GGFDYWGQGT LVTVSSGGGG   120
SGGGGSGGGG SQSVLTQPPS ASGTPGQRVT ISCSGSSSNI GSNYVYWYQQ LPGTAPKLLI   180
YRNNQRPSGV PDRFSGSKSG TSASLAISGL RSEDEADYYC AAYDSYSYVF GGGTKLTVLG   240

SEQ ID NO: 50            moltype = AA   length = 468
FEATURE                  Location/Qualifiers
source                   1..468
                         mol_type = protein
                         organism = synthetic construct
SEQUENCE: 50
EVQLLESGGG LVQPGGSLRL SCAASGFTFS SYMSWVRQAP GKGLEWVSSI GSGYYSTYYA    60
DSVKGRFTIS RDNSKNTLYL QMNSLRAEDT AVYYCARDYY GGFDYWGQGT LVTVSSGGGG   120
SGGGGSGGGG SQSVLTQPPS ASGTPGQRVT ISCSGSSSNI GSNYVYWYQQ LPGTAPKLLI   180
YRNNQRPSGV PDRFSGSKSG TSASLAISGL RSEDEADYYC AAYDSYSYVF GGGTKLTVLG   240
GQAGQTTTPA PRPPTPAPTI ASQPLSLRPE ACRPAAGGAV HTRGLDFACD IYIWAPLAGT   300
CGVLLLSLVI TLYCKRGRKK LLYIFKQPFM RPVQTTQEED GCSCRFPEEE EGGCELRVKF   360
SRSADAPAYQ QGQNQLYNEL NLGRREEYDV LDKRRGRDPE MGGKPRRKNP QEGLYNELQK   420
DKMAEAYSEI GMKGERRRGK GHDGLYQGLS TATKDTYDAL HMQALPPR              468

SEQ ID NO: 51            moltype = DNA   length = 12
FEATURE                  Location/Qualifiers
source                   1..12
                         mol_type = other DNA
                         organism = synthetic construct
SEQUENCE: 51
tcttacatga gc                                                                 12

SEQ ID NO: 52            moltype = DNA   length = 51
FEATURE                  Location/Qualifiers
source                   1..51
                         mol_type = other DNA
                         organism = synthetic construct
SEQUENCE: 52
tctatcggtt ctggttacta ctctacgtat tacgctgatt ctgtaaaagg t                      51

SEQ ID NO: 53            moltype = DNA   length = 24
FEATURE                  Location/Qualifiers
source                   1..24
                         mol_type = other DNA
                         organism = synthetic construct
```

-continued

```
SEQUENCE: 53
gactactacg gtggtttcga ctac                                                24

SEQ ID NO: 54           moltype = DNA   length = 39
FEATURE                 Location/Qualifiers
source                  1..39
                        mol_type = other DNA
                        organism = synthetic construct
SEQUENCE: 54
agtggctctt catctaatat tggctctaat tatgtctac                                39

SEQ ID NO: 55           moltype = DNA   length = 21
FEATURE                 Location/Qualifiers
source                  1..21
                        mol_type = other DNA
                        organism = synthetic construct
SEQUENCE: 55
agaaataacc agcggccaag c                                                   21

SEQ ID NO: 56           moltype = DNA   length = 21
FEATURE                 Location/Qualifiers
source                  1..21
                        mol_type = other DNA
                        organism = synthetic construct
SEQUENCE: 56
gctgcttacg actcttactc t                                                   21

SEQ ID NO: 57           moltype = DNA   length = 348
FEATURE                 Location/Qualifiers
source                  1..348
                        mol_type = other DNA
                        organism = synthetic construct
SEQUENCE: 57
gaggtgcagc tgttggagtc tggggggaggc ttggtacagc ctggggggtc cctgagactc        60
tcctgtgcag cctctggatt caccctttagc tcttacatga gctgggtccg ccaggctcca       120
gggaaggggc tggagtgggt ctcatctatc ggttctggtt actactctac gtattacgct       180
gattctgtaa aaggtcggtt caccatctcc agagacaatt ccaagaacac gctgtatctg       240
caaatgaaca gcctgagagc cgaggacacg gccgtgtatt actgtgcgcg tgactactac       300
ggtggtttcg actactgggg ccagggtaca ctggtcaccg tgagctca                    348

SEQ ID NO: 58           moltype = DNA   length = 327
FEATURE                 Location/Qualifiers
source                  1..327
                        mol_type = other DNA
                        organism = synthetic construct
SEQUENCE: 58
cagtctgtgc tgactcagcc accctcagcg tctgggaccc ccgggcagag ggtcaccatc        60
tcttgtagtg gctcttcatc taatattggc tctaattatg tctactggta ccagcagctc       120
ccaggaacgg cccccaaact cctcatctat agaaataacc agcggccaag cggggtccct       180
gaccgattct ctggctccaa gtctggcacc tcagcctccc tggccatcag tgggctccgg       240
tccgaggatg aggccgatta ttactgtgct gcttacgact cttactctta tgtcttcggc       300
ggaggcacca agctgacggt cctaggt                                            327

SEQ ID NO: 59           moltype = DNA   length = 720
FEATURE                 Location/Qualifiers
source                  1..720
                        mol_type = other DNA
                        organism = synthetic construct
SEQUENCE: 59
gaggtgcagc tgttggagtc tggggggaggc ttggtacagc ctggggggtc cctgagactc        60
tcctgtgcag cctctggatt cacctttagc tcttacatga gctgggtccg ccaggctcca       120
gggaaggggc tggagtgggt ctcatctatc ggttctggtt actactctac gtattacgct       180
gattctgtaa aaggtcggtt caccatctcc agagacaatt ccaagaacac gctgtatctg       240
caaatgaaca gcctgagagc cgaggacacg gccgtgtatt actgtgcgcg tgactactac       300
ggtggtttcg actactgggg ccagggtaca ctggtcaccg tgagctcagg tggaggcggt       360
tcaggcggag gtggatccgg cggtggcgga tcgcagtctg tgctgactca gccaccctca       420
gcgtctggga cccccgggca gagggtcacc atctcttgta gtggctcttc atctaatatt       480
ggctctaatt atgtctactg gtaccagcag ctcccaggaa cggcccccaa actcctcatc       540
tatagaaata accagcggcc aagcggggtc cctgaccgat tctctggctc caagtctggc       600
acctcagcct ccctggccat cagtgggctc cggtccgagg atgaggccga ttattactgt       660
gctgcttacg actcttactc ttatgtcttc ggcggaggca caagctgac ggtcctaggt       720

SEQ ID NO: 60           moltype = DNA   length = 1404
FEATURE                 Location/Qualifiers
source                  1..1404
                        mol_type = other DNA
                        organism = synthetic construct
SEQUENCE: 60
gaggtgcagc tgttggagtc tggggggaggc ttggtacagc ctggggggtc cctgagactc        60
```

-continued

```
tcctgtgcag cctctggatt caccttttagc tcttacatga gctgggtccg ccaggctcca   120
gggaaggggc tggagtgggt ctcatctatc ggttctggtt actactctac gtattacgct   180
gattctgtaa aaggtcggtt caccatctcc agagacaatt ccaagaacac gctgtatctg   240
caaatgaaca gcctgagagc cgaggacacg gccgtgtatt actgtgcgcg tgactactac   300
ggtggtttcg actactgggg ccagggtaca ctggtcaccg tgagctcagg tggaggcggt   360
tcaggcggag gtggatccgg cggtggcgga tcgcagtctg tgctgactca gccaccctca   420
gcgtctggga cccccgggca gagggtcacc atctcttgta gtggctcttc atctaatatt   480
ggctctaatt atgtctactg gtaccagcag ctcccaggaa cggcccccaa actcctcatc   540
tatagaaata accagcggcc aagcggggtc cctgaccgat tctctggctc caagtctggc   600
acctcagcct ccctggccat cagtgggctc cggtccgagg atgaggccga ttattactgt   660
gctgcttacg actcttactc ttatgtcttc ggcggaggca ccaagctgac ggtcctaggt   720
ggccaggccg gccagacaac gacacctgct cccagaccgc ctactcccgc cccaaccatt   780
gcatctcagc cactctctct gagacccgaa gcgtgtagac ctgcggccgg gggcgctgtc   840
cacacaagag gcttagactt cgcctgcgat atctatatct gggccccact cgcaggcact   900
tgtggagtgc tgctgctttc actcgtgata accctgtact gcaaaagggg gagaaagaag   960
ctgctgtata tttttaaaca accatttatg agacctgttc agactaccca ggaagaagac  1020
ggttgtagtt gcagattccc cgaggaggaa gaaggaggtg gcgagttgag agtaaagttc  1080
agcagatccg cagatgcccc tgcttaccag cagggtcaaa accagcttta caacgagctg  1140
aatttaggta gaagagagga atatgacgtg ttggataaaa gaagaggaag agacccggaa  1200
atgggcggca agcctcgaag aaaaaatccc caagagggac tctacaatga gctgcagaag  1260
gacaaaatgg ctgaagccta cagcgagatc ggcatgaagg gagaaagacg cagagggaaa  1320
gggcatgatg ggctttatca gggcttgtcc accgctacaa aggatactta tgacgcacta  1380
cacatgcagg ccctgccacc ccgt                                          1404
```

SEQ ID NO: 61          moltype = AA   length = 5
FEATURE                Location/Qualifiers
source                 1..5
                       mol_type = protein
                       organism = synthetic construct
SEQUENCE: 61
YYGMS                                                                     5

SEQ ID NO: 62          moltype = AA   length = 17
FEATURE                Location/Qualifiers
source                 1..17
                       mol_type = protein
                       organism = synthetic construct
SEQUENCE: 62
GIGSYSSYTY YADSVKG                                                       17

SEQ ID NO: 63          moltype = AA   length = 11
FEATURE                Location/Qualifiers
source                 1..11
                       mol_type = protein
                       organism = synthetic construct
SEQUENCE: 63
YASSPDAYFD Y                                                             11

SEQ ID NO: 64          moltype = AA   length = 13
FEATURE                Location/Qualifiers
source                 1..13
                       mol_type = protein
                       organism = synthetic construct
SEQUENCE: 64
SGSSSNIGSN YVY                                                           13

SEQ ID NO: 65          moltype = AA   length = 7
FEATURE                Location/Qualifiers
source                 1..7
                       mol_type = protein
                       organism = synthetic construct
SEQUENCE: 65
RNNQRPS                                                                   7

SEQ ID NO: 66          moltype = AA   length = 7
FEATURE                Location/Qualifiers
source                 1..7
                       mol_type = protein
                       organism = synthetic construct
SEQUENCE: 66
AAYYNYN                                                                   7

SEQ ID NO: 67          moltype = AA   length = 120
FEATURE                Location/Qualifiers
source                 1..120
                       mol_type = protein
                       organism = synthetic construct
SEQUENCE: 67
EVQLLESGGG LVQPGGSLRL SCAASGFTFS YYGMSWVRQA PGKGLEWVSG IGSYSSYTYY   60

```
ADSVKGRFTI SRDNSKNTLY LQMNSLRAED TAVYYCARYA SSPDAYFDYW GQGTLVTVSS  120

SEQ ID NO: 68           moltype = AA  length = 109
FEATURE                 Location/Qualifiers
source                  1..109
                        mol_type = protein
                        organism = synthetic construct
SEQUENCE: 68
QSVLTQPPSA SGTPGQRVTI SCSGSSSNIG SNYVYWYQQL PGTAPKLLIY RNNQRPSGVP  60
GRFSGSKSGT SASLAISGLR SEDEADYYCA AYYNYNYVFG GGTKLTVLG             109

SEQ ID NO: 69           moltype = AA  length = 244
FEATURE                 Location/Qualifiers
source                  1..244
                        mol_type = protein
                        organism = synthetic construct
SEQUENCE: 69
EVQLLESGGG LVQPGGSLRL SCAASGFTFS YYGMSWVRQA PGKGLEWVSG IGSYSSYTYY  60
ADSVKGRFTI SRDNSKNTLY LQMNSLRAED TAVYYCARYA SSPDAYFDYW GQGTLVTVSS  120
GGGGSGGGGS GGGGSQSVLT QPPSASGTPG QRVTISCSGS SSNIGSNYVY WYQQLPGTAP  180
KLLIYRNNQR PSGVPGRFSG SKSGTSASLA ISGLRSEDEA DYYCAAYYNY NYVFGGGTKL  240
TVLG                                                             244

SEQ ID NO: 70           moltype = AA  length = 472
FEATURE                 Location/Qualifiers
source                  1..472
                        mol_type = protein
                        organism = synthetic construct
SEQUENCE: 70
EVQLLESGGG LVQPGGSLRL SCAASGFTFS YYGMSWVRQA PGKGLEWVSG IGSYSSYTYY  60
ADSVKGRFTI SRDNSKNTLY LQMNSLRAED TAVYYCARYA SSPDAYFDYW GQGTLVTVSS  120
GGGGSGGGGS GGGGSQSVLT QPPSASGTPG QRVTISCSGS SSNIGSNYVY WYQQLPGTAP  180
KLLIYRNNQR PSGVPGRFSG SKSGTSASLA ISGLRSEDEA DYYCAAYYNY NYVFGGGTKL  240
TVLGGGQAGQT TTPAPRPPTP APTIASQPLS LRPEACRPAA GGAVHTRGLD FACDIYIWAP  300
LAGTCGVLLL SLVITLYCKR GRKKLLYIFK QPFMRPVQTT QEEDGCSCRF PEEEEGGCEL  360
RVKFSRSADA PAYQQGQNQL YNELNLGRRE EYDVLDKRRG RDPEMGGKPR RKNPQEGLYN  420
ELQKDKMAEA YSEIGMKGER RRGKGHDGLY QGLSTATKDT YDALHMQALP PR          472

SEQ ID NO: 71           moltype = DNA  length = 15
FEATURE                 Location/Qualifiers
source                  1..15
                        mol_type = other DNA
                        organism = synthetic construct
SEQUENCE: 71
tactatggta tgagc                                                  15

SEQ ID NO: 72           moltype = DNA  length = 51
FEATURE                 Location/Qualifiers
source                  1..51
                        mol_type = other DNA
                        organism = synthetic construct
SEQUENCE: 72
ggtatcggtt cttactcttc ttacacgtat tacgctgatt ctgtaaaagg t          51

SEQ ID NO: 73           moltype = DNA  length = 33
FEATURE                 Location/Qualifiers
source                  1..33
                        mol_type = other DNA
                        organism = synthetic construct
SEQUENCE: 73
tacgcttctt ctccggacgc ttacttcgac tac                             33

SEQ ID NO: 74           moltype = DNA  length = 39
FEATURE                 Location/Qualifiers
source                  1..39
                        mol_type = other DNA
                        organism = synthetic construct
SEQUENCE: 74
agtggctctt catctaatat tggctctaat tatgtctac                       39

SEQ ID NO: 75           moltype = DNA  length = 21
FEATURE                 Location/Qualifiers
source                  1..21
                        mol_type = other DNA
                        organism = synthetic construct
SEQUENCE: 75
agaaataacc agcggccaag c                                           21

SEQ ID NO: 76           moltype = DNA  length = 21
```

-continued

```
FEATURE              Location/Qualifiers
source               1..21
                     mol_type = other DNA
                     organism = synthetic construct
SEQUENCE: 76
gctgcttact acaactacaa c                                               21

SEQ ID NO: 77        moltype = DNA  length = 360
FEATURE              Location/Qualifiers
source               1..360
                     mol_type = other DNA
                     organism = synthetic construct
SEQUENCE: 77
gaggtgcagc tgttggagtc tggggggaggc ttggtacagc ctggggggtc cctgagactc   60
tcctgtgcag cctctggatt cacctttagc tactatggta tgagctgggt ccgccaggct  120
ccagggaagg ggctggagtg ggtctcaggt atcggttctt actcttctta cacgtattac  180
gctgattctg taaaaggtcg gttcaccatc tccagagaca attccaagaa cacgctgtat  240
ctgcaaatga acagcctgag agccgaggac acggccgtgt attactgtgc gcgttacgct  300
tcttctccgg acgcttactt cgactactgg ggccagggta cactggtcac cgtgagctca  360

SEQ ID NO: 78        moltype = DNA  length = 327
FEATURE              Location/Qualifiers
source               1..327
                     mol_type = other DNA
                     organism = synthetic construct
SEQUENCE: 78
cagtctgtgc tgactcagcc accctcagcg tctgggaccc ccgggcagag ggtcaccatc   60
tcttgtagtg gctcttcatc taatattggc tctaattatg tctactggta ccagcagctc  120
ccaggaacgg cccccaaact cctcatctat agaaataacc agcggccaag cggggtccct  180
ggccgattct ctggctccaa gtctggcacc tcagcctccc tggccatcag tgggctccgg  240
tccgaggatg aggccgatta ttactgtgct gcttactaca actacaacta tgtcttcggc  300
ggaggcacca agctgacggt cctaggt                                        327

SEQ ID NO: 79        moltype = DNA  length = 732
FEATURE              Location/Qualifiers
source               1..732
                     mol_type = other DNA
                     organism = synthetic construct
SEQUENCE: 79
gaggtgcagc tgttggagtc tgggggaggc ttggtacagc ctggggggtc cctgagactc   60
tcctgtgcag cctctggatt cacctttagc tactatggta tgagctgggt ccgccaggct  120
ccagggaagg ggctggagtg ggtctcaggt atcggttctt actcttctta cacgtattac  180
gctgattctg taaaaggtcg gttcaccatc tccagagaca attccaagaa cacgctgtat  240
ctgcaaatga acagcctgag agccgaggac acggccgtgt attactgtgc gcgttacgct  300
tcttctccgg acgcttactt cgactactgg ggccagggta cactggtcac cgtgagctca  360
ggtggaggcg gttcaggcgg aggtggatcc ggcggtggcg gatcgcagtc tgtgctgact  420
cagccaccct cagcgtctgg gacccccggg cagagggtca ccatctcttg tagtggctct  480
tcatctaata ttggctctaa ttatgtctac tggtaccagc agctcccagg aacggccccc  540
aaactcctca tctatagaaa taaccagcgg ccaagcgggg tccctggccg attctctggc  600
tccaagtctg gcacctcagc ctccctggcc atcagtgggc tccggtccga ggatgaggcc  660
gattattact gtgctgctta ctacaactac aactatgtct cggcggagg caccaagctg  720
acggtcctag gt                                                       732

SEQ ID NO: 80        moltype = DNA  length = 1416
FEATURE              Location/Qualifiers
source               1..1416
                     mol_type = other DNA
                     organism = synthetic construct
SEQUENCE: 80
gaggtgcagc tgttggagtc tgggggaggc ttggtacagc ctggggggtc cctgagactc   60
tcctgtgcag cctctggatt cacctttagc tactatggta tgagctgggt ccgccaggct  120
ccagggaagg ggctggagtg ggtctcaggt atcggttctt actcttctta cacgtattac  180
gctgattctg taaaaggtcg gttcaccatc tccagagaca attccaagaa cacgctgtat  240
ctgcaaatga acagcctgag agccgaggac acggccgtgt attactgtgc gcgttacgct  300
tcttctccgg acgcttactt cgactactgg ggccagggta cactggtcac cgtgagctca  360
ggtggaggcg gttcaggcgg aggtggatcc ggcggtggcg gatcgcagtc tgtgctgact  420
cagccaccct cagcgtctgg gacccccggg cagagggtca ccatctcttg tagtggctct  480
tcatctaata ttggctctaa ttatgtctac tggtaccagc agctcccagg aacggccccc  540
aaactcctca tctatagaaa taaccagcgg ccaagcgggg tccctggccg attctctggc  600
tccaagtctg gcacctcagc ctccctggcc atcagtgggc tccggtccga ggatgaggcc  660
gattattact gtgctgctta ctacaactac aactatgtct cggcggagg caccaagctg  720
acggtcctag gtgccaggc cggccagaca acgacacctg ctcccagacc gcctactccc  780
gccccaacca ttgcatctca gccactctct ctgagaccg aagcgtgtag acctgcggcc  840
ggggcgctg tccacacaag aggcttagac ttcgcctgcg atatctatat ctgggccca  900
ctcgcaggca cttgtggagt gctgctgctt cactcgtga taaccctgta ctgcaaaagg  960
gggagaaaga agctgctgta tattttttaaa caaccattta tgagacctgt tcagactacc 1020
caggaagaag acgttgtag ttgcagattc ccgaggagg aagaaggagg ttgcgagttg 1080
agagtaaagt tcagcagatc cgcagatgcc cctgcttacc agcagggtca aaaccagctt 1140
tacaacgagc tgaatttagg tagaagagag gaatatgacg tgttggataa aagaagagga 1200
```

```
agagacccgg aaatgggcgg caagcctcga agaaaaaatc cccaagaggg actctacaat   1260
gagctgcaga aggacaaaat ggctgaagcc tacagcgaga tcggcatgaa gggagaaaga   1320
cgcagaggga aagggcatga tgggctttat cagggcttgt ccaccgctac aaaggatact   1380
tatgacgcac tacacatgca ggccctgcca ccccgt                             1416
```

SEQ ID NO: 81      moltype = AA   length = 5
FEATURE      Location/Qualifiers
source      1..5
     mol_type = protein
     organism = synthetic construct
SEQUENCE: 81
SYGMS          5

SEQ ID NO: 82      moltype = AA   length = 17
FEATURE      Location/Qualifiers
source      1..17
     mol_type = protein
     organism = synthetic construct
SEQUENCE: 82
YISGGSYYTY YADSVKG          17

SEQ ID NO: 83      moltype = AA   length = 12
FEATURE      Location/Qualifiers
source      1..12
     mol_type = protein
     organism = synthetic construct
SEQUENCE: 83
YGYGYYDGSF DY          12

SEQ ID NO: 84      moltype = AA   length = 13
FEATURE      Location/Qualifiers
source      1..13
     mol_type = protein
     organism = synthetic construct
SEQUENCE: 84
SGSSSNIGSN YVY          13

SEQ ID NO: 85      moltype = AA   length = 7
FEATURE      Location/Qualifiers
source      1..7
     mol_type = protein
     organism = synthetic construct
SEQUENCE: 85
RNNQRPS          7

SEQ ID NO: 86      moltype = AA   length = 7
FEATURE      Location/Qualifiers
source      1..7
     mol_type = protein
     organism = synthetic construct
SEQUENCE: 86
AADGPYN          7

SEQ ID NO: 87      moltype = AA   length = 121
FEATURE      Location/Qualifiers
source      1..121
     mol_type = protein
     organism = synthetic construct
SEQUENCE: 87
EVQLLESGGG LVQPGGSLRL SCAASGFTFS SYGMSWVRQA PGKGLEWVSY ISGGSYYTYY   60
ADSVKGRFTI SRDNSKNTLY LQMNSLRAED TAVYYCARYG YGYYDGSFDY WGQGTLVTVS   120
S          121

SEQ ID NO: 88      moltype = AA   length = 109
FEATURE      Location/Qualifiers
source      1..109
     mol_type = protein
     organism = synthetic construct
SEQUENCE: 88
QSVLTQPPSA SGTPGQRVTI SCSGSSSNIG SNYVYWYQQL PGTAPKLLIY RNNQRPSGVP   60
DRFSGSKSGT SASLAISGLR SEDEADYYCA ADGPYNYVFG GGTKLTVLG      109

SEQ ID NO: 89      moltype = AA   length = 245
FEATURE      Location/Qualifiers
source      1..245
     mol_type = protein
     organism = synthetic construct
SEQUENCE: 89
EVQLLESGGG LVQPGGSLRL SCAASGFTFS SYGMSWVRQA PGKGLEWVSY ISGGSYYTYY   60

```
ADSVKGRFTI SRDNSKNTLY LQMNSLRAED TAVYYCARYG YGYYDGSFDY WGQGTLVTVS  120
SGGGGSGGGG SGGGGSQSVL TQPPSASGTP GQRVTISCSG SSSNIGSNYV YWYQQLPGTA  180
PKLLIYRNNQ RPSGVPDRFS GSKSGTSASL AISGLRSEDE ADYYCAADGP YNYVFGGGTK  240
LTVLG                                                              245

SEQ ID NO: 90              moltype = AA   length = 473
FEATURE                    Location/Qualifiers
source                     1..473
                           mol_type = protein
                           organism = synthetic construct
SEQUENCE: 90
EVQLLESGGG LVQPGGSLRL SCAASGFTFS SYGMSWVRQA PGKGLEWVSY ISGGSYYTYY   60
ADSVKGRFTI SRDNSKNTLY LQMNSLRAED TAVYYCARYG YGYYDGSFDY WGQGTLVTVS  120
SGGGGSGGGG SGGGGSQSVL TQPPSASGTP GQRVTISCSG SSSNIGSNYV YWYQQLPGTA  180
PKLLIYRNNQ RPSGVPDRFS GSKSGTSASL AISGLRSEDE ADYYCAADGP YNYVFGGGTK  240
LTVLGGQAGQ TTTPAPRPPT PAPTIASQPL SLRPEACRPA AGGAVHTRGL DFACDIYIWA  300
PLAGTCGVLL LSLVITLYCK RGRKKLLYIF KQPFMRPVQT TQEEDGCSCR FPEEEEGGCE  360
LRVKFSRSAD APAYQQGQNQ LYNELNLGRR EEYDVLDKRR GRDPEMGGKP RRKNPQEGLY  420
NELQKDKMAE AYSEIGMKGE RRRGKGHDGL YQGLSTATKD TYDALHMQAL PPR          473

SEQ ID NO: 91              moltype = DNA   length = 15
FEATURE                    Location/Qualifiers
source                     1..15
                           mol_type = other DNA
                           organism = synthetic construct
SEQUENCE: 91
tcttatggta tgagc                                                    15

SEQ ID NO: 92              moltype = DNA   length = 51
FEATURE                    Location/Qualifiers
source                     1..51
                           mol_type = other DNA
                           organism = synthetic construct
SEQUENCE: 92
tacatctctg gtggttctta ctacacgtat tacgctgatt ctgtaaaagg t            51

SEQ ID NO: 93              moltype = DNA   length = 36
FEATURE                    Location/Qualifiers
source                     1..36
                           mol_type = other DNA
                           organism = synthetic construct
SEQUENCE: 93
tacggttacg gttactacga cggttctttc gactac                             36

SEQ ID NO: 94              moltype = DNA   length = 39
FEATURE                    Location/Qualifiers
source                     1..39
                           mol_type = other DNA
                           organism = synthetic construct
SEQUENCE: 94
agtggctctt catctaatat tggctctaat tatgtctac                          39

SEQ ID NO: 95              moltype = DNA   length = 21
FEATURE                    Location/Qualifiers
source                     1..21
                           mol_type = other DNA
                           organism = synthetic construct
SEQUENCE: 95
agaaataacc agcggccaag c                                             21

SEQ ID NO: 96              moltype = DNA   length = 21
FEATURE                    Location/Qualifiers
source                     1..21
                           mol_type = other DNA
                           organism = synthetic construct
SEQUENCE: 96
gctgctgacg gtccgtacaa c                                             21

SEQ ID NO: 97              moltype = DNA   length = 363
FEATURE                    Location/Qualifiers
source                     1..363
                           mol_type = other DNA
                           organism = synthetic construct
SEQUENCE: 97
gaggtgcagc tgttggagtc tgggggaggc ttggtacagc ctggggggtc cctgagactc   60
tcctgtgcag cctctggatt cacctttagc tcttatggta tgagctgggt ccgccaggct  120
ccagggaagg ggctggagtg ggtctcatac atctctggtg gttcttacta cacgtattac  180
gctgattctg taaaaggtcg gttcaccatc tccagagaca attccaagaa cacgctgtat  240
ctgcaaatga acagcctgag agccgaggac acggccgtgt attactgtgc gcgttacggt  300
```

-continued

```
tacggttact acgacggttc tttcgactac tggggccagg gtacactggt caccgtgagc    360
tca                                                                  363

SEQ ID NO: 98          moltype = DNA   length = 327
FEATURE                Location/Qualifiers
source                 1..327
                       mol_type = other DNA
                       organism = synthetic construct
SEQUENCE: 98
cagtctgtgc tgactcagcc accctcagcg tctgggaccc ccgggcagag ggtcaccatc    60
tcttgtagtg gctcttcatc taatattggc tctaattatg tctactggta ccagcagctc    120
ccaggaacgg cccccaaact cctcatctat agaaataacc agcggccaag cggggtccct    180
gaccgattct ctggctccaa gtctggcacc tcagcctccc tggccatcag tgggctccgg    240
tccgaggatg aggccgatta ttactgtgct gctgacggtc cgtacaacta tgtcttcggc    300
ggaggcacca agctgacggt cctaggt                                        327

SEQ ID NO: 99          moltype = DNA   length = 735
FEATURE                Location/Qualifiers
source                 1..735
                       mol_type = other DNA
                       organism = synthetic construct
SEQUENCE: 99
gaggtgcagc tgttggagtc tggggggaggc ttggtacagc ctggggggtc cctgagactc    60
tcctgtgcag cctctggatt cacctttagc tcttatggta tgagctgggt ccgccaggct    120
ccagggaagg ggctggagtg ggtctcatac atctctggtg gttcttacta cacgtattac    180
gctgattctg taaaaggtcg gttcaccatc tccagagaca attccaagaa cacgctgtat    240
ctgcaaatga acagcctgag agccgaggac acggccgtgt attactgtgc gcgttacggt    300
tacggttact acgacggttc tttcgactac tggggccagg gtacactggt caccgtgagc    360
tcaggtggag gcggttcagg cggaggtgga tccggcggtg gcggatcgca gtctgtgctg    420
actcagccac cctcagcgtc tgggaccccc gggcagaggg tcaccatctc ttgtagtggc    480
tcttcatcta atattggctc taattatgtc tactggtacc agcagctccc aggaacggcc    540
cccaaactcc tcatctatag aaataaccag cggccaagcg gggtccctga ccgattctct    600
ggctccaagt ctggcacctc agcctccctg gccatcagtg ggctccggtc cgaggatgag    660
gccgattatt actgtgctgc tgacggtccg tacaactatg tcttcggcgg aggcaccaag    720
ctgacggtcc taggt                                                     735

SEQ ID NO: 100         moltype = DNA   length = 1419
FEATURE                Location/Qualifiers
source                 1..1419
                       mol_type = other DNA
                       organism = synthetic construct
SEQUENCE: 100
gaggtgcagc tgttggagtc tggggggaggc ttggtacagc ctggggggtc cctgagactc    60
tcctgtgcag cctctggatt cacctttagc tcttatggta tgagctgggt ccgccaggct    120
ccagggaagg ggctggagtg ggtctcatac atctctggtg gttcttacta cacgtattac    180
gctgattctg taaaaggtcg gttcaccatc tccagagaca attccaagaa cacgctgtat    240
ctgcaaatga acagcctgag agccgaggac acggccgtgt attactgtgc gcgttacggt    300
tacggttact acgacggttc tttcgactac tggggccagg gtacactggt caccgtgagc    360
tcaggtggag gcggttcagg cggaggtgga tccggcggtg gcggatcgca gtctgtgctg    420
actcagccac cctcagcgtc tgggaccccc gggcagaggg tcaccatctc ttgtagtggc    480
tcttcatcta atattggctc taattatgtc tactggtacc agcagctccc aggaacggcc    540
cccaaactcc tcatctatag aaataaccag cggccaagcg gggtccctga ccgattctct    600
ggctccaagt ctggcacctc agcctccctg gccatcagtg ggctccggtc cgaggatgag    660
gccgattatt actgtgctgc tgacggtccg tacaactatg tcttcggcgg aggcaccaag    720
ctgacggtcc taggtggcca ggccgcccag acaacgacac ctgctcccag accgcctact    780
cccgccccaa ccattgcatc tcagccactc tctctgagac cgaagcgtg tagacctgcg     840
gccggggggcg ctgtccacac aagaggctta gacttcgcct gcgatatcta tatctgggcc    900
ccactcgcag gcacttgtgg agtgctgctg ctttcactcg tgataaccct gtactgcaaa    960
agggggagaa agaagctgct gtatattttt aaacaaccat ttatgagacc tgttcagact   1020
acccaggaag aagacggttg tagttgcaga ttccccgagg aggaagaagg aggttgcgag   1080
ttgagagtaa agttcagcag atccgcagat gccctgctt accagcaggg tcaaaaccag    1140
ctttacaacg agctgaattt aggtagaaga gaggaatatg acgtgttgga taaaagaaga   1200
ggaagagacc cggaaatggg cggcaagcct cgaagaaaaa atcccaaga gggactctac    1260
aatgagctgc agaaggacaa aatggctgaa gcctacagcg aggtcggcat gaagggagaa   1320
agacgcagag ggaaagggca tgatgggctt tatcagggct tgtccaccgc tacaaaggat   1380
acttatgacg cactacacat gcaggccctg ccacccccgt                         1419

SEQ ID NO: 101         moltype = AA   length = 5
FEATURE                Location/Qualifiers
source                 1..5
                       mol_type = protein
                       organism = synthetic construct
SEQUENCE: 101
SYSMS                                                                  5

SEQ ID NO: 102         moltype = AA   length = 16
FEATURE                Location/Qualifiers
source                 1..16
                       mol_type = protein
```

-continued

```
                       organism = synthetic construct
SEQUENCE: 102
GIGYPYYTYY ADSVKG                                                      16

SEQ ID NO: 103         moltype = AA   length = 9
FEATURE                Location/Qualifiers
source                 1..9
                       mol_type = protein
                       organism = synthetic construct
SEQUENCE: 103
YYYDYGFDY                                                              9

SEQ ID NO: 104         moltype = AA   length = 13
FEATURE                Location/Qualifiers
source                 1..13
                       mol_type = protein
                       organism = synthetic construct
SEQUENCE: 104
SGSSSNIGSN YVY                                                         13

SEQ ID NO: 105         moltype = AA   length = 7
FEATURE                Location/Qualifiers
source                 1..7
                       mol_type = protein
                       organism = synthetic construct
SEQUENCE: 105
RNNQRPS                                                                7

SEQ ID NO: 106         moltype = AA   length = 7
FEATURE                Location/Qualifiers
source                 1..7
                       mol_type = protein
                       organism = synthetic construct
SEQUENCE: 106
AAYRSYD                                                                7

SEQ ID NO: 107         moltype = AA   length = 117
FEATURE                Location/Qualifiers
source                 1..117
                       mol_type = protein
                       organism = synthetic construct
SEQUENCE: 107
EVQLLESGGG LVQPGGSLRL SCAASGFTFS SYSMSWVRQA PGKGLEWVSG IGYPYYTYYA      60
DSVKGRFTIS RDNSKNTLYL QMNSLRAEDT AVYYCARYYY DYGFDYWGQG TLVTVSS         117

SEQ ID NO: 108         moltype = AA   length = 109
FEATURE                Location/Qualifiers
source                 1..109
                       mol_type = protein
                       organism = synthetic construct
SEQUENCE: 108
QSVLTQPPSA SGTPGQRVTI SCSGSSSNIG SNYVYWYQQL PGTAPKLLIY RNNQRPSGVP      60
DRFSGSKSGT SASLAISGLR SEDEADYYCA AYRSYDYVFG GGTKLTVLG                  109

SEQ ID NO: 109         moltype = AA   length = 241
FEATURE                Location/Qualifiers
source                 1..241
                       mol_type = protein
                       organism = synthetic construct
SEQUENCE: 109
EVQLLESGGG LVQPGGSLRL SCAASGFTFS SYSMSWVRQA PGKGLEWVSG IGYPYYTYYA      60
DSVKGRFTIS RDNSKNTLYL QMNSLRAEDT AVYYCARYYY DYGFDYWGQG TLVTVSSGGG      120
GSGGGGSGGG GSQSVLTQPP SASGTPGQRV TISCSGSSSN IGSNYVYWYQ QLPGTAPKLL      180
IYRNNQRPSG VPDRFSGSKS GTSASLAISG LRSEDEADYY CAAYRSYDYV FGGGTKLTVL      240
G                                                                     241

SEQ ID NO: 110         moltype = AA   length = 469
FEATURE                Location/Qualifiers
source                 1..469
                       mol_type = protein
                       organism = synthetic construct
SEQUENCE: 110
EVQLLESGGG LVQPGGSLRL SCAASGFTFS SYSMSWVRQA PGKGLEWVSG IGYPYYTYYA      60
DSVKGRFTIS RDNSKNTLYL QMNSLRAEDT AVYYCARYYY DYGFDYWGQG TLVTVSSGGG      120
GSGGGGSGGG GSQSVLTQPP SASGTPGQRV TISCSGSSSN IGSNYVYWYQ QLPGTAPKLL      180
IYRNNQRPSG VPDRFSGSKS GTSASLAISG LRSEDEADYY CAAYRSYDYV FGGGTKLTVL      240
GGQAGQTTTP APRPPTPAPT IASQPLSLRP EACRPAAGGA VHTRGLDFAC DIYIWAPLAG      300
TCGVLLLSLV ITLYCKRGRK KLLYIFKQPF MRPVQTTQEE DGCSCRFPEE EEGGCELRVK      360
FSRSADAPAY QQGQNQLYNE LNLGRREEYD VLDKRRGRDP EMGGKPRRKN PQEGLYNELQ      420
```

-continued

```
KDKMAEAYSE IGMKGERRRG KGHDGLYQGL STATKDTYDA LHMQALPPR        469

SEQ ID NO: 111          moltype = DNA   length = 15
FEATURE                 Location/Qualifiers
source                  1..15
                        mol_type = other DNA
                        organism = synthetic construct
SEQUENCE: 111
tcttattcta tgagc                                             15

SEQ ID NO: 112          moltype = DNA   length = 48
FEATURE                 Location/Qualifiers
source                  1..48
                        mol_type = other DNA
                        organism = synthetic construct
SEQUENCE: 112
ggtatcggtt acccttacta cacgtattac gctgattctg taaaaggt        48

SEQ ID NO: 113          moltype = DNA   length = 27
FEATURE                 Location/Qualifiers
source                  1..27
                        mol_type = other DNA
                        organism = synthetic construct
SEQUENCE: 113
tactactacg actacggttt cgactac                                27

SEQ ID NO: 114          moltype = DNA   length = 39
FEATURE                 Location/Qualifiers
source                  1..39
                        mol_type = other DNA
                        organism = synthetic construct
SEQUENCE: 114
agtggctctt catctaatat tggctctaat tatgtctac                  39

SEQ ID NO: 115          moltype = DNA   length = 21
FEATURE                 Location/Qualifiers
source                  1..21
                        mol_type = other DNA
                        organism = synthetic construct
SEQUENCE: 115
agaaataacc agcggccaag c                                      21

SEQ ID NO: 116          moltype = DNA   length = 21
FEATURE                 Location/Qualifiers
source                  1..21
                        mol_type = other DNA
                        organism = synthetic construct
SEQUENCE: 116
gctgcttacc gttcttacga c                                      21

SEQ ID NO: 117          moltype = DNA   length = 351
FEATURE                 Location/Qualifiers
source                  1..351
                        mol_type = other DNA
                        organism = synthetic construct
SEQUENCE: 117
gaggtgcagc tgttggagtc tggggggaggc ttggtacagc ctggggggtc cctgagactc   60
tcctgtgcag cctctggatt cacctttagc tcttattcta tgagctgggt ccgccaggct  120
ccagggaagg ggctggagtg ggtctcaggt atcggttacc cttactacac gtattacgct  180
gattctgtaa aaggtcggtt caccatctcc agagacaatt ccaagaacac gctgtatctg  240
caaatgaaca gcctgagagc cgaggacacg gccgtgtatt actgtgcgcg ttactactac  300
gactacggtt cgactactg gggccaggg acactggtca ccgtgagctc a              351

SEQ ID NO: 118          moltype = DNA   length = 327
FEATURE                 Location/Qualifiers
source                  1..327
                        mol_type = other DNA
                        organism = synthetic construct
SEQUENCE: 118
cagtctgtgc tgactcagcc accctcagcg tctgggaccc ccgggcagag ggtcaccatc   60
tcttgtagtg gctcttcatc taatattggc tctaattatg tctactgta ccagcagctc  120
ccaggaacgg ccccccaaact cctcatctat agaaataacc agcggccaag cggggtccct  180
gaccgattct ctggctccaa gtctggcacc tcagcctccc tggccatcag tgggctccgg  240
tccgaggatg aggccgatta ttactgtgct gcttaccgt cttacgacta tgtcttcggc  300
ggaggcacca agctgacggt cctaggt                               327

SEQ ID NO: 119          moltype = DNA   length = 723
FEATURE                 Location/Qualifiers
source                  1..723
```

```
                        mol_type = other DNA
                        organism = synthetic construct
SEQUENCE: 119
gaggtgcagc tgttggagtc tggggggaggc ttggtacagc ctggggggtc cctgagactc    60
tcctgtgcag cctctggatt caccttagc tcttattcta tgagctggct ccgccaggct   120
ccagggaagg ggctggagtg ggtctcaggt atcggttacc cttactacac gtattacgct   180
gattctgtaa aaggtcggtt caccatctcc agagacaatt ccaagaacac gctgtatctg   240
caaatgaaca gcctgagagc cgaggacacg gccgtgtatt actgtgcgcg ttactactac   300
gactacggtt tcgactactg gggccagggt acactggtca ccgtgagctc aggtggaggc   360
ggttcaggcg gaggtggatc cggcggtggc ggatcgcagt ctgtgctgac tcagccaccc   420
tcagcgtctg ggaccccggg gcagagggtc accatctctt gtagtggctc ttcatctaat   480
attggctcta attatgtcta ctggtaccag cagctcccag gaacggcccc caaactcctc   540
atctatagaa ataaccagcg gccaagcggg gtccctgacc gattctctgg ctccaagtct   600
ggcacctcag cctccctggc catcagtggg ctccggtccg aggatgaggc cgattattac   660
tgtgctgctt accgttctta cgactatgtc ttcggcggag gcaccaagct gaccggtccta   720
ggt                                                                   723

SEQ ID NO: 120          moltype = DNA  length = 1407
FEATURE                 Location/Qualifiers
source                  1..1407
                        mol_type = other DNA
                        organism = synthetic construct
SEQUENCE: 120
gaggtgcagc tgttggagtc tggggggaggc ttggtacagc ctggggggtc cctgagactc    60
tcctgtgcag cctctggatt caccttagc tcttattcta tgagctgggt ccgccaggct   120
ccagggaagg ggctggagtg ggtctcaggt atcggttacc cttactacac gtattacgct   180
gattctgtaa aaggtcggtt caccatctcc agagacaatt ccaagaacac gctgtatctg   240
caaatgaaca gcctgagagc cgaggacacg gccgtgtatt actgtgcgcg ttactactac   300
gactacggtt tcgactactg gggccagggt acactggtca ccgtgagctc aggtggaggc   360
ggttcaggcg gaggtggatc cggcggtggc ggatcgcagt ctgtgctgac tcagccaccc   420
tcagcgtctg ggaccccggg gcagagggtc accatctctt gtagtggctc ttcatctaat   480
attggctcta attatgtcta ctggtaccag cagctcccag gaacggcccc caaactcctc   540
atctatagaa ataaccagcg gccaagcggg gtccctgacc gattctctgg ctccaagtct   600
ggcacctcag cctccctggc catcagtggg ctccggtccg aggatgaggc cgattattac   660
tgtgctgctt accgttctta cgactatgtc ttcggcggag gcaccaagct gaccggtccta   720
ggtggccagg ccggccagac aacgacacct gctcccagac cgcctactcc cgccccaacc   780
attgcatctc agccactctc tctgagaccc gaagcgtgta gacctgcggc cggggggcgct   840
gtccacacaa gaggcttaga cttcgcctgc gatatctata tctgggcccc actcgcaggc   900
acttgtggag tgctgctgct ttcactcgtg ataaccctgt actgcaaaag ggggagaaag   960
aagctgctgt atatttttaa acaaccattt atgagacctg ttcagactac ccaggaagaa  1020
gacgttgta gttgcagatt ccccgaggag gaagaaggag gttgcgagtt gagagtaaag  1080
ttcagcagat ccgcagatgc ccctgcttac cagcagggtc aaaaaccagct ttacaacgag  1140
ctgaatttag gtagaagaga ggaatatgac gtgttggata aagaagagag aagagaccccg  1200
gaaatgggcg gcaagcctcg aagaaaaaat ccccaagagg gactctacaa tgagctgcag  1260
aaggacaaaa tggctgaagc ctacagcgag atcggcatga agggagaaag acgcagaggg  1320
aaagggcatg atgggcttta tcagggcttg tccaccgcta caaaggatac ttatgacgca  1380
ctacacatgc aggccctgcc accccgt                                      1407

SEQ ID NO: 121          moltype = AA  length = 5
FEATURE                 Location/Qualifiers
source                  1..5
                        mol_type = protein
                        organism = synthetic construct
SEQUENCE: 121
YYYMS                                                                   5

SEQ ID NO: 122          moltype = AA  length = 17
FEATURE                 Location/Qualifiers
source                  1..17
                        mol_type = protein
                        organism = synthetic construct
SEQUENCE: 122
YIGGGGSGTY YADSVKG                                                     17

SEQ ID NO: 123          moltype = AA  length = 9
FEATURE                 Location/Qualifiers
source                  1..9
                        mol_type = protein
                        organism = synthetic construct
SEQUENCE: 123
GPYYGYFDY                                                               9

SEQ ID NO: 124          moltype = AA  length = 13
FEATURE                 Location/Qualifiers
source                  1..13
                        mol_type = protein
                        organism = synthetic construct
SEQUENCE: 124
SGSSSNIGSN YVY                                                         13
```

-continued

```
SEQ ID NO: 125               moltype = AA   length = 7
FEATURE                      Location/Qualifiers
source                       1..7
                             mol_type = protein
                             organism = synthetic construct
SEQUENCE: 125
RNNQRPS                                                              7

SEQ ID NO: 126               moltype = AA   length = 8
FEATURE                      Location/Qualifiers
source                       1..8
                             mol_type = protein
                             organism = synthetic construct
SEQUENCE: 126
AAYPSYDS                                                             8

SEQ ID NO: 127               moltype = AA   length = 118
FEATURE                      Location/Qualifiers
source                       1..118
                             mol_type = protein
                             organism = synthetic construct
SEQUENCE: 127
EVQLLESGGG LVQPGGSLRL SCAASGFTFS YYYMSWVRQA PGKGLEWVSY IGGGGSGTYY    60
ADSVKGRFTI SRDNSKNTLY LQMNSLRAED TAVYYCARGP YYGYFDYWGQ GTLVTVSS     118

SEQ ID NO: 128               moltype = AA   length = 110
FEATURE                      Location/Qualifiers
source                       1..110
                             mol_type = protein
                             organism = synthetic construct
SEQUENCE: 128
QSVLTQPPSA SGTPGQRVTI SCSGSSSNIG SNYVYWYQQL PGTAPKLLIY RNNQRPSGVP    60
DRFSGSKSGT SASLAISGLR SEDEADYYCA AYPSYDSYVF GGGTKLTVLG             110

SEQ ID NO: 129               moltype = AA   length = 243
FEATURE                      Location/Qualifiers
source                       1..243
                             mol_type = protein
                             organism = synthetic construct
SEQUENCE: 129
EVQLLESGGG LVQPGGSLRL SCAASGFTFS YYYMSWVRQA PGKGLEWVSY IGGGGSGTYY    60
ADSVKGRFTI SRDNSKNTLY LQMNSLRAED TAVYYCARGP YYGYFDYWGQ GTLVTVSSGG   120
GGSGGGGSGG GGSQSVLTQP PSASGTPGQR VTISCSGSSS NIGSNYVYWY QQLPGTAPKL   180
LIYRNNQRPS GVPDRFSGSK SGTSASLAIS GLRSEDEADY YCAAYPSYDS YVFGGGTKLT   240
VLG                                                                243

SEQ ID NO: 130               moltype = AA   length = 471
FEATURE                      Location/Qualifiers
source                       1..471
                             mol_type = protein
                             organism = synthetic construct
SEQUENCE: 130
EVQLLESGGG LVQPGGSLRL SCAASGFTFS YYYMSWVRQA PGKGLEWVSY IGGGGSGTYY    60
ADSVKGRFTI SRDNSKNTLY LQMNSLRAED TAVYYCARGP YYGYFDYWGQ GTLVTVSSGG   120
GGSGGGGSGG GGSQSVLTQP PSASGTPGQR VTISCSGSSS NIGSNYVYWY QQLPGTAPKL   180
LIYRNNQRPS GVPDRFSGSK SGTSASLAIS GLRSEDEADY YCAAYPSYDS YVFGGGTKLT   240
VLGGQAGQTT TPAPRPPTPA PTIASQPLSL RPEACRPAAG GAVHTRGLDF ACDIYIWAPL   300
AGTCGVLLLS LVITLYCKRG RKKLLYIFKQ PFMRPVQTTQ EEDGCSCRFP EEEEGGCELR   360
VKFSRSADAP AYQQGQNQLY NELNLGRREE YDVLDKRRGR DPEMGGKPRR KNPQEGLYNE   420
LQKDKMAEAY SEIGMKGERR RGKGHDGLYQ GLSTATKDTY DALHMQALPP R            471

SEQ ID NO: 131               moltype = DNA   length = 15
FEATURE                      Location/Qualifiers
source                       1..15
                             mol_type = other DNA
                             organism = synthetic construct
SEQUENCE: 131
tactattaca tgagc                                                    15

SEQ ID NO: 132               moltype = DNA   length = 51
FEATURE                      Location/Qualifiers
source                       1..51
                             mol_type = other DNA
                             organism = synthetic construct
SEQUENCE: 132
tacatcggtg gtggtggttc tggtacgtat tacgctgatt ctgtaaaagg t            51

SEQ ID NO: 133               moltype = DNA   length = 27
```

-continued

```
FEATURE              Location/Qualifiers
source               1..27
                     mol_type = other DNA
                     organism = synthetic construct
SEQUENCE: 133
ggtccgtact acggttactt cgactac                                          27

SEQ ID NO: 134       moltype = DNA   length = 39
FEATURE              Location/Qualifiers
source               1..39
                     mol_type = other DNA
                     organism = synthetic construct
SEQUENCE: 134
agtggctctt catctaatat tggctctaat tatgtctac                             39

SEQ ID NO: 135       moltype = DNA   length = 21
FEATURE              Location/Qualifiers
source               1..21
                     mol_type = other DNA
                     organism = synthetic construct
SEQUENCE: 135
agaaataacc agcggccaag c                                                21

SEQ ID NO: 136       moltype = DNA   length = 24
FEATURE              Location/Qualifiers
source               1..24
                     mol_type = other DNA
                     organism = synthetic construct
SEQUENCE: 136
gctgcttacc cgtcttacga ctct                                             24

SEQ ID NO: 137       moltype = DNA   length = 354
FEATURE              Location/Qualifiers
source               1..354
                     mol_type = other DNA
                     organism = synthetic construct
SEQUENCE: 137
gaggtgcagc tgttggagtc tggggggaggc ttggtacagc ctggggggtc cctgagactc   60
tcctgtgcag cctctggatt caccttttagc tactattaca tgagctgggt ccgccaggct  120
ccagggaagg ggctggagtg ggtctctatc atcggtggtg gtggttctgg tacgtattac  180
gctgattctg taaaaggtcg gttcaccatc tccagagaca attccaagaa cacgctgtat  240
ctgcaaatga acagcctgag agccgaggac acggccgtgt attactgtgc gcgtggtccg  300
tactacggtt acttcgacta ctggggccag ggtacactgg tcaccgtgag ctca        354

SEQ ID NO: 138       moltype = DNA   length = 330
FEATURE              Location/Qualifiers
source               1..330
                     mol_type = other DNA
                     organism = synthetic construct
SEQUENCE: 138
cagtctgtgc tgactcagcc accctcagcg tctgggaccc ccgggcagag ggtcaccatc   60
tcttgtagtg gctcttcatc taatattggc tctaattatg tctactggta ccagcagctc  120
ccaggaacgg cccccaaact cctcatctat agaaataacc agcggccaag cggggtccct  180
gaccgattct ctggctccaa gtctggcacc tcagcctccc tggccatcag tgggctccgg  240
tccgaggatg aggccgatta ttactgtgct gcttacccgt cttacgactc ttatgtcttc  300
ggcggaggca ccaagctgac ggtcctaggt                                    330

SEQ ID NO: 139       moltype = DNA   length = 729
FEATURE              Location/Qualifiers
source               1..729
                     mol_type = other DNA
                     organism = synthetic construct
SEQUENCE: 139
gaggtgcagc tgttggagtc tggggggaggc ttggtacagc ctggggggtc cctgagactc   60
tcctgtgcag cctctggatt caccttttagc tactattaca tgagctgggt ccgccaggct  120
ccagggaagg ggctggagtg ggtctcatac atcggtggtg gtggttctgg tacgtattac  180
gctgattctg taaaaggtcg gttcaccatc tccagagaca attccaagaa cacgctgtat  240
ctgcaaatga acagcctgag agccgaggac acggccgtgt attactgtgc gcgtggtccg  300
tactacggtt acttcgacta ctggggccag ggtacactgg tcaccgtgag ctcaggtgga  360
ggcggttcag gcggaggtgg atccggcggt ggcggatcgc agtctgtgct gactcagcca  420
ccctcagcgt ctgggacccc cgggcagagg gtcaccatct cttgtagtgg ctcttcatct  480
aatattggct ctaattatgt ctactggtac cagcagctcc caggaacggc ccccaaactc  540
ctcatctata gaaataacca gcggccaagc ggggtccctg accgattctc tggctccaag  600
tctggcacct cagcctccct ggccatcagt gggctccggt ccgaggatga ggccgattat  660
tactgtgctg cttacccgtc ttacgactct tatgtcttcg gcggaggcac caagctgacg  720
gtcctaggt                                                            729

SEQ ID NO: 140       moltype = DNA   length = 1413
FEATURE              Location/Qualifiers
```

-continued

```
source                    1..1413
                          mol_type = other DNA
                          organism = synthetic construct
SEQUENCE: 140
gaggtgcagc tgttggagtc tggggggaggc ttggtacagc ctggggggtc cctgagactc   60
tcctgtgcag cctctggatt caccttagc tactattaca tgagctgggt ccgccaggct   120
ccagggaagg ggctggagtg ggtctcatac atcggtggtg gtggttctgg tacgtattac   180
gctgattctg taaaaggtcg gttcaccatc tccagagaca attccaagaa cacgctgtat   240
ctgcaaatga acagcctgag agccgaggac acggccgtgt attactgtgc gcgtggtccg   300
tactacggtt acttcgacta ctgggggccag ggtacactgg tcaccgtgag ctcaggtgga   360
ggcggttcag gcgggaggtgg atccggcgggt ggcggatcgc agtctgtgct gactcagcca   420
ccctcagcgt ctgggacccc cgggcagagg gtcaccatct cttgtagtgg ctcttcatct   480
aatattggct ctaattatgt ctactggtac cagcagctcc caggaacggc ccccaaactc   540
ctcatctata gaaataacca gcggccaagc ggggtccctg accgattctc tggctccaag   600
tctggcacct cagcctccct ggccatcagt gggctccggt ccgaggatga ggccgattat   660
tactgtgctg cttacccgtc ttacgactct tatgtcttcg gcggaggcac caagctgacg   720
gtcctaggtg gccaggccgg ccagacaacg acacctgctc ccagaccgcc tactcccgcc   780
ccaaccattg catctcagcc actctctctg agacccgaag cgtgtagacc tgcggcccggg   840
ggcgctgtcc acacaagagg cttagacttc gcctgcgata tctatatctg ggcccccactc   900
gcaggcactt gtggagtgct gctgctttca ctcgtgataa ccctgtactg caaaaggggg   960
agaaagaagc tgctgtatat tttttaaacaa ccatttatga gacctgttca gactacccag  1020
gaagaagacg gttgtagttg cagattcccc gaggaggaag aaggaggttg cgagttgaga  1080
gtaaagttca gcagatccgc agatgcccct gcttaccagc agggtcaaaa ccagctttac  1140
aacgagctga atttaggtag aagagaggaa tatgacgtgt tggataaaag aagaggaaga  1200
gacccggaaa tgggcggcaa gcctcgaaga aaaaatcccc aagagggact ctacaatgag  1260
ctgcagaagg acaaaatggc tgaagcctac agcgagatcg gcatgaaggg agaaagacgc  1320
agagggaaag ggcatgatgg gctttatcag ggcttgtcca ccgctacaaa ggatacttat  1380
gacgcactac acatgcaggc cctgccaccc cgt                               1413

SEQ ID NO: 141            moltype = AA  length = 5
FEATURE                   Location/Qualifiers
source                    1..5
                          mol_type = protein
                          organism = synthetic construct
SEQUENCE: 141
YYGMS                                                               5

SEQ ID NO: 142            moltype = AA  length = 17
FEATURE                   Location/Qualifiers
source                    1..17
                          mol_type = protein
                          organism = synthetic construct
SEQUENCE: 142
YISGYSSYTY YADSVKG                                                  17

SEQ ID NO: 143            moltype = AA  length = 9
FEATURE                   Location/Qualifiers
source                    1..9
                          mol_type = protein
                          organism = synthetic construct
SEQUENCE: 143
YNDSGSFDY                                                           9

SEQ ID NO: 144            moltype = AA  length = 13
FEATURE                   Location/Qualifiers
source                    1..13
                          mol_type = protein
                          organism = synthetic construct
SEQUENCE: 144
SGSSSNIGSN YVY                                                      13

SEQ ID NO: 145            moltype = AA  length = 7
FEATURE                   Location/Qualifiers
source                    1..7
                          mol_type = protein
                          organism = synthetic construct
SEQUENCE: 145
RNNQRPS                                                             7

SEQ ID NO: 146            moltype = AA  length = 7
FEATURE                   Location/Qualifiers
source                    1..7
                          mol_type = protein
                          organism = synthetic construct
SEQUENCE: 146
AADAGNR                                                             7

SEQ ID NO: 147            moltype = AA  length = 118
FEATURE                   Location/Qualifiers
```

```
source                     1..118
                           mol_type = protein
                           organism = synthetic construct
SEQUENCE: 147
EVQLLESGGG LVQPGGSLRL SCAASGFTFS YYGMSWVRQA PGKGLEWVSY ISGYSSYTYY    60
ADSVKGRFTI SRDNSKNTLY LQMNSLRAED TAVYYCARYN DSGSFDYWGQ GTLVTVSS      118

SEQ ID NO: 148            moltype = AA  length = 109
FEATURE                   Location/Qualifiers
source                    1..109
                          mol_type = protein
                          organism = synthetic construct
SEQUENCE: 148
QSVLTQPPSA SGTPGQRVTI SCSGSSSNIG SNYVYWYQQL PGTAPKLLIY RNNQRPSGVP    60
DRFSGSKSGT SASLAISGLR SEDEADYYCA ADAGNRYVFG GGTKLTVLG               109

SEQ ID NO: 149            moltype = AA  length = 242
FEATURE                   Location/Qualifiers
source                    1..242
                          mol_type = protein
                          organism = synthetic construct
SEQUENCE: 149
EVQLLESGGG LVQPGGSLRL SCAASGFTFS YYGMSWVRQA PGKGLEWVSY ISGYSSYTYY    60
ADSVKGRFTI SRDNSKNTLY LQMNSLRAED TAVYYCARYN DSGSFDYWGQ GTLVTVSSGG   120
GGSGGGGSGG GGSQSVLTQP PSASGTPGQR VTISCSGSSS NIGSNYVYWY QQLPGTAPKL   180
LIYRNNQRPS GVPDRFSGSK SGTSASLAIS GLRSEDEADY YCAADAGNRY VFGGGTKLTV   240
LG                                                                  242

SEQ ID NO: 150            moltype = AA  length = 470
FEATURE                   Location/Qualifiers
source                    1..470
                          mol_type = protein
                          organism = synthetic construct
SEQUENCE: 150
EVQLLESGGG LVQPGGSLRL SCAASGFTFS YYGMSWVRQA PGKGLEWVSY ISGYSSYTYY    60
ADSVKGRFTI SRDNSKNTLY LQMNSLRAED TAVYYCARYN DSGSFDYWGQ GTLVTVSSGG   120
GGSGGGGSGG GGSQSVLTQP PSASGTPGQR VTISCSGSSS NIGSNYVYWY QQLPGTAPKL   180
LIYRNNQRPS GVPDRFSGSK SGTSASLAIS GLRSEDEADY YCAADAGNRY VFGGGTKLTV   240
LGGQAGQTTT PAPRPPTPAP TIASQPLSLR PEACRPAAGG AVHTRGLDFA CDIYIWAPLA   300
GTCGVLLLSL VITLYCKRGR KKLLYIFKQP FMRPVQTTQE EDGCSCRFPE EEEGGCELRV   360
KFSRSADAPA YQQGQNQLYN ELNLGRREEY DVLDKRRGRD PEMGGKPRRK NPQEGLYNEL   420
QKDKMAEAYS EIGMKGERRR GKGHDGLYQG LSTATKDTYD ALHMQALPPR             470

SEQ ID NO: 151            moltype = DNA  length = 15
FEATURE                   Location/Qualifiers
source                    1..15
                          mol_type = other DNA
                          organism = synthetic construct
SEQUENCE: 151
tactatggta tgagc                                                    15

SEQ ID NO: 152            moltype = DNA  length = 51
FEATURE                   Location/Qualifiers
source                    1..51
                          mol_type = other DNA
                          organism = synthetic construct
SEQUENCE: 152
tacatctctg gttactcttc ttacacgtat tacgctgatt ctgtaaaagg t           51

SEQ ID NO: 153            moltype = DNA  length = 27
FEATURE                   Location/Qualifiers
source                    1..27
                          mol_type = other DNA
                          organism = synthetic construct
SEQUENCE: 153
tacaacgact ctggttcttt cgactac                                      27

SEQ ID NO: 154            moltype = DNA  length = 39
FEATURE                   Location/Qualifiers
source                    1..39
                          mol_type = other DNA
                          organism = synthetic construct
SEQUENCE: 154
agtggctctt catctaatat tggctctaat tatgtctac                         39

SEQ ID NO: 155            moltype = DNA  length = 21
FEATURE                   Location/Qualifiers
source                    1..21
                          mol_type = other DNA
```

```
                          organism = synthetic construct
SEQUENCE: 155
agaaataacc agcggccaag c                                                    21

SEQ ID NO: 156          moltype = DNA  length = 21
FEATURE                 Location/Qualifiers
source                  1..21
                        mol_type = other DNA
                        organism = synthetic construct
SEQUENCE: 156
gctgctgacg ctggtaaccg t                                                    21

SEQ ID NO: 157          moltype = DNA  length = 354
FEATURE                 Location/Qualifiers
source                  1..354
                        mol_type = other DNA
                        organism = synthetic construct
SEQUENCE: 157
gaggtgcagc tgttggagtc tggggggaggc ttggtacagc ctggggggtc cctgagactc    60
tcctgtgcag cctctggatt cacctttagc tactatggta tgagctgggt ccgccaggct   120
ccagggaagg ggctggagtg ggtctcatac atctctggtt actcttctta cacgtattac   180
gctgattctg taaaaggtcg gttcaccatc tccagagaca cacgctgtat              240
ctgcaaatga acagcctgag agccgaggac acggccgtgt attactgtgc gcgttacaac   300
gactctggtt ctttcgacta ctggggccag ggtacactgg tcaccgtgag ctca          354

SEQ ID NO: 158          moltype = DNA  length = 327
FEATURE                 Location/Qualifiers
source                  1..327
                        mol_type = other DNA
                        organism = synthetic construct
SEQUENCE: 158
cagtctgtgc tgactcagcc accctcagcg tctgggaccc ccgggcagag ggtcaccatc    60
tcttgtagtg gctcttcatc taatattggc tctaattatg tctactggta ccagcagctc   120
ccaggaacgg cccccaaact cctcatctat agaaataacc agcggccaag cggggtccct   180
gaccgattct ctggctccaa gtctggcacc tcagcctccc tggccatcag tgggctccgg   240
tccgaggatg aggccgatta ttactgtgct gctgacgctg gtaaccgtta tgtcttcggc   300
ggaggcacca agctgacggt cctaggt                                         327

SEQ ID NO: 159          moltype = DNA  length = 726
FEATURE                 Location/Qualifiers
source                  1..726
                        mol_type = other DNA
                        organism = synthetic construct
SEQUENCE: 159
gaggtgcagc tgttggagtc tggggggaggc ttggtacagc ctggggggtc cctgagactc    60
tcctgtgcag cctctggatt cacctttagc tactatggta tgagctgggt ccgccaggct   120
ccagggaagg ggctggagtg ggtctcatac atctctggtt actcttctta cacgtattac   180
gctgattctg taaaaggtcg gttcaccatc tccagagaca attccaagaa cacgctgtat   240
ctgcaaatga acagcctgag agccgaggac acggccgtgt attactgtgc gcgttacaac   300
gactctggtt ctttcgacta ctggggccag ggtacactgg tcaccgtgag ctcaggtgga   360
ggcggttcag gcggaggtgg atccggcggt ggcggatcgc agtctgtgct gactcagcca   420
ccctcagcgt ctgggacccc cgggcagagg gtcaccatct cttgtagtgg ctcttcatct   480
aatattggct ctaattatgt ctactggtac cagcagctcc caggaacggc ccccaaactc   540
ctcatctata gaaataacca gcggccaagc ggggtccctg accgattctc tggctccaag   600
tctggcacct cagcctccct ggccatcagt gggctccggt ccgaggatga ggccgattat   660
tactgtgctg ctgacgctgg taaccgttat gtcttcggcg gaggcaccaa gctgacggtc   720
ctaggt                                                               726

SEQ ID NO: 160          moltype = DNA  length = 1410
FEATURE                 Location/Qualifiers
source                  1..1410
                        mol_type = other DNA
                        organism = synthetic construct
SEQUENCE: 160
gaggtgcagc tgttggagtc tggggggaggc ttggtacagc ctggggggtc cctgagactc    60
tcctgtgcag cctctggatt cacctttagc tactatggta tgagctgggt ccgccaggct   120
ccagggaagg ggctggagtg ggtctcatac atctctggtt actcttctta cacgtattac   180
gctgattctg taaaaggtcg gttcaccatc tccagagaca attccaagaa cacgctgtat   240
ctgcaaatga acagcctgag agccgaggac acggccgtgt attactgtgc gcgttacaac   300
gactctggtt ctttcgacta ctggggccag ggtacactgg tcaccgtgag ctcaggtgga   360
ggcggttcag gcggaggtgg atccggcggt ggcggatcgc agtctgtgct gactcagcca   420
ccctcagcgt ctgggacccc cgggcagagg gtcaccatct cttgtagtgg ctcttcatct   480
aatattggct ctaattatgt ctactggtac cagcagctcc caggaacggc ccccaaactc   540
ctcatctata gaaataacca gcggccaagc ggggtccctg accgattctc tggctccaag   600
tctggcacct cagcctccct ggccatcagt gggctccggt ccgaggatga ggccgattat   660
tactgtgctg ctgacgctgg taaccgttat gtcttcggcg gaggcaccaa gctgacggtc   720
ctaggtggcc aggccggcca gacaacgaca cctgctccca gaccgcctac tcccgcccca   780
accattgcat ctcagccact ctctctgaga cccgaagcgt gtagacctgc ggccggggc    840
gctgtccaca caagaggctt agacttcgcc tgcgatatct atatctgggc cccactcgca   900
```

```
ggcacttgtg gagtgctgct gctttcactc gtgataaccc tgtactgcaa aaggggggaga    960
aagaagctgc tgtatatttt taaacaacca tttatgagac ctgttcagac tacccaggaa   1020
gaagacggtt gtagttgcag attccccgag gaggaagaag gaggttgcga gttgagagta   1080
aagttcagca gatccgcaga tgcccctgct taccagcagg gtcaaaacca gctttacaac   1140
gagctgaatt taggtagaag agaggaatat gacgtgttgg ataaaagaag aggaagagac   1200
ccggaaatgg gcggcaagcc tcgaagaaaa aatccccaag agggactcta caatgagctg   1260
cagaaggaca aaatggctga agcctacagc gagatcggca tgaagggaga aagacgcaga   1320
gggaaagggc atgatgggct ttatcagggc ttgtccaccg ctacaaagga tacttatgac   1380
gcactacaca tgcaggccct gccaccccgt                                    1410
```

```
SEQ ID NO: 161         moltype = AA   length = 5
FEATURE                Location/Qualifiers
source                 1..5
                       mol_type = protein
                       organism = synthetic construct
SEQUENCE: 161
YYDMS                                                                  5

SEQ ID NO: 162         moltype = AA   length = 16
FEATURE                Location/Qualifiers
source                 1..16
                       mol_type = protein
                       organism = synthetic construct
SEQUENCE: 162
GIYGSGSTYY ADSVKG                                                     16

SEQ ID NO: 163         moltype = AA   length = 13
FEATURE                Location/Qualifiers
source                 1..13
                       mol_type = protein
                       organism = synthetic construct
SEQUENCE: 163
YSYYDSYSDY FDY                                                        13

SEQ ID NO: 164         moltype = AA   length = 13
FEATURE                Location/Qualifiers
source                 1..13
                       mol_type = protein
                       organism = synthetic construct
SEQUENCE: 164
SGSSSNIGSN YVY                                                        13

SEQ ID NO: 165         moltype = AA   length = 7
FEATURE                Location/Qualifiers
source                 1..7
                       mol_type = protein
                       organism = synthetic construct
SEQUENCE: 165
RNNQRPS                                                                7

SEQ ID NO: 166         moltype = AA   length = 7
FEATURE                Location/Qualifiers
source                 1..7
                       mol_type = protein
                       organism = synthetic construct
SEQUENCE: 166
AAYSYGY                                                                7

SEQ ID NO: 167         moltype = AA   length = 121
FEATURE                Location/Qualifiers
source                 1..121
                       mol_type = protein
                       organism = synthetic construct
SEQUENCE: 167
EVQLLESGGG LVQPGGSLRL SCAASGFTFS YYDMSWVRQA PGKGLEWVSG IYGSGSTYYA     60
DSVKGRFTIS RDNSKNTLYL QMNSLRAEDT AVYYCARYSY YDSYSDYFDY WGQGTLVTVS    120
S                                                                    121

SEQ ID NO: 168         moltype = AA   length = 109
FEATURE                Location/Qualifiers
source                 1..109
                       mol_type = protein
                       organism = synthetic construct
SEQUENCE: 168
QSVLTQPPSA SGTPGQRVTI SCSGSSSNIG SNYVYWYQQL PGTAPKLLIY RNNQRPSGVP     60
DRFSGSKSGT SASLAISGLR SEDEADYYCA AYSGYYVFG GGTKLTVLG                 109

SEQ ID NO: 169         moltype = AA   length = 245
FEATURE                Location/Qualifiers
```

```
source                    1..245
                          mol_type = protein
                          organism = synthetic construct
SEQUENCE: 169
EVQLLESGGG LVQPGGSLRL SCAASGFTFS YYDMSWVRQA PGKGLEWVSG IYGSGSTYYA  60
DSVKGRFTIS RDNSKNTLYL QMNSLRAEDT AVYYCARYSY YDSYSDYFDY WGQGTLVTVS  120
SGGGGSGGGG SGGGGSQSVL TQPPSASGTP GQRVTISCSG SSSNIGSNYV YWYQQLPGTA  180
PKLLIYRNNQ RPSGVPDRFS GSKSGTSASL AISGLRSEDE ADYYCAAYSY GYYVFGGGTK  240
LTVLG                                                               245

SEQ ID NO: 170           moltype = AA   length = 473
FEATURE                  Location/Qualifiers
source                   1..473
                         mol_type = protein
                         organism = synthetic construct
SEQUENCE: 170
EVQLLESGGG LVQPGGSLRL SCAASGFTFS YYDMSWVRQA PGKGLEWVSG IYGSGSTYYA  60
DSVKGRFTIS RDNSKNTLYL QMNSLRAEDT AVYYCARYSY YDSYSDYFDY WGQGTLVTVS  120
SGGGGSGGGG SGGGGSQSVL TQPPSASGTP GQRVTISCSG SSSNIGSNYV YWYQQLPGTA  180
PKLLIYRNNQ RPSGVPDRFS GSKSGTSASL AISGLRSEDE ADYYCAAYSY GYYVFGGGTK  240
LTVLGGQAGQ TTTPAPRPPT PAPTIASQPL SLRPEACRPA AGGAVHTRGL DFACDIYIWA  300
PLAGTCGVLL LSLVITLYCK RGRKKLLYIF KQPFMRPVQT TQEEDGCSCR FPEEEEGGCE  360
LRVKFSRSAD APAYQQGQNQ LYNELNLGRR EEYDVLDKRR GRDPEMGGKP RRKNPQEGLY  420
NELQKDKMAE AYSEIGMKGE RRRGKGHDGL YQGLSTATKD TYDALHMQAL PPR         473

SEQ ID NO: 171           moltype = DNA   length = 15
FEATURE                  Location/Qualifiers
source                   1..15
                         mol_type = other DNA
                         organism = synthetic construct
SEQUENCE: 171
tactatgata tgagc                                                    15

SEQ ID NO: 172           moltype = DNA   length = 48
FEATURE                  Location/Qualifiers
source                   1..48
                         mol_type = other DNA
                         organism = synthetic construct
SEQUENCE: 172
ggtatctacg gttctggttc tacgtattac gctgattctg taaaaggt              48

SEQ ID NO: 173           moltype = DNA   length = 39
FEATURE                  Location/Qualifiers
source                   1..39
                         mol_type = other DNA
                         organism = synthetic construct
SEQUENCE: 173
tactcttact acgactctta ctctgactac ttcgactac                        39

SEQ ID NO: 174           moltype = DNA   length = 39
FEATURE                  Location/Qualifiers
source                   1..39
                         mol_type = other DNA
                         organism = synthetic construct
SEQUENCE: 174
agtggctctt catctaatat tggctctaat tatgtctac                        39

SEQ ID NO: 175           moltype = DNA   length = 21
FEATURE                  Location/Qualifiers
source                   1..21
                         mol_type = other DNA
                         organism = synthetic construct
SEQUENCE: 175
agaaataacc agcggccaag c                                            21

SEQ ID NO: 176           moltype = DNA   length = 21
FEATURE                  Location/Qualifiers
source                   1..21
                         mol_type = other DNA
                         organism = synthetic construct
SEQUENCE: 176
gctgcttact cttacggtta c                                            21

SEQ ID NO: 177           moltype = DNA   length = 363
FEATURE                  Location/Qualifiers
source                   1..363
                         mol_type = other DNA
                         organism = synthetic construct
SEQUENCE: 177
```

```
gaggtgcagc tgttggagtc tggggaggc ttggtacagc ctggggggtc cctgagactc   60
tcctgtgcag cctctggatt cacctttagc tactatgata tgagctgggt ccgccaggct  120
ccagggaagg ggctggagtg ggtctcaggt atctacggtt ctggttctac gtattacgct  180
gattctgtaa aagtcggtt caccatctcc agagacaatt ccaagaacac gctgtatctg   240
caaatgaaca gcctgagagc cgaggacacg gccgtgtatt actgtgcgcg ttactcttac  300
tacgactctt actctgacta cttcgactac tggggccagg gtacactggt caccgtgagc  360
tca                                                                363
```

SEQ ID NO: 178        moltype = DNA   length = 327
FEATURE               Location/Qualifiers
source                1..327
                      mol_type = other DNA
                      organism = synthetic construct
SEQUENCE: 178

```
cagtctgtgc tgactcagcc accctcagcg tctgggaccc ccgggcagag ggtcaccatc   60
tcttgtagtg gctcttcatc taatattggc tctaattatg tctactggta ccagcagctc  120
ccaggaacgg cccccaaact cctcatctat agaaataacc agcggccaag cggggtccct  180
gaccgattct ctggctccaa gtctggcacc tcagcctccc tggccatcag tgggctccgg  240
tccgaggatg aggccgatta ttactgtgct gcttactctt acgttactta tgtcttcggc  300
ggaggcacca agctgacggt cctaggt                                      327
```

SEQ ID NO: 179        moltype = DNA   length = 735
FEATURE               Location/Qualifiers
source                1..735
                      mol_type = other DNA
                      organism = synthetic construct
SEQUENCE: 179

```
gaggtgcagc tgttggagtc tggggaggc ttggtacagc ctggggggtc cctgagactc   60
tcctgtgcag cctctggatt cacctttagc tactatgata tgagctgggt ccgccaggct  120
ccagggaagg ggctggagtg ggtctcaggt atctacggtt ctggttctac gtattacgct  180
gattctgtaa aagtcggtt caccatctcc agagacaatt ccaagaacac gctgtatctg   240
caaatgaaca gcctgagagc cgaggacacg gccgtgtatt actgtgcgcg ttactcttac  300
tacgactctt actctgacta cttcgactac tggggccagg gtacactggt caccgtgagc  360
tcaggtggag gcggttcagg cggaggtgga tccggcggtg gcggatcgca gtctgtgctg  420
actcagccac cctcagcgtc tgggaccccc gggcagaggg tcaccatctc ttgtagtggc  480
tcttcatcta atattggctc taattatgtc tactggtacc agcagctccc aggaacggcc  540
cccaaactcc tcatctatag aaataaccag cggccaagcg gggtccctga ccgattctct  600
ggctccaagt ctggcacctc agcctccctg gccatcagtg ggctccggtc cgaggatgag  660
gccgattatt actgtgctgc ttactcttac ggttactatg tcttcggcgg aggcaccaag  720
ctgacggtcc taggt                                                   735
```

SEQ ID NO: 180        moltype = DNA   length = 1419
FEATURE               Location/Qualifiers
source                1..1419
                      mol_type = other DNA
                      organism = synthetic construct
SEQUENCE: 180

```
gaggtgcagc tgttggagtc tggggaggc ttggtacagc ctggggggtc cctgagactc   60
tcctgtgcag cctctggatt cacctttagc tactatgata tgagctgggt ccgccaggct  120
ccagggaagg ggctggagtg ggtctcaggt atctacggtt ctggttctac gtattacgct  180
gattctgtaa aagtcggtt caccatctcc agagacaatt ccaagaacac gctgtatctg   240
caaatgaaca gcctgagagc cgaggacacg gccgtgtatt actgtgcgcg ttactcttac  300
tacgactctt actctgacta cttcgactac tggggccagg gtacactggt caccgtgagc  360
tcaggtggag gcggttcagg cggaggtgga tccggcggtg gcggatcgca gtctgtgctg  420
actcagccac cctcagcgtc tgggaccccc gggcagaggg tcaccatctc ttgtagtggc  480
tcttcatcta atattggctc taattatgtc tactggtacc agcagctccc aggaacggcc  540
cccaaactcc tcatctatag aaataaccag cggccaagcg gggtccctga ccgattctct  600
ggctccaagt ctggcacctc agcctccctg gccatcagtg ggctccggtc cgaggatgag  660
gccgattatt actgtgctgc ttactcttac ggttactatg tcttcggcgg aggcaccaag  720
ctgacggtcc taggtggcca ggccggccag acaacgacac ctgctcccag accgcctact  780
cccgccccaa ccattgcatc tcagccactc tctctgagac ccgaagcgtg tagacctgcg  840
gccgggggcg ctgtccacac aagaggctta gacttcgcct gcgatatcta tatctgggcc  900
ccactcgcag gcacttgtgg agtgctgctg ctttcactcg tgataaccct gtactgcaaa  960
aggggggaa agaagctgct gtatattttt aaacaaccat ttatgagacc tgttcagact  1020
acccaggaag aagacggttg tagttgcaga ttccccgagg aggaagaagg aggttgcgag  1080
ttgagagtaa agttcagcag atccgcagat gcccctgctt accagcaggg tcaaaaccag  1140
ctttacaacg agctgaattt aggtagaaga gaggaatatg acgtgttgga taaaagaaga  1200
ggaagagacc cggaaatggg cggcaagcct cgaagaaaaa atccccaaga gggactctac  1260
aatgagctgc agaaggacaa aatggctgaa gcctacagcg agatcggcat gaagggagaa  1320
agacgcagag ggaaagggca tgatgggctt tatcagggct tgtccaccgc tacaaaggat  1380
acttatgacg cactacacat gcaggccctg ccacccgt                          1419
```

SEQ ID NO: 181        moltype = AA   length = 5
FEATURE               Location/Qualifiers
source                1..5
                      mol_type = protein
                      organism = synthetic construct
SEQUENCE: 181
SYGMS                                                               5

```
SEQ ID NO: 182          moltype = AA   length = 17
FEATURE                 Location/Qualifiers
source                  1..17
                        mol_type = protein
                        organism = synthetic construct
SEQUENCE: 182
SIYYYSGGTY YADSVKG                                                    17

SEQ ID NO: 183          moltype = AA   length = 11
FEATURE                 Location/Qualifiers
source                  1..11
                        mol_type = protein
                        organism = synthetic construct
SEQUENCE: 183
NDYRNNSDFD Y                                                          11

SEQ ID NO: 184          moltype = AA   length = 13
FEATURE                 Location/Qualifiers
source                  1..13
                        mol_type = protein
                        organism = synthetic construct
SEQUENCE: 184
SGSSSNIGSN YVY                                                        13

SEQ ID NO: 185          moltype = AA   length = 7
FEATURE                 Location/Qualifiers
source                  1..7
                        mol_type = protein
                        organism = synthetic construct
SEQUENCE: 185
RNNQRPS                                                               7

SEQ ID NO: 186          moltype = AA   length = 7
FEATURE                 Location/Qualifiers
source                  1..7
                        mol_type = protein
                        organism = synthetic construct
SEQUENCE: 186
AAYYPYY                                                               7

SEQ ID NO: 187          moltype = AA   length = 120
FEATURE                 Location/Qualifiers
source                  1..120
                        mol_type = protein
                        organism = synthetic construct
SEQUENCE: 187
EVQLLESGGG LVQPGGSLRL SCAASGFTFS SYGMSWVRQA PGKGLEWVSS IYYYSGGTYY     60
ADSVKGRFTI SRDNSKNTLY LQMNSLRAED TAVYYCARND YRNNSDFDYW GQGTLVTVSS     120

SEQ ID NO: 188          moltype = AA   length = 109
FEATURE                 Location/Qualifiers
source                  1..109
                        mol_type = protein
                        organism = synthetic construct
SEQUENCE: 188
QSVLTQPPSA SGTPGQRVTI SCSGSSSNIG SNYVYWYQQL PGTAPKLLIY RNNQRPSGVP     60
DRFSGSKSGT SASLAISGLR SEDEADYYCA AYYPYYVFG GGTKLTVLG                  109

SEQ ID NO: 189          moltype = AA   length = 244
FEATURE                 Location/Qualifiers
source                  1..244
                        mol_type = protein
                        organism = synthetic construct
SEQUENCE: 189
EVQLLESGGG LVQPGGSLRL SCAASGFTFS SYGMSWVRQA PGKGLEWVSS IYYYSGGTYY     60
ADSVKGRFTI SRDNSKNTLY LQMNSLRAED TAVYYCARND YRNNSDFDYW GQGTLVTVSS     120
GGGGSGGGGS GGGGSQSVLT QPPSASGTPG QRVTISCSGS SSNIGSNYVY WYQQLPGTAP     180
KLLIYRNNQR PSGVPDRFSG SKSGTSASLA ISGLRSEDEA DYYCAAYYPY YVFGGGTKL     240
TVLG                                                                 244

SEQ ID NO: 190          moltype = AA   length = 472
FEATURE                 Location/Qualifiers
source                  1..472
                        mol_type = protein
                        organism = synthetic construct
SEQUENCE: 190
EVQLLESGGG LVQPGGSLRL SCAASGFTFS SYGMSWVRQA PGKGLEWVSS IYYYSGGTYY     60
ADSVKGRFTI SRDNSKNTLY LQMNSLRAED TAVYYCARND YRNNSDFDYW GQGTLVTVSS     120
```

```
GGGGSGGGGS GGGGSQSVLT QPPSASGTPG QRVTISCSGS SSNIGSNYVY WYQQLPGTAP  180
KLLIYRNNQR PSGVPDRFSG SKSGTSASLA ISGLRSEDEA DYYCAAYYPY YYVFGGGTKL  240
TVLGGQAGQT TTPAPRPPTP APTIASQPLS LRPEACRPAA GGAVHTRGLD FACDIYIWAP  300
LAGTCGVLLL SLVITLYCKR GRKKLLYIFK QPFMRPVQTT QEEDGCSCRF PEEEEGGCEL  360
RVKFSRSADA PAYQQGQNQL YNELNLGRRE EYDVLDKRRG RDPEMGGKPR RKNPQEGLYN  420
ELQKDKMAEA YSEIGMKGER RRGKGHDGLY QGLSTATKDT YDALHMQALP PR          472

SEQ ID NO: 191          moltype = DNA  length = 15
FEATURE                 Location/Qualifiers
source                  1..15
                        mol_type = other DNA
                        organism = synthetic construct
SEQUENCE: 191
tcttatggta tgagc                                                    15

SEQ ID NO: 192          moltype = DNA  length = 51
FEATURE                 Location/Qualifiers
source                  1..51
                        mol_type = other DNA
                        organism = synthetic construct
SEQUENCE: 192
tctatctact actactctgg tggtacgtat tacgctgatt ctgtaaaagg t            51

SEQ ID NO: 193          moltype = DNA  length = 33
FEATURE                 Location/Qualifiers
source                  1..33
                        mol_type = other DNA
                        organism = synthetic construct
SEQUENCE: 193
aacgactacc gtaacaactc tgacttcgac tac                                33

SEQ ID NO: 194          moltype = DNA  length = 39
FEATURE                 Location/Qualifiers
source                  1..39
                        mol_type = other DNA
                        organism = synthetic construct
SEQUENCE: 194
agtggctctt catctaatat tggctctaat tatgtctac                          39

SEQ ID NO: 195          moltype = AA  length = 21
FEATURE                 Location/Qualifiers
source                  1..21
                        mol_type = protein
                        organism = synthetic construct
SEQUENCE: 195
AGAAATAACC AGCGGCCAAG C                                             21

SEQ ID NO: 196          moltype = DNA  length = 21
FEATURE                 Location/Qualifiers
source                  1..21
                        mol_type = other DNA
                        organism = synthetic construct
SEQUENCE: 196
gctgcttact acccgtacta c                                             21

SEQ ID NO: 197          moltype = DNA  length = 360
FEATURE                 Location/Qualifiers
source                  1..360
                        mol_type = other DNA
                        organism = synthetic construct
SEQUENCE: 197
gaggtgcagc tgttggagtc tggggggaggc ttggtacagc ctggggggtc cctgagactc  60
tcctgtgcag cctctggatt caccttttagc tcttatggta tgagctgggt ccgccaggct  120
ccaggggaagg ggctggagtg ggtctcatct atctactact actctggtgg tacgtattac  180
gctgattctg taaaaggtcg gttcaccatc tccagagaca attccaagaa cacgctgtat  240
ctgcaaatga acagcctgag agccgaggac acggccgtgt attactgtgc gcgtaacgac  300
taccgtaaca actctgactt cgactactgg ggccagggta cactggtcac cgtgagctca  360

SEQ ID NO: 198          moltype = DNA  length = 327
FEATURE                 Location/Qualifiers
source                  1..327
                        mol_type = other DNA
                        organism = synthetic construct
SEQUENCE: 198
cagtctgtgc tgactcagcc accctcagcg tctgggaccc ccgggcagag ggtcaccatc  60
tcttgtagtg gctcttcatc taatattggc tctaattatg tctactggta ccagcagctc  120
ccaggaacgg cccccaaact cctcatctat agaaataacc agcggccaag cggggtccct  180
gaccgattct ctggctccaa gtctggcacc tcagcctccc tggccatcag tgggctccgg  240
tccgaggatg aggccgatta ttactgtgct gcttactacc cgtactacta tgtcttcggc  300
```

-continued

```
ggaggcacca agctgacggt cctaggt                                    327

SEQ ID NO: 199          moltype = DNA   length = 732
FEATURE                 Location/Qualifiers
source                  1..732
                        mol_type = other DNA
                        organism = synthetic construct
SEQUENCE: 199
gaggtgcagc tgttggagtc tggggggaggc ttggtacagc ctggggggtc cctgagactc   60
tcctgtgcag cctctggatt caccttttagc tcttatggta tgagctgggt ccgccaggct  120
ccagggaagg ggctggagtg ggtctcatct atctactact actctggtgg tacgtattac  180
gctgattctg taaaaggtcg gttcaccatc tccagagaca attccaagaa cacgctgtat  240
ctgcaaatga acagcctgag agccgaggac acggccgtgt attactgtgc gcgtaacgac  300
taccgtaaca actctgactt cgactactgg ggccaggta cactggtcac cgtgagctca  360
ggtggaggcg gttcaggcgg aggtggatcc ggcggtggcg gatcgcagtc tgtgctgact  420
cagccaccct cagcgtctgg gaccccccggg cagagggtca ccatctcttg tagtggctct  480
tcatctaata ttggctctaa ttatgtctac tggtaccagc agctcccagg aacggcccc  540
aaactcctca tctatagaaa taaccagcgg ccaagcgggg tccctgaccg attctctggc  600
tccaagtctg gcacctcagc ctcccctggcc atcagtgggg tccggtccga ggatgaggcc  660
gattattact gtgctgctta ctacccgtac tactatgtct tcggcggagg caccaagctg  720
acggtcctag gt                                                   732

SEQ ID NO: 200          moltype = DNA   length = 1416
FEATURE                 Location/Qualifiers
source                  1..1416
                        mol_type = other DNA
                        organism = synthetic construct
SEQUENCE: 200
gaggtgcagc tgttggagtc tggggggaggc ttggtacagc ctggggggtc cctgagactc   60
tcctgtgcag cctctggatt caccttttagc tcttatggta tgagctgggt ccgccaggct  120
ccagggaagg ggctggagtg ggtctcatct atctactact actctggtgg tacgtattac  180
gctgattctg taaaaggtcg gttcaccatc tccagagaca attccaagaa cacgctgtat  240
ctgcaaatga acagcctgag agccgaggac acggccgtgt attactgtgc gcgtaacgac  300
taccgtaaca actctgactt cgactactgg ggccaggta cactggtcac cgtgagctca  360
ggtggaggcg gttcaggcgg aggtggatcc ggcggtggcg gatcgcagtc tgtgctgact  420
cagccaccct cagcgtctgg gaccccccggg cagagggtca ccatctcttg tagtggctct  480
tcatctaata ttggctctaa ttatgtctac tggtaccagc agctcccagg aacggcccc  540
aaactcctca tctatagaaa taaccagcgg ccaagcgggg tccctgaccg attctctggc  600
tccaagtctg gcacctcagc ctcccctggcc atcagtgggg tccggtccga ggatgaggcc  660
gattattact gtgctgctta ctacccgtac tactatgtct tcggcggagg caccaagctg  720
acggtcctag gtggccaggc cggccagaca acgacacctg ctcccagacc gcctactccc  780
gccccaacca ttgcatctca gccactctct ctgagacccg aagcgtgtag acctgcggcc  840
gggggcgctg tccacacaag aggcttagac ttcgcctgca atatctatat ctgggcccca  900
ctcgcaggca cttgtggagt gctgctgctt tcactcgtga taaccctgta ctgcaaaagg  960
gggagaaaga agctgctgta tattttttaaa caaccattta tgagacctgt tcagactacc 1020
caggaagaag acgttgtag ttgcagattc cccgaggagg aagaaggagg ttgcgagttg 1080
agagtaaagt tcagcagatc cgcagatgcc cctgcttacc agcaggggtca aaaccagctt 1140
tacaacgagc tgaatttagg tagaagagag gaatatgacg tgttggataa aagaagagga 1200
agagacccgg aaatgggcgg caagcctcga agaaaaaatc cccaagaggg actctacaat 1260
gagctgcaga aggacaaaat ggctgaagcc tacagcgaga tcggcatgaa gggagaaaga 1320
cgcagaggga aagggcatga tgggctttat cagggcttgt ccaccgctac aaaggatact 1380
tatgacgcac tacacatgca ggccctgcca ccccgt                          1416

SEQ ID NO: 201          moltype = AA   length = 5
FEATURE                 Location/Qualifiers
source                  1..5
                        mol_type = protein
                        organism = synthetic construct
SEQUENCE: 201
SYHMS                                                            5

SEQ ID NO: 202          moltype = AA   length = 17
FEATURE                 Location/Qualifiers
source                  1..17
                        mol_type = protein
                        organism = synthetic construct
SEQUENCE: 202
GIGYGHGGTY YADSVKG                                               17

SEQ ID NO: 203          moltype = AA   length = 9
FEATURE                 Location/Qualifiers
source                  1..9
                        mol_type = protein
                        organism = synthetic construct
SEQUENCE: 203
YDYDYSFDY                                                        9

SEQ ID NO: 204          moltype = AA   length = 13
FEATURE                 Location/Qualifiers
```

-continued

```
source                    1..13
                          mol_type = protein
                          organism = synthetic construct
SEQUENCE: 204
SGSSSNIGSN YVY                                                          13

SEQ ID NO: 205            moltype = AA  length = 7
FEATURE                   Location/Qualifiers
source                    1..7
                          mol_type = protein
                          organism = synthetic construct
SEQUENCE: 205
RNNQRPS                                                                 7

SEQ ID NO: 206            moltype = AA  length = 7
FEATURE                   Location/Qualifiers
source                    1..7
                          mol_type = protein
                          organism = synthetic construct
SEQUENCE: 206
AVSSPYS                                                                 7

SEQ ID NO: 207            moltype = AA  length = 118
FEATURE                   Location/Qualifiers
source                    1..118
                          mol_type = protein
                          organism = synthetic construct
SEQUENCE: 207
EVQLLESGGG LVQPGGSLRL SCAASGFTFS SYHMSWVRQA PGKGLEWVSG IGYGHGGTYY       60
ADSVKGRFTI SRDNSKNTLY LQMNSLRAED TAVYYCARYD YDYSFDYWGQ GTLVTVSS        118

SEQ ID NO: 208            moltype = AA  length = 109
FEATURE                   Location/Qualifiers
source                    1..109
                          mol_type = protein
                          organism = synthetic construct
SEQUENCE: 208
QSVLTQPPSA SGTPGQRVTI SCSGSSSNIG SNYVYWYQQL PGTAPKLLIY RNNQRPSGVP       60
DRFSGSKSGT SASLAISGLR SEDEADYYCA VSSPYSYVFG GGTKLTVLG                  109

SEQ ID NO: 209            moltype = AA  length = 242
FEATURE                   Location/Qualifiers
source                    1..242
                          mol_type = protein
                          organism = synthetic construct
SEQUENCE: 209
EVQLLESGGG LVQPGGSLRL SCAASGFTFS SYHMSWVRQA PGKGLEWVSG IGYGHGGTYY       60
ADSVKGRFTI SRDNSKNTLY LQMNSLRAED TAVYYCARYD YDYSFDYWGQ GTLVTVSSGG      120
GGSGGGGSGG GGSQSVLTQP PSASGTPGQR VTISCSGSSS NIGSNYVYWY QQLPGTAPKL      180
LIYRNNQRPS GVPDRFSGSK SGTSASLAIS GLRSEDEADY YCAVSSPYSY VFGGGTKLTV      240
LG                                                                    242

SEQ ID NO: 210            moltype = AA  length = 470
FEATURE                   Location/Qualifiers
source                    1..470
                          mol_type = protein
                          organism = synthetic construct
SEQUENCE: 210
EVQLLESGGG LVQPGGSLRL SCAASGFTFS SYHMSWVRQA PGKGLEWVSG IGYGHGGTYY       60
ADSVKGRFTI SRDNSKNTLY LQMNSLRAED TAVYYCARYD YDYSFDYWGQ GTLVTVSSGG      120
GGSGGGGSGG GGSQSVLTQP PSASGTPGQR VTISCSGSSS NIGSNYVYWY QQLPGTAPKL      180
LIYRNNQRPS GVPDRFSGSK SGTSASLAIS GLRSEDEADY YCAVSSPYSY VFGGGTKLTV      240
LGGQAGQTTT PAPRPPTPAP TIASQPLSLR PEACRPAAGG AVHTRGLDFA CDIYIWAPLA      300
GTCGVLLLSL VITLYCKRGR KKLLYIFKQP FMRPVQTTQE EDGCSCRFPE EEEGGCELRV      360
KFSRSADAPA YQQGQNQLYN ELNLGRREEY DVLDKRRGRD PEMGGKPRRK NPQEGLYNEL      420
QKDKMAEAYS EIGMKGERRR GKGHDGLYQG LSTATKDTYD ALHMQALPPR                 470

SEQ ID NO: 211            moltype = DNA  length = 15
FEATURE                   Location/Qualifiers
source                    1..15
                          mol_type = other DNA
                          organism = synthetic construct
SEQUENCE: 211
tcttatcaca tgagc                                                       15

SEQ ID NO: 212            moltype = DNA  length = 51
FEATURE                   Location/Qualifiers
source                    1..51
                          mol_type = other DNA
```

-continued

```
                                organism = synthetic construct
SEQUENCE: 212
ggtatcggtt acggtcacgg tggtacgtat tacgctgatt ctgtaaaagg t              51

SEQ ID NO: 213             moltype = DNA   length = 27
FEATURE                    Location/Qualifiers
source                     1..27
                           mol_type = other DNA
                           organism = synthetic construct
SEQUENCE: 213
tacgactacg actactcttt cgactac                                         27

SEQ ID NO: 214             moltype = DNA   length = 39
FEATURE                    Location/Qualifiers
source                     1..39
                           mol_type = other DNA
                           organism = synthetic construct
SEQUENCE: 214
tcctgctctt catctaatat tggctctaat tatgtctac                            39

SEQ ID NO: 215             moltype = DNA   length = 21
FEATURE                    Location/Qualifiers
source                     1..21
                           mol_type = other DNA
                           organism = synthetic construct
SEQUENCE: 215
agaaataacc agcggccaag c                                               21

SEQ ID NO: 216             moltype = DNA   length = 21
FEATURE                    Location/Qualifiers
source                     1..21
                           mol_type = other DNA
                           organism = synthetic construct
SEQUENCE: 216
gctgtttctt ctccgtactc t                                               21

SEQ ID NO: 217             moltype = DNA   length = 354
FEATURE                    Location/Qualifiers
source                     1..354
                           mol_type = other DNA
                           organism = synthetic construct
SEQUENCE: 217
gaggtgcagc tgttggagtc tggggaggc ttggtacagc ctggggggtc cctgagactc     60
tcctgtgcag cctctggatt caccttttagc tcttatcaca tgagctgggt ccgccaggct    120
ccagggaagg ggctggagtg ggtctcaggt atcggttacg gtcacggtgg tacgtattac    180
gctgattctg taaaaggtcg gttcaccatc tccagagaca attccaagaa cacgctgtat    240
ctgcaaatga acagcctgag agccgaggac acggccgtgt attactgtgc gcgttacgac    300
tacgactact ctttcgacta ctggggccag ggtacactgg tcaccgtgag ctca          354

SEQ ID NO: 218             moltype = DNA   length = 327
FEATURE                    Location/Qualifiers
source                     1..327
                           mol_type = other DNA
                           organism = synthetic construct
SEQUENCE: 218
cagtctgtgc tgactcagcc accctcagcg tctgggaccc ccgggcagag ggtcaccatc    60
tcttgttcct gctcttcatc taatattggc tctaattatg tctactggta ccagcagctc    120
ccaggaacgg cccccaaact cctcatctat agaaataacc agcggccaag cggggtccct    180
gaccgattct ctggctccaa gtctggcacc tcagcctccc tggccatcag tgggctccgg    240
tccgaggatg aggccgatta ttactgtgct gtttcttctc gtactcttta tgtcttcggc    300
ggaggcacca agctgacggt cctaggt                                         327

SEQ ID NO: 219             moltype = DNA   length = 726
FEATURE                    Location/Qualifiers
source                     1..726
                           mol_type = other DNA
                           organism = synthetic construct
SEQUENCE: 219
gaggtgcagc tgttggagtc tggggaggc ttggtacagc ctggggggtc cctgagactc     60
tcctgtgcag cctctggatt caccttttagc tcttatcaca tgagctgggt ccgccaggct    120
ccagggaagg ggctggagtg ggtctcaggt atcggttacg gtcacggtgg tacgtattac    180
gctgattctg taaaaggtcg gttcaccatc tccagagaca attccaagaa cacgctgtat    240
ctgcaaatga acagcctgag agccgaggac acggccgtgt attactgtgc gcgttacgac    300
tacgactact ctttcgacta ctggggccag ggtacactgg tcaccgtgag ctcaggtgga    360
ggcggttcag gcggaggtgg atccggcggg ggcggatcgc agtctgtgct gactcagcca    420
ccctcagcgt ctgggacccc cgggcagagg gtcaccatct cttgtagtgg ctcttcatct    480
aatattggct ctaattatgt ctactggtac cagcagctcc caggaacggc ccccaaactc    540
ctcatctata gaaataacca gcggccaagc ggggtccctg accgattctc tggctccaag    600
tctggcacct cagcctccct ggccatcagt gggctccggt ccgaggatga ggccgattat    660
```

```
tactgtgctg tttcttctcc gtactcttat gtcttcggcg gaggcaccaa gctgacggtc   720
ctaggt                                                              726

SEQ ID NO: 220        moltype = DNA  length = 1410
FEATURE               Location/Qualifiers
source                1..1410
                      mol_type = other DNA
                      organism = synthetic construct
SEQUENCE: 220
gaggtgcagc tgttggagtc tggggggaggc ttggtacagc ctggggggtc cctgagactc   60
tcctgtgcag cctctggatt cacctttagc tcttatcaca tgagctgggt ccgccaggct   120
ccagggaagg ggctggagtg ggtctcaggt atcggttacg gtcacggtgg tacgtattac   180
gctgattctg taaaaggtcg gttcaccatc tccagagaca attccaagaa cacgctgtat   240
ctgcaaatga acagcctgag agccgaggac acggccgtgt attactgtgc gcgttacgac   300
tacgactact ctttcgacta ctggggccag ggtacactgg tcaccgtgag ctcaggtgga   360
ggcggttcag gcggaggtgg atccggcggt ggcggatcgc agtctgtgct gactcagcca   420
ccctcagcgt ctgggacccc cgggcagagg gtcaccatct cttgtagtgg ctcttcatct   480
aatattggct ctaattatgt ctactggtac cagcagctcc caggaacggc ccccaaactc   540
ctcatctata gaaataacca gcggccaagc ggggtccctg accgattctc tggctccaag   600
tctggcacct cagcctccct ggccatcagt gggctccggt ccgaggatga ggccgattat   660
tactgtgctg tttcttctcc gtactcttat gtcttcggcg gaggcaccaa gctgacggtc   720
ctaggtggcc aggccggcca gacaacgaca cctgctccca gaccgcctac tcccgcccca   780
accattgcat ctcagccact ctctctgaga cccgaaccgt gtagacctgc ggccgggggc   840
gctgtccaca caagaggctt agacttcgcc tgcgatatct atatctgggc cccactcgca   900
ggcacttgtg gagtgctgct gctttcactc gtgataaccc tgtactgcaa aagggggaga   960
aagaagctgc tgtatatttt taaacaacca tttatgaagc ctgttcagac tacccaggaa  1020
gaagacggtt gtagttgcag attccccgag gaggaagaag gaggttgcga gttgagagta  1080
aagttcagca gatccgcaga tgccctgct taccagcagg gtcaaaacca gctttacaac   1140
gagctgaatt taggtagaag agaggaatat gacgtgttgg ataaaagaag aggaagagac  1200
ccggaaatgg gcggcaagcc tcgaagaaaa aatccccaag agggactcta caatgagctg  1260
cagaaggaca aaatggctga agcctacagc gagatcggca tgaagggaga aagacgcaga  1320
gggaaagggc atgatgggct ttatcagggc ttgtccaccg ctacaaagga tacttatgac  1380
gcactacaca tgcaggccct gccacccgt                                    1410

SEQ ID NO: 221        moltype = DNA  length = 1184
FEATURE               Location/Qualifiers
source                1..1184
                      mol_type = other DNA
                      organism = synthetic construct
SEQUENCE: 221
tgtgaggctc cggtgcccgt cagtgggcag agcgcacatc gcccacagtc cccgagaagt   60
tgggggggagg ggtcggcaat tgaaccggtg cctagagaag gtggcgcggg gtaaactggg   120
aaagtgatgt cgtgtactgg ctccgccttt ttcccgaggg tggggggagaa ccgtatataa   180
gtgcagtagt cgccgtgaac gttctttttc gcaacgggtt tgccgccaga acacaggtaa   240
gtgccgtgtg tggttcccgc gggcctggcc tctttacggg ttatgccct tgcgtgcctt   300
gaattacttc cacctggctg cagtacgtga ttcttgatcc cgagcttcgg gttggaagtg   360
ggtgggagag ttcgaggcct tgcgcttaag gagccccttc gcctcgtgct tgagttgagg   420
cctggcctgg gcgctggggc cgccgcgtgc gaatctggtg gcaccttcgc gcctgtctcg   480
ctgctttcga taagtctcta gccatttaaa attttttgatg acctgctgcg acgctttttt   540
tctggcaaga tagtcttgta aatgcgggcc aagatctgca cactggtatt tcggtttttg   600
gggccgggcg cggcgacggg gcccgtgcgt cccagcgcac atgttcggcg aggcggggcc   660
tgcgagcgcg gccaccgaga atcggacggg ggtagtctca agctggccgg cctgctctgg   720
tgcctggcct cgcgccgccg tgtatcgccc cgccctgggc ggcaaggctg gcccggtcgg   780
caccagttgc gtgagcggaa agatggccgc ttccccggccc tgctgcaggg agctcaaaat   840
ggaggacgcg gcgctcggga gagcgggcgg gtgagtcacc cacacaaagg aaaagggcct   900
ttccgtcctc agccgtcgct tcatgtgact ccacggagta ccgggcgccg tccaggcacc   960
tcgattagtt ctcgagcttt tggagtacgt cgtctttagg ttggggggag gggtttttatg  1020
cgatggagtt tccccacact gagtgggtgg agactgaagt taggccagct tggcacttga   1080
tgtaattctc cttggaattt gcccttttgg agtttggatc ttggttcatt ctcaagcctc   1140
agacagtggt tcaaagtttt tttcttccat ttcaggtgtc gtga                   1184

SEQ ID NO: 222        moltype = DNA  length = 684
FEATURE               Location/Qualifiers
source                1..684
                      mol_type = other DNA
                      organism = synthetic construct
SEQUENCE: 222
ggccaggccg gccagacaac gacacctgct cccagaccgc ctactcccgc cccaaccatt   60
gcatctcagc cactctctct gagacccgaa gcgtgtagac ctgcggccgg gggcgctgtc   120
cacacaagag gcttagactt cgcctgcgat atctatatct gggcccccact cgcaggcact   180
tgtgtggagtgc tgctgctttc actcgtgata accctgtact gcaaaagggg gagaaagaag   240
ctgctgtata ttttttaaaca accatttatg agacctggttc agactacccca ggaagaagac   300
ggttgtagtt gcagattccc cgaggaggaa gaaggaggt gcgagttgag agtaaagttc   360
agcagatccg cagatgcccc tgcttaccag cagggtcaaa accagcttta caacgagctg   420
aatttaggta gaagagagga atatgacgtg ttggataaaa gaagaggaag agacccggaa   480
atgggcggca agcctcgaag aaaaaatccc caagagggac tctacaatga gctgcagaag   540
gacaaaatg ctgaagccta cagcgagatc ggcatgaagg gagaaagacg cagagggaaa   600
gggcatgatg ggctttatca gggcttgtcc accgctacaa aggatactta tgacgcacta   660
cacatgcagg ccctgccacc ccgt                                         684
```

-continued

```
SEQ ID NO: 223          moltype = AA  length = 361
FEATURE                 Location/Qualifiers
source                  1..361
                        mol_type = protein
                        organism = synthetic construct
SEQUENCE: 223
FPQDRPFEDT CHGNPSHYYD KAVRRCCYRC PMGLFPTQQC PQRPTDCRKQ CEPDYYLDEA   60
DRCTACVTCS RDDLVEKTPC AWNSSRVCEC RPGMFCSTSA VNSCARCFFH SVCPAGMIVK  120
FPGTAQKNTV CEPASPGVSP ACASPENCKE PSSGTIPQAK PTPVSPATSS ASTMPVRGGT  180
RLAQEAASKL TRAPDSPSSV GRPSSDPGLS PTQPCPEGSG DCRKQCEPDY YLDEAGRCTA  240
CVSCSRDDLV EKTPCAWNSS RTCECRPGMI CATSATNSCA RCVPYPICAA ETVTKPQDMA  300
EKDTTFEAPP LGTQPDCNPT PENGEAPAST SPTQSLLVDS QASKTLPIPT SAPVALSSTG  360
K                                                                  361

SEQ ID NO: 224          moltype = AA  length = 226
FEATURE                 Location/Qualifiers
source                  1..226
                        mol_type = protein
                        organism = synthetic construct
SEQUENCE: 224
FPQDRPFEDT CHGNPSHYYD KAVRRCCYRC PMGLFPTQQC PQRPTDCRKQ CEPDYYLDEA   60
DRCTACVTCS RDDLVEKTPC AWNSSRVCEC RPGMFCSTSA VNSCARCFFH SVCPAGMIVK  120
FPGTAQKNTV CEPASPGVSP ACASPENCKE PSSGTIPQAK PTPVSPATSS ASTMPVRGGT  180
RLAQEAASKL TRAPDSPSSV GRPSSDPGLS PTQPCPEGSG DCRKQC                 226

SEQ ID NO: 225          moltype = AA  length = 226
FEATURE                 Location/Qualifiers
source                  1..226
                        mol_type = protein
                        organism = synthetic construct
SEQUENCE: 225
PGVSPACASP ENCKEPSSGT IPQAKPTPVS PATSSASTMP VRGGTRLAQE AASKLTRAPD   60
SPSSVGRPSS DPGLSPTQPC PEGSGDCRKQ CEPDYYLDEA GRCTACVSCS RDDLVEKTPC  120
AWNSSRTCEC RPGMICATSA TNSCARCVPY PICAAETVTK PQDMAEKDTT FEAPPLGTQP  180
DCNPTPENGE APASTSPTQS LLVDSQASKT LPIPTSAPVA LSSTGK                 226

SEQ ID NO: 226          moltype = AA  length = 270
FEATURE                 Location/Qualifiers
source                  1..270
                        mol_type = protein
                        organism = synthetic construct
SEQUENCE: 226
FPQDRPFEDT CHGNPSHYYD KAVRRCCYRC PMGLFPTQQC PQRPTDCRKQ CEPDYYLDEA   60
DRCTACVTCS RDDLVEKTPC AWNSSRVCEC RPGMFCSTSA VNSCARCFFH SVCPAGMIVK  120
FPGTAQKNTV CEPASEPDYY LDEAGRCTAC VSCSRDDLVE KTPCAWNSSR TCECRPGMIC  180
ATSATNSCAR CVPYPICAAE TVTKPQDMAE KDTTFEAPPL GTQPDCNPTP ENGEAPASTS  240
PTQSLLVDSQ ASKTLPIPTS APVALSSTGK                                   270
```

ANTI-CD30 ANTIBODY AND CHIMERIC ANTIGEN RECEPTOR COMPRISING THEREOF

SEQUENCE LISTING

This application contains references to amino acid sequences and/or nucleic acid sequences which have been submitted concurrently herewith as the sequence listing XML file entitled "000341 us_SequenceListing.XML", file size 236 kilobytes, created on 18 May 2023. The aforementioned sequence listing is hereby incorporated by reference in its entirety pursuant to 37 C.F.R. § 1.52(e)(5).

FIELD

The present disclosure relates to a novel antibody or an antigen binding fragment thereof for use in targeting CD30 to treat cancer, a chimeric antigen receptor including same, and uses thereof.

BACKGROUND

B cell malignancies are tumors generated in B cells, which are a type of cell lineage responsible for the immune system of the body. Such a B cell malignancy breaks a normal immune system to decrease the immunity against antigens invading from the outside, finally causing the death of patients. For example, acute lymphocytic leukemia (ALL), which is one of B cell malignancies, refers to a disease in which the lymphoid line of white blood cells becomes malignant, grows in the bone marrow, and spreads to peripheral blood, thus invading the liver, the spleen, the lymph, the cerebrum, the cerebellum, the spinal cord, and so on. Acute lymphocytic leukemia is predicted to have a global incidence of 161,000 and a death number of 110,000 in 2015, and both outbreaks of acute lymphocytic leukemia and deaths from acute lymphocytic leukemia are more prevalent in men than women. Representative of therapies for acute lymphocytic leukemia are chemotherapy, targeted therapy, and allogeneic stem cell transplantation. These therapies have been improved to carry the survival rate of child patients to over 85%.

CD30 is attracting attention as a target for these diseases. The CD30 cell surface molecule is a member of the tumor necrosis factor receptor (TNF-R) superfamily. CD30 is a type I transmembrane glycoprotein with six (human) or three (murine and rat) cysteine-rich repeats with a central hinge sequence. CD30 exists as a 120 kDa membrane molecule which develops from an intercellular precursor protein of 90 kDa.

CD30 is preferentially expressed by activated lymphoid cells. Specifically, stimulation of CD30 in lymphoid cells has been shown to induce pleiotropic biological effects, including proliferation, activation, differentiation, and cell death, depending on cell type, stage of differentiation and presence of other stimuli. CD30 was originally identified by the monoclonal antibody Ki-1, which is reactive with antigens expressed on Hodgkin and Reed-Sternberg cells of Hodgkin's disease. Accordingly, CD30 is widely used as a clinical marker for Hodgkin's lymphoma and related hematological malignancies.

CD30 was subsequently shown to be expressed on a subset of non-Hodgkin's lymphomas (NHL), including Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), and entroblastic/centrocytic (cb/cc) follicular lymphomas, as well as several virally-transformed lines such as human T-Cell Lymphotrophic Virus I or II transformed T-cells, and Epstein-Barr Virus transformed B-cells.

Since the percentage of CD30-positive cells in normal individuals is quite small, the expression of CD30 in tumor cells renders it an important target for antibody mediated therapy to specifically target therapeutic agents against CD30-positive neoplastic cells. However, while the results obtained to date clearly establish CD30 as a useful target for immunotherapy, they also show that currently available murine antibodies do not constitute ideal therapeutic agents. Accordingly, the need exists for anti-CD antibodies effective for treating or preventing diseases related with CD30-expressing cells.

BRIEF DESCRIPTION OF THE DRAWINGS

The above and other aspects, features and advantages of the present disclosure will be more apparent from the following detailed description taken in conjunction with the accompanying drawings, in which:

FIG. 5 is a schematic view of CAR structures including an CD30 antibody and an HRS antibody used as a control.

DETAILED DESCRIPTION

Figure 1:
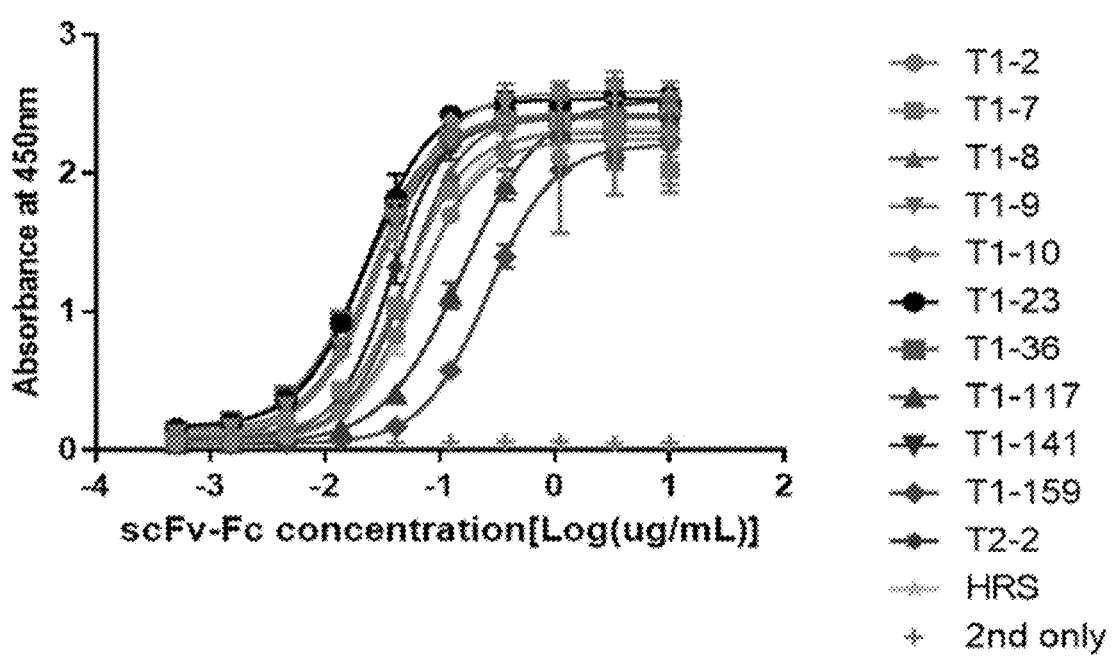
FIG. 1 is a plot quantitatively analyzing binding affinity of 11 Fc-linked antibodies for CD30.

The present inventors have conducted intensive and thorough research into development of a novel antibody specifically binding to CD30 and a chimeric antigen receptor using the same, in order to treat tumorigenic diseases and immune diseases. As a result, the present inventors have discovered, among other things, that an anti-CD30 antibody or an antigen-binding fragment thereof that specifically binds to CD30 antigen or an effector cell expressing a chimeric antigen receptor comprising same retains cytotoxic activity and antitumoral effects, which leads to the present disclosure.

Therefore, an aspect of the present disclosure is to provide an anti-CD30 antibody or an antigen-binding fragment thereof.

Another aspect of the present disclosure is to provide a nucleic acid molecule encoding the anti-CD30 antibody or the antigen-binding fragment thereof.

Another aspect of the present disclosure is to provide a CD30-specific chimeric antigen receptor comprising: an extracellular domain comprising an anti-CD30 antibody or an antigen-binding fragment thereof; a transmembrane domain; and an intracellular signaling domain.

In an aspect thereof, the present disclosure provides an anti-CD30 antibody or an antigen binding fragment thereof, comprising an immunoglobulin heavy-chain variable region domain and an immunoglobulin light-chain variable region domain, wherein:

i) the heavy-chain variable region domain comprises HCDR1, HCDR2, and HCDR3, wherein the HCDR1, HCDR2, and HCDR3 comprise the amino acid sequence of SEQ ID NO: 1, 2, and 3, respectively; and the light-chain variable region domain comprises LCDR1, LCDR2, and LCDR3, wherein the LCDR1, LCDR2, and LCDR3 comprise the amino acid sequence of SEQ ID NO: 4, 5, and 6, respectively;

ii) the heavy-chain variable region domain comprises HCDR1, HCDR2, and HCDR3, wherein the HCDR1, HCDR2, and HCDR3 comprise the amino acid sequence of SEQ ID NO: 21, 22, and 23, respectively; and the light-chain variable region domain comprises LCDR1, LCDR2, and LCDR3, wherein the LCDR1, LCDR2, and LCDR3 comprise the amino acid sequence of SEQ ID NO: 24, 25, and 26, respectively;

iii) the heavy-chain variable region domain comprises HCDR1, HCDR2, and HCDR3, wherein the HCDR1, HCDR2, and HCDR3 comprise the amino acid sequence of SEQ ID NO: 41, 42, and 43, respectively; and the light-chain variable region domain comprises LCDR1, LCDR2, and LCDR3, wherein the LCDR1, LCDR2, and LCDR3 comprise the amino acid sequence of SEQ ID NO: 44, 45, and 46, respectively;

iv) the heavy-chain variable region domain comprises HCDR1, HCDR2, and HCDR3, wherein the HCDR1, HCDR2, and HCDR3 comprise the amino acid sequence of SEQ ID NO: 61, 62, and 63, respectively; and the light-chain variable region domain comprises LCDR1, LCDR2, and LCDR3, wherein the LCDR1, LCDR2, and LCDR3 comprise the amino acid sequence of SEQ ID NO: 64, 65, and 66, respectively;

v) the heavy-chain variable region domain comprises HCDR1, HCDR2, and HCDR3, wherein the HCDR1, HCDR2, and HCDR3 comprise the amino acid sequence of SEQ ID NO: 81, 82, and 83, respectively; and the light-chain variable region domain comprises LCDR1, LCDR2, and LCDR3, wherein the LCDR1, LCDR2, and LCDR3 comprise the amino acid sequence of SEQ ID NO: 84, 85, and 86, respectively;

vi) the heavy-chain variable region domain comprises HCDR1, HCDR2, and HCDR3, wherein the HCDR1, HCDR2, and HCDR3 comprise the amino acid sequence of SEQ ID NO: 101, 102, and 103, respectively; and the light-chain variable region domain comprises LCDR1, LCDR2, and LCDR3, wherein the LCDR1, LCDR2, and LCDR3 comprise the amino acid sequence of SEQ ID NO: 104, 105, and 106, respectively;

vii) the heavy-chain variable region domain comprises HCDR1, HCDR2, and HCDR3, wherein the HCDR1, HCDR2, and HCDR3 comprise the amino acid sequence of SEQ ID NO: 121, 122, and 123, respectively; and the light-chain variable region domain comprises LCDR1, LCDR2, and LCDR3, wherein the LCDR1, LCDR2, and LCDR3 comprise the amino acid sequence of SEQ ID NO: 124, 125, and 126, respectively;

viii) the heavy-chain variable region domain comprises HCDR1, HCDR2, and HCDR3, wherein the HCDR1, HCDR2, and HCDR3 comprise the amino acid sequence of SEQ ID NO: 141, 142, and 143, respectively; and the light-chain variable region domain comprises LCDR1, LCDR2, and LCDR3, wherein the LCDR1, LCDR2, and LCDR3 comprise the amino acid sequence of SEQ ID NO: 144, 145, and 146, respectively;

ix) the heavy-chain variable region domain comprises HCDR1, HCDR2, and HCDR3, wherein the HCDR1, HCDR2, and HCDR3 comprise the amino acid sequence of SEQ ID NO: 161, 162, and 163, respectively; and the light-chain variable region domain comprises LCDR1, LCDR2, and LCDR3, wherein the LCDR1, LCDR2, and LCDR3 comprise the amino acid sequence of SEQ ID NO: 164, 165, and 166, respectively;

x) the heavy-chain variable region domain comprises HCDR1, HCDR2, and HCDR3, wherein the HCDR1, HCDR2, and HCDR3 comprise the amino acid sequence of SEQ ID NO: 181, 182, and 183, respectively; and the light-chain variable region domain comprises LCDR1, LCDR2, and LCDR3, wherein the LCDR1, LCDR2, and LCDR3 comprise the amino acid sequence of SEQ ID NO: 184, 185, and 186, respectively; or xi) the heavy-chain variable region domain comprises HCDR1, HCDR2, and HCDR3, wherein the HCDR1, HCDR2, and HCDR3 comprise the amino acid sequence of SEQ ID NO: 201, 202, and 203, respectively; and the light-chain variable region domain comprises LCDR1, LCDR2, and LCDR3, wherein the LCDR1, LCDR2, and LCDR3 comprise the amino acid sequence of SEQ ID NO: 204, 205, and 206, respectively.

Intensive and thorough research conducted by the present inventors into the development of a novel antibody binding specifically to CD30 and a chimeric antigen receptor using same for use in treating tumorigenic diseases or immune diseases resulted in the finding that the anti-CD30 antibody binding selectively to the CD30 antigen and an effector cell expressing a chimeric antigen receptor including a fragment of the antibody bring about cytolytic and antitumor effects.

As used herein, the term "CD30", also known as a member of the TNF receptor (TNF-R) superfamily, refers to a cell membrane protein of the tumor necrosis factor receptor family. This family of molecules has variable homology among its members and includes nerve growth factor receptor (NGFR), CD120 (a), CD120 (b), CD27, CD40, and CD95. These molecules are typically characterized by the presence of multiple cysteine-rich repeats in the extracyto-plasmic region. Members of this family are considered crucial for regulating proliferation and differentiation of lymphocytes.

As used herein, the term "antibody" used in context of CD30 refers to an antibody specific for CD30 and is intended to encompass not only a whole antibody form, but also an antigen-binding fragment thereof.

A whole antibody includes two full length light chain and two full length heavy chains where each light chain is linked to the heavy chain by disulfide bonds. The heavy chain constant region is divided into isotypes of gamma (γ), mu (μ), alpha (α), delta (δ), and epsilon (ε) types, which are further subtyped into gamma1 (γ1), gamma2 (γ2), gamma3 (γ3), gamma4 (γ4), alpha 1 (α1), and alpha 2 (α2). The light chain constant region is divided into kappa (κ) and lambda (λ) types.

As used herein, the term "antigen-binding fragment" refers to a fragment retaining the function of binding to an antigen and includes Fab, F(ab'), F(ab')$_2$, and Fv. Of them, Fab (fragment antigen binding) is composed of one constant and one variable domain of each of the heavy and the light chain, the constant domain of the heavy chain being the first constant domain (CH1), and thus contains one antigen-binding site. Fab' is different from Fab in that the former comprises a hinge region including at least one cysteine residue at the C-terminal of the CH1 domain of a heavy chain. F(ab')$_2$ is produced by a disulfide bond formation between cysteine residues in the hinge region of Fab'. Fv is an antibody fragment composed only of variable regions of a heavy and a light chain, which may be produced by a recombinant technology disclosed in the art. In Fv (two-chain Fv), variable regions of a light and heavy chain are linked by a non-covalent bond, and in a single chain Fv, variable regions of a light and heavy chain are linked by a covalent bond through a peptide linker or it may form a dimer structure like a two chain FV through a direct linkage at the C-terminal. These antibody fragments can be obtained through a proteinase treatment (for example, a whole anti-body may be treated with a papain to obtain Fab fragments or with pepsin to obtain F(ab')$_2$ fragment) or preferably constructed using a recombinant DNA technology.

Herein, examples of the antibody include a monoclonal antibody, a multispecific antibody, a human antibody, a humanized antibody, a chimeric antibody, a single-chain Fv (scFv), a single-chain antibody, an Fab, an F(ab'), a disulfide-linked Fv (sdFv), an anti-idiotype (anti-Id) antibody, and an epitope-binding fragment thereof, but are not limited thereto.

The term "heavy chain", as used herein, refers to a full-length chain comprising three constant regions CH1, CH2 and CH3 and one variable region VH comprising an amino acid sequence which is sufficient for conferring specificity to an antigen as well fragments thereof. Also the term "light chain" as used herein refers to a full length chain comprising one constant region CL and one variable region VL comprising an amino acid sequence which is sufficient for conferring specificity to an antigen as well fragments thereof.

The term "variable region" or "variable domain", as used herein, refers to a domain on a heavy or a light chain of an antibody, which is responsible for binding the antibody to an antigen. Variable domains on the heavy and the light chain of a native antibody (VH and VL, respectively) are generally similar in structure and each include four conserved frame-work regions (FRs) and three hypervariable regions (HVRs) (Kindt et al., Kuby Immunology, 6$^{th}$ edition, W. H. Freeman and Co., page 91 (2007)).

As used herein, the term "CDR" (complementarity determining region) refers to an amino acid sequence of the hypervariable regions on the immunoglobulin heavy and light chains (Kabat et al., Sequences of Proteins of Immunological Interest, 4th Ed., U. S. Department of Health and Human Services, National Institutes of Health (1987)). Three CDRs are included in each of the heavy chain (CDRH1, CDRH2, and CDRH3) and the light chain (CDRL1, CDRL2, and CDRL3). CDRs provide important contact residues with which the antibody binds to an antigen or an epitope.

As used herein, the term "framework" or "FR" refers to variable domain residues other than hypervariable region (HVR) residues. The FR of the variable domain generally consists of four FR domains: FR1, FR2, FR3, and FR4. Thus, the HVR and FR sequences generally appear in the following sequence in VH:

FRH1 (framework region 1 of heavy chain)-CDRH1 (complementarity determining region 1 of heavy chain)-FRH2-CDRH2-FRH3-CDRH3-FRH4.

Also, HVR and FR sequences in VL (or Vk) are arranged in the order as follows: FRL1 (framework region 1 of light chain)-CDRL1 (complementarity determining region 1 of light chain)-FRL2-CDRL2-FRL3-CDRL3-FRL4.

By the term "specifically binding" or wordings relevant thereto, it is intended that an antibody or a constituent thereof, such as an antigen binding fragment or scFv, forms a complex with an antigen that is relatively stable under physiologic conditions. Specific binding can be characterized by an equilibrium dissociation constant of at least about $1 \times 10^{-6}$ M or less (e.g., less KD means more strong binding). Methods for determining whether two molecules specifically bind are well known in the art and include, for example, equilibrium dialysis, surface plasmon resonance, and the like.

The term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

The term "human antibody" or "humanized antibody", as used herein, refers to an antibody which possesses an amino acid sequence which corresponds to that of an antibody produced by a human or a human cell or derived from a non-human source that utilizes human antibody repertoires or other human antibody-encoding sequences.

As used herein, the term "chimeric antibody" refers to an antibody in which a portion of the heavy and/or light chain is derived from a particular source or species, while the remainder of the heavy and/or light chain is derived from a different source or species.

In the context of specifically recognizing CD30, variants of the amino acid sequences, as recognized by a person skilled in the art, may fall within the scope of the anti-CD30 antibody or an antigen-binding fragment thereof according to the present disclosure. For example, a variation may be given to the amino acid sequence of an antibody in order to improve the binding affinity and/or other biological properties of the antibody. The variation includes a deletion, an addition, and/or a substitution of an amino acid residue on the amino acid sequence of the antibody.

Such amino acid variations may be provided on the basis of a relative similarity of amino acid side chains, e.g., hydrophobicity, hydrophilicity, charge, and size. As analyzed for size, shape, and type of amino acid side chains, it is clear that all of arginine, lysine, and histidine residues are positively charged; alanine, glycine, and serine are similar in size; phenylalanine, tryptophan, and tyrosine have similar shapes. Accordingly, based on this consideration, arginine, lysine and histidine; alanine, glycine and serine; and phenylalanine, tryptophan and tyrosine may be considered to be biologically functional equivalents.

In making such variations, the hydropathic index of amino acids may be considered. Each amino acid has been assigned a hydropathic index on the basis of their hydrophobicity and charge characteristics: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art. It is known that similar biological activity is retained only upon substitution of certain amino acids for other amino acids having a similar hydropathic index. In making variations based upon the hydropathic index, the substitution of amino acids whose hydropathic indices are within ±2 is preferred, those which are within ±1 are particularly preferred, and those within ±0.5 are even more particularly preferred.

It is also understood in the art that substitutions between amino acids having similar hydrophilicity values may result in the generation of proteins having biologically equivalent activities. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4).

In making variations based upon similar hydrophilicity values, the substitution of amino acids whose hydrophilicity values are within ±2 is preferred, those which are within ±1 are particularly preferred, and those within ±0.5 are even more particularly preferred.

The amino acid exchanges in proteins that do not substantially change the activity of the molecule are well known in the art (H. Neurath, R. L. Hill, The Proteins, Academic Press, New York, 1979). The most common exchanges are found between amino acid residues: Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

In an embodiment of the present disclosure, the anti-CD30 antibody or the antigen binding fragment thereof comprises a heavy chain variable region domain and a light chain variable region domain, wherein:

i) the heavy-chain variable region domain comprises the amino acid sequence of SEQ ID NO: 7; and the light-chain variable region domain comprises the amino acid sequence of SEQ ID NO: 8;

ii) the heavy-chain variable region domain comprises the amino acid sequence of SEQ ID NO: 27; and the light-chain variable region domain comprises the amino acid sequence of SEQ ID NO: 28;

iii) the heavy-chain variable region domain comprises the amino acid sequence of SEQ ID NO: 47; and the light-chain variable region domain comprises the amino acid sequence of SEQ ID NO: 48;

iv) the heavy-chain variable region domain comprises the amino acid sequence of SEQ ID NO: 67; and the light-chain variable region domain comprises the amino acid sequence of SEQ ID NO: 68;

v) the heavy-chain variable region domain comprises the amino acid sequence of SEQ ID NO: 87; and the light-chain variable region domain comprises the amino acid sequence of SEQ ID NO: 88;

vi) the heavy-chain variable region domain comprises the amino acid sequence of SEQ ID NO: 107; and the light-chain variable region domain comprises the amino acid sequence of SEQ ID NO: 108;

vii) the heavy-chain variable region domain comprises the amino acid sequence of SEQ ID NO: 127; and the light-chain variable region domain comprises the amino acid sequence of SEQ ID NO: 128;

viii) the heavy-chain variable region domain comprises the amino acid sequence of SEQ ID NO: 147; and the light-chain variable region domain comprises the amino acid sequence of SEQ ID NO: 148;

ix) the heavy-chain variable region domain comprises the amino acid sequence of SEQ ID NO: 167; and the light-chain variable region domain comprises the amino acid sequence of SEQ ID NO: 168;

x) the heavy-chain variable region domain comprises the amino acid sequence of SEQ ID NO: 187; and the light-chain variable region domain comprises the amino acid sequence of SEQ ID NO: 188; or xi) the heavy-chain variable region domain comprises the amino acid sequence of SEQ ID NO: 207; and the light-chain variable region domain comprises the amino acid sequence of SEQ ID NO: 208.

In an embodiment of the present disclosure, the anti-CD30 antibody or the antigen binding fragment thereof comprises scFv, wherein the scFv comprises an amino acid sequence selected from the group consisting of the amino acid sequence of SEQ ID NO: 9, the amino acid sequence of SEQ ID NO: 29, the amino acid sequence of SEQ ID NO: 49, the amino acid sequence of SEQ ID NO: 69, the amino acid sequence of SEQ ID NO: 89, the amino acid sequence of SEQ ID NO: 109, the amino acid sequence of SEQ ID NO: 129, the amino acid sequence of SEQ ID NO: 149, the amino acid sequence of SEQ ID NO: 169, the amino acid sequence of SEQ ID NO: 189, and the amino acid sequence of SEQ ID NO: 209.

In an embodiment of the present disclosure, the antigen binding fragment is Fab, Fab', F(ab')$_2$, Fv, scFV, or chemically linked F(ab') 2.

An aspect of the present invention provides a nucleic acid molecule coding for the anti-CD30 antibody or an antigen-binding fragment thereof.

The term "nucleic acid molecule", as used herein, is intended to encompass DNA (gDNA and cDNA) and RNA molecules. Nucleotides are the basic building block of the nucleic acid molecule and include sugar or base-modified analogues as well as natural nucleotides (Scheit, *Nucleotide Analogs*, John Wiley, New York (1980); Uhlman and Peyman, *Chemical Reviews*, 90:543-584 (1990)).

It should be understood to a person skilled in the art that the nucleotide sequence coding for the antibody, the antigen-biding fragment thereof, or the chimeric antigen receptor polypeptide according to the present disclosure is any nucleotide sequence that encode an amino acid sequence constituting the chimeric antigen receptor molecule and is not limited to particular nucleotide sequences.

The reason is that even if the nucleotide sequence undergoes mutation, the expression of the mutated nucleotide sequence into a protein may not cause a change in the protein sequence. This is called the degeneracy of codons. Therefore, the nucleotide sequence includes nucleotide sequences containing functionally equivalent codons, codons encoding the same amino acids (e.g., arginine or serine are six different codons due to the degeneracy of codons), or codons containing biologically equivalent amino acids.

According to an embodiment of the present disclosure, nucleotide sequences of nucleic acids coding for polypeptides of heavy chain CDRs, light chain CDRs, heavy chain variable regions, light chain variable regions, heavy chains, or light chains in the antibody to CD30 or the antigen-binding fragment thereof according to the present disclosure are listed in the sequence listing appended.

The nucleic acid molecule of the present disclosure which encodes the anti-CD30 antibody or the antigen-binding fragment thereof is construed to encompass nucleotide sequences having substantial identity to the nucleic acid molecule. In this context, the term "substantial identity" refers to an identity of at least 80%, more preferably at least 90%, and most preferably at least 95% between the nucleotide sequence of the present disclosure and any other sequences as analyzed by commonly used algorithm when alignment therebetween is made as much correspondingly as possible.

Considering the above-described mutations having biologically equivalent activity, it should be construed that nucleic acid molecules encoding the antibody or the antigen-binding fragment; or the chimeric antigen receptor polypeptide according to the present disclosure also include sequences having substantial identity therewith. In this regard, the substantial identity refers to an identity of at least 61%, more preferably at least 70%, still more preferably 80%, and most preferably at least 90% between the nucleotide sequence of the present disclosure and any other sequences as analyzed by commonly used algorithm when alignment therebetween is made as much correspondingly as possible. Methods of alignment for sequence comparison are known in the art. Various methods and algorithms for alignment are disclosed in Smith and Waterman, Adv. Appl. Math. 2:482 (1981); Needleman and Wunsch, J. Mol. Bio. 48:443 (1970); Pearson and Lipman, Methods in Mol. Biol. 24:307-31 (1988); Higgins and Sharp, Gene 73:237-44 (1988); Higgins and Sharp, CABIOS 5:151-3 (1989); Corpet et al., Nuc. Acids Res. 16:10881-90 (1988); Huang et al., Comp. Appl. BioSci. 8:155-65 (1992) and Pearson et al., Meth. Mol. Biol. 24:307-31 (1994). The NCBI Basic Local Alignment Search Tool (BLAST; Altschul, et al., *J. Mol. Biol.* 215:403-10 (1990)) is available from, for example, the NBCI (National Center for Biological Information), and can be used in connection with sequence analysis programs, such as blastp, blasm, blastx, tblastn and tblastx, on the Internet. The use of the program in comparing sequence similarity can be available on the BLAST help page at the NCBI website. The BLAST is available from, for example, the BLAST page of the NBCI website on the Internet. The use of the program in comparing sequence similarity can be available on the BLAST help page at the NCBI website.

In an embodiment of the present disclosure, the nucleic acid molecule comprises nucleotide sequences selected from the group consisting of:

i) the nucleotide sequence of SEQ ID NO: 11, the nucleotide sequence of SEQ ID NO: 12, the nucleotide sequence of SEQ ID NO: 13, the nucleotide sequence of SEQ ID NO: 14, the nucleotide sequence of SEQ ID NO: 15, and the nucleotide sequence of SEQ ID NO: 16, wherein the nucleotide sequence encodes HCDR1, HCDR2, HCDR3, LCDR1, LCDR2, and LCDR3, respectively;

ii) the nucleotide sequence of SEQ ID NO: 31, the nucleotide sequence of SEQ ID NO: 32, the nucleotide sequence of SEQ ID NO: 33, the nucleotide sequence of SEQ ID NO: 34, the nucleotide sequence of SEQ ID NO: 35, and the nucleotide sequence of SEQ ID NO: 36, wherein the nucleotide sequence encodes HCDR1, HCDR2, HCDR3, LCDR1, LCDR2, and LCDR3, respectively;

iii) the nucleotide sequence of SEQ ID NO: 51, the nucleotide sequence of SEQ ID NO: 52, the nucleotide sequence of SEQ ID NO: 53, the nucleotide sequence of SEQ ID NO: 54, the nucleotide sequence of SEQ ID NO: 55, and the nucleotide sequence of SEQ ID NO: 56, wherein the nucleotide sequence encodes HCDR1, HCDR2, HCDR3, LCDR1, LCDR2, and LCDR3, respectively;

iv) the nucleotide sequence of SEQ ID NO: 71, the nucleotide sequence of SEQ ID NO: 72, the nucleotide sequence of SEQ ID NO: 73, the nucleotide sequence of SEQ ID NO: 74, the nucleotide sequence of SEQ ID NO: 75, and the nucleotide sequence of SEQ ID NO: 76, wherein the nucleotide sequence encodes HCDR1, HCDR2, HCDR3, LCDR1, LCDR2, and LCDR3, respectively;

v) the nucleotide sequence of SEQ ID NO: 91, the nucleotide sequence of SEQ ID NO: 92, the nucleotide sequence of SEQ ID NO: 93, the nucleotide sequence of SEQ ID NO: 94, the nucleotide sequence of SEQ ID NO: 95, and the nucleotide sequence of SEQ ID NO: 96, wherein the nucleotide sequence encodes HCDR1, HCDR2, HCDR3, LCDR1, LCDR2, and LCDR3, respectively;

vi) the nucleotide sequence of SEQ ID NO: 111, the nucleotide sequence of SEQ ID NO: 112, the nucleotide sequence of SEQ ID NO: 113, the nucleotide sequence of SEQ ID NO: 114, the nucleotide sequence of SEQ ID NO: 115, and the nucleotide sequence of SEQ ID NO: 116, wherein the nucleotide sequence encodes HCDR1, HCDR2, HCDR3, LCDR1, LCDR2, and LCDR3, respectively;

vii) the nucleotide sequence of SEQ ID NO: 131, the nucleotide sequence of SEQ ID NO: 132, the nucleotide sequence of SEQ ID NO: 133, the nucleotide sequence of SEQ ID NO: 134, the nucleotide sequence of SEQ ID NO: 135, and the nucleotide sequence of SEQ ID NO: 136, wherein the nucleotide sequence encodes HCDR1, HCDR2, HCDR3, LCDR1, LCDR2, and LCDR3, respectively;

viii) the nucleotide sequence of SEQ ID NO: 151, the nucleotide sequence of SEQ ID NO: 152, the nucleotide sequence of SEQ ID NO: 153, the nucleotide sequence of SEQ ID NO: 154, the nucleotide sequence of SEQ ID NO: 155, and the nucleotide sequence of SEQ ID NO: 156, wherein the nucleotide sequence encodes HCDR1, HCDR2, HCDR3, LCDR1, LCDR2, and LCDR3, respectively;

ix) the nucleotide sequence of SEQ ID NO: 171, the nucleotide sequence of SEQ ID NO: 172, the nucleotide sequence of SEQ ID NO: 173, the nucleotide sequence of SEQ ID NO: 174, the nucleotide sequence of SEQ ID NO: 175, and the nucleotide sequence of SEQ ID NO: 176, wherein the nucleotide sequence encodes HCDR1, HCDR2, HCDR3, LCDR1, LCDR2, and LCDR3, respectively;

x) the nucleotide sequence of SEQ ID NO: 191, the nucleotide sequence of SEQ ID NO: 192, the nucleotide sequence of SEQ ID NO: 193, the nucleotide sequence of SEQ ID NO: 194, the nucleotide sequence of SEQ ID NO: 195, and the nucleotide sequence of SEQ ID NO: 196, wherein the nucleotide sequence encodes HCDR1, HCDR2, HCDR3, LCDR1, LCDR2, and LCDR3, respectively; and xi) the nucleotide sequence of SEQ ID NO: 211, the nucleotide sequence of SEQ ID NO: 212, the nucleotide sequence of SEQ ID NO: 213, the nucleotide sequence of SEQ ID NO: 214, the nucleotide sequence of SEQ ID NO: 215, and the nucleotide sequence of SEQ ID NO: 216, wherein the nucleotide sequence encodes HCDR1, HCDR2, HCDR3, LCDR1, LCDR2, and LCDR3, respectively.

In an embodiment of the present disclosure, the nucleic acid molecule comprises nucleotide sequences selected from the group consisting of:

i) the nucleotide sequence of SEQ ID NO: 17 and the nucleotide sequence of SEQ ID NO: 18, wherein the nucleotide sequence encodes heavy chain variable domain and light chain variable domain, respectively;

ii) the nucleotide sequence of SEQ ID NO: 37 and the nucleotide sequence of SEQ ID NO: 38, wherein the nucleotide sequence encodes heavy chain variable domain and light chain variable domain, respectively;

iii) the nucleotide sequence of SEQ ID NO: 57 and the nucleotide sequence of SEQ ID NO: 58, wherein the nucleotide sequence encodes heavy chain variable domain and light chain variable domain, respectively;

iv) the nucleotide sequence of SEQ ID NO: 77 and the nucleotide sequence of SEQ ID NO: 78, wherein the nucleotide sequence encodes heavy chain variable domain and light chain variable domain, respectively;

v) the nucleotide sequence of SEQ ID NO: 97 and the nucleotide sequence of SEQ ID NO: 98, wherein the nucleotide sequence encodes heavy chain variable domain and light chain variable domain, respectively;

vi) the nucleotide sequence of SEQ ID NO: 117 and the nucleotide sequence of SEQ ID NO: 118, wherein the nucleotide sequence encodes heavy chain variable domain and light chain variable domain, respectively;

vii) the nucleotide sequence of SEQ ID NO: 137 and the nucleotide sequence of SEQ ID NO: 138, wherein the nucleotide sequence encodes heavy chain variable domain and light chain variable domain, respectively;

viii) the nucleotide sequence of SEQ ID NO: 157 and the nucleotide sequence of SEQ ID NO: 158, wherein the nucleotide sequence encodes heavy chain variable domain and light chain variable domain, respectively;

ix) the nucleotide sequence of SEQ ID NO: 177 and the nucleotide sequence of SEQ ID NO: 178, wherein the nucleotide sequence encodes heavy chain variable domain and light chain variable domain, respectively;

x) the nucleotide sequence of SEQ ID NO: 197 and the nucleotide sequence of SEQ ID NO: 198, wherein the nucleotide sequence encodes heavy chain variable domain and light chain variable domain, respectively; and xi) the nucleotide sequence of SEQ ID NO: 217 and the nucleotide sequence of SEQ ID NO: 218, wherein the nucleotide sequence encodes heavy chain variable domain and light chain variable domain, respectively.

In an embodiment of the present disclosure, the nucleic acid molecule comprises a nucleotide sequence selected from the group consisting of the nucleotide sequence of SEQ ID NO: 19, the nucleotide sequence of SEQ ID NO: 39, the nucleotide sequence of SEQ ID NO: 59, the nucleotide sequence of SEQ ID NO: 79, the nucleotide sequence of SEQ ID NO: 99, the nucleotide sequence of SEQ ID NO: 119, the nucleotide sequence of SEQ ID NO: 139, the nucleotide sequence of SEQ ID NO: 159, the nucleotide sequence of SEQ ID NO: 179, the nucleotide sequence of SEQ ID NO: 199, and the nucleotide sequence of SEQ ID NO: 219, wherein the nucleotide sequence encodes scFv.

Another aspect of the present disclosure provides a recombinant vector carrying the nucleic acid molecule.

According to another aspect thereof, the present disclosure provides a host cell transformed with the recombinant vector.

So long as it allows a vector to be cloned thereto and expressed sequentially, any host cell can be used in the present disclosure. Such host cells are well known in the art. For example, eukaryotic host cells suitable for the vector include monkey kidney cell 7 (COS7), NSO cells, SP2/0, Chinese hamster ovary (CHO) cells, W138, baby hamster kidney (BHK) cells, MDCK, myeloma cell lines, HuT 78 cells, and HEK-293 cells, but are not limited thereto.

According to another aspect thereof, the present disclosure provides a CD30-specific chimeric antigen receptor comprising an anti-CD30 antibody or an antigen-binding fragment thereof; a transmembrane domain; and an intracellular signaling domain.

The anti-CD30 antibody or an antigen binding fragment thereof comprises an immunoglobulin heavy-chain variable region domain and an immunoglobulin light-chain variable region domain, wherein:

i) the heavy-chain variable region domain comprises HCDR1, HCDR2, and HCDR3, wherein the HCDR1, HCDR2, and HCDR3 comprise the amino acid sequence of SEQ ID NO: 1, 2, and 3, respectively; and the light-chain variable region domain comprises LCDR1, LCDR2, and LCDR3, wherein the LCDR1, LCDR2, and LCDR3 comprise the amino acid sequence of SEQ ID NO: 4, 5, and 6, respectively;

ii) the heavy-chain variable region domain comprises HCDR1, HCDR2, and HCDR3, wherein the HCDR1, HCDR2, and HCDR3 comprise the amino acid sequence of SEQ ID NO: 21, 22, and 23, respectively; and the light-chain variable region domain comprises LCDR1, LCDR2, and LCDR3, wherein the LCDR1, LCDR2, and LCDR3 comprise the amino acid sequence of SEQ ID NO: 24, 25, and 26, respectively;

iii) the heavy-chain variable region domain comprises HCDR1, HCDR2, and HCDR3, wherein the HCDR1, HCDR2, and HCDR3 comprise the amino acid sequence of SEQ ID NO: 41, 42, and 43, respectively; and the light-chain variable region domain comprises LCDR1, LCDR2, and LCDR3, wherein the LCDR1, LCDR2, and LCDR3 comprise the amino acid sequence of SEQ ID NO: 44, 45, and 46, respectively;

iv) the heavy-chain variable region domain comprises HCDR1, HCDR2, and HCDR3, wherein the HCDR1, HCDR2, and HCDR3 comprise the amino acid sequence of SEQ ID NO: 61, 62, and 63, respectively; and the light-chain variable region domain comprises LCDR1, LCDR2, and LCDR3, wherein the LCDR1, LCDR2, and LCDR3 comprise the amino acid sequence of SEQ ID NO: 64, 65, and 66, respectively;

v) the heavy-chain variable region domain comprises HCDR1, HCDR2, and HCDR3, wherein the HCDR1, HCDR2, and HCDR3 comprise the amino acid sequence of SEQ ID NO: 81, 82, and 83, respectively; and the light-chain variable region domain comprises LCDR1, LCDR2, and LCDR3, wherein the LCDR1, LCDR2, and LCDR3 comprise the amino acid sequence of SEQ ID NO: 84, 85, and 86, respectively;

vi) the heavy-chain variable region domain comprises HCDR1, HCDR2, and HCDR3, wherein the HCDR1, HCDR2, and HCDR3 comprise the amino acid sequence of SEQ ID NO: 101, 102, and 103, respectively; and the light-chain variable region domain comprises LCDR1, LCDR2, and LCDR3, wherein the LCDR1, LCDR2, and LCDR3 comprise the amino acid sequence of SEQ ID NO: 104, 105, and 106, respectively;

vii) the heavy-chain variable region domain comprises HCDR1, HCDR2, and HCDR3, wherein the HCDR1, HCDR2, and HCDR3 comprise the amino acid sequence of SEQ ID NO: 121, 122, and 123, respectively; and the light-chain variable region domain comprises LCDR1, LCDR2, and LCDR3, wherein the LCDR1, LCDR2, and LCDR3 comprise the amino acid sequence of SEQ ID NO: 124, 125, and 126, respectively;

viii) the heavy-chain variable region domain comprises HCDR1, HCDR2, and HCDR3, wherein the HCDR1, HCDR2, and HCDR3 comprise the amino acid sequence of SEQ ID NO: 141, 142, and 143, respectively; and the light-chain variable region domain comprises LCDR1, LCDR2, and LCDR3, wherein the LCDR1, LCDR2, and LCDR3 comprise the amino acid sequence of SEQ ID NO: 144, 145, and 146, respectively;

ix) the heavy-chain variable region domain comprises HCDR1, HCDR2, and HCDR3, wherein the HCDR1, HCDR2, and HCDR3 comprise the amino acid sequence of SEQ ID NO: 161, 162, and 163, respectively; and the light-chain variable region domain comprises LCDR1, LCDR2, and LCDR3, wherein the LCDR1, LCDR2, and LCDR3 comprise the amino acid sequence of SEQ ID NO: 164, 165, and 166, respectively;

x) the heavy-chain variable region domain comprises HCDR1, HCDR2, and HCDR3, wherein the HCDR1, HCDR2, and HCDR3 comprise the amino acid sequence of SEQ ID NO: 181, 182, and 183, respectively; and the light-chain variable region domain comprises LCDR1, LCDR2, and LCDR3, wherein the LCDR1, LCDR2, and LCDR3 comprise the amino acid sequence of SEQ ID NO: 184, 185, and 186, respectively; or xi) the heavy-chain variable region domain comprises HCDR1, HCDR2, and HCDR3, wherein the HCDR1, HCDR2, and HCDR3 comprise the amino acid sequence of SEQ ID NO: 201, 202, and 203, respectively; and the light-chain variable region domain comprises LCDR1, LCDR2, and LCDR3, wherein the LCDR1, LCDR2, and LCDR3 comprise the amino acid sequence of SEQ ID NO: 204, 205, and 206, respectively.

In an embodiment of the present disclosure, the anti-CD30 antibody or the antigen binding fragment thereof comprises a heavy chain variable region domain and a light chain variable region domain, wherein:

i) the heavy-chain variable region domain comprises the amino acid sequence of SEQ ID NO: 7; and the light-chain variable region domain comprises the amino acid sequence of SEQ ID NO: 8;

ii) the heavy-chain variable region domain comprises the amino acid sequence of SEQ ID NO: 27; and the light-chain variable region domain comprises the amino acid sequence of SEQ ID NO: 28;

iii) the heavy-chain variable region domain comprises the amino acid sequence of SEQ ID NO: 47; and the light-chain variable region domain comprises the amino acid sequence of SEQ ID NO: 48;

iv) the heavy-chain variable region domain comprises the amino acid sequence of SEQ ID NO: 67; and the light-chain variable region domain comprises the amino acid sequence of SEQ ID NO: 68;

v) the heavy-chain variable region domain comprises the amino acid sequence of SEQ ID NO: 87; and the light-chain variable region domain comprises the amino acid sequence of SEQ ID NO: 88;

vi) the heavy-chain variable region domain comprises the amino acid sequence of SEQ ID NO: 107; and the light-chain variable region domain comprises the amino acid sequence of SEQ ID NO: 108;

vii) the heavy-chain variable region domain comprises the amino acid sequence of SEQ ID NO: 127; and the light-chain variable region domain comprises the amino acid sequence of SEQ ID NO: 128;

viii) the heavy-chain variable region domain comprises the amino acid sequence of SEQ ID NO: 147; and the light-chain variable region domain comprises the amino acid sequence of SEQ ID NO: 148;

ix) the heavy-chain variable region domain comprises the amino acid sequence of SEQ ID NO: 167; and the light-chain variable region domain comprises the amino acid sequence of SEQ ID NO: 168;

x) the heavy-chain variable region domain comprises the amino acid sequence of SEQ ID NO: 187; and the light-chain variable region domain comprises the amino acid sequence of SEQ ID NO: 188; or xi) the heavy-chain variable region domain comprises the amino acid sequence of SEQ ID NO: 207; and the light-chain variable region domain comprises the amino acid sequence of SEQ ID NO: 208.

As used herein, the term "chimeric antigen receptor (CAR)" refers to an artificially constructed hybrid protein or polypeptide in which an antigen-binding domain (e.g., single-chain variable fragment (scFv)) of an antibody is linked to a T-cell signaling or T-cell activating domain. Taking advantage of the antigen-binding function of a monoclonal antibody, chimeric antigen receptors give T cells the new ability to retarget a specific protein in a non-MHC-restricted manner.

Non-MHC-restricted antigen recognition provides CAR-expressing T cells with an ability to recognize irrespective of antigen processing, thus avoiding main tumor escape mechanisms. In addition, when expressed in T cells, CAR does advantageously not dimerize with intrinsic T-cell receptor (TCR) alpha and beta chains.

The chimeric antigen receptor of the present disclosure comprises an extracellular domain containing an antibody induced against CD30, known as a B lymphocyte antigen, or against an antigen-binding fragment thereof. In the present disclosure, the antibody induced against CD30 or an anti-gen-binding fragment thereof is as defined above for the anti-CD30 antibody or the antigen-binding fragment thereof.

In an embodiment of the present disclosure, the anti-CD30 antibody or the antigen binding fragment thereof comprises scFv, wherein the scFv comprises an amino acid sequence selected from the group consisting of the amino acid sequence of SEQ ID NO: 9, the amino acid sequence of SEQ ID NO: 29, the amino acid sequence of SEQ ID NO: 49, the amino acid sequence of SEQ ID NO: 69, the amino acid sequence of SEQ ID NO: 89, the amino acid sequence of SEQ ID NO: 109, the amino acid sequence of SEQ ID NO: 129, the amino acid sequence of SEQ ID NO: 149, the amino acid sequence of SEQ ID NO: 169, the amino acid sequence of SEQ ID NO: 189, and the amino acid sequence of SEQ ID NO: 209.

In an embodiment of the present disclosure, the CD30-specific chimeric antigen receptor comprises scFv CAR, wherein the scFv CAR comprises an amino acid sequence selected from the group consisting of the amino acid sequence of SEQ ID NO:10, the amino acid sequence of SEQ ID NO: 30, the amino acid sequence of SEQ ID NO: 50, the amino acid sequence of SEQ ID NO: 70, the amino acid sequence of SEQ ID NO: 90, the amino acid sequence of SEQ ID NO: 110, the amino acid sequence of SEQ ID NO: 130, the amino acid sequence of SEQ ID NO: 150, the amino acid sequence of SEQ ID NO: 170, the amino acid sequence of SEQ ID NO: 190, and the amino acid sequence of SEQ ID NO: 210.

According to an embodiment of the present disclosure, the intracellular signaling domain includes functional sig-naling of 4-1BB, CD28, OX40, CD3 zeta, or a combination thereof.

According to an embodiment of the present disclosure, the chimeric antigen receptor of the present disclosure is expressed on cell surfaces. Hence, the chimeric antigen receptor may comprise a transmembrane domain. The trans-membrane domain may be derived from natural or synthetic sources known in the art. By way of example, the trans-membrane domain may be a transmembrane domain of the protein selected from the group consisting of alpha, beta, or zeta chains of T-cell receptor, CD27, CD28, CD3 epsilon, CD45, CD4, CD5, CD8 (CD8α, CD8β, CD8γ), CD9, CD16, CD22, CD33, CD37, CD64, CD80, CD86, CD134, CD137, and CD154 (CD154α, CD154β, CD154ζ), but is not limited thereto.

The term "intracellular signaling domain", as used herein, refers to a functional protein domain that produces a $2^{nd}$ messenger or functions as an effector in response to the $2^{nd}$ messenger to intracellularly transfer information so as to regulate cellular activity via a defined signaling pathway.

According to another embodiment of the present disclo-sure, the chimeric antigen receptor of the present disclosure may comprise an intracellular signaling domain. The intra-cellular signaling domain is responsible for intracellular signaling following the binding of extracellular ligand bind-ing domain to the target (e.g., CD30) resulting in the activation of the immune cell and immune response. In other words, the signal transducing domain is responsible for the activation of at least one of the normal effector functions of the immune cell in which the chimeric antigen receptor is expressed. For example, the effector function of a T cell can be a cytolytic activity or helper activity including the secretion of cytokines. Preferred examples of signal trans-ducing domain for use in a chimeric antigen receptor can be the cytoplasmic sequences of the T cell receptor and co-receptors that act in concert to initiate signal transduction following antigen receptor engagement, as well as any derivate or variant of these sequences and any synthetic sequence that has the same functional capability.

According to an exemplary embodiment, the intracellular signaling domain of the chimeric antigen receptor is a domain derived from CD3ζ (CD3 zeta) chain.

According to another exemplary embodiment of the pres-ent disclosure, the intracellular signaling domain of chimeric antigen receptor further comprises at least one intracellular (cytoplasmic) region of a costimulatory molecule selected from the group consisting of OX40 (CD134), CD2, CD27, CD28, CDS, ICAM-1, LFA-1 (CD11a/CD18), and 4-1BB (CD137). The intracellular signaling domain may be obtained or derived from an intracellular signaling molecule and may include an entirety or a part of the molecule from which the intracellular signaling domain is derived, as well as the domain described above.

According to an exemplary embodiment of the present disclosure, the costimulatory molecule (domain) comprises a functional signaling domain obtained from a protein selected from the group consisting of CD28, OX40, 4-1BB (CD137), and/or ICOS (CD278) and, more particularly, a functional signaling domain of CD28 and/or OX40.

According to another embodiment of the present disclo-sure, the intracellular signaling domain comprises a func-tional signaling domain of 4-1BB, CD28, OX40, CD3 zeta, or a combination thereof. Most particularly, the intracellular signaling domain is a functional signaling domain of CD3 zeta.

The transmembrane domain and intracellular signaling domain in the chimeric antigen receptor of the present disclosure may be at least one combination selected from among the transmembrane domains and intracellular signal-ing domains described above. For example, the chimeric antigen receptor of the present disclosure may comprise the CD8a transmembrane domain and the intracellular signaling domains of CD28 and CD3ζ.

Another aspect of the present disclosure provides a nucleic acid molecule encoding the chimeric antigen recep-tor described above.

The above-mentioned anti-CD30 antibody or the antigen-binding fragment (polypeptide) thereof, the nucleic acid molecule coding therefor, the chimeric antigen receptor comprising the anti-CD30 antibody or the antigen-binding fragment thereof, and the nucleic acid molecule coding for the chimeric antigen receptor are each in an isolated state.

As used herein, the term "isolated" means altered or removed from the natural/native state. For example, a nucleic acid or a peptide naturally present in a living animal is not "isolated", but the same nucleic acid or peptide partially or completely separated from the coexisting mate-rials of its natural state is "isolated". An isolated nucleic acid or protein can exist in substantially purified form, or can exist in a non-native environment such as, for example, a host cell.

According to another aspect thereof, the present disclo-sure provides a recombinant vector carrying the above-mentioned nucleic acid molecule. For the "vector" to be described hereinafter, the antibody or the antigen-binding fragment thereof, or the nucleic acid molecule encoding a chimeric antigen receptor are commonly applied.

The term "vector" is intended to encompass a transfer vector and an expression vector.

As used herein, the term "transfer vector" refers to a composition of matter which comprises an isolated nucleic acid and which can be used to deliver the isolated nucleic acid into the interior of a cell. Examples of the transfer vector include, but are not limited to, linear polynucleotides, polynucleotides associated with ionic or amphiphilic compounds, plasmids, and viruses. More particularly, the transfer vector includes an autonomously replicating plasmid or virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adeno-viral vectors, adeno-associated virus vectors, retroviral vectors, lentiviral vectors, and the like.

The term "expression vector", as used herein, refers to a vector comprising a recombinant polynucleotide comprising expression control sequences operatively linked to a nucleotide sequence to be expressed in a host cell. An expression vector comprises sufficient cis-acting elements for expression; other elements for expression can be supplied by the host cell or in an in vitro expression system. Expression vectors include plasmids; cosmids; and viruses, such as bacteriophages, adenoviruses, lentiviruses, retroviruses, and adeno-associated viruses, which all incorporate the recombinant polynucleotide. According to an exemplary embodiment of the present disclosure, a nucleic acid molecule coding for the antibody or antigen-binding fragment, or the chimeric antigen receptor is operatively linked to a promoter in the vector of the present disclosure. As used herein, the term "operatively linked" means a functional linkage between a regulatory sequence for nucleic acid expression (example: a promoter, a signal sequence, or array of positions to which transcriptional factors bind) and other nucleic acid sequences, and by which the regulatory sequences are able to control the transcription and/or translation of the other nucleic acid sequence.

The recombinant vector system of the present disclosure can be constructed using various methods known in the art. With respect to concrete methods, reference may be made to Sambrook et al., Molecular Cloning, A Laboratory Manual, Cold Spring Harbor Laboratory Press (2001), which is incorporated herein by reference.

The vector of the present disclosure may be constructed as a vector for gene cloning, for protein expression, or for gene transfer. Also, the vectors of the present disclosure may be constructed for eukaryotic or prokaryotic cells serving as host cells.

For example, when the present vector is an expression vector in a eukaryotic cell, promoters derived from genomes of mammalian cells (e.g., a metallothionein promoter, β-actin promoter, human hemoglobin promoter and human muscle creatinine promoter) or promoters derived from mammalian viruses (e.g., an adenovirus late promoter, a vaccinia virus 7.5K promoter, SV40 promoter, cytomegalo-virus promoter, a tk promoter of HSV, a promoter of mouse mammary tumor virus (MMTV), a LTR promoter of HIV, a promoter of moloney virus, a promoter of Epstein Barr Virus (EBV), a promoter of Rous Sarcoma Virus (RSV)) may be use. Generally, the vectors include a polyadenylate sequence as a transcriptional termination sequence.

According to an embodiment of the present disclosure, when used as a transfer vector, the vector may be "retroviral vector". Retroviruses provide a convenient platform for gene delivery systems. A selected gene can be inserted into a vector and packaged in retroviral particles. The recombinant virus can then be delivered to cells of the subject either in vivo or in vitro. A number of retroviral systems are known in the art. In some exemplary embodiments, the retroviral vector may be a pMT retroviral vector, which is an MLV-based retroviral vector, but is not limited thereto.

According to an embodiment of the present disclosure, the vector may be a lentivirus vector or an adenovirus vector.

The recombinant vector of the present disclosure may be fused with additional nucleotide sequences to facilitate the isolation and purification of the polypeptide expressed from the vector. The nucleotide sequences to be fused with the present vector include, for example, glutathione S-transferase (Pharmacia, USA), maltose binding protein (NEB, USA), FLAG (IBI, USA) and 6×His (hexahistidine; Qiagen, USA) and the like. The expression vector of the present disclosure may also comprise a selectable marker gene and/or a reporter gene as a selection marker for evaluating the expression of the antibody or the antigen-binding fragment and the CAR polypeptide containing the antibody. The selectable marker gene may be an antibiotic resistant gene typically used in the art, examples of which include genes resistant to ampicillin, gentamicin, carbenicillin, chloramphenicol, streptomycin, kanamycin, geneticin, neomycin, and tetracycline. The reporter gene may be exemplified by luciferase, beta-galactosidase, chloramphenicol acetyl transferase, and green fluorescent protein genes.

Methods of introducing and expressing genes into a cell are known in the art. In the context of an expression vector, the vector can be readily introduced into a host cell, e.g., mammalian, bacterial, yeast, or insect cell by any method known in the art. For example, the expression vector can be transferred into a host cell by physical, chemical, or biological means. The physical means include calcium phosphate precipitation, lipofection, particle bombardment, microinjection, electroporation, and the like. The chemical means include colloidal dispersion systems, such as macromolecule complexes, nanocapsules, microspheres, beads, and lipid-based systems including oil-in-water emulsions, micelles, mixed micelles, and liposomes. Within the biological means are the use of DNA or RNA vectors such as lentivirus, retrovirus, and the like.

According to an aspect thereof, the present disclosure provides an effector cell expressing the chimeric antigen receptor.

In one embodiment of the present disclosure, the effector cell refers to a cell of hematopoietic origin functionally involved in the initiation and/or execution of an innate and/or adaptive immune response.

The immune cell according to the present disclosure may be derived from a stem cell. The stem cells may be adult stem cell, non-human embryonic stem cells, cord blood stem cells, bone marrow stem cells, induced pluripotent stem cells, or hematopoietic stem cells. More particularly, the immune cells may be selected from the group consisting of dendritic cells, killer dendritic cells, mast cells, NK-cells, B-cells or inflammatory T-lymphocytes, cytotoxic T-lymphocytes, regulatory T-lymphocytes, and helper T-lymphocytes, but are not limited thereto.

The effector cells include a population of autologous or allogeneic cells. In other words, the effector cells include a population of autologous or allogeneic cells expressing CAR specific for CD30.

According to an embodiment of the present disclosure, the effector cells include a population of cells transduced or transfected with a vector carrying a nucleic acid molecular coding for a CD30-specific CAR. The transfection or transduction can be achieved by various means known in the art as described above, without limitations.

Hence, according to an exemplary embodiment of the present disclosure, after being delivered into the effector cells, e.g., T lymphocytes or natural killer cells, the nucleic acid molecule coding for the CD30-specific CAR is transcribed into mRNA from which a CD30-specific CAR polypeptide is then translated, and expressed on the cell surface.

Also, another aspect of the present disclosure provides a pharmaceutical composition comprising the anti-CD30 antibody of the present disclosure or an antigen-binding fragment thereof or a pharmaceutical composition comprising a cell expressing the chimeric antigen receptor of the present disclosure.

The pharmaceutical composition may be provided in the form of a pharmaceutical composition comprising: the anti-CD30 antibody of the present disclosure or an antigen-binding fragment thereof or the chimeric antigen receptor-expressing cell; and a pharmaceutically acceptable carrier.

When administered in the form of a pharmaceutical composition, the cell expressing the chimeric antigen receptor of the present disclosure may be a cell derived from an animal allogenic to the subject, or a cell autologous cell.

The pharmaceutical composition of the present disclosure may comprise a population of cells expressing the chimeric antigen receptor of the present disclosure.

The pharmaceutical composition of the present disclosure comprises the anti-CD30 antibody of the present disclosure or an antigen-binding fragment thereof or the chimeric antigen receptor-expressing cell as an effective ingredient. Accordingly, the common descriptions between them are omitted in order to avoid undue redundancy leading to the complexity of this specification.

As will be proven in the following Example, when the chimeric antigen receptor T cells containing the CD30 antibody fragment of the present disclosure and a CD30 antigen-expressing cell line are co-cultured, the CD30 antigen on the surface of the CD30-positive cell line is recognized to induce the activation of the chimeric antigen receptor. Thus, the pharmaceutical composition of the present disclosure is expected to find advantageous applications in the treatment of CD30 antigen-related diseases.

The pharmaceutically acceptable carrier contained in the pharmaceutical composition of the present disclosure is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present disclosure may further comprise a lubricant, a wetting agent, a sweetening agent, a flavoring agent, an emulsifier, a suspending agent, a preservative, and the like in addition to the above ingredients. Suitable pharmaceutically acceptable carriers and preparations are described in detail in Remington's Pharmaceutical Sciences (19th ed., 1995).

The pharmaceutical composition of the present disclosure may be administered orally or parenterally, for example, by intravenous injection, subcutaneous injection, intramuscular injection, intraperitoneal injection, intrasternal injection, intratumoral injection, topical administration, intranasal administration, intrapulmonary administration, and rectal administration.

The appropriate dose of the pharmaceutical composition of the present disclosure varies depending on factors, such as a formulating method, a manner of administration, patient's age, body weight, gender, and morbidity, food, a time of administration, a route of administration, an excretion rate, and response sensitivity. An ordinarily skilled practitioner can easily determine and prescribe an effective dose for desired treatment or prevention. According to a preferable embodiment of the present disclosure, the daily dose of the pharmaceutical composition of the present disclosure is 0.0001-100 mg/kg. As used herein, the term "pharmaceutically effective amount" refers to an amount sufficient to prevent or treat the above-described diseases.

As used herein, the term "prevention" refers to a prophylactic or protective treatment of a disease or a disease condition. As used herein, the term "treatment" refers to a reduction, suppression, relief, or eradication of a disease condition.

The pharmaceutical composition of the present disclosure may be formulated into a unit dosage form or may be prepared in a multi-dose container by using a pharmaceutically acceptable carrier and/or excipient according to a method that can be easily implemented by a person having an ordinary skill in the art to which the present disclosure pertains. Here, the formulation may be in the form of a solution in an oily or aqueous medium, a suspension, an emulsion, an extract, a pulvis, a suppository, a powder, a granule, a tablet, or a capsule, and may further contain a dispersant or a stabilizer.

The pharmaceutical composition of the present disclosure may further comprise other pharmaceutically active agents or drugs, for example, chemotherapeutic agents such as asparaginase, busulfane, carboplatin, cisplatin, daunorubicin, doxorubicin, fluorouracil, gemcitabine, hydroxyurea, methotrexate, paclitaxel, rituximab, vinblastine, vincristine, and the like; targeted therapeutic agents such as bevacizumab, olaparib, and the like; or immune checkpoint inhibitors such as nivolumab, pembrolizumab, and the like, in addition to the above-described chimeric antigen receptor-expressing cells, or may be administered in combination therewith.

According to another aspect thereof, the present disclosure provides a method for prevention or treatment of a CD30-expressing cell-associated disease, the method comprising a step of administering to a subject in need thereof a composition comprising an anti-CD30 antibody or an antigen-binding fragment thereof; or a composition comprising a cell expressing the chimeric antigen receptor.

Accordingly, human antibodies of the present invention can be used to treat and/or prevent a variety of CD30 mediated diseases by administering the anti-CD30 antibody or the effector cell harboring the chimeric antigen receptor to patients suffering from various CD30-mediated diseases. Exemplary diseases that can be treated (e.g., ameliorated) or prevented include, but are not limited to, tumorigenic diseases and autoimmune diseases. Examples of tumorigenic diseases which can be treated and/or prevented include B cell malignancy selected from the group consisting of chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin's lymphoma, diffuse large B cell lymphoma (DLBCL), anaplastic large-cell lymphoma, multiple myeloma, follicular lymphoma, splenic lymphoma, marginal zone lymphoma, mantle cell lymphoma, indolent B cell lymphoma, and Hodgkin lymphoma, Hodgkin's disease, anaplastic large cell lymphoma (ALCL), adult T-cell lymphoma (ATL), angioimmunoblastic lymphadenopathy (AILD)-like T cell lymphoma, peripheral T-cell lymphoma, cutaneous T-cell lymphoma (CTCL), NK/T cell lymphoma, HIV associated body cavity-based lymphomas, embryonal carcinomas, undifferentiated carcinomas of the rhino-pharynx (e.g., Schmincke's tumor), Castleman's disease, Kaposi's Sarcoma and other T-cell or B-cell lymphomas. Germ cell tumor may also be included. Examples of autoimmune diseases which can be treated and/or prevented include rheumatoid arthritis, systemic lupus erythematosus, systemic sclerosis, atopic dermatitis, Graves' disease, Hashimoto's thyroiditis, Wegner's granulomatosis, Omen's syndrome, chronic renal failure, acute infectious mononucleosis, HIV and herpes virus associated diseases.

In an embodiment of the present invention, the subject is a mammalian animal or a human.

Since the method for the prevention or treatment of cancer or inflammatory disease according to the present disclosure employs the above-described antibody or antigen-binding fragment; or the chimeric antigen receptor-expressing effector cell as an effective ingredient, the overlapping descriptions thereof are omitted to avoid undue complexity of the specification.

Features and advantages of the present disclosure are summarized as follows:

(a) The present disclosure provides an anti-CD30 antibody or an antigen-binding fragment thereof.

(b) The present disclosure provides a nucleic acid molecule encoding an anti-CD30 antibody or an antigen-binding fragment thereof.

(c) The present disclosure provides a CD30-specific chimeric antigen receptor comprising: an anti-CD30 antibody or an antigen-binding fragment thereof; a transmembrane domain; and intracellular signaling domain.

(d) The antibody of the present disclosure binds specifically to CD30 that is highly expressed in cancer cells (particularly, blood cancer) and has very low CDR sequence homology to conventional CD30 target antibodies. Thus, the antibody of the present disclosure has a characteristic sequence. Inducing immune cell activation in response to stimulation with CD30-positive cells, cells expressing the chimeric antigen receptor containing the anti-CD30 antibody or the antigen-binding fragment (e.g., scFv) of the present disclosure can be advantageously used as a CAR-immune cell therapy product.

Information about the amino acid and nucleotide sequences used in this specification is provided below.

| SEQ ID NO: | Type | Name | Sequence |
|---|---|---|---|
| 1 | Protein | CDRH1 of anti CD30 antibody (T1-2) | GYGMS |
| 2 | Protein | CDRH2 of anti CD30 antibody (T1-2) | YISGYSYYTYYADSVKG |
| 3 | Protein | CDRH3 of anti CD30 antibody (T1-2) | YDGNGFDY |
| 4 | Protein | CDRL1 of anti CD30 antibody (T1-2) | SGSSSNIGSNYVY |
| 5 | Protein | CDRL2 of anti CD30 antibody (T1-2) | RNNQRPS |
| 6 | Protein | CDRL3 of anti CD30 antibody (T1-2) | AADSSDDS |
| 7 | Protein | Heavy chain variable domain of anti CD30 antibody (T1-2) | EVQLLESGGGLVQPGGSLRLSCAASGFTFSGYGMSWVR QAPGKGLEWVSYISGYSYYTYYADSVKGRFTFSRDNSKN TLYLQMNSLRAEDTAVYYCARYDGNGFDYWGQGTLVTV SS |
| 8 | Protein | Light chain variable domain of anti CD30 antibody (T1-2) | QSVLTQPPSASGTPGQRVTISCSGSSSNIGSNYVYWYQQ LPGTAPKLLIYRNNQRPSGVPDRFSGSKSGTSASLAISGL RSEDEADYYCAADSSDDSYVFGGGTKLTVLG |
| 9 | Protein | scFv of anti CD30 antibody (T1-2) | EVQLLESGGGLVQPGGSLRLSCAASGFTFSGYGMSWVR QAPGKGLEWVSYISGYSYYTYYADSVKGRFTFSRDNSKN TLYLQMNSLRAEDTAVYYCARYDGNGFDYWGQGTLVTV SSGGGGSGGGGSGGGGSQSVLTQPPSASGTPGQRVTI SCSGSSSNIGSNYVYWYQQLPGTAPKLLIYRNNQRPSGV PDRFSGSKSGTSASLAISGLRSEDEADYYCAADSSDDSY VFGGGTKLTVLG |
| 10 | Protein | scFv CAR of anti CD30 antibody (T1-2) | EVQLLESGGGLVQPGGSLRLSCAASGFTFSGYGMSWVR QAPGKGLEWVSYISGYSYYTYYADSVKGRFTFSRDNSKN TLYLQMNSLRAEDTAVYYCARYDGNGFDYWGQGTLVTV SSGGGGSGGGGSGGGGSQSVLTQPPSASGTPGQRVTI SCSGSSSNIGSNYVYWYQQLPGTAPKLLIYRNNQRPSGV PDRFSGSKSGTSASLAISGLRSEDEADYYCAADSSDDSY VFGGGTKLTVLGGQAGQTTTPAPRPPTPAPTIASQPLSLR PEACRPAAGGAVHTRGLDFACDIYIWAPLAGTCGVLLLSL VITLYCKRGRKKLLYIFKQPFMRPVQTTQEEDGCSCRFPE EEEGGCELRVKFSRSADAPAYQQGQNQLYNELNLGRRE EYDVLDKRRGRDPEMGGKPRRKNPQEGLYNELQKDKM AEAYSEIGMKGERRRGKGHDGLYQGLSTATKDTYDALH MQALPPR |

-continued

| SEQ ID NO: | Type | Name | Sequence |
|---|---|---|---|
| 11 | DNA | Nucleotide sequence for encoding CDRH1 of anti CD30 antibody (T1-2) | GGTTATGGTATGAGC |
| 12 | DNA | Nucleotide sequence for encoding CDRH2 of anti CD30 antibody (T1-2) | TACATCTCTGGTTACTCTTACTACACGTATTACGCTGAT TCTGTAAAAGGT |
| 13 | DNA | Nucleotide sequence for encoding CDRH3 of anti CD30 antibody (T1-2) | TACGACGGTAACGGTTTCGACTAC |
| 14 | DNA | Nucleotide sequence for encoding CDRL1 of anti CD30 antibody (T1-2) | AGTGGCTCTTCATCTAATATTGGCTCTAATTATGTCTAC |
| 15 | DNA | Nucleotide sequence for encoding CDRL2 of anti CD30 antibody (T1-2) | AGAAATAACCAGCGGCCAAGC |
| 16 | DNA | Nucleotide sequence for encoding CDRL3 of anti CD30 antibody (T1-2) | GCTGCTGACTCTTCTGACGACTCT |
| 17 | DNA | Nucleotide sequence for encoding heavy chain variable domain of anti CD30 antibody (T1-2) | GAGGTGCAGCTGTTGGAGTCTGGGGGAGGCTTGGTAC AGCCTGGGGGGTCCCTGAGACTCTCCTGTGCAGCCTC TGGATTCACCTTTAGCGGTTATGGTATGAGCTGGGTCC GCCAGGCTCCAGGGAAGGGGCTGGAGTGGGTCTCAT ACATCTCTGGTTACTCTTACTACACGTATTACGCTGATT CTGTAAAAGGTCGGTTCACCTTCTCCAGAGACAATTCC AAGAACACGCTGTATCTGCAAATGAACAGCCTGAGAGC CGAGGACACGGCCGTGTATTACTGTGCGCGTTACGAC GGTAACGGTTTCGACTACTGGGGCCAGGGTACACTGG TCACCGTGAGCTCA |
| 18 | DNA | Nucleotide sequence for encoding light chain variable domain of anti CD30 antibody (T1-2) | CAGTCTGTGCTGACTCAGCCACCCTCAGCGTCTGGGA CCCCCGGGCAGAGGGTCACCATCTCTTGTAGTGGCTC TTCATCTAATATTGGCTCTAATTATGTCTACTGGTACCA GCAGCTCCCAGGAACGGCCCCCAAACTCCTCATCTAT AGAAATAACCAGCGGCCAAGCGGGGTCCCTGACCGAT TCTCTGGCTCCAAGTCTGGCACCTCAGCCTCCCTGGC CATCAGTGGGCTCCGGTCCGAGGATGAGGCCGATTAT TACTGTGCTGCTGACTCTTCTGACGACTCTTATGTCTTC GGCGGAGGCACCAAGCTGACGGTCCTAGGT |
| 19 | DNA | Nucleotide sequence for encoding scFv of anti CD30 antibody (T1-2) | GAGGTGCAGCTGTTGGAGTCTGGGGGAGGCTTGGTAC AGCCTGGGGGGTCCCTGAGACTCTCCTGTGCAGCCTC TGGATTCACCTTTAGCGGTTATGGTATGAGCTGGGTCC GCCAGGCTCCAGGGAAGGGGCTGGAGTGGGTCTCAT ACATCTCTGGTTACTCTTACTACACGTATTACGCTGATT CTGTAAAAGGTCGGTTCACCTTCTCCAGAGACAATTCC AAGAACACGCTGTATCTGCAAATGAACAGCCTGAGAGC CGAGGACACGGCCGTGTATTACTGTGCGCGTTACGAC GGTAACGGTTTCGACTACTGGGGCCAGGGTACACTGG TCACCGTGAGCTCAGGTGGAGGCGGTTCAGGCGGAG GTGGATCCGGCGGTGGCGGATCGCAGTCTGTGCTGAC TCAGCCACCCTCAGCGTCTGGGACCCCCGGGCAGAG GGTCACCATCTCTTGTAGTGGCTCTTCATCTAATATTG GCTCTAATTATGTCTACTGGTACCAGCAGCTCCCAGGA ACGGCCCCCAAACTCCTCATCTATAGAAATAACCAGCG GCCAAGCGGGGTCCCTGACCGATTCTCTGGCTCCAAG TCTGGCACCTCAGCCTCCCTGGCCATCAGTGGGCTCC GGTCCGAGGATGAGGCCGATTATTACTGTGCTGCTGA CTCTTCTGACGACTCTTATGTCTTCGGCGGAGGCACCA AGCTGACGGTCCTAGGT |
| 20 | DNA | Nucleotide sequence for encoding scFv CAR of anti CD30 antibody | GAGGTGCAGCTGTTGGAGTCTGGGGGAGGCTTGGTAC AGCCTGGGGGGTCCCTGAGACTCTCCTGTGCAGCCTC TGGATTCACCTTTAGCGGTTATGGTATGAGCTGGGTCC GCCAGGCTCCAGGGAAGGGGCTGGAGTGGGTCTCAT |

-continued

| SEQ ID NO: | Type | Name | Sequence |
|---|---|---|---|
| | | (T1-2) | ACATCTCTGGTTACTCTTACTACACGTATTACGCTGATT<br>CTGTAAAAGGTCGGTTCACCTTCTCCAGAGACAATTCC<br>AAGAACACGCTGTATCTGCAAATGAACAGCCTGAGAGC<br>CGAGGACACGGCCGTGTATTACTGTGCGCGTTACGAC<br>GGTAACGGTTTCGACTACTGGGGCCAGGGTACACTGG<br>TCACCGTGAGCTCAGGTGGAGGCGGTTCAGGCGGAG<br>GTGGATCCGGCGGTGGCGGATCGCAGTCTGTGCTGAC<br>TCAGCCACCCTCAGCGTCTGGGACCCCCGGGCAGAG<br>GGTCACCATCTCTTGTAGTGGCTCTTCATCTAATATTG<br>GCTCTAATTATGTCTACTGGTACCAGCAGCTCCCAGGA<br>ACGGCCCCCAAACTCCTCATCTATAGAAATAACCAGCG<br>GCCAAGCGGGGTCCCTGACCGATTCTCTGGCTCCAAG<br>TCTGGCACCTCAGCCTCCCTGGCCATCAGTGGGCTCC<br>GGTCCGAGGATGAGGCCGATTATTACTGTGCTGCTGA<br>CTCTTCTGACGACTCTTATGTCTTCGGCGGAGGCACCA<br>AGCTGACGGTCCTAGGTGGCCAGGCCGGCCAGACAA<br>CGACACCTGCTCCCAGACCGCCTACTCCCGCCCCAAC<br>CATTGCATCTCAGCCACTCTCTCTGAGACCCGAAGCGT<br>GTAGACCTGCGGCCGGGGGCGCTGTCCACACAAGAG<br>GCTTAGACTTCGCCTGCGATATCTATATCTGGGCCCCA<br>CTCGCAGGCACTTGTGGAGTGCTGCTGCTTTCACTCGT<br>GATAACCCTGTACTGCAAAAGGGGGAGAAAGAAGCTG<br>CTGTATATTTTTAAACAACCATTTATGAGACCTGTTCAG<br>ACTACCCAGGAAGAAGACGGTTGTAGTTGCAGATTCCC<br>CGAGGAGGAAGAAGGAGGTTGCGAGTTGAGAGTAAAG<br>TTCAGCAGATCCGCAGATGCCCCTGCTTACCAGCAGG<br>GTCAAAACCAGCTTTACAACGAGCTGAATTTAGGTAGA<br>AGAGAGGAATATGACGTGTTGGATAAAAGAAGAGGAA<br>GAGACCCGGAAATGGGCGGCAAGCCTCGAAGAAAAAA<br>TCCCCAAGAGGGACTCTACAATGAGCTGCAGAAGGAC<br>AAAATGGCTGAAGCCTACAGCGAGATCGGCATGAAGG<br>GAGAAAGACGCAGAGGGAAAGGGCATGATGGGCTTTA<br>TCAGGGCTTGTCCACCGCTACAAAGGATACTTATGACG<br>CACTACACATGCAGGCCCTGCCACCCCGT |
| 21 | Protein | CDRH1 of anti CD30 antibody (T1-7) | GYGMS |
| 22 | Protein | CDRH2 of anti CD30 antibody (T1-7) | YISSGSYYTYYADSVKG |
| 23 | Protein | CDRH3 of anti CD30 antibody (T1-7) | YRGDNDYYGYFDY |
| 24 | Protein | CDRL1 of anti CD30 antibody (T1-7) | SCSSSNIGNNAVS |
| 25 | Protein | CDRL2 of anti CD30 antibody (T1-7) | RNNQRPS |
| 26 | Protein | CDRL3 of anti CD30 antibody (T1-7) | AADYGSD |
| 27 | Protein | Heavy chain variable domain of anti CD30 antibody (T1-7) | EVQLLESGGGLVQPGGSLRLSCAASGFTFSGYGMSWVR<br>QAPGKGLEWVSYISSGSYYTYYADSVKGRFTISRDNSKN<br>TLYLQMNSLRAEDTAVYYCARYRGDNDYYGYFDYWGQG<br>TLVTVSS |
| 28 | Protein | Light chain variable domain of anti CD30 antibody (T1-7) | QSVLTQPPSASGTPGQRVTISCSCSSSNIGNNAVSWYQQ<br>LPGTAPKLLIYRNNQRPSGVPDRFSGSKSGTSASLAISGL<br>RSEDEADYYCAADYGSDYVFGGGTKLTVLG |
| 29 | Protein | scFv of anti CD30 antibody (T1-7) | EVQLLESGGGLVQPGGSLRLSCAASGFTFSGYGMSWVR<br>QAPGKGLEWVSYISSGSYYTYYADSVKGRFTISRDNSKN<br>TLYLQMNSLRAEDTAVYYCARYRGDNDYYGYFDYWGQG<br>TLVTVSSGGGGSGGGGSGGGGSQSVLTQPPSASGTPG<br>QRVTISCSCSSSNIGNNAVSWYQQLPGTAPKLLIYRNNQ<br>RPSGVPDRFSGSKSGTSASLAISGLRSEDEADYYCAADY<br>GSDYVFGGGTKLTVLG |
| 30 | Protein | scFv CAR of anti CD30 antibody (T1-7) | EVQLLESGGGLVQPGGSLRLSCAASGFTFSGYGMSWVR<br>QAPGKGLEWVSYISSGSYYTYYADSVKGRFTISRDNSKN<br>TLYLQMNSLRAEDTAVYYCARYRGDNDYYGYFDYWGQG<br>TLVTVSSGGGGSGGGGSGGGGSQSVLTQPPSASGTPG<br>QRVTISCSCSSSNIGNNAVSWYQQLPGTAPKLLIYRNNQ<br>RPSGVPDRFSGSKSGTSASLAISGLRSEDEADYYCAADY<br>GSDYVFGGGTKLTVLG |

-continued

| SEQ ID NO:Type | Name | Sequence |
|---|---|---|
| | | GQAGQTTTPAPRPPTPAPTIASQPLSLRPEACRPAAGGA<br>VHTRGLDFACDIYIWAPLAGTCGVLLLSLVITLYCKR-<br>GRKK<br>LLYIFKQPFMRPVQTTQEEDGCSCRFPEEEEGGCELRVK<br>FSRSADAPAYQQGQNQLYNELNLGRREEYDVLDKRRGR<br>DPEMGGKPRRKNPQEGLYNELQKDKMAEAYSEIGMKGE<br>RRRGKGHDGLYQGLSTATKDTYDALHMQALPPR |
| 31 DNA | Nucleotide sequence<br>for encoding CDRH1<br>of anti CD30 antibody<br>(T1-7) | GGTTATGGTATGAGC |
| 32 DNA | Nucleotide sequence<br>for encoding CDRH2<br>of anti CD30 antibody<br>(T1-7) | TACATCTCTTCTGGTTCTTACTACACGTATTACGCTGAT<br>TCTGTAAAAGGT |
| 33 DNA | Nucleotide sequence<br>for encoding CDRH3<br>of anti CD30 antibody<br>(T1-7) | TACCGTGGTGACAACGATTACTACGGTTACTTCGACTA<br>C |
| 34 DNA | Nucleotide sequence<br>for encoding CDRL1 of<br>anti CD30 antibody<br>(T1-7) | AGTTGCTCTTCATCTAATATTGGCAATAATGCTGTCTCC |
| 35 DNA | Nucleotide sequence<br>for encoding CDRL2 of<br>anti CD30 antibody<br>(T1-7) | AGAAATAACCAGCGGCCAAGC |
| 36 DNA | Nucleotide sequence<br>for encoding CDRL3 of<br>anti CD30 antibody<br>(T1-7) | GCTGCTGACTACGGTTCTGAC |
| 37 DNA | Nucleotide sequence<br>for encoding heavy<br>chain variable domain<br>of anti CD30 antibody<br>(T1-7) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCGGTTATGGTATGAGCTGGGTCC<br>GCCAGGCTCCAGGGAAGGGGCTGGAGTGGGTCTCAT<br>ACATCTCTTCTGGTTCTTACTACACGTATTACGCTGATT<br>CTGTAAAAGGTCGGTTCACCATCTCCAGAGACAATTCC<br>AAGAACACGCTGTATCTGCAAATGAACAGCCTGAGAGC<br>CGAGGACACGGCCGTGTATTACTGTGCGCGTTACCGT<br>GGTGACAACGATTACTACGGTTACTTCGACTACTGGGG<br>CCAGGGTACACTGGTCACCGTGAGCTCA |
| 38 DNA | Nucleotide sequence<br>for encoding light<br>chain variable domain<br>of anti CD30 antibody<br>(T1-7) | CAGTCTGTGCTGACTCAGCCACCCTCAGCGTCTGGGA<br>CCCCCGGGCAGAGGGTCACCATCTCTTGTAGTTGCTC<br>TTCATCTAATATTGGCAATAATGCTGTCTCCTGGTACCA<br>GCAGCTCCCAGGAACGGCCCCCAAACTCCTCATCTAT<br>AGAAATAACCAGCGGCCAAGCGGGGTCCCTGACCGAT<br>TCTCTGGCTCCAAGTCTGGCACCTCAGCCTCCCTGGC<br>CATCAGTGGGCTCCGGTCCGAGGATGAGGCCGATTAT<br>TACTGTGCTGCTGACTACGGTTCTGACTATGTCTTCGG<br>CGGAGGCACCAAGCTGACGGTCCTAGGT |
| 39 DNA | Nucleotide sequence<br>for encoding scFv of<br>anti CD30 antibody<br>(T1-7) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCGGTTATGGTATGAGCTGGGTCC<br>GCCAGGCTCCAGGGAAGGGGCTGGAGTGGGTCTCAT<br>ACATCTCTTCTGGTTCTTACTACACGTATTACGCTGATT<br>CTGTAAAAGGTCGGTTCACCATCTCCAGAGACAATTCC<br>AAGAACACGCTGTATCTGCAAATGAACAGCCTGAGAGC<br>CGAGGACACGGCCGTGTATTACTGTGCGCGTTACCGT<br>GGTGACAACGATTACTACGGTTACTTCGACTACTGGGG<br>CCAGGGTACACTGGTCACCGTGAGCTCAGGTGGAGGC<br>GGTTCAGGCGGAGGTGGATCCGGCGGTGGCGGATCG<br>CAGTCTGTGCTGACTCAGCCACCCTCAGCGTCTGGGA<br>CCCCCGGGCAGAGGGTCACCATCTCTTGTAGTTGCTC<br>TTCATCTAATATTGGCAATAATGCTGTCTCCTGGTACCA<br>GCAGCTCCCAGGAACGGCCCCCAAACTCCTCATCTAT<br>AGAAATAACCAGCGGCCAAGCGGGGTCCCTGACCGAT<br>TCTCTGGCTCCAAGTCTGGCACCTCAGCCTCCCTGGC |

| SEQ ID NO: Type | Name | Sequence |
|---|---|---|
| | | CATCAGTGGGCTCCGGTCCGAGGATGAGGCCGATTAT<br>TACTGTGCTGCTGACTACGGTTCTGACTATGTCTTCGG<br>CGGAGGCACCAAGCTGACGGTCCTAGGT |
| 40  DNA | Nucleotide sequence for encoding scFv CAR of anti CD30 antibody (T1-7) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCGGTTATGGTATGAGCTGGGTCC<br>GCCAGGCTCCAGGGAAGGGGCTGGAGTGGGTCTCAT<br>ACATCTCTTCTGGTTCTTACTACACGTATTACGCTGATT<br>CTGTAAAAGGTCGGTTCACCATCTCCAGAGACAATTCC<br>AAGAACACGCTGTATCTGCAAATGAACAGCCTGAGAGC<br>CGAGGACACGGCCGTGTATTACTGTGCGCGTTACCGT<br>GGTGACAACGATTACTACGGTTACTTCGACTACTGGGG<br>CCAGGGTACACTGGTCACCGTGAGCTCAGGTGGAGGC<br>GGTTCAGGCGGAGGTGGATCCGGCGGTGGCGGATCG<br>CAGTCTGTGCTGACTCAGCCACCCTCAGCGTCTGGGA<br>CCCCCGGGCAGAGGGTCACCATCTCTTGTAGTTGCTC<br>TTCATCTAATATTGGCAATAATGCTGTCTCCTGGTACCA<br>GCAGCTCCCAGGAACGGCCCCCAAACTCCTCATCTAT<br>AGAAATAACCAGCGGCCAAGCGGGGTCCCTGACCGAT<br>TCTCTGGCTCCAAGTCTGGCACCTCAGCCTCCCTGGC<br>CATCAGTGGGCTCCGGTCCGAGGATGAGGCCGATTAT<br>TACTGTGCTGCTGACTACGGTTCTGACTATGTCTTCGG<br>CGGAGGCACCAAGCTGACGGTCCTAGGT<br>GGCCAGGCCGGCCAGACAACGACACCTGCTCCCAGA<br>CCGCCTACTCCCGCCCCAACCATTGCATCTCAGCCACT<br>CTCTCTGAGACCCGAAGCGTGTAGACCTGCGGCCGGG<br>GGCGCTGTCCACACAAGAGGCTTAGACTTCGCCTGCG<br>ATATCTATATCTGGGCCCCACTCGCAGGCACTTGTGGA<br>GTGCTGCTGCTTTCACTCGTGATAACCCTGTACTGCAA<br>AAGGGGGGAGAAAGAAGCTGCTGTATATTTTTAAACAAC<br>CATTTATGAGACCTGTTCAGACTACCCAGGAAGAAGAC<br>GGTTGTAGTTGCAGATTCCCCGAGGAGGAAGAAGGAG<br>GTTGCGAGTTGAGAGTAAAGTTCAGCAGATCCGCAGAT<br>GCCCCTGCTTACCAGCAGGGTCAAAACCAGCTTTACAA<br>CGAGCTGAATTTAGGTAGAAGAGAGGAATATGACGTGT<br>TGGATAAAAGAAGAGGAAGAGACCCGGAAATGGGCGG<br>CAAGCCTCGAAGAAAAAATCCCCAAGAGGGACTCTACA<br>ATGAGCTGCAGAAGGACAAAATGGCTGAAGCCTACAG<br>CGAGATCGGCATGAAGGGAGAAAGACGCAGAGGGAAA<br>GGGCATGATGGGCTTTATCAGGGCTTGTCCACCGCTA<br>CAAAGGATACTTATGACGCACTACACATGCAGGCCCTG<br>CCACCCCGT |
| 41  Protein | CDRH1 of anti CD30 antibody (T1-8) | SYMS |
| 42  Protein | CDRH2 of anti CD30 antibody (T1-8) | SIGSGYYSTYYADSVKG |
| 43  Protein | CDRH3 of anti CD30 antibody (T1-8) | DYYGGFDY |
| 44  Protein | CDRL1 of anti CD30 antibody (T1-8) | SGSSSNIGSNYVY |
| 45  Protein | CDRL2 of anti CD30 antibody (T1-8) | RNNQRPS |
| 46  Protein | CDRL3 of anti CD30 antibody (T1-8) | AAYDSYS |
| 47  Protein | Heavy chain variable domain of anti CD30 antibody (T1-8) | EVQLLESGGGLVQPGGSLRLSCAASGFTFSSYMSWVRQ<br>APGKGLEWVSSIGSGYYSTYYADSVKGRFTISRDNSKNT<br>LYLQMNSLRAEDTAVYYCARDYYGGFDYWGQGTLVTVS<br>S |
| 48  Protein | Light chain variable domain of anti CD30 antibody (T1-8) | QSVLTQPPSASGTPGQRVTISCSGSSSNIGSNYVYWYQQ<br>LPGTAPKLLIYRNNQRPSGVPDRFSGSKSGTSASLAISGL<br>RSEDEADYYCAAYDSYSYVFGGGTKLTVLG |
| 49  Protein | scFv of anti CD30 antibody (T1-8) | EVQLLESGGGLVQPGGSLRLSCAASGFTFSSYMSWVRQ<br>APGKGLEWVSSIGSGYYSTYYADSVKGRFTISRDNSKNT<br>LYLQMNSLRAEDTAVYYCARDYYGGFDYWGQGTLVTVS<br>SGGGGSGGGGSGGGGSQSVLTQPPSASGTPGQRVTIS<br>CSGSSSNIGSNYVYWYQQLPGTAPKLLIYRNNQRPSGVP |

-continued

| SEQ ID NO: | Type | Name | Sequence |
|---|---|---|---|
| | | | DRFSGSKSGTSASLAISGLRSEDEADYYCAAYDSYSYVF |
| | | | GGGTKLTVLG |
| 50 | Protein | scFv CAR of anti CD30 antibody (T1-8) | EVQLLESGGGLVQPGGSLRLSCAASGFTFSSYMSWVRQ |
| | | | APGKGLEWVSSIGSGYYSTYYADSVKGRFTISRDNSKNT |
| | | | LYLQMNSLRAEDTAVYYCARDYYGGFDYWGQGTLVTVS |
| | | | SGGGGSGGGGSGGGGSQSVLTQPPSASGTPGQRVTIS |
| | | | CSGSSSNIGSNYVYWYQQLPGTAPKLLIYRNNQRPSGVP |
| | | | DRFSGSKSGTSASLAISGLRSEDEADYYCAAYDSYSYVF |
| | | | GGGTKLTVLGGQAGQTTTPAPRPPTPAPTIASQPLSLRP |
| | | | EACRPAAGGAVHTRGLDFACDIYIWAPLAGTCGVLLLSLV |
| | | | ITLYCKRGRKKLLYIFKQPFMRPVQTTQEEDGCSCRFPEE |
| | | | EEGGCELRVKFSRSADAPAYQQGQNQLYNELNLGRREE |
| | | | YDVLDKRRGRDPEMGGKPRRKNPQEGLYNELQKDKMA |
| | | | EAYSEIGMKGERRRGKGHDGLYQGLSTATKDTYDALHM |
| | | | QALPPR |
| 51 | DNA | Nucleotide sequence for encoding CDRH1 of anti CD30 antibody (T1-8) | TCTTACATGAGC |
| 52 | DNA | Nucleotide sequence for encoding CDRH2 of anti CD30 antibody (T1-8) | TCTATCGGTTCTGGTTACTACTCTACGTATTACGCTGAT TCTGTAAAAGGT |
| 53 | DNA | Nucleotide sequence for encoding CDRH3 of anti CD30 antibody (T1-8) | GACTACTACGGTGGTTTCGACTAC |
| 54 | DNA | Nucleotide sequence for encoding CDRL1 of anti CD30 antibody (T1-8) | AGTGGCTCTTCATCTAATATTGGCTCTAATTATGTCTAC |
| 55 | DNA | Nucleotide sequence for encoding CDRL2 of anti CD30 antibody (T1-8) | AGAAATAACCAGCGGCCAAGC |
| 56 | DNA | Nucleotide sequence for encoding CDRL3 of anti CD30 antibody (T1-8) | GCTGCTTACGACTCTTACTCT |
| 57 | DNA | Nucleotide sequence for encoding heavy chain variable domain of anti CD30 antibody (T1-8) | GAGGTGCAGCTGTTGGAGTCTGGGGGAGGCTTGGTAC |
| | | | AGCCTGGGGGGTCCCTGAGACTCTCCTGTGCAGCCTC |
| | | | TGGATTCACCTTTAGCTCTTACATGAGCTGGGTCCGCC |
| | | | AGGCTCCAGGGAAGGGGCTGGAGTGGGTCTCATCTAT |
| | | | CGGTTCTGGTTACTACTCTACGTATTACGCTGATTCTGT |
| | | | AAAAGGTCGGTTCACCATCTCCAGAGACAATTCCAAGA |
| | | | ACACGCTGTATCTGCAAATGAACAGCCTGAGAGCCGA |
| | | | GGACACGGCCGTGTATTACTGTGCGCGTGACTACTAC |
| | | | GGTGGTTTCGACTACTGGGGCCAGGGTACACTGGTCA |
| | | | CCGTGAGCTCA |
| 58 | DNA | Nucleotide sequence for encoding light chain variable domain of anti CD30 antibody (T1-8) | CAGTCTGTGCTGACTCAGCCACCCTCAGCGTCTGGGA |
| | | | CCCCCGGGCAGAGGGTCACCATCTCTTGTAGTGGCTC |
| | | | TTCATCTAATATTGGCTCTAATTATGTCTACTGGTACCA |
| | | | GCAGCTCCCAGGAACGGCCCCCAAACTCCTCATCTAT |
| | | | AGAAATAACCAGCGGCCAAGCGGGGTCCCTGACCGAT |
| | | | TCTCTGGCTCCAAGTCTGGCACCTCAGCCTCCCTGGC |
| | | | CATCAGTGGGCTCCGGTCCGAGGATGAGGCCGATTAT |
| | | | TACTGTGCTGCTTACGACTCTTACTCTTATGTCTTCGGC |
| | | | GGAGGCACCAAGCTGACGGTCCTAGGT |
| 59 | DNA | Nucleotide sequence for encoding scFv of anti CD30 antibody (T1-8) | GAGGTGCAGCTGTTGGAGTCTGGGGGAGGCTTGGTAC |
| | | | AGCCTGGGGGGTCCCTGAGACTCTCCTGTGCAGCCTC |
| | | | TGGATTCACCTTTAGCTCTTACATGAGCTGGGTCCGCC |
| | | | AGGCTCCAGGGAAGGGGCTGGAGTGGGTCTCATCTAT |
| | | | CGGTTCTGGTTACTACTCTACGTATTACGCTGATTCTGT |
| | | | AAAAGGTCGGTTCACCATCTCCAGAGACAATTCCAAGA |
| | | | ACACGCTGTATCTGCAAATGAACAGCCTGAGAGCCGA |
| | | | GGACACGGCCGTGTATTACTGTGCGCGTGACTACTAC |
| | | | GGTGGTTTCGACTACTGGGGCCAGGGTACACTGGTCA |

-continued

| SEQ ID NO: | Type | Name | Sequence |
|---|---|---|---|
| | | | CCGTGAGCTCAGGTGGAGGCGGTTCAGGCGGAGGTG GATCCGGCGGTGGCGGATCGCAGTCTGTGCTGACTCA GCCACCCTCAGCGTCTGGGACCCCCGGGCAGAGGGT CACCATCTCTTGTAGTGGCTCTTCATCTAATATTGGCTC TAATTATGTCTACTGGTACCAGCAGCTCCCAGGAACGG CCCCCAAACTCCTCATCTATAGAAATAACCAGCGGCCA AGCGGGGTCCCTGACCGATTCTCTGGCTCCAAGTCTG GCACCTCAGCCTCCCTGGCCATCAGTGGGCTCCGGTC CGAGGATGAGGCCGATTATTACTGTGCTGCTTACGACT CTTACTCTTATGTCTTCGGCGGAGGCACCAAGCTGACG GTCCTAGGT |
| 60 | DNA | Nucleotide sequence for encoding scFv CAR of anti CD30 antibody (T1-8) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTCTTACATGAGCTGGGTCCGCC AGGCTCCAGGGAAGGGGCTGGAGTGGGTCTCATCTAT CGGTTCTGGTTACTACTCTACGTATTACGCTGATTCTGT AAAAGGTCGGTTCACCATCTCCAGAGACAATTCCAAGA ACACGCTGTATCTGCAAATGAACAGCCTGAGAGCCGA GGACACGGCCGTGTATTACTGTGCGCGTGACTACTAC GGTGGTTTCGACTACTGGGGCCAGGGTACACTGGTCA CCGTGAGCTCAGGTGGAGGCGGTTCAGGCGGAGGTG GATCCGGCGGTGGCGGATCGCAGTCTGTGCTGACTCA GCCACCCTCAGCGTCTGGGACCCCCGGGCAGAGGGT CACCATCTCTTGTAGTGGCTCTTCATCTAATATTGGCTC TAATTATGTCTACTGGTACCAGCAGCTCCCAGGAACGG CCCCCAAACTCCTCATCTATAGAAATAACCAGCGGCCA AGCGGGGTCCCTGACCGATTCTCTGGCTCCAAGTCTG GCACCTCAGCCTCCCTGGCCATCAGTGGGCTCCGGTC CGAGGATGAGGCCGATTATTACTGTGCTGCTTACGACT CTTACTCTTATGTCTTCGGCGGAGGCACCAAGCTGACG GTCCTAGGTGGCCAGGCCGGCCAGACAACGACACCTG CTCCCAGACCGCCTACTCCCGCCCCAACCATTGCATCT CAGCCACTCTCTCTGAGACCCGAAGCGTGTAGACCTG CGGCCGGGGGCGCTGTCCACACAAGAGGCTTAGACTT CGCCTGCGATATCTATATCTGGGCCCCACTCGCAGGC ACTTGTGGAGTGCTGCTGCTTTCACTCGTGATAACCCT GTACTGCAAAAGGGGGAGAAAGAAGCTGCTGTATATTT TTAAACAACCATTTATGAGACCTGTTCAGACTACCCAG GAAGAAGACGGTTGTAGTTGCAGATTCCCCGAGGAGG AAGAAGGAGGTTGCGAGTTGAGAGTAAAGTTCAGCAG ATCCGCAGATGCCCCTGCTTACCAGCAGGGTCAAAAC CAGCTTTACAACGAGCTGAATTTAGGTAGAAGAGAGGA ATATGACGTGTTGGATAAAAGAGAGGAAGAGACCCG GAAATGGGCGGCAAGCCTCGAAGAAAAAATCCCCAAG AGGGACTCTACAATGAGCTGCAGAAGGACAAAATGGC TGAAGCCTACAGCGAGATCGGCATGAAGGGAGAAAGA CGCAGAGGGAAAGGGCATGATGGGCTTTATCAGGGCT TGTCCACCGCTACAAAGGATACTTATGACGCACTACAC ATGCAGGCCCTGCCACCCCGT |
| 61 | Protein | CDRH1 of anti CD30 antibody (T1-9) | YYGMS |
| 62 | Protein | CDRH2 of anti CD30 antibody (T1-9) | GIGSYSSYTYYADSVKG |
| 63 | Protein | CDRH3 of anti CD30 antibody (T1-9) | YASSPDAYFDY |
| 64 | Protein | CDRL1 of anti CD30 antibody (T1-9) | SGSSSNIGSNYVY |
| 65 | Protein | CDRL2 of anti CD30 antibody (T1-9) | RNNQRPS |
| 66 | Protein | CDRL3 of anti CD30 antibody (T1-9) | AAYYNYN |
| 67 | Protein | Heavy chain variable domain of anti CD30 antibody (T1-9) | EVQLLESGGGLVQPGGSLRLSCAASGFTFSYYGMSWVR QAPGKGLEWVSGIGSYSSYTYYADSVKGRFTISRDNSKN TLYLQMNSLRAEDTAVYYCARYASSPDAYFDYWGQGTL VTVSS |

-continued

| SEQ ID NO: | Type | Name | Sequence |
|---|---|---|---|
| 68 | Protein | Light chain variable domain of anti CD30 antibody (T1-9) | QSVLTQPPSASGTPGQRVTISCSGSSSNIGSNYVYWYQQ LPGTAPKLLIYRNNQRPSGVPGRFSGSKSGTSASLAISGL RSEDEADYYCAAYYNYNYVFGGGTKLTVLG |
| 69 | Protein | scFv of anti CD30 antibody (T1-9) | EVQLLESGGGLVQPGGSLRLSCAASGFTFSYYGMSWVR QAPGKGLEWVSGIGSYSSYTYYADSVKGRFTISRDNSKN TLYLQMNSLRAEDTAVYYCARYASSPDAYFDYWGQGTL VTVSSGGGGSGGGGSGGGGSQSVLTQPPSASGTPGQR VTISCSGSSSNIGSNYVYWYQQLPGTAPKLLIYRNNQRPS GVPGRFSGSKSGTSASLAISGLRSEDEADYYCAAYYNYN YVFGGGTKLTVLG |
| 70 | Protein | scFv CAR of anti CD30 antibody (T1-9) | EVQLLESGGGLVQPGGSLRLSCAASGFTFSYYGMSWVR QAPGKGLEWVSGIGSYSSYTYYADSVKGRFTISRDNSKN TLYLQMNSLRAEDTAVYYCARYASSPDAYFDYWGQGTL VTVSSGGGGSGGGGSGGGGSQSVLTQPPSASGTPGQR VTISCSGSSSNIGSNYVYWYQQLPGTAPKLLIYRNNQRPS GVPGRFSGSKSGTSASLAISGLRSEDEADYYCAAYYNYN YVFGGGTKLTVLGGGQAGQTTTPAPRPPTPAPTIASQPLSL RPEACRPAAGGAVHTRGLDFACDIYIWAPLAGTCGVLLLS LVITLYCKRGRKKLLYIFKQPFMRPVQTTQEEDGCSCRFP EEEEGGCELRVKFSRSADAPAYQQGQNQLYNELNLGRR EEYDVLDKRRGRDPEMGGKPRRKNPQEGLYNELQKDK MAEAYSEIGMKGERRRGKGHDGLYQGLSTATKDTYDAL HMQALPPR |
| 71 | DNA | Nucleotide sequence for encoding CDRH1 of anti CD30 antibody (T1-9) | TACTATGGTATGAGC |
| 72 | DNA | Nucleotide sequence for encoding CDRH2 of anti CD30 antibody (T1-9) | GGTATCGGTTCTTACTCTTCTTACACGTATTACGCTGAT TCTGTAAAAGGT |
| 73 | DNA | Nucleotide sequence for encoding CDRH3 of anti CD30 antibody (T1-9) | TACGCTTCTTCTCCGGACGCTTACTTCGACTAC |
| 74 | DNA | Nucleotide sequence for encoding CDRL1 of anti CD30 antibody (T1-9) | AGTGGCTCTTCATCTAATATTGGCTCTAATTATGTCTAC |
| 75 | DNA | Nucleotide sequence for encoding CDRL2 of anti CD30 antibody (T1-9) | AGAAATAACCAGCGGCCAAGC |
| 76 | DNA | Nucleotide sequence for encoding CDRL3 of anti CD30 antibody (T1-9) | GCTGCTTACTACAACTACAAC |
| 77 | DNA | Nucleotide sequence for encoding heavy chain variable domain of anti CD30 antibody (T1-9) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTACTATGGTATGAGCTGGGTCC GCCAGGCTCCAGGGAAGGGGCTGGAGTGGGTCTCAG GTATCGGTTCTTACTCTTCTTACACGTATTACGCTGATT CTGTAAAAGGTCGGTTCAC1ATCTCCAGAGACAATTCC AAGAACACGCTGTATCTGCAAATGAACAGCCTGAGAGC CGAGGACACGGCCGTGTATTACTGTGCGCGTTACGCT TCTTCTCCGGACGCTTACTTCGACTACTGGGGCCAGG GTACACTGGTCACCGTGAGCTCA |
| 78 | DNA | Nucleotide sequence for encoding light chain variable domain of anti CD30 antibody (T1-9) | CAGTCTGTGCTGACTCAGCCACCCTCAGCGTCTGGGA CCCCCGGGCAGAGGGTCACCATCTCTTGTAGTGGCTC TTCATCTAATATTGGCTCTAATTATGTCTACTGGTACCA GCAGCTCCCAGGAACGGCCCCCAAACTCCTCATCTAT AGAAATAACCAGCGGCCAAGCGGGGTCCCTGGCCGAT TCTCTGGCTCCAAGTCTGGCACCTCAGCCTCCCTGGC CATCAGTGGGCTCCGGTCCGAGGATGAGGCCGATTAT TACTGTGCTGCTTACTACAACTACAACTATGTCTTCGG CGGAGGCACCAAGCTGACGGTCCTAGGT |

| SEQ ID NO: | Type | Name | Sequence |
|---|---|---|---|
| 79 | DNA | Nucleotide sequence for encoding scFv of anti CD30 antibody (T1-9) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCTACTATGGTATGAGCTGGGTCC<br>GCCAGGCTCCAGGGAAGGGGCTGGAGTGGGTCTCAG<br>GTATCGGTTCTTACTCTTCTTACACGTATTACGCTGATT<br>CTGTAAAAGGTCGGTTCACCATCTCCAGAGACAATTCC<br>AAGAACACGCTGTATCTGCAAATGAACAGCCTGAGAGC<br>CGAGGACACGGCCGTGTATTACTGTGCGCGTTACGCT<br>TCTTCTCCGGACGCTTACTTCGACTACTGGGGCCAGG<br>GTACACTGGTCACCGTGAGCTCAGGTGGAGGCGGTTC<br>AGGCGGAGGTGGATCCGGCGGTGGCGGATCGCAGTC<br>TGTGCTGACTCAGCCACCCTCAGCGTCTGGGACCCCC<br>GGGCAGAGGGTCACCATCTCTTGTAGTGGCTCTTCATC<br>TAATATTGGCTCTAATTATGTCTACTGGTACCAGCAGCT<br>CCCAGGAACGGCCCCCAAACTCCTCATCTATAGAAATA<br>ACCAGCGGCCAAGCGGGGTCCCTGGCCGATTCTCTGG<br>CTCCAAGTCTGGCACCTCAGCCTCCCTGGCCATCAGT<br>GGGCTCCGGTCCGAGGATGAGGCCGATTATTACTGTG<br>CTGCTTACTACAACTACAACTATGTCTTCGGCGGAGGC<br>ACCAAGCTGACGGTCCTAGGT |
| 80 | DNA | Nucleotide sequence for encoding scFv CAR of anti CD30 antibody (T1-9) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCTACTATGGTATGAGCTGGGTCC<br>GCCAGGCTCCAGGGAAGGGGCTGGAGTGGGTCTCAG<br>GTATCGGTTCTTACTCTTCTTACACGTATTACGCTGATT<br>CTGTAAAAGGTCGGTTCACCATCTCCAGAGACAATTCC<br>AAGAACACGCTGTATCTGCAAATGAACAGCCTGAGAGC<br>CGAGGACACGGCCGTGTATTACTGTGCGCGTTACGCT<br>TCTTCTCCGGACGCTTACTTCGACTACTGGGGCCAGG<br>GTACACTGGTCACCGTGAGCTCAGGTGGAGGCGGTTC<br>AGGCGGAGGTGGATCCGGCGGTGGCGGATCGCAGTC<br>TGTGCTGACTCAGCCACCCTCAGCGTCTGGGACCCCC<br>GGGCAGAGGGTCACCATCTCTTGTAGTGGCTCTTCATC<br>TAATATTGGCTCTAATTATGTCTACTGGTACCAGCAGCT<br>CCCAGGAACGGCCCCCAAACTCCTCATCTATAGAAATA<br>ACCAGCGGCCAAGCGGGGTCCCTGGCCGATTCTCTGG<br>CTCCAAGTCTGGCACCTCAGCCTCCCTGGCCATCAGT<br>GGGCTCCGGTCCGAGGATGAGGCCGATTATTACTGTG<br>CTGCTTACTACAACTACAACTATGTCTTCGGCGGAGGC<br>ACCAAGCTGACGGTCCTAGGTGGCCAGGCCGGCCAG<br>ACAACGACACCTGCTCCCAGACCGCCTACTCCCGCCC<br>CAACCATTGCATCTCAGCCACTCTCTCTGAGACCCGAA<br>GCGTGTAGACCTGCGGCCGGGGGCGCTGTCCACACA<br>AGAGGCTTAGACTTCGCCTGCGATATCTATATCTGGGC<br>CCCACTCGCAGGCACTTGTGGAGTGCTGCTGCTTTCA<br>CTCGTGATAACCCTGTACTGCAAAAGGGGGAGAAAGA<br>AGCTGCTGTATATTTTTAAACAACCATTTATGAGACCTG<br>TTCAGACTACCCAGGAAGAAGACGGTTGTAGTTGCAGA<br>TTCCCCGAGGAGGAAGAAGGAGGTTGCGAGTTGAGAG<br>TAAAGTTCAGCAGATCCGCAGATGCCCCTGCTTACCAG<br>CAGGGTCAAAACCAGCTTTACAACGAGCTGAATTTAGG<br>TAGAAGAGAGGAATATGACGTGTTGGATAAAAGAAGAG<br>GAAGAGACCCGGAAATGGGGGGCAAGCCTCGAAGAAA<br>AAATCCCCAAGAGGGACTCTACAATGAGCTGCAGAAG<br>GACAAAATGGCTGAAGCCTACAGCGAGATCGGCATGA<br>AGGGAGAAAGACGCAGAGGGAAAGGGCATGATGGGC<br>TTTATCAGGGCTTGTCCACCGCTACAAAGGATACTTAT<br>GACGCACTACACATGCAGGCCCTGCCACCCCGT |
| 81 | Protein | CDRH1 of anti CD30 antibody (T1-10) | SYGMS |
| 82 | Protein | CDRH2 of anti CD30 antibody (T1-10) | YISGGSYYTYYADSVKG |
| 83 | Protein | CDRH3 of anti CD30 antibody (T1-10) | YGYGYYDGSFDY |
| 84 | Protein | CDRL1 of anti CD30 antibody (T1-10) | SGSSSNIGSNYVY |
| 85 | Protein | CDRL2 of anti CD30 antibody (T1-10) | RNNQRPS |

-continued

| SEQ ID NO: | Type | Name | Sequence |
|---|---|---|---|
| 86 | Protein | CDRL3 of anti CD30 antibody (T1-10) | AADGPYN |
| 87 | Protein | Heavy chain variable domain of anti CD30 antibody (T1-10) | EVQLLESGGGLVQPGGSLRLSCAASGFTFSSYGMSWVR QAPGKGLEWVSYISGGSYYTYYADSVKGRFTISRDNSKN TLYLQMNSLRAEDTAVYYCARYGYGYYDGSFDYWGQGT LVTVSS |
| 88 | Protein | Light chain variable domain of anti CD30 antibody (T1-10) | QSVLTQPPSASGTPGQRVTISCSGSSSNIGSNYVYWYQQ LPGTAPKLLIYRNNQRPSGVPDRFSGSKSGTSASLAISGL RSEDEADYYCAADGPYNYVFGGGTKLTVLG |
| 89 | Protein | scFv of anti CD30 antibody (T1-10) | EVQLLESGGGLVQPGGSLRLSCAASGFTFSSYGMSWVR QAPGKGLEWVSYISGGSYYTYYADSVKGRFTISRDNSKN TLYLQMNSLRAEDTAVYYCARYGYGYYDGSFDYWGQGT LVTVSSGGGGSGGGGSGGGGSQSVLTQPPSASGTPGQ RVTISCSGSSSNIGSNYVYWYQQLPGTAPKLLIYRNNQRP SGVPDRFSGSKSGTSASLAISGLRSEDEADYYCAADGPY NYVFGGGTKLTVLG |
| 90 | Protein | scFv CAR of anti CD30 antibody (T1-10) | EVQLLESGGGLVQPGGSLRLSCAASGFTFSSYGMSWVR QAPGKGLEWVSYISGGSYYTYYADSVKGRFTISRDNSKN TLYLQMNSLRAEDTAVYYCARYGYGYYDGSFDYWGQGT LVTVSSGGGGSGGGGSGGGGSQSVLTQPPSASGTPGQ RVTISCSGSSSNIGSNYVYWYQQLPGTAPKLLIYRNNQRP SGVPDRFSGSKSGTSASLAISGLRSEDEADYYCAADGPY NYVFGGGTKLTVLGGQAGQTTTPAPRPPTPAPTIASQPL SLRPEACRPAAGGAVHTRGLDFACDIYIWAPLAGTCGVLL LSLVITLYCKRGRKKLLYIFKQPFMRPVQTTQEEDGCSCR FPEEEEGGCELRVKFSRSADAPAYQQGQNQLYNELNLG RREEYDVLDKRRGRDPEMGGKPRRKNPQEGLYNELQK DKMAEAYSEIGMKGERRRGKGHDGLYQGLSTATKDTYD ALHMQALPPR |
| 91 | DNA | Nucleotide sequence for encoding CDRH1 of anti CD30 antibody (T1-10) | TCTTATGGTATGAGC |
| 92 | DNA | Nucleotide sequence for encoding CDRH2 of anti CD30 antibody (T1-10) | TACATCTCTGGTGGTTCTTACTACACGTATTACGCTGAT TCTGTAAAAGGT |
| 93 | DNA | Nucleotide sequence for encoding CDRH3 of anti CD30 antibody (T1-10) | TACGGTTACGGTTACTACGACGGTTCTTTCGACTAC |
| 94 | DNA | Nucleotide sequence for encoding CDRL1 of anti CD30 antibody (T1-10) | AGTGGCTCTTCATCTAATATTGGCTCTAATTATGTCTAC |
| 95 | DNA | Nucleotide sequence for encoding CDRL2 of anti CD30 antibody (T1-10) | AGAAATAACCAGCGGCCAAGC |
| 96 | DNA | Nucleotide sequence for encoding CDRL3 of anti CD30 antibody (T1-10) | GCTGCTGACGGTCCGTACAAC |
| 97 | DNA | Nucleotide sequence for encoding heavy chain variable domain of anti CD30 antibody (T1-10) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTCTTATGGTATGAGCTGGGTCC GCCAGGCTCCAGGGAAGGGGCTGGAGTGGGTCTCAT ACATCTCTGGTGGTTCTTACTACACGTATTACGCTGATT CTGTAAAAGGTCGGTTCACCATCTCCAGAGACAATTCC AAGAACACGCTGTATCTGCAAATGAACAGCCTGAGAGC CGAGGACACGGCCGTGTATTACTGTGCGCGTTACGGT TACGGTTACTACGACGGTTCTTTCGACTACTGGGGCCA GGGTACACTGGTCACCGTGAGCTCA |
| 98 | DNA | Nucleotide sequence for encoding light | CAGTCTGTGCTGACTCAGCCACCCTCAGCGTCTGGGA CCCCCGGGCAGAGGGTCACCATCTCTTGTAGTGGCTC |

-continued

| SEQ ID NO:Type | | Name | Sequence |
|---|---|---|---|
| | | chain variable domain of anti CD30 antibody (T1-10) | TTCATCTAATATTGGCTCTAATTATGTCTACTGGTACCA GCAGCTCCCAGGAACGGCCCCCAAACTCCTCATCTAT AGAAATAACCAGCGGCCAAGCGGGGTCCCTGACCGAT TCTCTGGCTCCAAGTCTGGCACCTCAGCCTCCCTGGC CATCAGTGGGCTCCGGTCCGAGGATGAGGCCGATTAT TACTGTGCTGCTGACGGTCCGTACAACTATGTCTTCGG CGGAGGCACCAAGCTGACGGTCCTAGGT |
| 99 | DNA | Nucleotide sequence for encoding scFv of anti CD30 antibody (T1-10) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTCTTATGGTATGAGCTGGGTCC GCCAGGCTCCAGGGAAGGGGCTGGAGTGGGTCTCAT ACATCTCTGGTGGTTCTTACTACACGTATTACGCTGATT CTGTAAAAGGTCGGTTCACCATCTCCAGAGACAATTCC AAGAACACGCTGTATCTGCAAATGAACAGCCTGAGAGC CGAGGACACGGCCGTGTATTACTGTGCGCGTTACGGT TACGGTTACTACGACGGTTCTTTCGACTACTGGGGCCA GGGTACACTGGTCACCGTGAGCTCAGGTGGAGGCGGT TCAGGCGGAGGTGGATCCGGCGGTGGCGGATCGCAG TCTGTGCTGACTCAGCCACCCTCAGCGTCTGGGACCC CCGGGCAGAGGGTCACCATCTCTTGTAGTGGCTCTTC ATCTAATATTGGCTCTAATTATGTCTACTGGTACCAGCA GCTCCCAGGAACGGCCCCCAAACTCCTCATCTATAGAA ATAACCAGCGGCCAAGCGGGGTCCCTGACCGATTCTC TGGCTCCAAGTCTGGCACCTCAGCCTCCCTGGCCATC AGTGGGCTCCGGTCCGAGGATGAGGCCGATTATTACT GTGCTGCTGACGGTCCGTACAACTATGTCTTCGGCGG AGGCACCAAGCTGACGGTCCTAGGT |
| 100 | DNA | Nucleotide sequence for encoding scFv CAR of anti CD30 antibody (T1-10) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTCTTATGGTATGAGCTGGGTCC GCCAGGCTCCAGGGAAGGGGCTGGAGTGGGTCTCAT ACATCTCTGGTGGTTCTTACTACACGTATTACGCTGATT CTGTAAAAGGTCGGTTCACCATCTCCAGAGACAATTCC AAGAACACGCTGTATCTGCAAATGAACAGCCTGAGAGC CGAGGACACGGCCGTGTATTACTGTGCGCGTTACGGT TACGGTTACTACGACGGTTCTTTCGACTACTGGGGCCA GGGTACACTGGTCACCGTGAGCTCAGGTGGAGGCGGT TCAGGCGGAGGTGGATCCGGCGGTGGCGGATCGCAG TCTGTGCTGACTCAGCCACCCTCAGCGTCTGGGACCC CCGGGCAGAGGGTCACCATCTCTTGTAGTGGCTCTTC ATCTAATATTGGCTCTAATTATGTCTACTGGTACCAGCA GCTCCCAGGAACGGCCCCCAAACTCCTCATCTATAGAA ATAACCAGCGGCCAAGCGGGGTCCCTGACCGATTCTC TGGCTCCAAGTCTGGCACCTCAGCCTCCCTGGCCATC AGTGGGCTCCGGTCCGAGGATGAGGCCGATTATTACT GTGCTGCTGACGGTCCGTACAACTATGTCTTCGGCGG AGGCACCAAGCTGACGGTCCTAGGTGGCCAGGCCGG CCAGACAACGACACCTGCTCCCAGACCGCCTACTCCC GCCCCAACCATTGCATCTCAGCCACTCTCTCTGAGACC CGAAGCGTGTAGACCTGCGGCCGGGGGCGCTGTCCA CACAAGAGGCTTAGACTTCGCCTGCGATATCTATATCT GGGCCCCACTCGCAGGCACTTGTGGAGTGCTGCTGCT TTCACTCGTGATAACCCTGTACTGCAAAAGGGGGAGAA AGAAGCTGCTGTATATTTTTAAACAACCATTTATGAGAC CTGTTCAGACTACCCAGGAAGAAGACGGTTGTAGTTGC AGATTCCCCGAGGAGGAAGAAGGAGGTTGCGAGTTGA GAGTAAAGTTCAGCAGATCCGCAGATGCCCCTGCTTAC CAGCAGGGTCAAAACCAGCTTTACAACGAGCTGAATTT AGGTAGAAGAGAGGAATATGACGTGTTGGATAAAAGAA GAGGAAGAGACCCGGAAATGGGGGGCAAGCCTCGAA GAAAAAATCCCCAAGAGGGACTCTACAATGAGCTGCA GAAGGACAAAATGGCTGAAGCCTACAGCGAGATCGGC ATGAAGGGAGAAAGACGCAGAGGGAAAGGGCATGATG GGCTTTATCAGGGCTTGTCCACCGCTACAAAGGATACT TATGACGCACTACACATGCAGGCCCTGCCACCCCGT |
| 101 | Protein | CDRH1 of anti CD30 antibody (T1-23) | SYSMS |
| 102 | Protein | CDRH2 of anti CD30 antibody (T1-23) | GIGYPYYTYYADSVKG |
| 103 | Protein | CDRH3 of anti CD30 antibody (T1-23) | YYYDYGFDY |

-continued

| SEQ ID NO: | Type | Name | Sequence |
|---|---|---|---|
| 104 | Protein | CDRL1 of anti CD30 antibody (T1-23) | SGSSSNIGSNYVY |
| 105 | Protein | CDRL2 of anti CD30 antibody (T1-23) | RNNQRPS |
| 106 | Protein | CDRL3 of anti CD30 antibody (T1-23) | AAYRSYD |
| 107 | Protein | Heavy chain variable domain of anti CD30 antibody (T1-23) | EVQLLESGGGLVQPGGSLRLSCAASGFTFSSYSMSWVR QAPGKGLEWVSGIGYPYYTYYADSVKGRFTISRDNSKNT LYLQMNSLRAEDTAVYYCARYYYDYGFDYWGQGTLVTV SS |
| 108 | Protein | Light chain variable domain of anti CD30 antibody (T1-23) | QSVLTQPPSASGTPGQRVTISCSGSSSNIGSNYVYWYQQ LPGTAPKLLIYRNNQRPSGVPDRFSGSKSGTSASLAISGL RSEDEADYYCAAYRSYDYVFGGGTKLTVLG |
| 109 | Protein | scFv of anti CD30 antibody (T1-23) | EVQLLESGGGLVQPGGSLRLSCAASGFTFSSYSMSWVR QAPGKGLEWVSGIGYPYYTYYADSVKGRFTISRDNSKNT LYLQMNSLRAEDTAVYYCARYYYDYGFDYWGQGTLVTV SSGGGGSGGGGSGGGGSQSVLTQPPSASGTPGQRVTI SCSGSSSNIGSNYVYWYQQLPGTAPKLLIYRNNQRPSGV PDRFSGSKSGTSASLAISGLRSEDEADYYCAAYRSYDYV FGGGTKLTVLG |
| 110 | Protein | scFv CAR of anti CD30 antibody (T1-23) | EVQLLESGGGLVQPGGSLRLSCAASGFTFSSYSMSWVR QAPGKGLEWVSGIGYPYYTYYADSVKGRFTISRDNSKNT LYLQMNSLRAEDTAVYYCARYYYDYGFDYWGQGTLVTV SSGGGGSGGGGSGGGGSQSVLTQPPSASGTPGQRVTI SCSGSSSNIGSNYVYWYQQLPGTAPKLLIYRNNQRPSGV PDRFSGSKSGTSASLAISGLRSEDEADYYCAAYRSYDYV FGGGTKLTVLGGQAGQTTTPAPRPPTPAPTIASQPLSLRP EACRPAAGGAVHTRGLDFACDIYIWAPLAGTCGVLLLSLV ITLYCKRGRKKLLYIFKQPFMRPVQTTQEEDGCSCRFPEE EEGGCELRVKFSRSADAPAYQQGQNQLYNELNLGRREE YDVLDKRRGRDPEMGGKPRRKNPQEGLYNELQKDKMA EAYSEIGMKGERRRGKGHDGLYQGLSTATKDTYDALHM QALPPR |
| 111 | DNA | Nucleotide sequence for encoding CDRH1 of anti CD30 antibody (T1-23) | TCTTATTCTATGAGC |
| 112 | DNA | Nucleotide sequence for encoding CDRH2 of anti CD30 antibody (T1-23) | GGTATCGGTTACCCTTACTACACGTATTACGCTGATTC TGTAAAAGGT |
| 113 | DNA | Nucleotide sequence for encoding CDRH3 of anti CD30 antibody (T1-23) | TACTACTACGACTACGGTTTCGACTAC |
| 114 | DNA | Nucleotide sequence for encoding CDRL1 of anti CD30 antibody (T1-23) | AGTGGCTCTTCATCTAATATTGGCTCTAATTATGTCTAC |
| 115 | DNA | Nucleotide sequence for encoding CDRL2 of anti CD30 antibody (T1-23) | AGAAATAACCAGCGGCCAAGC |
| 116 | DNA | Nucleotide sequence for encoding CDRL3 of anti CD30 antibody (T1-23) | GCTGCTTACCGTTCTTACGAC |
| 117 | DNA | Nucleotide sequence for encoding heavy chain variable domain of anti CD30 antibody (T1-23) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTCTTATTCTATGAGCTGGGTCC GCCAGGCTCCAGGGAAGGGGCTGGAGTGGGTCTCAG GTATCGGTTACCCTTACTACACGTATTACGCTGATTCT GTAAAAGGTCGGTTCACCATCTCCAGAGACAATTCCAA |

-continued

| SEQ ID NO: | Type | Name | Sequence |
|---|---|---|---|
| | | | GAACACGCTGTATCTGCAAATGAACAGCCTGAGAGCC<br>GAGGACACGGCCGTGTATTACTGTGCGCGTTACTACTA<br>CGACTACGGTTTCGACTACTGGGGCCAGGGTACACTG<br>GTCACCGTGAGCTCA |
| 118 | DNA | Nucleotide sequence<br>for encoding light<br>chain variable domain<br>of anti CD30<br>antibody (T1-23) | CAGTCTGTGCTGACTCAGCCACCCTCAGCGTCTGGGA<br>CCCCCGGGCAGAGGGTCACCATCTCTTGTAGTGGCTC<br>TTCATCTAATATTGGCTCTAATTATGTCTACTGGTACCA<br>GCAGCTCCCAGGAACGGCCCCCAAACTCCTCATCTAT<br>AGAAATAACCAGCGGCCAAGCGGGGTCCCTGACCGAT<br>TCTCTGGCTCCAAGTCTGGCACCTCAGCCTCCCTGGC<br>CATCAGTGGGCTCCGGTCCGAGGATGAGGCCGATTAT<br>TACTGTGCTGCTTACCGTTCTTACGACTATGTCTTCGG<br>CGGAGGCACCAAGCTGACGGTCCTAGGT |
| 119 | DNA | Nucleotide sequence<br>for encoding scFv of<br>anti CD30 antibody<br>(T1-23) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCTCTTATTCTATGAGCTGGGTCC<br>GCCAGGCTCCAGGGAAGGGGCTGGAGTGGGTCTCAG<br>GTATCGGTTACCCTTACTACACGTATTACGCTGATTCT<br>GTAAAAGGTCGGTTCACCATCTCCAGAGACAATTCCAA<br>GAACACGCTGTATCTGCAAATGAACAGCCTGAGAGCC<br>GAGGACACGGCCGTGTATTACTGTGCGCGTTACTACTA<br>CGACTACGGTTTCGACTACTGGGGCCAGGGTACACTG<br>GTCACCGTGAGCTCAGGTGGAGGCGGTTCAGGCGGA<br>GGTGGATCCGGCGGTGGCGGATCGCAGTCTGTGCTG<br>ACTCAGCCACCCTCAGCGTCTGGGACCCCCGGGCAGA<br>GGGTCACCATCTCTTGTAGTGGCTCTTCATCTAATATT<br>GGCTCTAATTATGTCTACTGGTACCAGCAGCTCCCAGG<br>AACGGCCCCCAAACTCCTCATCTATAGAAATAACCAGC<br>GGCCAAGCGGGGTCCCTGACCGATTCTCTGGCTCCAA<br>GTCTGGCACCTCAGCCTCCCTGGCCATCAGTGGGCTC<br>CGGTCCGAGGATGAGGCCGATTATTACTGTGCTGCTTA<br>CCGTTCTTACGACTATGTCTTCGGCGGAGGCACCAAG<br>CTGACGGTCCTAGGT |
| 120 | DNA | Nucleotide sequence<br>for encoding scFv<br>CAR of anti CD30<br>antibody<br>(T1-23) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCTCTTATTCTATGAGCTGGGTCC<br>GCCAGGCTCCAGGGAAGGGGCTGGAGTGGGTCTCAG<br>GTATCGGTTACCCTTACTACACGTATTACGCTGATTCT<br>GTAAAAGGTCGGTTCACCATCTCCAGAGACAATTCCAA<br>GAACACGCTGTATCTGCAAATGAACAGCCTGAGAGCC<br>GAGGACACGGCCGTGTATTACTGTGCGCGTTACTACTA<br>CGACTACGGTTTCGACTACTGGGGCCAGGGTACACTG<br>GTCACCGTGAGCTCAGGTGGAGGCGGTTCAGGCGGA<br>GGTGGATCCGGCGGTGGCGGATCGCAGTCTGTGCTG<br>ACTCAGCCACCCTCAGCGTCTGGGACCCCCGGGCAGA<br>GGGTCACCATCTCTTGTAGTGGCTCTTCATCTAATATT<br>GGCTCTAATTATGTCTACTGGTACCAGCAGCTCCCAGG<br>AACGGCCCCCAAACTCCTCATCTATAGAAATAACCAGC<br>GGCCAAGCGGGGTCCCTGACCGATTCTCTGGCTCCAA<br>GTCTGGCACCTCAGCCTCCCTGGCCATCAGTGGGCTC<br>CGGTCCGAGGATGAGGCCGATTATTACTGTGCTGCTTA<br>CCGTTCTTACGACTATGTCTTCGGCGGAGGCACCAAG<br>CTGACGGTCCTAGGTGGCCAGGCCGGCCAGACAACG<br>ACACCTGCTCCCAGACCGCCTACTCCCGCCCCAACCA<br>TTGCATCTCAGCCACTCTCTCTGAGACCCGAAGCGTGT<br>AGACCTGCGGCCGGGGGCGCTGTCCACACAAGAGGC<br>TTAGACTTCGCCTGCGATATCTATATCTGGGCCCCACT<br>CGCAGGCACTTGTGGAGTGCTGCTGCTTTCACTCGTG<br>ATAACCCTGTACTGCAAAAGGGGGAGAAAGAAGCTGC<br>TGTATATTTTTAAACAACCATTTATGAGACCTGTTCAGA<br>CTACCCAGGAAGAAGACGGTTGTAGTTGCAGATTCCC<br>CGAGGAGGAAGAAGGAGGTTGCGAGTTGAGAGTAAAG<br>TTCAGCAGATCCGCAGATGCCCCTGCTTACCAGCAGG<br>GTCAAAACCAGCTTTACAACGAGCTGAATTTAGGTAGA<br>AGAGAGGAATATGACGTGTTGGATAAAAGAAGAGGAA<br>GAGACCCGGAAATGGGCGGCAAGCCTCGAAGAAAAA<br>TCCCCAAGAGGGACTCTACAATGAGCTGCAGAAGGAC<br>AAAATGGCTGAAGCCTACAGCGAGATCGGCATGAAGG<br>GAGAAAGACGCAGAGGGAAAGGGCATGATGGGCTTTA<br>TCAGGGCTTGTCCACCGCTACAAAGGATACTTATGACG<br>CACTACACATGCAGGCCCTGCCACCCCGT |
| 121 | Protein | CDRH1 of anti CD30<br>antibody (T1-36) | YYYMS |

-continued

| SEQ ID NO: | Type | Name | Sequence |
|---|---|---|---|
| 122 | Protein | CDRH2 of anti CD30 antibody (T1-36) | YIGGGGSGTYYADSVKG |
| 123 | Protein | CDRH3 of anti CD30 antibody (T1-36) | GPYYGYFDY |
| 124 | Protein | CDRL1 of anti CD30 antibody (T1-36) | SGSSSNIGSNYVY |
| 125 | Protein | CDRL2 of anti CD30 antibody (T1-36) | RNNQRPS |
| 126 | Protein | CDRL3 of anti CD30 antibody (T1-36) | AAYPSYDS |
| 127 | Protein | Heavy chain variable domain of anti CD30 antibody (T1-36) | EVQLLESGGGLVQPGGSLRLSCAASGFTFSYYYMSWVR QAPGKGLEWVSYIGGGGSGTYYADSVKGRFTISRDNSK NTLYLQMNSLRAEDTAVYYCARGPYYGYFDYWGQGTLV TVSS |
| 128 | Protein | Light chain variable domain of anti CD30 antibody (T1-36) | QSVLTQPPSASGTPGQRVTISCSGSSSNIGSNYVYWYQQ LPGTAPKLLIYRNNQRPSGVPDRFSGSKSGTSASLAISGL RSEDEADYYCAAYPSYDSYVFGGGTKLTVLG |
| 129 | Protein | scFv of anti CD30 antibody (T1-36) | EVQLLESGGGLVQPGGSLRLSCAASGFTFSYYYMSWVR QAPGKGLEWVSYIGGGGSGTYYADSVKGRFTISRDNSK NTLYLQMNSLRAEDTAVYYCARGPYYGYFDYWGQGTLV TVSSGGGGSGGGGSGGGGSQSVLTQPPSASGTPGQRV TISCSGSSSNIGSNYVYWYQQLPGTAPKLLIYRNNQRPSG VPDRFSGSKSGTSASLAISGLRSEDEADYYCAAYPSYDS YVFGGGTKLTVLG |
| 130 | Protein | scFv CAR of anti CD30 antibody (T1-36) | EVQLLESGGGLVQPGGSLRLSCAASGFTFSYYYMSWVR QAPGKGLEWVSYIGGGGSGTYYADSVKGRFTISRDNSK NTLYLQMNSLRAEDTAVYYCARGPYYGYFDYWGQGTLV TVSSGGGGSGGGGSGGGGSQSVLTQPPSASGTPGQRV TISCSGSSSNIGSNYVYWYQQLPGTAPKLLIYRNNQRPSG VPDRFSGSKSGTSASLAISGLRSEDEADYYCAAYPSYDS YVFGGGTKLTVLGGQAGQTTTPAPRPPTPAPTIASQPLSL RPEACRPAAGGAVHTRGLDFACDIYIWAPLAGTCGVLLLS LVITLYCKRGRKKLLYIFKQPFMRPVQTTQEEDGCSCRFP EEEEGGCELRVKFSRSADAPAYQQGQNQLYNELNLGRR EEYDVLDKRRGRDPEMGGKPRRKNPQEGLYNELQKDK MAEAYSEIGMKGERRRGKGHDGLYQGLSTATKDTYDAL HMQALPPR |
| 131 | DNA | Nucleotide sequence for encoding CDRH1 of anti CD30 antibody (T1-36) | TACTATTACATGAGC |
| 132 | DNA | Nucleotide sequence for encoding CDRH2 of anti CD30 antibody (T1-36) | TACATCGGTGGTGGTGGTTCTGGTACGTATTACGCTGA TTCTGTAAAAGGT |
| 133 | DNA | Nucleotide sequence for encoding CDRH3 of anti CD30 antibody (T1-36) | GGTCCGTACTACGGTTACTTCGACTAC |
| 134 | DNA | Nucleotide sequence for encoding CDRL1 of anti CD30 antibody (T1-36) | AGTGGCTCTTCATCTAATATTGGCTCTAATTATGTCTAC |
| 135 | DNA | Nucleotide sequence for encoding CDRL2 of anti CD30 antibody (T1-36) | AGAAATAACCAGCGGCCAAGC |
| 136 | DNA | Nucleotide sequence for encoding CDRL3 of anti CD30 antibody (T1-36) | GCTGCTTACCCGTCTTACGACTCT |

-continued

| SEQ ID NO:Type | Name | Sequence |
|---|---|---|
| 137    DNA | Nucleotide sequence for encoding heavy chain variable domain of anti CD30 antibody (T1-36) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTACTATTACATGAGCTGGGTCC GCCAGGCTCCAGGGAAGGGGCTGGAGTGGGTCTCAT ACATCGGTGGTGGTGGTTCTGGTACGTATTACGCTGAT TCTGTAAAAGGTCGGTTCACCATCTCCAGAGACAATTC CAAGAACACGCTGTATCTGCAAATGAACAGCCTGAGAG CCGAGGACACGGCCGTGTATTACTGTGCGCGTGGTCC GTACTACGGTTACTTCGACTACTGGGGCCAGGGTACA CTGGTCACCGTGAGCTCA |
| 138    DNA | Nucleotide sequence for encoding light chain variable domain of anti CD30 antibody (T1-36) | CAGTCTGTGCTGACTCAGCCACCCTCAGCGTCTGGGA CCCCCGGGCAGAGGGTCACCATCTCTTGTAGTGGCTC TTCATCTAATATTGGCTCTAATTATGTCTACTGGTACCA GCAGCTCCCAGGAACGGCCCCCAAACTCCTCATCTAT AGAAATAACCAGCGGCCAAGCGGGGTCCCTGACCGAT TCTCTGGCTCCAAGTCTGGCACCTCAGCCTCCCTGGC CATCAGTGGGCTCCGGTCCGAGGATGAGGCCGATTAT TACTGTGCTGCTTACCGTCTTACGACTCTTATGTCTTC GGCGGAGGCACCAAGCTGACGGTCCTAGGT |
| 139    DNA | Nucleotide sequence for encoding scFv of anti CD30 antibody (T1-36) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTACTATTACATGAGCTGGGTCC GCCAGGCTCCAGGGAAGGGGCTGGAGTGGGTCTCAT ACATCGGTGGTGGTGGTTCTGGTACGTATTACGCTGAT TCTGTAAAAGGTCGGTTCACCATCTCCAGAGACAATTC CAAGAACACGCTGTATCTGCAAATGAACAGCCTGAGAG CCGAGGACACGGCCGTGTATTACTGTGCGCGTGGTCC GTACTACGGTTACTTCGACTACTGGGGCCAGGGTACA CTGGTCACCGTGAGCTCAGGTGGAGGCGGTTCAGGC GGAGGTGGATCCGGCGGTGGCGGATCGCAGTCTGTG CTGACTCAGCCACCCTCAGCGTCTGGGACCCCCGGGC AGAGGGTCACCATCTCTTGTAGTGGCTCTTCATCTAAT ATTGGCTCTAATTATGTCTACTGGTACCAGCAGCTCCC AGGAACGGCCCCCAAACTCCTCATCTATAGAAATAACC AGCGGCCAAGCGGGGTCCCTGACCGATTCTCTGGCTC CAAGTCTGGCACCTCAGCCTCCCTGGCCATCAGTGGG CTCCGGTCCGAGGATGAGGCCGATTATTACTGTGCTG CTTACCGTCTTACGACTCTTATGTCTTCGGCGGAGGC ACCAAGCTGACGGTCCTAGGT |
| 140    DNA | Nucleotide sequence for encoding scFv CAR of anti CD30 antibody (T1-36) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTACTATTACATGAGCTGGGTCC GCCAGGCTCCAGGGAAGGGGCTGGAGTGGGTCTCAT ACATCGGTGGTGGTGGTTCTGGTACGTATTACGCTGAT TCTGTAAAAGGTCGGTTCACCATCTCCAGAGACAATTC CAAGAACACGCTGTATCTGCAAATGAACAGCCTGAGAG CCGAGGACACGGCCGTGTATTACTGTGCGCGTGGTCC GTACTACGGTTACTTCGACTACTGGGGCCAGGGTACA CTGGTCACCGTGAGCTCAGGTGGAGGCGGTTCAGGC GGAGGTGGATCCGGCGGTGGCGGATCGCAGTCTGTG CTGACTCAGCCACCCTCAGCGTCTGGGACCCCCGGGC AGAGGGTCACCATCTCTTGTAGTGGCTCTTCATCTAAT ATTGGCTCTAATTATGTCTACTGGTACCAGCAGCTCCC AGGAACGGCCCCCAAACTCCTCATCTATAGAAATAACC AGCGGCCAAGCGGGGTCCCTGACCGATTCTCTGGCTC CAAGTCTGGCACCTCAGCCTCCCTGGCCATCAGTGGG CTCCGGTCCGAGGATGAGGCCGATTATTACTGTGCTG CTTACCGTCTTACGACTCTTATGTCTTCGGCGGAGGC ACCAAGCTGACGGTCCTAGGTGGCCAGGCCGGCCAG ACAACGACACCTGCTCCCAGACCGCCTACTCCCGCCC CAACCATTGCATCTCAGCCACTCTCTCTGAGACCCGAA GCGTGTAGACCTGCGGCCGGGGGCGCTGTCCACACA AGAGGCTTAGACTTCGCCTGCGATATCTATATCTGGGC CCCACTCGCAGGCACTTGTGGAGTGCTGCTGCTTTCA CTCGTGATAACCCTGTACTGCAAAAGGGGGAGAAAGA AGCTGCTGTATATTTTTAAACAACCATTTATGAGACCTG TTCAGACTACCCAGGAAGAAGACGGTTGTAGTTGCAGA TTCCCCGAGGAGGAAGAAGGAGGTTGCGAGTTGAGAG TAAAGTTCAGCAGATCCGCAGATGCCCCTGCTTACCAG CAGGGTCAAAACCAGCTTTACAACGAGCTGAATTTAGG TAGAAGAGAGGAATATGACGTGTTGGATAAAAGAAGAG GAAGAGACCCGGAAATGGGCGGCAAGCCTCGAAGAAA AAATCCCCAAGAGGGACTCTACAATGAGCTGCAGAAG |

-continued

| SEQ ID NO: | Type | Name | Sequence |
|---|---|---|---|
| | | | GACAAAATGGCTGAAGCCTACAGCGAGATCGGCATGA AGGGAGAAAGACGCAGAGGGAAAGGGCATGATGGGC TTTATCAGGGCTTGTCCACCGCTACAAAGGATACTTAT GACGCACTACACATGCAGGCCCTGCCACCCCGT |
| 141 | Protein | CDRH1 of anti CD30 antibody (T1-117) | YYGMS |
| 142 | Protein | CDRH2 of anti CD30 antibody (T1-117) | YISGYSSYTYYADSVKG |
| 143 | Protein | CDRH3 of anti CD30 antibody (T1-117) | YNDSGSFDY |
| 144 | Protein | CDRL1 of anti CD30 antibody (T1-117) | SGSSSNIGSNYVY |
| 145 | Protein | CDRL2 of anti CD30 antibody (T1-117) | RNNQRPS |
| 146 | Protein | CDRL3 of anti CD30 antibody (T1-117) | AADAGNR |
| 147 | Protein | Heavy chain variable domain of anti CD30 antibody (T1-117) | EVQLLESGGGLVQPGGSLRLSCAASGFTFSYYGMSWVR QAPGKGLEWVSYISGYSSYTYYADSVKGRFTISRDNSKN TLYLQMNSLRAEDTAVYYCARYNDSGSFDYWGQGTLVT VSS |
| 148 | Protein | Light chain variable domain of anti CD30 antibody (T1-117) | QSVLTQPPSASGTPGQRVTISCSGSSSNIGSNYVYWYQQ LPGTAPKLLIYRNNQRPSGVPDRFSGSKSGTSASLAISGL RSEDEADYYCAADAGNRYVFGGGTKLTVLG |
| 149 | Protein | scFv of anti CD30 antibody (T1-117) | EVQLLESGGGLVQPGGSLRLSCAASGFTFSYYGMSWVR QAPGKGLEWVSYISGYSSYTYYADSVKGRFTISRDNSKN TLYLQMNSLRAEDTAVYYCARYNDSGSFDYWGQGTLVT VSSGGGGSGGGGSGGGGSQSVLTQPPSASGTPGQRVT ISCSGSSSNIGSNYVYWYQQLPGTAPKLLIYRNNQRPSG VPDRFSGSKSGTSASLAISGLRSEDEADYYCAADAGNRY VFGGGTKLTVLG |
| 150 | Protein | scFv CAR of anti CD30 antibody (T1-117) | EVQLLESGGGLVQPGGSLRLSCAASGFTFSYYGMSWVR QAPGKGLEWVSYISGYSSYTYYADSVKGRFTISRDNSKN TLYLQMNSLRAEDTAVYYCARYNDSGSFDYWGQGTLVT VSSGGGGSGGGGSGGGGSQSVLTQPPSASGTPGQRVT ISCSGSSSNIGSNYVYWYQQLPGTAPKLLIYRNNQRPSG VPDRFSGSKSGTSASLAISGLRSEDEADYYCAADAGNRY VFGGGTKLTVLGGQAGQTTTPAPRPPTPAPTIASQPLSLR PEACRPAAGGAVHTRGLDFACDIYIWAPLAGTCGVLLLSL VITLYCKRGRKKLLYIFKQPFMRPVQTTQEEDGCSCRFPE EEEGGCELRVKFSRSADAPAYQQGQNQLYNELNLGRRE EYDVLDKRRGRDPEMGGKPRRKNPQEGLYNELQKDKM AEAYSEIGMKGERRRGKGHDGLYQGLSTATKDTYDALH MQALPPR |
| 151 | DNA | Nucleotide sequence for encoding CDRH1 of anti CD30 antibody (T1-117) | TACTATGGTATGAGC |
| 152 | DNA | Nucleotide sequence for encoding CDRH2 of anti CD30 antibody (T1-117) | TACATCTCTGGTTACTCTTCTTACACGTATTACGCTGAT TCTGTAAAAGGT |
| 153 | DNA | Nucleotide sequence for encoding CDRH3 of anti CD30 antibody (T1-117) | TACAACGACTCTGGTTCTTTCGACTAC |
| 154 | DNA | Nucleotide sequence for encoding CDRL1 of anti CD30 antibody (T1-117) | AGTGGCTCTTCATCTAATATTGGCTCTAATTATGTCTAC |
| 155 | DNA | Nucleotide sequence for encoding CDRL2 | AGAAATAACCAGCGGCCAAGC |

-continued

| SEQ ID NO:Type | | Name | Sequence |
|---|---|---|---|
| | | of anti CD30 antibody (T1-117) | |
| 156 | DNA | Nucleotide sequence for encoding CDRL3 of anti CD30 antibody (T1-117) | GCTGCTGACGCTGGTAACCGT |
| 157 | DNA | Nucleotide sequence for encoding heavy chain variable domain of anti CD30 antibody (T1-117) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCTACTATGGTATGAGCTGGGTCC<br>GCCAGGCTCCAGGGAAGGGGCTGGAGTGGGTCTCAT<br>ACATCTCTGGTTACTCTTCTTACACGTATTACGCTGATT<br>CTGTAAAAGGTCGGTTCACCATCTCCAGAGACAATTCC<br>AAGAACACGCTGTATCTGCAAATGAACAGCCTGAGAGC<br>CGAGGACACGGCCGTGTATTACTGTGCGCGTTACAAC<br>GACTCTGGTTCTTTCGACTACTGGGGCCAGGGTACACT<br>GGTCACCGTGAGCTCA |
| 158 | DNA | Nucleotide sequence for encoding light chain variable domain of anti CD30 antibody(T1-117) | CAGTCTGTGCTGACTCAGCCACCCTCAGCGTCTGGGA<br>CCCCCGGGCAGAGGGTCACCATCTCTTGTAGTGGCTC<br>TTCATCTAATATTGGCTCTAATTATGTCTACTGGTACCA<br>GCAGCTCCCAGGAACGGCCCCCAAACTCCTCATCTAT<br>AGAAATAACCAGCGGCCAAGCGGGGTCCCTGACCGAT<br>TCTCTGGCTCCAAGTCTGGCACCTCAGCCTCCCTGGC<br>CATCAGTGGGCTCCGGTCCGAGGATGAGGCCGATTAT<br>TACTGTGCTGCTGACGCTGGTAACCGTTATGTCTTCGG<br>CGGAGGCACCAAGCTGACGGTCCTAGGT |
| 159 | DNA | Nucleotide sequence for encoding scFv of anti CD30 antibody (T1-117) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCTACTATGGTATGAGCTGGGTCC<br>GCCAGGCTCCAGGGAAGGGGCTGGAGTGGGTCTCAT<br>ACATCTCTGGTTACTCTTCTTACACGTATTACGCTGATT<br>CTGTAAAAGGTCGGTTCACCATCTCCAGAGACAATTCC<br>AAGAACACGCTGTATCTGCAAATGAACAGCCTGAGAGC<br>CGAGGACACGGCCGTGTATTACTGTGCGCGTTACAAC<br>GACTCTGGTTCTTTCGACTACTGGGGCCAGGGTACACT<br>GGTCACCGTGAGCTCAGGTGGAGGCGGTTCAGGCGG<br>AGGTGGATCCGGCGGTGGCGGATCGCAGTCTGTGCT<br>GACTCAGCCACCCTCAGCGTCTGGGACCCCCGGGCA<br>GAGGGTCACCATCTCTTGTAGTGGCTCTTCATCTAATA<br>TTGGCTCTAATTATGTCTACTGGTACCAGCAGCTCCCA<br>GGAACGGCCCCCAAACTCCTCATCTATAGAAATAACCA<br>GCGGCCAAGCGGGGTCCCTGACCGATTCTCTGGCTCC<br>AAGTCTGGCACCTCAGCCTCCCTGGCCATCAGTGGGC<br>TCCGGTCCGAGGATGAGGCCGATTATTACTGTGCTGC<br>TGACGCTGGTAACCGTTATGTCTTCGGCGGAGGCACC<br>AAGCTGACGGTCCTAGGT |
| 160 | DNA | Nucleotide sequence for encoding scFv CAR of anti CD30 antibody (T1-117) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCTACTATGGTATGAGCTGGGTCC<br>GCCAGGCTCCAGGGAAGGGGCTGGAGTGGGTCTCAT<br>ACATCTCTGGTTACTCTTCTTACACGTATTACGCTGATT<br>CTGTAAAAGGTCGGTTCACCATCTCCAGAGACAATTCC<br>AAGAACACGCTGTATCTGCAAATGAACAGCCTGAGAGC<br>CGAGGACACGGCCGTGTATTACTGTGCGCGTTACAAC<br>GACTCTGGTTCTTTCGACTACTGGGGCCAGGGTACACT<br>GGTCACCGTGAGCTCAGGTGGAGGCGGTTCAGGCGG<br>AGGTGGATCCGGCGGTGGCGGATCGCAGTCTGTGCT<br>GACTCAGCCACCCTCAGCGTCTGGGACCCCCGGGCA<br>GAGGGTCACCATCTCTTGTAGTGGCTCTTCATCTAATA<br>TTGGCTCTAATTATGTCTACTGGTACCAGCAGCTCCCA<br>GGAACGGCCCCCAAACTCCTCATCTATAGAAATAACCA<br>GCGGCCAAGCGGGGTCCCTGACCGATTCTCTGGCTCC<br>AAGTCTGGCACCTCAGCCTCCCTGGCCATCAGTGGGC<br>TCCGGTCCGAGGATGAGGCCGATTATTACTGTGCTGC<br>TGACGCTGGTAACCGTTATGTCTTCGGCGGAGGCACC<br>AAGCTGACGGTCCTAGGTGGCCAGGCCGGCCAGACAA<br>CGACACCTGCTCCCAGACCGCCTACTCCCGCCCCAAC<br>CATTGCATCTCAGCCACTCTCTCTGAGACCCGAAGCGT<br>GTAGACCTGCGGCCGGGGGCGCTGTCCACACAAGAG<br>GCTTAGACTTCGCCTGCGATATCTATATCTGGGCCCCA<br>CTCGCAGGCACTTGTGGAGTGCTGCTGCTTTCACTCGT<br>GATAACCCTGTACTGCAAAAGGGGGAGAAAGAAGCTG<br>CTGTATATTTTTAAACAACCATTTATGAGACCTGTTCAG |

-continued

| SEQ ID NO:Type | | Name | Sequence |
|---|---|---|---|
| | | | ACTACCCAGGAAGAAGACGGTTGTAGTTGCAGATTCCC<br>CGAGGAGGAAGAAGGAGGTTGCGAGTTGAGAGTAAAG<br>TTCAGCAGATCCGCAGATGCCCCTGCTTACCAGCAGG<br>GTCAAAACCAGCTTTACAACGAGCTGAATTTAGGTAGA<br>AGAGAGGAATATGACGTGTTGGATAAAAGAAGAGGAA<br>GAGACCCGGAAATGGGCGGCAAGCCTCGAAGAAAAAA<br>TCCCCAAGAGGGACTCTACAATGAGCTGCAGAAGGAC<br>AAAATGGCTGAAGCCTACAGCGAGATCGGCATGAAGG<br>GAGAAAGACGCAGAGGGAAAGGGCATGATGGGCTTTA<br>TCAGGGCTTGTCCACCGCTACAAAGGATACTTATGACG<br>CACTACACATGCAGGCCCTGCCACCCCGT |
| 161 | Protein | CDRH1 of anti CD30<br>antibody (T1-141) | YYDMS |
| 162 | Protein | CDRH2 of anti CD30<br>antibody (T1-141) | GIYGSGSTYYADSVKG |
| 163 | Protein | CDRH3 of anti CD30<br>antibody (T1-141) | YSYYDSYSDYFDY |
| 164 | Protein | CDRL1 of anti CD30<br>antibody (T1-141) | SGSSSNIGSNYVY |
| 165 | Protein | CDRL2 of anti CD30<br>antibody (T1-141) | RNNQRPS |
| 166 | Protein | CDRL3 of anti CD30<br>antibody (T1-141) | AAYSYGY |
| 167 | Protein | Heavy chain variable<br>domain of anti CD30<br>antibody<br>(T1-141) | EVQLLESGGGLVQPGGSLRLSCAASGFTFSYYDMSWVR<br>QAPGKGLEWVSGIYGSGSTYYADSVKGRFTISRDNSKNT<br>LYLQMNSLRAEDTAVYYCARYSYYDSYSDYFDYWGQGT<br>LVTVSS |
| 168 | Protein | Light chain variable<br>domain of anti CD30<br>antibody<br>(T1-141) | QSVLTQPPSASGTPGQRVTISCSGSSSNIGSNYVYWYQQ<br>LPGTAPKLLIYRNNQRPSGVPDRFSGSKSGTSASLAISGL<br>RSEDEADYYCAAYSYGYYVFGGGTKLTVLG |
| 169 | Protein | scFv of anti CD30<br>antibody<br>(T1-141) | EVQLLESGGGLVQPGGSLRLSCAASGFTFSYYDMSWVR<br>QAPGKGLEWVSGIYGSGSTYYADSVKGRFTISRDNSKNT<br>LYLQMNSLRAEDTAVYYCARYSYYDSYSDYFDYWGQGT<br>LVTVSSGGGGSGGGGSGGGGSQSVLTQPPSASGTPGQ<br>RVTISCSGSSSNIGSNYVYWYQQLPGTAPKLLIYRNNQRP<br>SGVPDRFSGSKSGTSASLAISGLRSEDEADYYCAAYSYG<br>YYVFGGGTKLTVLG |
| 170 | Protein | scFv CAR of anti<br>CD30 antibody<br>(T1-141) | EVQLLESGGGLVQPGGSLRLSCAASGFTFSYYDMSWVR<br>QAPGKGLEWVSGIYGSGSTYYADSVKGRFTISRDNSKNT<br>LYLQMNSLRAEDTAVYYCARYSYYDSYSDYFDYWGQGT<br>LVTVSSGGGGSGGGGSGGGGSQSVLTQPPSASGTPGQ<br>RVTISCSGSSSNIGSNYVYWYQQLPGTAPKLLIYRNNQRP<br>SGVPDRFSGSKSGTSASLAISGLRSEDEADYYCAAYSYG<br>YYVFGGGTKLTVLGGQAGQTTTPAPRPPTPAPTIASQPL<br>SLRPEACRPAAGGAVHTRGLDFACDIYIWAPLAGTCGVLL<br>LSLVITLYCKRGRKKLLYIFKQPFMRPVQTTQEEDGCSCR<br>FPEEEEGGCELRVKFSRSADAPAYQQGQNQLYNELNLG<br>RREEYDVLDKRRGRDPEMGGKPRRKNPQEGLYNELQK<br>DKMAEAYSEIGMKGERRRGKGHDGLYQGLSTATKDTYD<br>ALHMQALPPR |
| 171 | DNA | Nucleotide sequence<br>for encoding CDRH1<br>of anti CD30<br>antibody (T1-141) | TACTATGATATGAGC |
| 172 | DNA | Nucleotide sequence<br>for encoding CDRH2<br>of anti CD30<br>antibody (T1-141) | GGTATCTACGGTTCTGGTTCTACGTATTACGCTGATTC<br>TGTAAAAGGT |
| 173 | DNA | Nucleotide sequence<br>for encoding CDRH3<br>of anti CD30<br>antibody (T1-141) | TACTCTTACTACGACTCTTACTCTGACTACTTCGACTAC |

-continued

| SEQ ID NO: | Type | Name | Sequence |
|---|---|---|---|
| 174 | DNA | Nucleotide sequence for encoding CDRL1 of anti CD30 antibody (T1-141) | AGTGGCTCTTCATCTAATATTGGCTCTAATTATGTCTAC |
| 175 | DNA | Nucleotide sequence for encoding CDRL2 of anti CD30 antibody (T1-141) | AGAAATAACCAGCGGCCAAGC |
| 176 | DNA | Nucleotide sequence for encoding CDRL3 of anti CD30 antibody (T1-141) | GCTGCTTACTCTTACGGTTAC |
| 177 | DNA | Nucleotide sequence for encoding heavy chain variable domain of anti CD30 antibody (T1-141) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCTACTATGATATGAGCTGGGTCC<br>GCCAGGCTCCAGGGAAGGGGCTGGAGTGGGTCTCAG<br>GTATCTACGGTTCTGGTTCTACGTATTACGCTGATTCT<br>GTAAAAGGTCGGTTCACCATCTCCAGAGACAATTCCAA<br>GAACACGCTGTATCTGCAAATGAACAGCCTGAGAGCC<br>GAGGACACGGCCGTGTATTACTGTGCGCGTTACTCTTA<br>CTACGACTCTTACTCTGACTACTTCGACTACTGGGGCC<br>AGGGTACACTGGTCACCGTGAGCTCA |
| 178 | DNA | Nucleotide sequence for encoding light chain variable domain of anti CD30 antibody (T1-141) | CAGTCTGTGCTGACTCAGCCACCCTCAGCGTCTGGGA<br>CCCCCGGGCAGAGGGTCACCATCTCTTGTAGTGGCTC<br>TTCATCTAATATTGGCTCTAATTATGTCTACTGGTACCA<br>GCAGCTCCCAGGAACGGCCCCCAAACTCCTCATCTAT<br>AGAAATAACCAGCGGCCAAGCGGGGTCCCTGACCGAT<br>TCTCTGGCTCCAAGTCTGGCACCTCAGCCTCCCTGGC<br>CATCAGTGGGCTCCGGTCCGAGGATGAGGCCGATTAT<br>TACTGTGCTGCTTACTCTTACGGTTACTATGTCTTCGG<br>CGGAGGCACCAAGCTGACGGTCCTAGGT |
| 179 | DNA | Nucleotide sequence for encoding scFv of anti CD30 antibody (T1-141) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCTACTATGATATGAGCTGGGTCC<br>GCCAGGCTCCAGGGAAGGGGCTGGAGTGGGTCTCAG<br>GTATCTACGGTTCTGGTTCTACGTATTACGCTGATTCT<br>GTAAAAGGTCGGTTCACCATCTCCAGAGACAATTCCAA<br>GAACACGCTGTATCTGCAAATGAACAGCCTGAGAGCC<br>GAGGACACGGCCGTGTATTACTGTGCGCGTTACTCTTA<br>CTACGACTCTTACTCTGACTACTTCGACTACTGGGGCC<br>AGGGTACACTGGTCACCGTGAGCTCAGGTGGAGGCG<br>GTTCAGGCGGAGGTGGATCCGGCGGTGGCGGATCGC<br>AGTCTGTGCTGACTCAGCCACCCTCAGCGTCTGGGAC<br>CCCCGGGCAGAGGGTCACCATCTCTTGTAGTGGCTCT<br>TCATCTAATATTGGCTCTAATTATGTCTACTGGTACCAG<br>CAGCTCCCAGGAACGGCCCCCAAACTCCTCATCTATA<br>GAAATAACCAGCGGCCAAGCGGGGTCCCTGACCGATT<br>CTCTGGCTCCAAGTCTGGCACCTCAGCCTCCCTGGCC<br>ATCAGTGGGCTCCGGTCCGAGGATGAGGCCGATTATT<br>ACTGTGCTGCTTACTCTTACGGTTACTATGTCTTCGGC<br>GGAGGCACCAAGCTGACGGTCCTAGGT |
| 180 | DNA | Nucleotide sequence for encoding scFv CAR of anti CD30 antibody (T1-141) | GAGGTGCAGCTGTTGGAGTCTGGGGGAGGCTTGGTAC<br>AGCCTGGGGGGTCCCTGAGACTCTCCTGTGCAGCCTC<br>TGGATTCACCTTTAGCTACTATGATATGAGCTGGGTCC<br>GCCAGGCTCCAGGGAAGGGGCTGGAGTGGGTCTCAG<br>GTATCTACGGTTCTGGTTCTACGTATTACGCTGATTCT<br>GTAAAAGGTCGGTTCACCATCTCCAGAGACAATTCCAA<br>GAACACGCTGTATCTGCAAATGAACAGCCTGAGAGCC<br>GAGGACACGGCCGTGTATTACTGTGCGCGTTACTCTTA<br>CTACGACTCTTACTCTGACTACTTCGACTACTGGGGCC<br>AGGGTACACTGGTCACCGTGAGCTCAGGTGGAGGCG<br>GTTCAGGCGGAGGTGGATCCGGCGGTGGCGGATCGC<br>AGTCTGTGCTGACTCAGCCACCCTCAGCGTCTGGGAC<br>CCCCGGGCAGAGGGTCACCATCTCTTGTAGTGGCTCT<br>TCATCTAATATTGGCTCTAATTATGTCTACTGGTACCAG<br>CAGCTCCCAGGAACGGCCCCCAAACTCCTCATCTATA<br>GAAATAACCAGCGGCCAAGCGGGGTCCCTGACCGATT<br>CTCTGGCTCCAAGTCTGGCACCTCAGCCTCCCTGGCC<br>ATCAGTGGGCTCCGGTCCGAGGATGAGGCCGATTATT<br>ACTGTGCTGCTTACTCTTACGGTTACTATGTCTTCGGC<br>GGAGGCACCAAGCTGACGGTCCTAGGTGGCCAGGCC |

| SEQ ID NO: | Type | Name | Sequence |
|---|---|---|---|
| | | | GGCCAGACAACGACACCTGCTCCCAGACCGCCTACTC<br>CCGCCCCAACCATTGCATCTCAGCCACTCTCTCTGAGA<br>CCCGAAGCGTGTAGACCTGCGGCCGGGGGCGCTGTC<br>CACACAAGAGGCTTAGACTTCGCCTGCGATATCTATAT<br>CTGGGCCCCACTCGCAGGCACTTGTGGAGTGCTGCTG<br>CTTTCACTCGTGATAACCCTGTACTGCAAAAGGGGGAG<br>AAAGAAGCTGCTGTATATTTTTAAACAACCATTTATGAG<br>ACCTGTTCAGACTACCCAGGAAGAAGACGGTTGTAGTT<br>GCAGATTCCCCGAGGAGGAAGAAGGAGGTTGCGAGTT<br>GAGAGTAAAGTTCAGCAGATCCGCAGATGCCCCTGCT<br>TACCAGCAGGGTCAAAACCAGCTTTACAACGAGCTGAA<br>TTTAGGTAGAAGAGAGGAATATGACGTGTTGGATAAAA<br>GAAGAGGAAGAGACCCGGAAATGGGCGGCAAGCCTC<br>GAAGAAAAAATCCCCAAGAGGGACTCTACAATGAGCTG<br>CAGAAGGACAAAATGGCTGAAGCCTACAGCGAGATCG<br>GCATGAAGGGAGAAAGACGCAGAGGGAAAGGGCATG<br>ATGGGCTTTATCAGGGCTTGTCCACCGCTACAAAGGAT<br>ACTTATGACGCACTACACATGCAGGCCCTGCCACCCC<br>GT |
| 181 | Protein | CDRH1 of anti CD30<br>antibody (T1-159) | SYGMS |
| 182 | Protein | CDRH2 of anti CD30<br>antibody (T1-159) | SIYYYSGGTYYADSVKG |
| 183 | Protein | CDRH3 of anti CD30<br>antibody (T1-159) | NDYRNNSDFDY |
| 184 | Protein | CDRL1 of anti CD30<br>antibody (T1-159) | SGSSSNIGSNYVY |
| 185 | Protein | CDRL2 of anti CD30<br>antibody (T1-159) | RNNQRPS |
| 186 | Protein | CDRL3 of anti CD30<br>antibody (T1-159) | AAYYPYY |
| 187 | Protein | Heavy chain variable<br>domain of anti CD30<br>antibody<br>(T1-159) | EVQLLESGGGLVQPGGSLRLSCAASGFTFSSYGMSWVR<br>QAPGKGLEWVSSIYYYSGGTYYADSVKGRFTISRDNSKN<br>TLYLQMNSLRAEDTAVYYCARNDYRNNSDFDYWGQGTL<br>VTVSS |
| 188 | Protein | Light chain variable<br>domain of anti CD30<br>antibody<br>(T1-159) | QSVLTQPPSASGTPGQRVTISCSGSSSNIGSNYVYWYQQ<br>LPGTAPKLLIYRNNQRPSGVPDRFSGSKSGTSASLAISGL<br>RSEDEADYYCAAYYPYYVFGGGTKLTVLG |
| 189 | Protein | scFv of anti CD30<br>antibody<br>(T1-159) | EVQLLESGGGLVQPGGSLRLSCAASGFTFSSYGMSWVR<br>QAPGKGLEWVSSIYYYSGGTYYADSVKGRFTISRDNSKN<br>TLYLQMNSLRAEDTAVYYCARNDYRNNSDFDYWGQGTL<br>VTVSSGGGGSGGGGSGGGGSQSVLTQPPSASGTPGQR<br>VTISCSGSSSNIGSNYVYWYQQLPGTAPKLLIYRNNQRPS<br>GVPDRFSGSKSGTSASLAISGLRSEDEADYYCAAYYPYY<br>YVFGGGTKLTVLG |
| 190 | Protein | scFv CAR of anti<br>CD30 antibody<br>(T1-159) | EVQLLESGGGLVQPGGSLRLSCAASGFTFSSYGMSWVR<br>QAPGKGLEWVSSIYYYSGGTYYADSVKGRFTISRDNSKN<br>TLYLQMNSLRAEDTAVYYCARNDYRNNSDFDYWGQGTL<br>VTVSSGGGGSGGGGSGGGGSQSVLTQPPSASGTPGQR<br>VTISCSGSSSNIGSNYVYWYQQLPGTAPKLLIYRNNQRPS<br>GVPDRFSGSKSGTSASLAISGLRSEDEADYYCAAYYPYY<br>YVFGGGTKLTVLGGQAGQTTTPAPRPPTPAPTIASQPLSL<br>RPEACRPAAGGAVHTRGLDFACDIYIWAPLAGTCGVLLLS<br>LVITLYCKRGRKKLLYIFKQPFMRPVQTTQEEDGCSCRFP<br>EEEEGGCELRVKFSRSADAPAYQQGQNQLYNELNLGRR<br>EEYDVLDKRRGRDPEMGGKPRRKNPQEGLYNELQKDK<br>MAEAYSEIGMKGERRRGKGHDGLYQGLSTATKDTYDAL<br>HMQALPPR |
| 191 | DNA | Nucleotide sequence<br>for encoding CDRH1<br>of anti CD30<br>antibody (T1-159) | TCTTATGGTATGAGC |
| 192 | DNA | Nucleotide sequence<br>for encoding CDRH2 | TCTATCTACTACTACTCTGGTGGTACGTATTACGCTGAT<br>TCTGTAAAAGGT |

-continued

| SEQ ID NO:Type | | Name | Sequence |
|---|---|---|---|
| | | of anti CD30 antibody (T1-159) | |
| 193 | DNA | Nucleotide sequence for encoding CDRH3 of anti CD30 antibody (T1-159) | AACGACTACCGTAACAACTCTGACTTCGACTAC |
| 194 | DNA | Nucleotide sequence for encoding CDRL1 of anti CD30 antibody (T1-159) | AGTGGCTCTTCATCTAATATTGGCTCTAATTATGTCTAC |
| 195 | DNA | Nucleotide sequence for encoding CDRL2 of anti CD30 antibody (T1-159) | AGAAATAACCAGCGGCCAAGC |
| 196 | DNA | Nucleotide sequence for encoding CDRL3 of anti CD30 antibody (T1-159) | GCTGCTTACTACCCGTACTAC |
| 197 | DNA | Nucleotide sequence for encoding heavy chain variable domain of anti CD30 antibody (T1-159) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTCTTATGGTATGAGCTGGGTCC GCCAGGCTCCAGGGAAGGGGCTGGAGTGGGTCTCAT CTATCTACTACTACTCTGGTGGTACGTATTACGCTGATT CTGTAAAAGGTCGGTTCACCATCTCCAGAGACAATTCC AAGAACACGCTGTATCTGCAAATGAACAGCCTGAGAGC CGAGGACACGGCCGTGTATTACTGTGCGCGTAACGAC TACCGTAACAACTCTGACTTCGACTACTGGGGCCAGG GTACACTGGTCACCGTGAGCTCA |
| 198 | DNA | Nucleotide sequence for encoding light chain variable domain of anti CD30 antibody (T1-159) | CAGTCTGTGCTGACTCAGCCACCCTCAGCGTCTGGGA CCCCCGGGCAGAGGGTCACCATCTCTTGTAGTGGCTC TTCATCTAATATTGGCTCTAATTATGTCTACTGGTACCA GCAGCTCCCAGGAACGGCCCCCAAACTCCTCATCTAT AGAAATAACCAGCGGCCAAGCGGGGTCCCTGACCGAT TCTCTGGCTCCAAGTCTGGCACCTCAGCCTCCCTGGC CATCAGTGGGCTCCGGTCCGAGGATGAGGCCGATTAT TACTGTGCTGCTTACTACCCGTACTACTATGTCTTCGG CGGAGGCACCAAGCTGACGGTCCTAGGT |
| 199 | DNA | Nucleotide sequence for encoding scFv of anti CD30 antibody (T1-159) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTCTTATGGTATGAGCTGGGTCC GCCAGGCTCCAGGGAAGGGGCTGGAGTGGGTCTCAT CTATCTACTACTACTCTGGTGGTACGTATTACGCTGATT CTGTAAAAGGTCGGTTCACCATCTCCAGAGACAATTCC AAGAACACGCTGTATCTGCAAATGAACAGCCTGAGAGC CGAGGACACGGCCGTGTATTACTGTGCGCGTAACGAC TACCGTAACAACTCTGACTTCGACTACTGGGGCCAGG GTACACTGGTCACCGTGAGCTCAGGTGGAGGCGGTTC AGGCGGAGGTGGATCCGGCGGTGGCGGATCGCAGTC TGTGCTGACTCAGCCACCCTCAGCGTCTGGGACCCCC GGGCAGAGGGTCACCATCTCTTGTAGTGGCTCTTCATC TAATATTGGCTCTAATTATGTCTACTGGTACCAGCAGCT CCCAGGAACGGCCCCCAAACTCCTCATCTATAGAAATA ACCAGCGGCCAAGCGGGGTCCCTGACCGATTCTCTGG CTCCAAGTCTGGCACCTCAGCCTCCCTGGCCATCAGT GGGCTCCGGTCCGAGGATGAGGCCGATTATTACTGTG CTGCTTACTACCCGTACTACTATGTCTTCGGCGGAGGC ACCAAGCTGACGGTCCTAGGT |
| 200 | DNA | Nucleotide sequence for encoding scFv CAR of anti CD30 antibody (T1-159) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTCTTATGGTATGAGCTGGGTCC GCCAGGCTCCAGGGAAGGGGCTGGAGTGGGTCTCAT CTATCTACTACTACTCTGGTGGTACGTATTACGCTGATT CTGTAAAAGGTCGGTTCACCATCTCCAGAGACAATTCC AAGAACACGCTGTATCTGCAAATGAACAGCCTGAGAGC CGAGGACACGGCCGTGTATTACTGTGCGCGTAACGAC TACCGTAACAACTCTGACTTCGACTACTGGGGCCAGG GTACACTGGTCACCGTGAGCTCAGGTGGAGGCGGTTC AGGCGGAGGTGGATCCGGCGGTGGCGGATCGCAGTC TGTGCTGACTCAGCCACCCTCAGCGTCTGGGACCCCC |

-continued

| SEQ ID NO:Type | Name | Sequence |
|---|---|---|
| | | GGGCAGAGGGTCACCATCTCTTGTAGTGGCTCTTCATC<br>TAATATTGGCTCTAATTATGTCTACTGGTACCAGCAGCT<br>CCCAGGAACGGCCCCCAAACTCCTCATCTATAGAAATA<br>ACCAGCGGCCAAGCGGGGTCCCTGACCGATTCTCTGG<br>CTCCAAGTCTGGCACCTCAGCCTCCCTGGCCATCAGT<br>GGGCTCCGGTCCGAGGATGAGGCCGATTATTACTGTG<br>CTGCTTACTACCCGTACTACTATGTCTTCGGCGGAGGC<br>ACCAAGCTGACGGTCCTAGGTGGCCAGGCCGGCCAG<br>ACAACGACACCTGCTCCCAGACCGCCTACTCCCGCCC<br>CAACCATTGCATCTCAGCCACTCTCTCTGAGACCCGAA<br>GCGTGTAGACCTGCGGCCGGGGGCGCTGTCCACACA<br>AGAGGCTTAGACTTCGCCTGCGATATCTATATCTGGGC<br>CCCACTCGCAGGCACTTGTGGAGTGCTGCTGCTTTCA<br>CTCGTGATAACCCTGTACTGCAAAAGGGGGAGAAAGA<br>AGCTGCTGTATATTTTTAAACAACCATTTATGAGACCTG<br>TTCAGACTACCCAGGAAGAAGACGGTTGTAGTTGCAGA<br>TTCCCCGAGGAGGAAGAAGGAGGTTGCGAGTTGAGAG<br>TAAAGTTCAGCAGATCCGCAGATGCCCCTGCTTACCAG<br>CAGGGTCAAAACCAGCTTTACAACGAGCTGAATTTAGG<br>TAGAAGAGAGGAATATGACGTGTTGGATAAAAGAAGAG<br>GAAGAGACCCGGAAATGGGGGGCAAGCCTCGAAGAAA<br>AAATCCCCAAGAGGGACTCTACAATGAGCTGCAGAAG<br>GACAAAATGGCTGAAGCCTACAGCGAGATCGGCATGA<br>AGGGAGAAAGACGCAGAGGGAAAGGGCATGATGGGC<br>TTTATCAGGGCTTGTCCACCGCTACAAAGGATACTTAT<br>GACGCACTACACATGCAGGCCCTGCCACCCCGT |
| 201 | Protein | CDRH1 of anti CD30<br>antibody (T2-2) | SYHMS |
| 202 | Protein | CDRH2 of anti CD30<br>antibody (T2-2) | GIGYGHGGTYYADSVKG |
| 203 | Protein | CDRH3 of anti CD30<br>antibody (T2-2) | YDYDYSFDY |
| 204 | Protein | CDRL1 of anti CD30<br>antibody (T2-2) | SGSSSNIGSNYVY |
| 205 | Protein | CDRL2 of anti CD30<br>antibody (T2-2) | RNNQRPS |
| 206 | Protein | CDRL3 of anti CD30<br>antibody (T2-2) | AVSSPYS |
| 207 | Protein | Heavy chain variable<br>domain of anti CD30<br>antibody (T2-2) | EVQLLESGGGLVQPGGSLRLSCAASGFTFSSYHMSWVR<br>QAPGKGLEWVSGIGYGHGGTYYADSVKGRFTISRDNSK<br>NTLYLQMNSLRAEDTAVYYCARYDYDYSFDYWGQGTLV<br>TVSS |
| 208 | Protein | Light chain variable<br>domain of anti CD30<br>antibody (T2-2) | QSVLTQPPSASGTPGQRVTISCSGSSSNIGSNYVYWYQQ<br>LPGTAPKLLIYRNNQRPSGVPDRFSGSKSGTSASLAISGL<br>RSEDEADYYCAVSSPYSYVFGGGTKLTVLG |
| 209 | Protein | scFv of anti CD30<br>antibody<br>(T2-2) | EVQLLESGGGLVQPGGSLRLSCAASGFTFSSYHMSWVR<br>QAPGKGLEWVSGIGYGHGGTYYADSVKGRFTISRDNSK<br>NTLYLQMNSLRAEDTAVYYCARYDYDYSFDYWGQGTLV<br>TVSSGGGGSGGGGSGGGGSQSVLTQPPSASGTPGQRV<br>TISCSGSSSNIGSNYVYWYQQLPGTAPKLLIYRNNQRPSG<br>VPDRFSGSKSGTSASLAISGLRSEDEADYYCAVSSPYSY<br>VFGGGTKLTVLG |
| 210 | Protein | scFv CAR of anti<br>CD30 antibody<br>(T2-2) | EVQLLESGGGLVQPGGSLRLSCAASGFTFSSYHMSWVR<br>QAPGKGLEWVSGIGYGHGGTYYADSVKGRFTISRDNSK<br>NTLYLQMNSLRAEDTAVYYCARYDYDYSFDYWGQGTLV<br>TVSSGGGGSGGGGSGGGGSQSVLTQPPSASGTPGQRV<br>TISCSGSSSNIGSNYVYWYQQLPGTAPKLLIYRNNQRPSG<br>VPDRFSGSKSGTSASLAISGLRSEDEADYYCAVSSPYSY<br>VFGGGTKLTVLGGQAGQTTTPAPRPPTPAPTIASQPLSLR<br>PEACRPAAGGAVHTRGLDFACDIYIWAPLAGTCGVLLLSL<br>VITLYCKRGRKKLLYIFKQPFMRPVQTTQEEDGCSCRFPE<br>EEEGGCELRVKFSRSADAPAYQQGQNQLYNELNLGRRE<br>EYDVLDKRRGRDPEMGGKPRRKNPQEGLYNELQKDKM<br>AEAYSEIGMKGERRRGKGHDGLYQGLSTATKDTYDALH<br>MQALPPR |

-continued

| SEQ ID NO: | Type | Name | Sequence |
|---|---|---|---|
| 211 | DNA | Nucleotide sequence for encoding CDRH1 of anti CD30 antibody (T2-2) | TCTTATCACATGAGC |
| 212 | DNA | Nucleotide sequence for encoding CDRH2 of anti CD30 antibody (T2-2) | GGTATCGGTTACGGTCACGGTGGTACGTATTACGCTG ATTCTGTAAAAGGT |
| 213 | DNA | Nucleotide sequence for encoding CDRH3 of anti CD30 antibody (T2-2) | TACGACTACGACTACTCTTTCGACTAC |
| 214 | DNA | Nucleotide sequence for encoding CDRL1 of anti CD30 antibody (T2-2) | TCCTGCTCTTCATCTAATATTGGCTCTAATTATGTCTAC |
| 215 | DNA | Nucleotide sequence for encoding CDRL2 of anti CD30 antibody (T2-2) | AGAAATAACCAGCGGCCAAGC |
| 216 | DNA | Nucleotide sequence for encoding CDRL3 of anti CD30 antibody (T2-2) | GCTGTTTCTTCTCCGTACTCT |
| 217 | DNA | Nucleotide sequence for encoding heavy chain variable domain of anti CD30 antibody (T2-2) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTCTTATCACATGAGCTGGGTCC GCCAGGCTCCAGGGAAGGGGCTGGAGTGGGTCTCAG GTATCGGTTACGGTCACGGTGGTACGTATTACGCTGAT TCTGTAAAAGGTCGGTTCACCATCTCCAGAGACAATTC CAAGAACACGCTGTATCTGCAAATGAACAGCCTGAGAG CCGAGGACACGGCCGTGTATTACTGTGCGCGTTACGA CTACGACTACTCTTTCGACTACTGGGGCCAGGGTACAC TGGTCACCGTGAGCTCA |
| 218 | DNA | Nucleotide sequence for encoding light chain variable domain of anti CD30 antibody (T2-2) | CAGTCTGTGCTGACTCAGCCACCCTCAGCGTCTGGGA CCCCCGGGCAGAGGGTCACCATCTCTTGTTCCTGCTC TTCATCTAATATTGGCTCTAATTATGTCTACTGGTACCA GCAGCTCCCAGGAACGGCCCCCAAACTCCTCATCTAT AGAAATAACCAGCGGCCAAGCGGGGTCCCTGACCGAT TCTCTGGCTCCAAGTCTGGCACCTCAGCCTCCCTGGC CATCAGTGGGCTCCGGTCCGAGGATGAGGCCGATTAT TACTGTGCTGTTTCTTCTCCGTACTCTTATGTCTTCGGC GGAGGCACCAAGCTGACGGTCCTAGGT |
| 219 | DNA | Nucleotide sequence for encoding scFv of anti CD30 antibody (T2-2) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTCTTATCACATGAGCTGGGTCC GCCAGGCTCCAGGGAAGGGGCTGGAGTGGGTCTCAG GTATCGGTTACGGTCACGGTGGTACGTATTACGCTGAT TCTGTAAAAGGTCGGTTCACCATCTCCAGAGACAATTC CAAGAACACGCTGTATCTGCAAATGAACAGCCTGAGAG CCGAGGACACGGCCGTGTATTACTGTGCGCGTTACGA CTACGACTACTCTTTCGACTACTGGGGCCAGGGTACAC TGGTCACCGTGAGCTCAGGTGGAGGCGGTTCAGGCG GAGGTGGATCCGGCGGTGGCGGATCGCAGTCTGTGC TGACTCAGCCACCCTCAGCGTCTGGGACCCCCGGGCA GAGGGTCACCATCTCTTGTAGTGGCTCTTCATCTAATA TTGGCTCTAATTATGTCTACTGGTACCAGCAGCTCCCA GGAACGGCCCCCAAACTCCTCATCTATAGAAATAACCA GCGGCCAAGCGGGGTCCCTGACCGATTCTCTGGCTCC AAGTCTGGCACCTCAGCCTCCCTGGCCATCAGTGGGC TCCGGTCCGAGGATGAGGCCGATTATTACTGTGCTGTT TCTTCTCCGTACTCTTATGTCTTCGGCGGAGGCACCAA GCTGACGGTCCTAGGT |
| 220 | DNA | Nucleotide sequence for encoding scFv CAR of anti CD30 antibody (T2-2) | GAGGTGCAGCTGTTGGAGTCTGGGGGAGGCTTGGTAC AGCCTGGGGGGTCCCTGAGACTCTCCTGTGCAGCCTC TGGATTCACCTTTAGCTCTTATCACATGAGCTGGGTCC GCCAGGCTCCAGGGAAGGGGCTGGAGTGGGTCTCAG GTATCGGTTACGGTCACGGTGGTACGTATTACGCTGAT |

-continued

| SEQ ID NO:Type | | Name | Sequence |
|---|---|---|---|
| | | | TCTGTAAAAGGTCGGTTCACCATCTCCAGAGACAATTC |
| | | | CAAGAACACGCTGTATCTGCAAATGAACAGCCTGAGAG |
| | | | CCGAGGACACGGCCGTGTATTACTGTGCGCGTTACGA |
| | | | CTACGACTACTCTTTCGACTACTGGGGCCAGGGTACAC |
| | | | TGGTCACCGTGAGCTCAGGTGGAGGCGGTTCAGGCG |
| | | | GAGGTGGATCCGGCGGTGGCGGATCGCAGTCTGTGC |
| | | | TGACTCAGCCACCCTCAGCGTCTGGGACCCCCGGGCA |
| | | | GAGGGTCACCATCTCTTGTAGTGGCTCTTCATCTAATA |
| | | | TTGGCTCTAATTATGTCTACTGGTACCAGCAGCTCCCA |
| | | | GGAACGGCCCCCAAACTCCTCATCTATAGAAATAACCA |
| | | | GCGGCCAAGCGGGGTCCCTGACCGATTCTCTGGCTCC |
| | | | AAGTCTGGCACCTCAGCCTCCCTGGCCATCAGTGGGC |
| | | | TCCGGTCCGAGGATGAGGCCGATTATTACTGTGCTGTT |
| | | | TCTTCTCCGTACTCTTATGTCTTCGGCGGAGGCACCAA |
| | | | GCTGACGGTCCTAGGTGGCCAGGCCGGCCAGACAAC |
| | | | GACACCTGCTCCCAGACCGCCTACTCCCGCCCCAACC |
| | | | ATTGCATCTCAGCCACTCTCTCTGAGACCCGAAGCGTG |
| | | | TAGACCTGCGGCCGGGGGCGCTGTCCACACAAGAGG |
| | | | CTTAGACTTCGCCTGCGATATCTATATCTGGGCCCCAC |
| | | | TCGCAGGCACTTGTGGAGTGCTGCTGCTTTCACTCGT |
| | | | GATAACCCTGTACTGCAAAAGGGGGAGAAAGAAGCTG |
| | | | CTGTATATTTTTAAACAACCATTTATGAGACCTGTTCAG |
| | | | ACTACCCAGGAAGAAGACGGTTGTAGTTGCAGATTCCC |
| | | | CGAGGAGGAAGAAGGAGGTTGCGAGTTGAGAGTAAAG |
| | | | TTCAGCAGATCCGCAGATGCCCCTGCTTACCAGCAGG |
| | | | GTCAAAACCAGCTTTACAACGAGCTGAATTTAGGTAGA |
| | | | AGAGAGGAATATGACGTGTTGGATAAAAGAAGAGGAA |
| | | | GAGACCCGGAAATGGGCGGCAAGCCTCGAAGAAAAAA |
| | | | TCCCCAAGAGGGACTCTACAATGAGCTGCAGAAGGAC |
| | | | AAAATGGCTGAAGCCTACAGCGAGATCGGCATGAAGG |
| | | | GAGAAAGACGCAGAGGGAAAGGGCATGATGGGCTTTA |
| | | | TCAGGGCTTGTCCACCGCTACAAAGGATACTTATGACG |
| | | | CACTACACATGCAGGCCCTGCCACCCCGT |
| 221 | DNA | Nucleotide sequence for encoding EF-1 alpha promoter | TGTGAGGCTCCGGTGCCCGTCAGTGGGCAGAGCGCA |
| | | | CATCGCCCACAGTCCCCGAGAAGTTGGGGGGAGGGG |
| | | | TCGGCAATTGAACCGGTGCCTAGAGAAGGTGGCGCGG |
| | | | GGTAAACTGGGAAAGTGATGTCGTGTACTGGCTCCGC |
| | | | CTTTTTCCCGAGGGTGGGGGAGAACCGTATATAAGTG |
| | | | CAGTAGTCGCCGTGAACGTTCTTTTTCGCAACGGGTTT |
| | | | GCCGCCAGAACACAGGTAAGTGCCGTGTGTGGTTCCC |
| | | | GCGGGCCTGGCCTCTTTACGGGTTATGGCCCTTGCGT |
| | | | GCCTTGAATTACTTCCACCTGGCTGCAGTACGTGATTC |
| | | | TTGATCCCGAGCTTCGGGTTGGAAGTGGGTGGGAGAG |
| | | | TTCGAGGCCTTGCGCTTAAGGAGCCCCTTCGCCTCGT |
| | | | GCTTGAGTTGAGGCCTGGCCTGGGCGCTGGGGCCGC |
| | | | CGCGTGCGAATCTGGTGGCACCTTCGCGCCTGTCTCG |
| | | | CTGCTTTCGATAAGTCTCTAGCCATTTAAAATTTTTGAT |
| | | | GACCTGCTGCGACGCTTTTTTTTCTGGCAAGATAGTCTT |
| | | | GTAAATGCGGGCCAAGATCTGCACACTGGTATTTCGGT |
| | | | TTTTGGGGCCGCGGGGGGCGACGGGGCCCGTGCGTC |
| | | | CCAGCGCACATGTTCGGCGAGGCGGGGCCTGCGAGC |
| | | | GCGGCCACCGAGAATCGGACGGGGGTAGTCTCAAGCT |
| | | | GGCCGGCCTGCTCTGGTGCCTGGCCTCGCGCCGCCG |
| | | | TGTATCGCCCCGCCCTGGGCGGCAAGGCTGGCCCGG |
| | | | TCGGCACCAGTTGCGTGAGCGGAAAGATGGCCGCTTC |
| | | | CCGGCCCTGCTGCAGGGAGCTCAAAATGGAGGACGC |
| | | | GGCGCTCGGGAGAGCGGGCGGGTGAGTCACCCACAC |
| | | | AAAGGAAAAGGGCCTTTCCGTCCTCAGCCGTCGCTTC |
| | | | ATGTGACTCCACGGAGTACCGGGCGCCGTCCAGGCAC |
| | | | CTCGATTAGTTCTCGAGCTTTTGGAGTACGTCGTCTTT |
| | | | AGGTTGGGGGGAGGGGTTTTATGCGATGGAGTTTCCC |
| | | | CACACTGAGTGGGTGGAGACTGAAGTTAGGCCAGCTT |
| | | | GGCACTTGATGTAATTCTCCTTGGAATTTGCCCTTTTTG |
| | | | AGTTTGGATCTTGGTTCATTCTCAAGCCTCAGACAGTG |
| | | | GTTCAAAGTTTTTTTCTTCCATTTCAGGTGTCGTGA |
| 222 | DNA | Nucleotide sequence for encoding CAR construct | GGCCAGGCCGGCCAGACAACGACACCTGCTCCCAGA |
| | | | CCGCCTACTCCCGCCCCAACCATTGCATCTCAGCCACT |
| | | | CTCTCTGAGACCCGAAGCGTGTAGACCTGCGGCCGGG |
| | | | GGCGCTGTCCACACAAGAGGCTTAGACTTCGCCTGCG |
| | | | ATATCTATATCTGGGCCCCACTCGCAGGCACTTGTGGA |
| | | | GTGCTGCTGCTTTCACTCGTGATAACCCTGTACTGCAA |
| | | | AAGGGGGAGAAAGAAGCTGCTGTATATTTTTAAACAAC |
| | | | CATTTATGAGACCTGTTCAGACTACCCAGGAAGAAGAC |
| | | | GGTTGTAGTTGCAGATTCCCCGAGGAGGAAGAAGGAG |
| | | | GTTGCGAGTTGAGAGTAAAGTTCAGCAGATCCGCAGAT |

| SEQ ID NO: | Type | Name | Sequence |
|---|---|---|---|
| | | | GCCCCTGCTTACCAGCAGGGTCAAAACCAGCTTTACAA CGAGCTGAATTTAGGTAGAAGAGAGGAATATGACGTGT TGGATAAAAGAAGAGGAAGAGACCCGGAAATGGGGGG CAAGCCTCGAAGAAAAAATCCCCAAGAGGGACTCTACA ATGAGCTGCAGAAGGACAAAATGGCTGAAGCCTACAG CGAGATCGGCATGAAGGGAGAAAGACGCAGAGGGAAA GGGCATGATGGGCTTTATCAGGGCTTGTCCACCGCTA CAAAGGATACTTATGACGCACTACACATGCAGGCCCTG CCACCCCGT |
| 223 | Protein | CD30 extracellular region (CD30 domain 1, linker, CD30 domain 2) | FPQDRPFEDTCHGNPSHYYDKAVRRCCYRCPMGLFPTQ QCPQRPTDCRKQCEPDYYLDEADRCTACVTCSRDDLVE KTPCAWNSSRVCECRPGMFCSTSAVNSCARCFFHSVCP AGMIVKFPGTAQKNTVCEPASPGVSPACASPENCKEPSS GTIPQAKPTPVSPATSSASTMPVRGGTRLAQEAASKLTR APDSPSSVGRPSSDPGLSPTQPCPEGSGDCRKQCEPDY YLDEAGRCTACVSCSRDDLVEKTPCAWNSSRTCECRPG MICATSATNSCARCVPYPICAAETVTKPQDMAEKDTTFEA PPLGTQPDCNPTPENGEAPASTSPTQSLLVDSQASKTLPI PTSAPVALSSTGK |
| 224 | Protein | CD30 D1L (CD30 domain 1, linker) | FPQDRPFEDTCHGNPSHYYDKAVRRCCYRCPMGLFPTQ QCPQRPTDCRKQCEPDYYLDEADRCTACVTCSRDDLVE KTPCAWNSSRVCECRPGMFCSTSAVNSCARCFFHSVCP AGMIVKFPGTAQKNTVCEPASPGVSPACASPENCKEPSS GTIPQAKPTPVSPATSSASTMPVRGGTRLAQEAASKLTR APDSPSSVGRPSSDPGLSPTQPCPEGSGDCRKQC |
| 225 | Protein | CD30 LD2 (linker, CD30 domain 2) | PGVSPACASPENCKEPSSGTIPQAKPTPVSPATSSASTM PVRGGTRLAQEAASKLTRAPDSPSSVGRPSSDPGLSPTQ PCPEGSGDCRKQCEPDYYLDEAGRCTACVSCSRDDLVE KTPCAWNSSRTCECRPGMICATSATNSCARCVPYPICAA ETVTKPQDMAEKDTTFEAPPLGTQPDCNPTPENGEAPAS TSPTQSLLVDSQASKTLPIPTSAPVALSSTGK |
| 226 | Protein | CD30 D1D2 (CD30 domain 1, CD30 domain 2) | FPQDRPFEDTCHGNPSHYYDKAVRRCCYRCPMGLFPTQ QCPQRPTDCRKQCEPDYYLDEADRCTACVTCSRDDLVE KTPCAWNSSRVCECRPGMFCSTSAVNSCARCFFHSVCP AGMIVKFPGTAQKNTVCEPASEPDYYLDEAGRCTACVSC SRDDLVEKTPCAWNSSRTCECRPGMICATSATNSCARC VPYPICAAETVTKPQDMAEKDTTFEAPPLGTQPDCNPTP ENGEAPASTSPTQSLLVDSQASKTLPIPTSAPVALSSTGK |

A better understanding of the present disclosure may be obtained through the following examples which are set forth to illustrate, but are not to be construed as limiting, the present disclosure.

EXAMPLES

Example 1: Development of Antibody Binding to CD30

Example 1-1. Selection of Antibody Through Panning

Selection was made of clones binding specifically to CD30 from the Rz library (Korean Patent No. 10-1694832 B, Jan. 12, 2017) by a panning process using the protein CD30-His (Sino Biological, 10777-H08H).

From the Rz library, phage rescue was done using VCSM13 helper phage, and the rescued phages were used in the panning. More than $10^{13}$ library phages were employed in the first round of binding to the antigen, and a total of five panning rounds was conducted. In the strategy for selectively selecting phages of high affinity, the amount of the antigen is reduced (20 μg, 10 μg, 10 μg, 5 μg, 5 μg), and the number of washes is increased (3, 5, 7, and 10 times) with the increase of the panning round.

Binder phages obtained in each panning round were infected into ER2537 to form colonies which were then examined for binding to the antibody by ELISA. The colonies obtained after infection of the binder phages were inoculated into SB medium (MOPS 10 g/L, Bacto YEAST extract 20 g/L, Trypton 30 g/L) and then grown until reaching an OD600 of 0.8, followed by shaking incubation at 30° C. in the presence of 1 mM IPTG (LPS Solution, IPTG025) to allow the overexpression of the antibody. Periplasmic extraction was conducted using a BBS buffer (200 mM boric acid, 150 mM NaCl, 1 mM EDTA). Binders were screened by ELISA using the extract. For ELISA, the scFv periplasmic extract was applied to a plate coated with 2 μg/mL of CD30-His protein and treated with a secondary antibody (anti-HA-HRP (Roche, 12013819001)). After color development with TMB (BioFx, TMBC-1000-01), $OD_{450}$ values were read using an ELISA reader (Perkin Elmer, Victor3). The ELISA data exhibited affibodies specifically binding to CD30 protein and 11 unique clones were identified by sequencing (Table 1 and Table 2).

TABLE 1

Light chain CDR sequences of the candidate antibodies

| Antibody | 1st Light Chain (LCDR1) | 2nd Light Chain (LCDR2) | 3rd Light Chain (LCDR3) |
|---|---|---|---|
| T1-2 | SGSSSNIGSNYVY (SEQ ID NO: 4) | RNNQRPS (SEQ ID NO: 5) | AADSSDDS (SEQ ID NO: 6) |
| T1-7 | SCSSSNIGNNAVS (SEQ ID NO: 24) | RNNQRPS (SEQ ID NO: 25) | AADYGSD (SEQ ID NO: 26) |
| T1-8 | SGSSSNIGSNYVY (SEQ ID NO: 44) | RNNQRPS (SEQ ID NO: 45) | AAYDSYS (SEQ ID NO: 46) |
| T1-9 | SGSSSNIGSNYVY (SEQ ID NO: 64) | RNNQRPS (SEQ ID NO: 65) | AAYYNYN (SEQ ID NO: 66) |
| T1-10 | SGSSSNIGSNYVY (SEQ ID NO: 84) | RNNQRPS (SEQ ID NO: 85) | AADGPYN (SEQ ID NO: 86) |
| T1-23 | SGSSSNIGSNYVY (SEQ ID NO: 104) | RNNQRPS (SEQ ID NO: 105) | AAYRSYD (SEQ ID NO: 106) |
| T1-36 | SGSSSNIGSNYVY (SEQ ID NO: 124) | RNNQRPS (SEQ ID NO: 125) | AAYPSYDS (SEQ ID NO: 126) |
| T1-117 | SGSSSNIGSNYVY (SEQ ID NO: 144) | RNNQRPS (SEQ ID NO: 145) | AADAGNR (SEQ ID NO: 146) |
| T1-141 | SGSSSNIGSNYVY (SEQ ID NO: 164) | RNNQRPS (SEQ ID NO: 165) | AAYSYGY (SEQ ID NO: 166) |
| T1-159 | SGSSSNIGSNYVY (SEQ ID NO: 184) | RNNQRPS (SEQ ID NO: 185) | AAYYPYY (SEQ ID NO: 186) |
| T2-2 | SGSSSNIGSNYVY (SEQ ID NO: 204) | RNNQRPS (SEQ ID NO: 205) | AVSSPYS (SEQ ID NO: 206) |

TABLE 2

Heavy chain CDR sequences of the candidate antibodies

| Antibody | 1st Heavy Chain (HCDR1) | 2nd Heavy Chain (HCDR2) | 3rd Heavy Chain (HCDR3) |
|---|---|---|---|
| T1-2 | GYGMS (SEQ ID NO: 1) | YISGYSYTYYADSVKG (SEQ ID NO: 2) | YDGNGFDY (SEQ ID NO: 3) |
| T1-7 | GYGMS (SEQ ID NO: 21) | YISSGSYYTYYADSVKG (SEQ ID NO: 22) | YRGDNDYYGYFDY (SEQ ID NO: 23) |
| T1-8 | SYMS (SEQ ID NO: 41) | SIGSGYYSTYYADSVKG (SEQ ID NO: 42) | DYYGGFDY (SEQ ID NO: 43) |
| T1-9 | YYGMS (SEQ ID NO: 61) | GIGSYSSYTYYADSVKG (SEQ ID NO: 62) | YASSPDAYFDY (SEQ ID NO: 63) |
| T1-10 | SYGMS (SEQ ID NO: 81) | YISGGSYYTYYADSVKG (SEQ ID NO: 82) | YGYGYYDGSFDY (SEQ ID NO: 83) |
| T1-23 | SYSMS (SEQ ID NO: 101) | GIGYPYYTYYADSVKG (SEQ ID NO: 102) | YYYDYGFDY (SEQ ID NO: 103) |
| T1-36 | YYYMS (SEQ ID NO: 121) | YIGGGGSGTYYADSVKG (SEQ ID NO: 122) | GPYYGYFDY (SEQ ID NO: 123) |

TABLE 2-continued

Heavy chain CDR sequences of the candidate antibodies

| Antibody | 1st Heavy Chain (HCDR1) | 2nd Heavy Chain (HCDR2) | 3rd Heavy Chain (HCDR3) |
|---|---|---|---|
| T1-117 | YYGMS (SEQ ID NO: 141) | YISGYSSYTYYADSVKG (SEQ ID NO: 142) | YNDSGSFDY (SEQ ID NO: 143) |
| T1-141 | YYDMS (SEQ ID NO: 161) | GIYGSGSTYYADSVKG (SEQ ID NO: 162) | YSYYDSYSDYFDY (SEQ ID NO: 163) |
| T1-159 | SYGMS (SEQ ID NO: 181) | SIYYYSGGTYYADSVKG (SEQ ID NO: 182) | NDYRNNSDFDY (SEQ ID NO: 183) |
| T2-2 | SYHMS (SEQ ID NO: 201) | GIGYGHGGTYYADSVKG (SEQ ID NO: 202) | YDYDYSFDY (SEQ ID NO: 203) |

Example 1-2. Identification of Binding Affinity of Selected Antibody

The eleven selected antibodies and the positive control HRS antibody (Protein Eng Des Sel. 2004 December; 17 (12):847-60.) were cloned in an scFv-Fc-conjugated form (Zb-Fc) and analyzed for binding to CD30 protein and for affinity for CD30-expressing cells.

For ELISA, the eleven purified anti-CD30 scFv-Fc forms and the positive control HRS scFV-Fc were 1/3 diluted for 10 points starting from 10 μg/mL in a plate coated with 1 μg/mL CD30-His protein. After treatment with a secondary antibody (anti-hIgG-Fc-HRP (Invitrogen, H10007)), a color was developed with TMB. $OD_{450}$ values were read using an ELISA reader, and $EC_{50}$ values were measured by means of Graph prism (FIG. 1, Table 3).

As shown in FIG. 1 and Table 3, most of the 11 candidate antibodies had high binding to CD30 compared to the positive control HRS antibody.

TABLE 3

Analyze the binding of candidate antibodies to CD30

| Antibody | $EC_{50}$(μg/mL) |
|---|---|
| T1-2 | 0.060 |
| T1-7 | 0.048 |
| T1-8 | 0.051 |
| T1-9 | 0.026 |
| T1-10 | 0.031 |
| T1-23 | 0.023 |
| T1-36 | 0.021 |
| T1-117 | 0.157 |
| T1-141 | 0.026 |
| T1-159 | 0.260 |
| T2-2 | 0.038 |
| HRS | 0.067 |

The selected antibodies were analyzed for binding affinity in CD30-expressing cells. For use in this experiment, CD30-293T cell line was established by introducing CD30-over-expressing lentivirus into the 293T cell line that does not express CD30. The CD30-293T cell line and the WT 293T cell line were each prepared at a density of $3 \times 10^5$ cells/tube. The cells were harvested by centrifugation at 1,200 rpm for 3 min and washed with PBS containing 5% FBS. Thereafter, the cells were incubated at 4° C. for 1 hour in the presence of 2 μg/mL of each of the eleven antibodies. The cells were washed three times by three rounds of centrifugation with 200 μL of 5% FBS-containing PBS at 1200 rpm for 3 min. Afterwards, the cells were incubated with 1 μg/mL of anti-human-Fc-FITC (Life Technologies, A11013) at 4° C. for 45 min in a light-shielded condition. After being washed three times through three rounds of centrifugation with 200 μL of 5% FBS-containing PBS at 1200 rpm for 3 min, the cells were measured for fluorescence intensity by FACS (FIG. 2).

Figure 2:
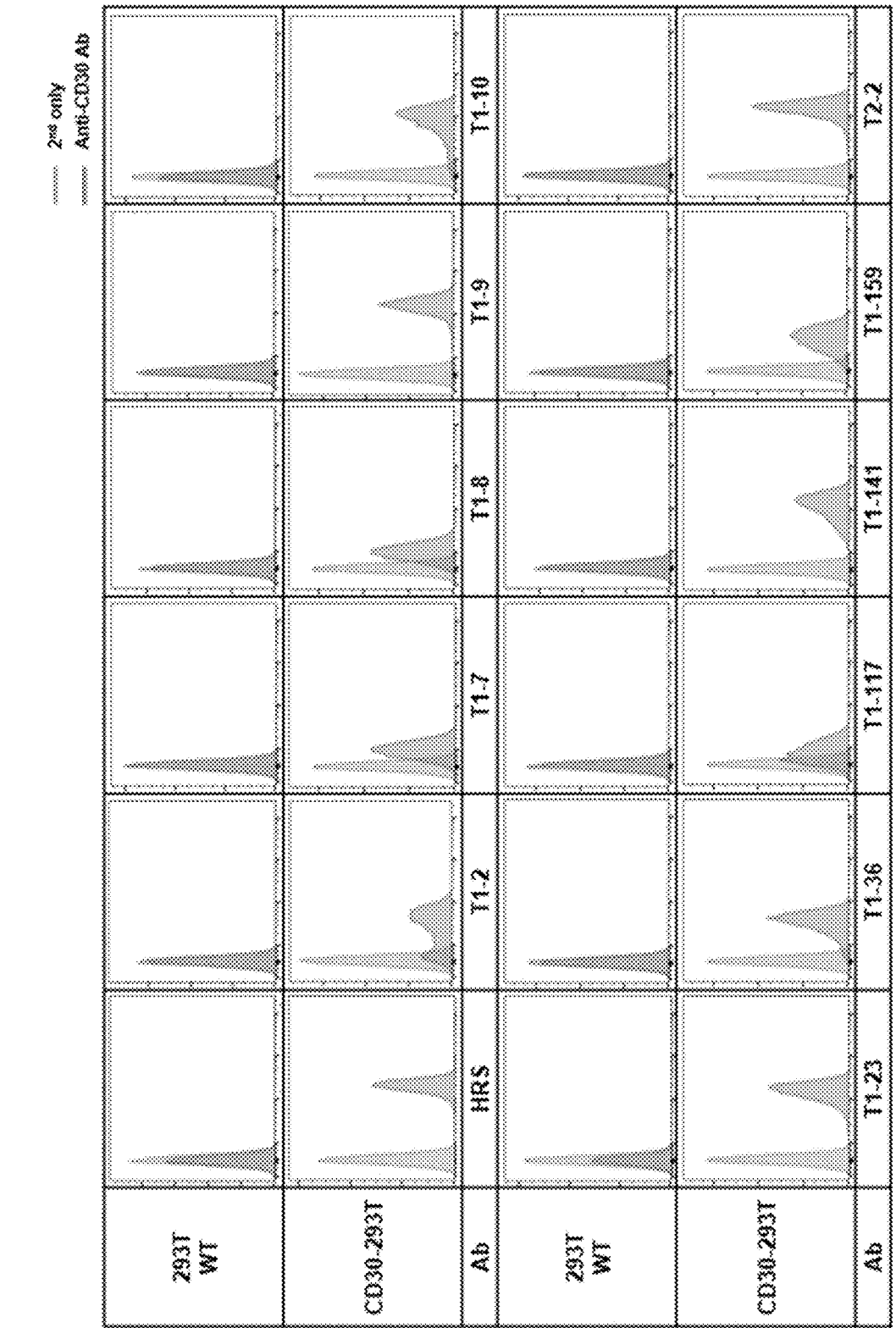
FIG. 2 shows graphs quantitatively analyzing the binding affinity of the CD30-binding antibodies for CD30-overexpressing CD30-293T cells.

As shown in FIG. 2, 11 candidate antibodies were found to bind to the CD30-293T cell line expressing CD30. In particular, T1-9, T1-23, and T2-2 demonstrated binding to CD30-expressing cells at levels equivalent to the positive control, HRS.

Example 1-3. Identification of CD30-Specific Binding Affinity of Selected Antibody Examination was made to see whether the selected eleven antibodies bind specifically to CD30. In this regard, the antibodies were measured for binding affinity for the TNFR family members CD27, CD270, CD134, CD137, CD359, and CD30 by ELISA.

For ELISA, the eleven purified anti-CD30 scFv-Fc forms and the positive control HRS scFV-Fc were each applied at a density of 1 μg/mL to plates coated with TNFR family proteins (CD27-His: Sino Biological, 10039-H08B1; CD134-His: Sino Biological, 10481-H08H; CD137-His: in-house produced; CD270-His: Sino Biological, 10334-H08H; CD357-His: Sino Biological, 13643-H08H; and CD30-His: Sino Biological, 10777-H08H). After treatment with a secondary antibody (anti-hIgG-Fc-HRP (Invitrogen, H10007)), a color was developed with TMB. $OD_{450}$ values were read using an ELISA reader (FIG. 3).

Figure 3:
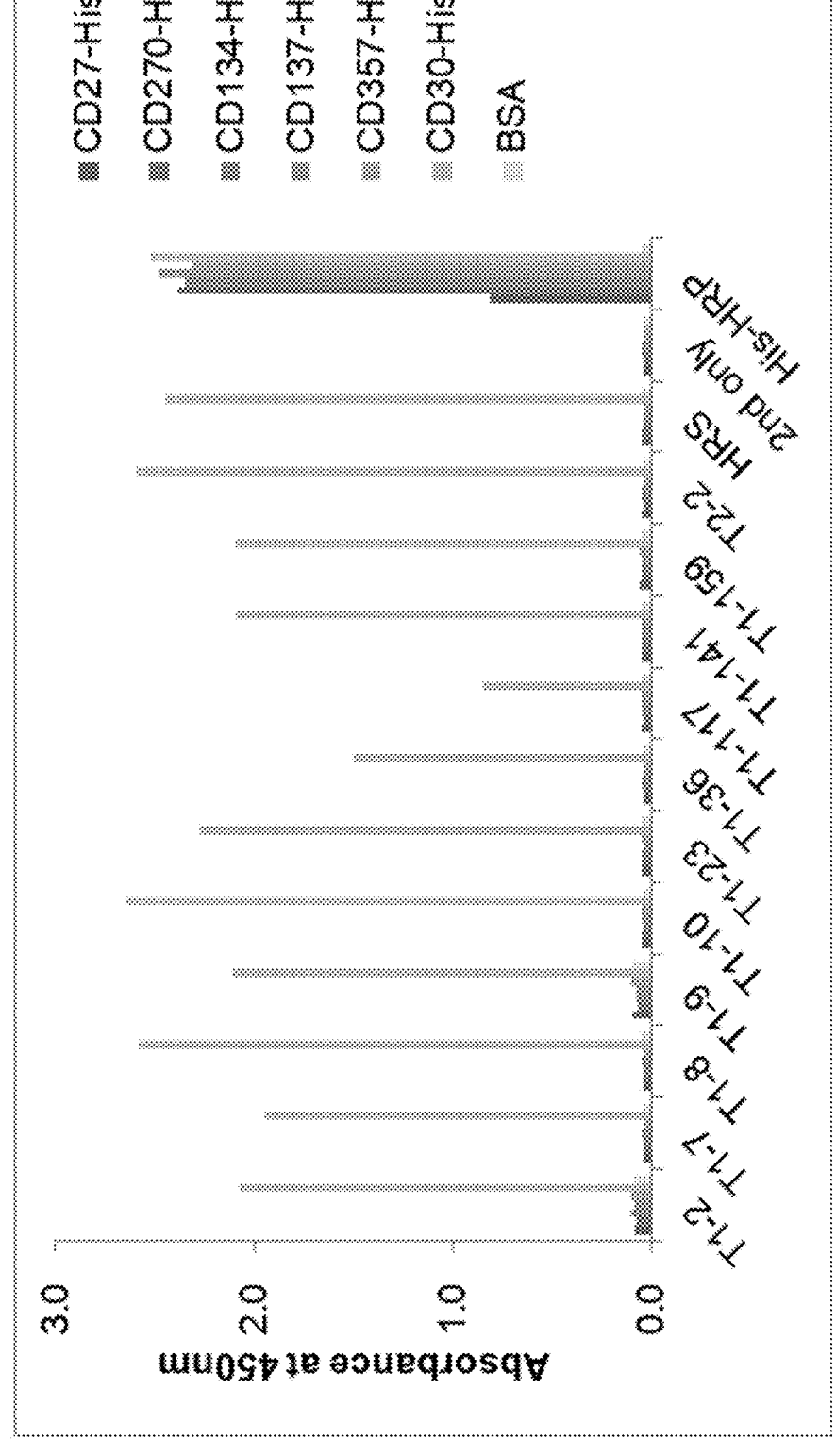
FIG. 3 is a graph showing the specific binding affinity of the 11 antibodies for CD30 as measured by ELISA for the TNFR family members including CD30 (CD27, CD270, CD134, CD137, CD357, and CD30).

As shown in FIG. 3, all 11 candidate antibodies had high affinity for CD30 only, thus confirming that the candidate antibodies all bind specifically to CD30.

Example 1-4. Identification of Binding Site of CD30 for Selected Antibody

Figure 4:
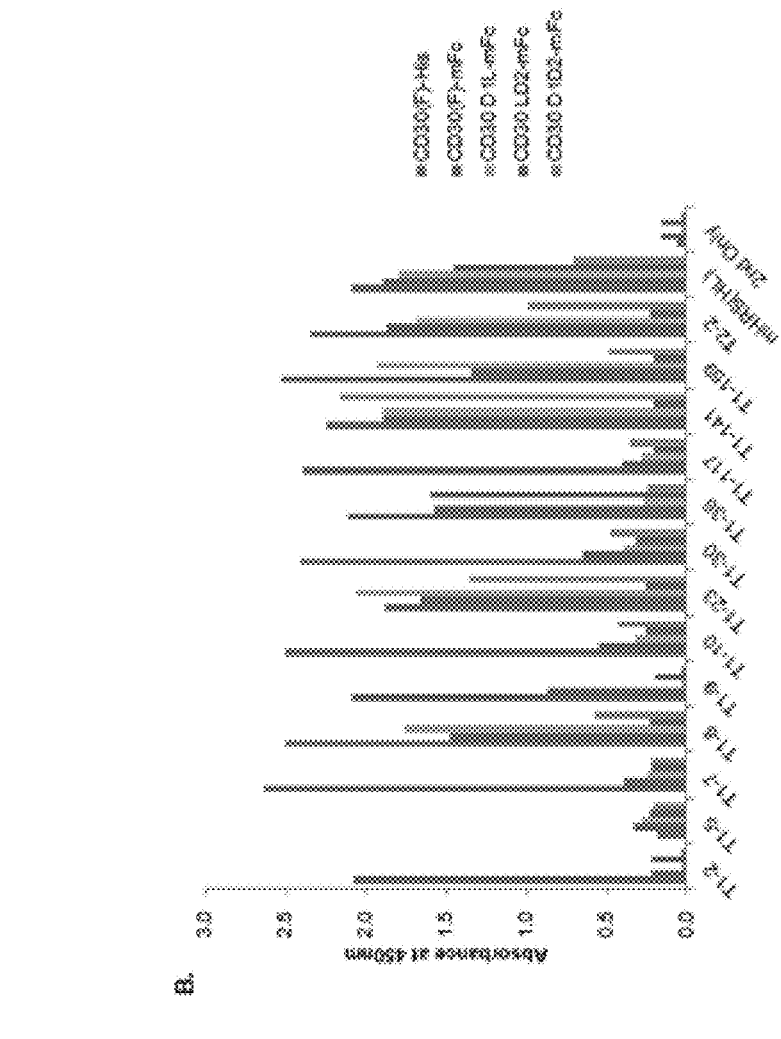
FIG. 4 shows the binding of the 11 antibodies to the chimeric extracellular domains of CD30 protein (CD30 (F), CD30 (D1L), CD30 (LD2), and CD30 (D1D2)) to identify a binding site on the extracellular domain of CD30 protein (A. schematic view of CD30 chimeric extracellular domain protein, B. data of binding to chimeric extracellular domain protein as measured by ELISA).

The binding sites of 11 candidate antibodies to the extracellular domain of the CD30 protein were identified by ELISA. To perform the ELISA, the extracellular domain of the CD30 protein was produced in animal cells and used as an antigen. In brief, a DNA structured to link the hinge and Fc region (CH2-CH3) of murine IgG1 to the C-terminus of ECD was cloned into pCEP4 vector (Invitrogen, V044-50) after digestion with the restriction enzymes HindIII and BamHI. Subsequently, the cloned vector was transiently transfected into FreeStyle™ 293F cells (Invitrogen, R790-07) with the aid of polyethylenimine (Polyscience Inc., 23966). From the cell culture, CD30 (F)-mFc, CD30 D1L-mFc, CD30 LD2-mFc, and CD30 D1D2-mFc fusion proteins were purified using Mabselect SuRe resin (Cytiva, 17-5438-01) (FIG. 4A). The purified proteins were quantitated using a protein assay dye (Bio-Rad, 500-0006). Their concentrations and purities were determined by SDS-PAGE with Coomassie blue staining.

The fusion proteins CD30 (F)-mFc, CD30 D1L-mFc, CD30 LD2-mFc, and CD30 D1D2-mFc were each fixed at a concentration of 1 μg/mL overnight, 4° C. to Costar 96-well plates (Corning, 3690). After three washes with TBS-T (0.05% Triton X-100), the protein in each well was blocked at room temperature for one hour with 100 μl of TBS-T/BSA (5% BSA). The blocked plates were washed three times, after which an anti-CD30 antibody was added and incubated at room temperature for one hour to bind to the antigens. The plates were washed three times and then incubated at room temperature for one hour with a 1:3,000 dilution of the secondary antibody anti-human IgG-HRP in TBS-T/BSA to form an antibody conjugate. Three rounds of wash were followed by color development with TMB (SurModics, TMBC-1000-01) at room temperature for 5 min until 1 N sulfuric acid (DukSan, 254) was added to stop the color development. Absorbance at 450 nm was read on Victor X3 (PerkinElmer, 2030-0030) (FIG. 4B).

The positive control HRS antibody was observed to exhibit strong binding strength for CD30 D1L and CD30 LD2 and weak binding strength for CD30 D1D2, indicating that even the linker of CD30 as well as D1 and D2 has influence on the binding. On the other hand, strong binding strength was measured from the T1-36 antibody LD2, T1-8 and T1-159 for D1L, and T1-23 and T1-141 for D1L and D1D2. From this analysis, these antibodies were identified to differ from the positive control HRS antibody in binding site.

Example 2: Development of Anti-CD30 scFv-Bearing Chimeric Antigen Receptor and Identification of Activity Thereof

Figure 5:
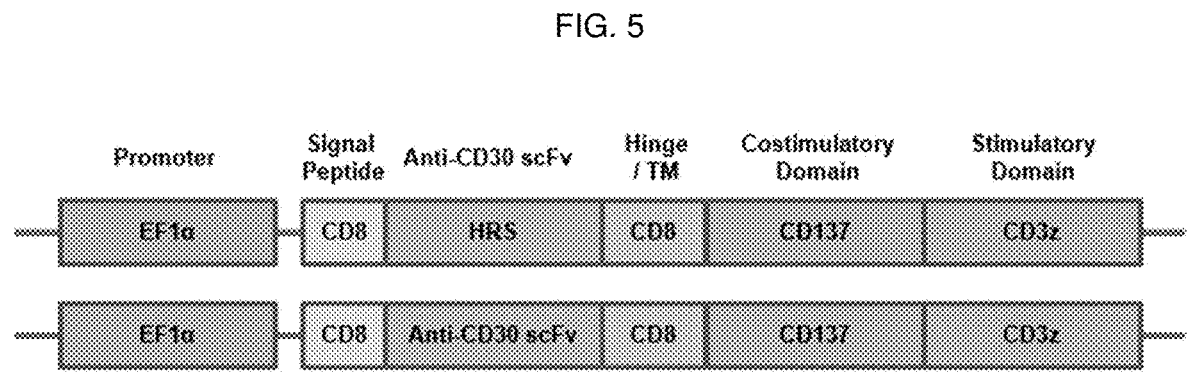

Example 2-1. Construction of Lentivirus Containing Anti-CD30 Antibody Fragment-Linked Chimeric Antigen Receptor A chimeric antigen receptor was developed using an anti-CD30 antibody fragment. After being subjected to codon optimization for a CD8 leader, a scFv-type anti-CD30, a CD8 hinge and transmembrane region, a CD137 cytoplasmic region, and a CD3 zeta cytoplasmic region in the chimeric antigen receptor, the gene was cut with SpeI/XhoI and ligated to pLenti6-V5/DEST lentiviral vector (Invitrogen, V53306). The constructs thus obtained were identified by base sequencing (FIG. 5).

Each of the prepared lentiviral constructs was transduced, together with the plasmid pCMV-dR8.91 carrying the viral coat protein VSV-G (vesicular stomatitis Indiana virus G protein), gag, pol, and rev genes, into Lenti-X 293T cells (Takara Bio Inc., 632180). Transduction was performed using Lipofectamine 2000 (Invitrogen, 11668019) according to the manufacturer's protocol. After 72 hours, the cell culture containing lentivirus was 10-fold enriched by a centrifugal filter (Millipore, UFC910024) and stored.

Example 2-2. Preparation of Cytotoxic T Cell Presenting Anti-CD30 Antibody-Bearing Chimeric Antigen Receptor on Surface (CD30-CAR-T)

Cytotoxic T cells on which anti-CD30 antibody fragment-bearing chimeric antigen receptors were presented were prepared using the lentivirus obtained in Example 2-1.

Figure 6:
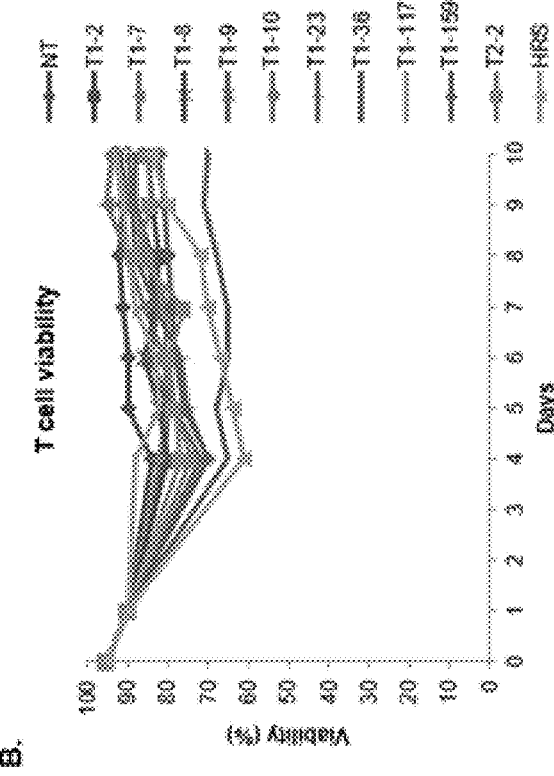
FIG. 6 shows cell proliferation (A) and viability (B) of CAR-T including CD30 antibodies.
Figure 6:
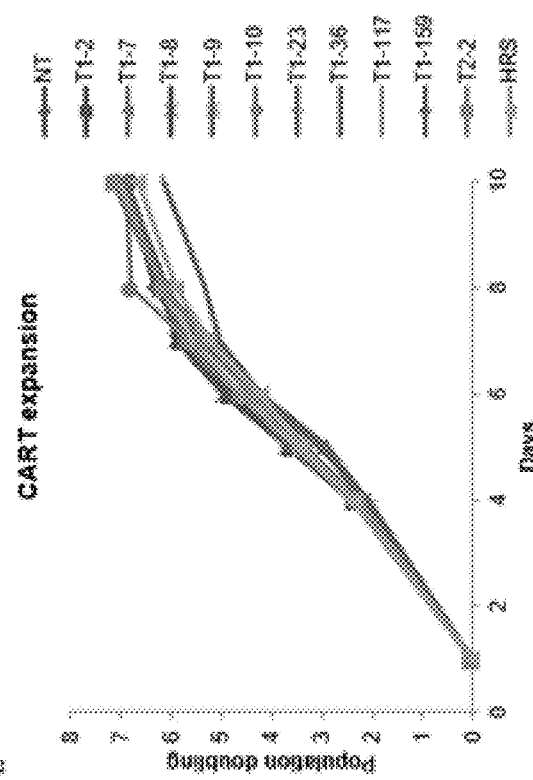

First, human T cells were isolated and stimulated with T cell TransAct (Miltenyi Biotec, 130-111-160) for 24 hours. Thereafter, the lentivirus was transduced for 24 hours into the cells. Then, the medium was exchanged with a medium containing IL-2 (Miltenyi Biotec, 170-076-146), followed by incubation at 37° C. in a 5% $CO_2$ atmosphere. After being cultured, the CD30-CAR-T was analyzed for proliferation and viability. CD30-CAR-T was prepared, for the most part, with high viability without any specificity in the CAR-T construction process. (FIG. 6, Table 4). The prepared CD30-CAR-Ts were stored in a frozen state at −130° C.

TABLE 4

| | Analyze proliferation and viability of candidate antibodies | |
|---|---|---|
| Antibody | Cell viability (%, Day 10) | Population doubling (Day 10) |
| T1-2 | 85 | 7.0 |
| T1-7 | 94 | 6.9 |
| T1-8 | 92 | 6.9 |
| T1-9 | 88 | 6.9 |
| T1-10 | 93 | 6.9 |
| T1-23 | 90 | 6.9 |
| T1-36 | 70 | 6.1 |
| T1-117 | 93 | 7.1 |
| T1-159 | 82 | 7.2 |
| T2-2 | 85 | 7.1 |
| HRS | 84 | 6.6 |

Under different conditions, an examination was made again of the proliferative ability of T1-159 observed to exhibit a high cell proliferation rate.

Figure 7:
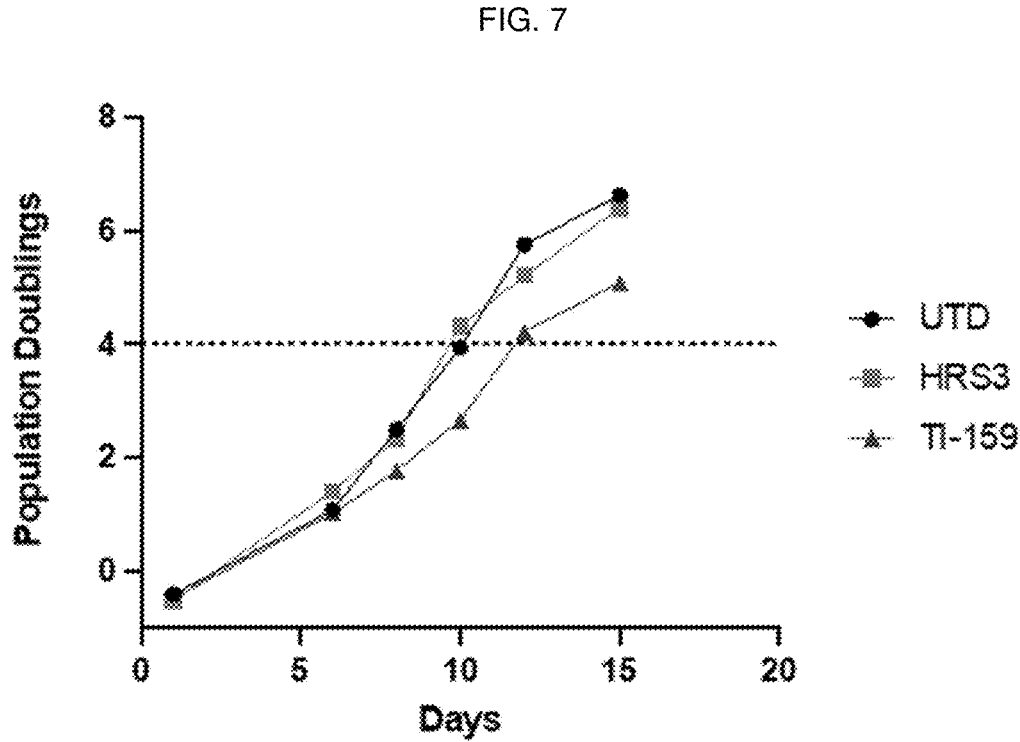
FIG. 7 shows results of an assay for cell proliferation ability of CD30 CAR-T containing T1-159.

To this end, $2 \times 10^6$ human T cells (CD4:CD8=1:1) were stimulated anti-CD3/CD28 Dynabeads (3:1 bead:T cell) for five days (120 hours). Twenty-four hours after stimulation, lentivirus containing a T1-159 construct was transduced into the T cells (MOI=2). On day 5 (120 hours after stimulation), beads of the CD30-CAR-T cells were removed and a cell concentration of 500,000 T cell/mL was maintained in a cytokine supplemented R10 medium (RPMI1640+10% FBS+20 ng/ml IL7+20 ng/ml IL15). The cell concentration was measured using an OrFlo MoxiGo II benchtop cell counter and a Beckman coulter counter. The results are depicted in FIG. 7. As shown in FIG. 7, the T1-159-containing CAR-T was superb in terms of proliferative rate, proving its proliferative ability sufficient for mass production of CAR-T.

Example 2-3. Verifying the Manufactured CAR-T Expresses an Anti-CD30 Antibody Fragment Before evaluating the activity of the CD30-CAR-T, we verified that the manufactured CAR-T was properly expressing the anti-CD30 antibody fragment. Briefly, the CD30-CAR-T cells obtained above were prepared at a density of $3 \times 10^5$ cells/tube, and harvested by centrifugation at 1,200 rpm for 3 min. After a wash with PBS containing 5% FBS, the cells were incubated at 4° C. for 30 min with 2 µg/mL mouse anti-Linker antibody (Clone 163, USA, U.S. Patent No. US 2019/0093101 A, Mar. 28, 2019). The cells were washed three times by three rounds of centrifugation with 200 µL of 5% FBS-containing PBS at 1200 rpm for 3 min. Afterwards, the cells were incubated with 1 µg/mL of anti-mouse-Fc-PE (BioLegend, 405307) at 4° C. for 30 min in a light-shielded condition. After being washed three times through three rounds of centrifugation with 200 µL of 5% FBS-containing PBS at 1200 rpm for 3 min, the expression of CAR was measured in terms of fluorescence intensity by FACS. The results are shown in FIG. 8 and Table 5.

Figure 8:
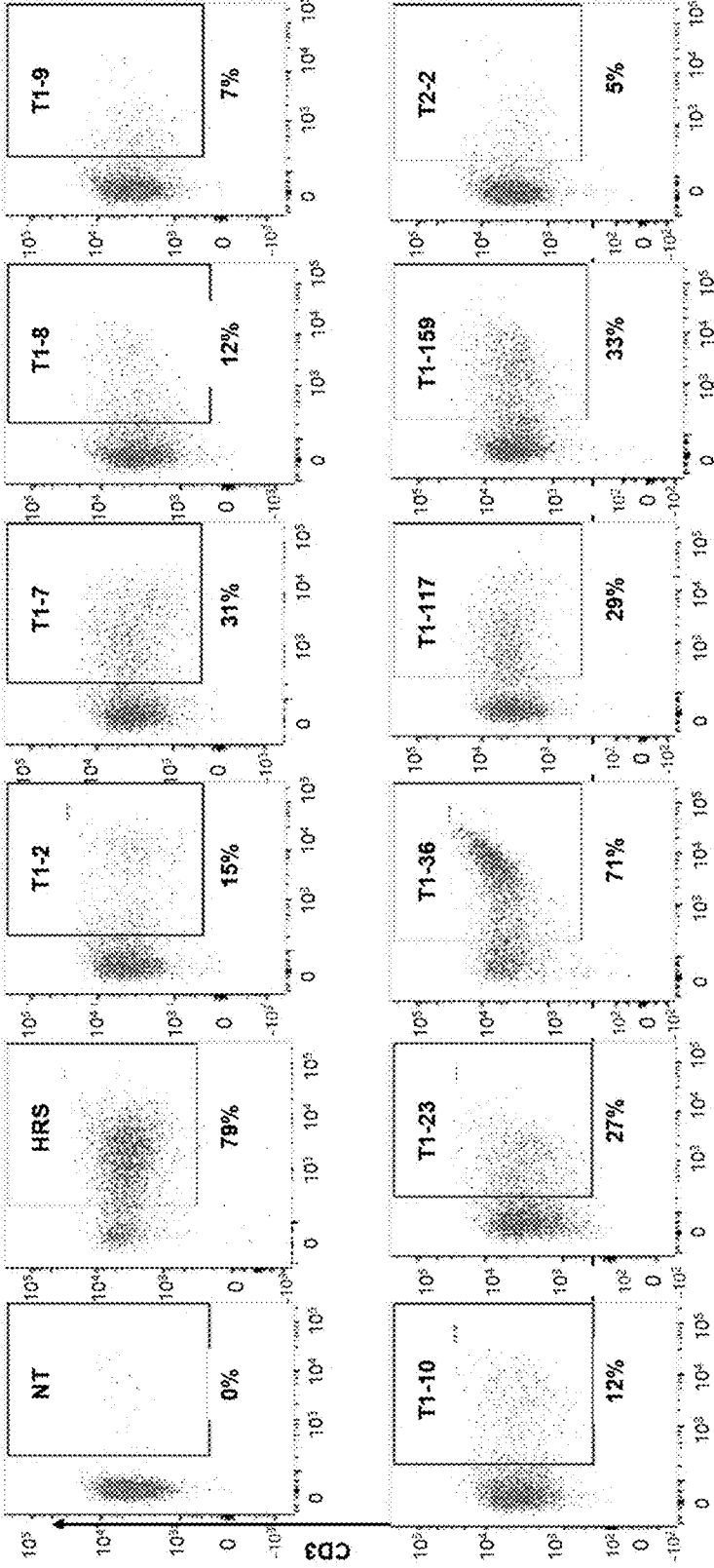
FIG. 8 shows ratios of expressing anti-CD30 CAR in the CAR-T constructed in the present disclosure.

As shown in FIG. 8, the anti-CD30 antibody fragment was expressed in the prepared CAR-T cells, although there were differences in expression levels. In particular, T1-36 had the highest expression levels.

TABLE 5

| | Expression of the anti-CD30 antibody fragment in the manufactured CAR-T cells. |
|---|---|
| | CAR Expression (%) |
| NT | 0 |
| T1-2 | 15 |
| T1-7 | 31 |
| T1-8 | 12 |
| T1-9 | 7 |
| T1-10 | 12 |
| T1-23 | 27 |
| T1-36 | 71 |
| T1-117 | 29 |
| T1-159 | 33 |
| T2-2 | 5 |
| HRS | 79 |

Example 3: Identification of Activity of CD30-CAR-T

Example 3-1. Confirm Cytotoxicity Against CD30+ Cell Lines

To determine whether the CD30-CAR-T prepared in Example 2-2 recognizes CD30 on the cell surface and induces activation of chimeric antigen receptor cells.

The activity of CD30-CAR-T was evaluated by measuring cytotoxicity and IFN release in CD30-positive cells and CD30-CAR-T. Briefly, GFP-Luciferase-expressing lentivirus (Biosettia, GlowCell-16p-1) was introduced into the CD30-positive cell line SUDHL1 (ATCC, 22268) and CD30-overexpressing CD30-293T cells to establish SUDHL1-ffLuc and CD30-293T-ffLuc cell lines for use in experiments. First, SUDHL1-ffLuc and CD30-293T-ffLuc cells were each seeded at a density of $1 \times 10^4$ cells/well into 96-well plates. The prepared cytotoxic T cells were added at a suitable rate per well to the Luc cells-seeded plate and incubated 37° C. for 24 hours in a 5% $CO_2$ atmosphere. Thereafter, cytotoxicity of the cytotoxic T cells was measured using a luciferase assay (Bio-Glo Luciferase assay system, Promega, G7941). For measurement of cytotoxic effects, the cytotoxic T cells and the ffLuc cells were co-cultured after which the remaining SUDHL1-ffLuc and CD30-293T-ffLuc cells were lysed with 3× Lysis buffer (75 mM Tris (pH8.0), 30% glycerol, 3% Triton X100) to release a luciferase which was then reacted with a substrate. Relative lysis rates were given when the signal from the wells where only ffLuc cells had been cultured was set forth as 100%.

Figure 9:
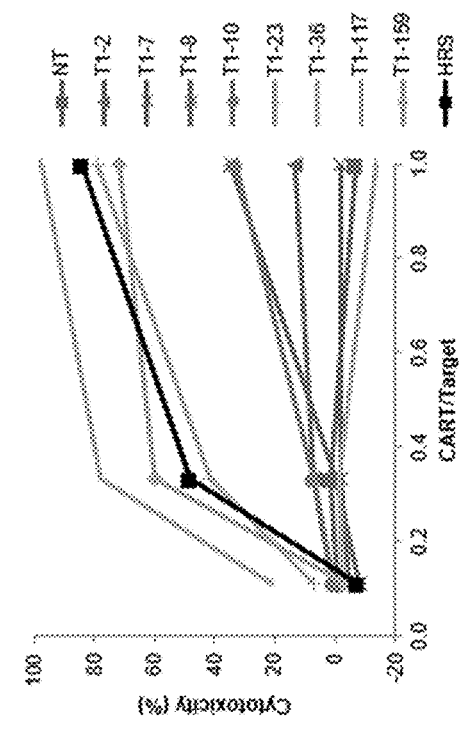
FIG. 9 shows plots of cytotoxicity effects of CD30-CAR-T on the CD30-positive cells SUDHL1 (A) and CD30-293T (B).
Figure 9:
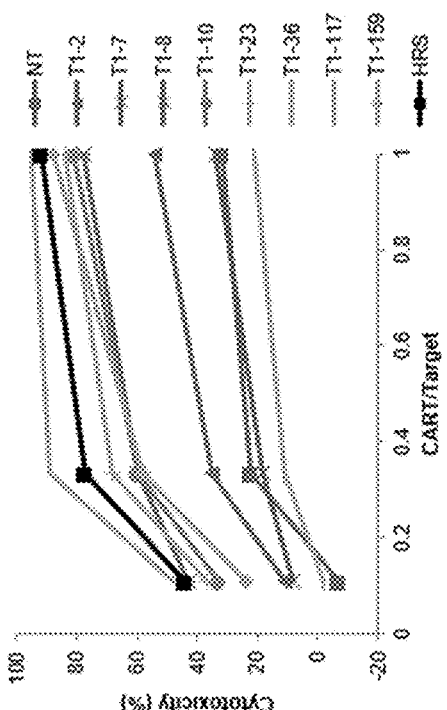

The results are shown in FIG. 9, Table 6, and Table 7. As shown in FIG. 9, the cytotoxic effects were increased in a cytotoxic T cell concentration-dependent manner. Relatively high cytotoxicity was observed in T1-23, T1-36, and T1-159.

TABLE 6

| | Cytotoxicity (%) of Candidate Antibody against CD30-Expressing Cell (SUDHL1) | | |
|---|---|---|---|
| | CAR-T/Target | | |
| | 0.11 | 0.33 | 1 |
| NT | −7 | 22 | 32 |
| T1-2 | 11 | 35 | 54 |
| T1-7 | 8 | 18 | 34 |

TABLE 6-continued

Cytotoxicity (%) of Candidate Antibody against
CD30-Expressing Cell (SUDHL1)

| | CAR-T/Target | | |
|---|---|---|---|
| | 0.11 | 0.33 | 1 |
| T1-8 | 43 | 60 | 78 |
| T1-10 | 33 | 60 | 81 |
| T1-23 | 37 | 68 | 84 |
| T1-36 | 48 | 89 | 95 |
| T1-117 | −2 | 11 | 21 |
| T1-159 | 24 | 58 | 88 |
| HRS | 44 | 77 | 92 |

TABLE 7

Cytotoxicity (%) of Candidate Antibody against
CD30-Expressing Cell (CD30-293T)

| | CAR-T/Target | | |
|---|---|---|---|
| | 0.11 | 0.33 | 1 |
| NT | −1 | 2 | −7 |
| T1-2 | 1 | 7 | 13 |
| T1-7 | −5 | −2 | −2 |
| T1-8 | −8 | 0 | 35 |
| T1-10 | 1 | 7 | 33 |
| T1-23 | 7 | 41 | 79 |
| T1-36 | 21 | 78 | 98 |
| T1-117 | −3 | −1 | −14 |
| T1-159 | −4 | 60 | 72 |
| HRS | −8 | 48 | 84 |

T1-36 and T1-159 that exhibited excellent cytotoxicity effects were reexamined for cytotoxicity against HDLM-2 cells (CD30+ cHL cell line).

HDLM-2 cells (CD30+ cHL) were seeded, together with 50,000 CBG (click-beetle green), into 96-well plates, with the target and effector cells set at various ratios. UTD, HRS3, and T1-36 or T1-159 CD30-CAR-T cells of the same donor (ND578) were treated. After 72 hours, 20 μL of luciferin (GoldBio, diluted to 150 μg/mL in PBS) was added to each well and incubated for 10 minutes in an incubator (37° C.+5% $CO_2$). Then, luminance was acquired using BioTek Synergy H4, and a tumor death effect in each well was evaluated according to Equation 1, below.

$$\text{Tumor Death (\%)} = \text{(maximal luminance} \qquad \text{[Equation 1]}$$
$$\text{(cancer alone)} - \text{coculture well)/(maximal luminance (cancer}$$
$$\text{alone)} - \text{background signal)} * 100$$

Figure 10:
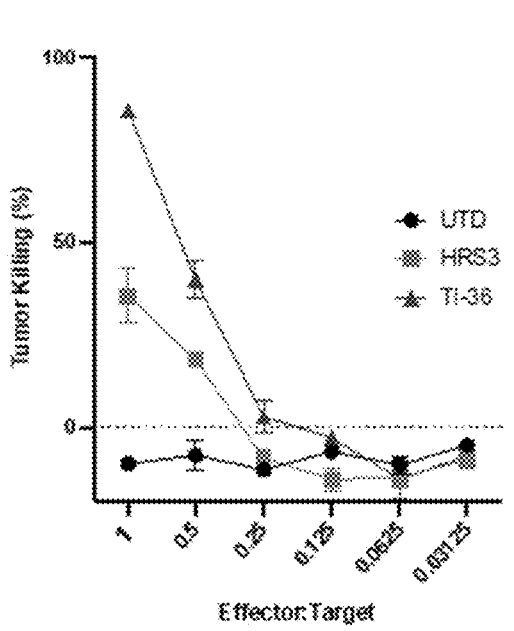
FIG. 10 shows results of an assay for tumor death effects of CD30 CAR-T containing T1-36 or T1-159.
Figure 10:
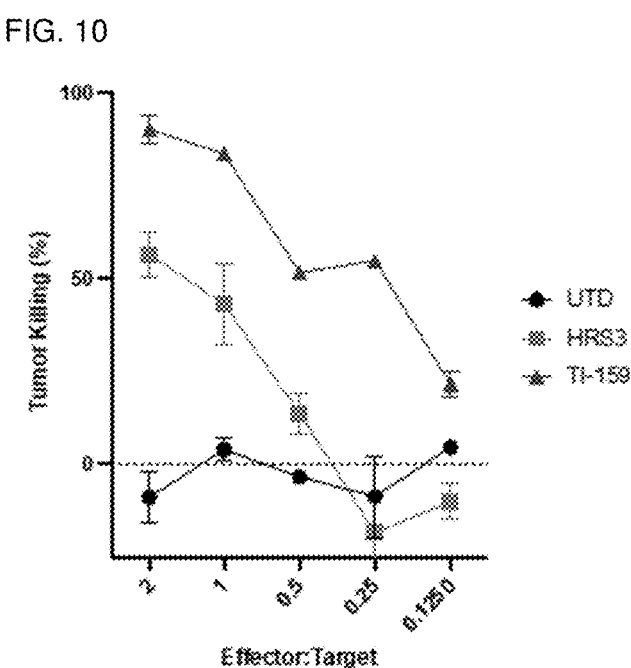

Results of the assay for tumor death effects are depicted in FIG. 10.

As shown in FIG. 10, CD30-CAR-T containing T1-36 and T1-159 were both observed to exhibit excellent tumor death effects. In particularly, T1-159 exhibited a tumor death rate of 50% or higher even when the ratio of CAR-T to the target was 0.25, proving its relatively high ability to kill tumors even at a low concentration.

Example 3-2. Assay for Cytotoxicity Against CD30-Cell Line

T1-159, observed to have excellent cytotoxic effect, was assayed for an off-target effect by examining it has cytotoxicity against the CD30-cell line.

OCI-Ly18 cells (CD19+ DLBCL) or Nalm6 cells (CD19+ B-ALL) were seeded, together with 50,000 CBG (click-beetle green), into 96-well plates, with the target and effector cells set at various ratios. UTD, HRS3, and T1-159 CD30-CAR-T cells of the same donor (ND578) were treated. After 48 hours, 20 μL of luciferin (GoldBio, diluted to 150 μg/mL in PBS) was added to each well and incubated for 10 minutes in an incubator (37° C.+5% $CO_2$). Then, luminance was acquired using BioTek Synergy H4, and a tumor death effect in each well was evaluated according to Equation 1, above.

Figure 11:
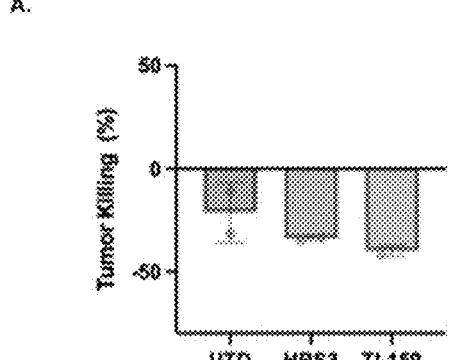
FIG. 11 shows the presence or absence of an off-target effect of the CD30 CAR-T containing T1-159 by examining whether CD30 CAR-T containing T1-159 has cell death effects on CD30⁻ cells.
Figure 11:
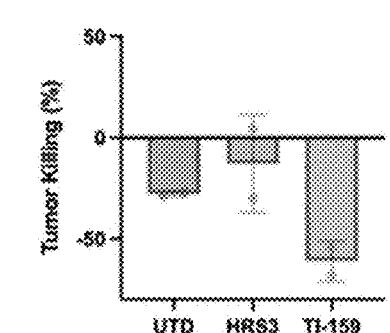

Results are depicted in FIG. 11. As shown in FIG. 11, the T1-159-containing CD30-CAR-T did not cytotoxicity against OCI-Ly18 and Nalm6 cells, which did not express CD30, indicating that T1-159 is very specific for CD30, with a low plausibility of off-target effect.

Example 3-3. Validate the Effectiveness of Stimulating Interferon-Gamma Release

Figure 12:
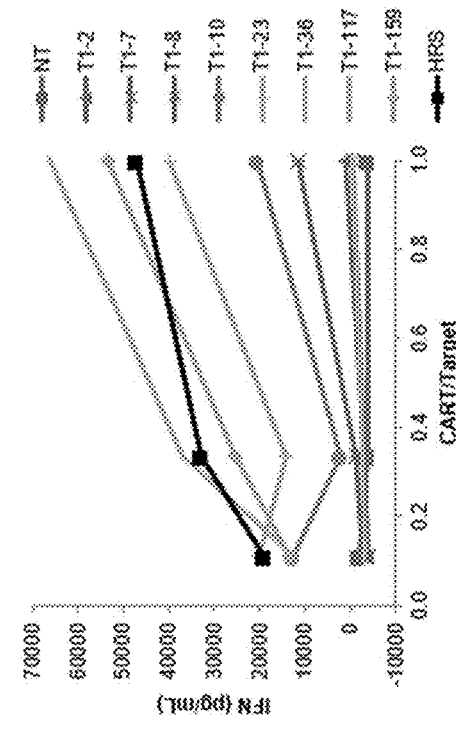
FIG. 12 are plots of IFN release from CD30-CAR-T for the CD30-positive cells SUDHL1 (A) and CD30-293T (B).
Figure 12:
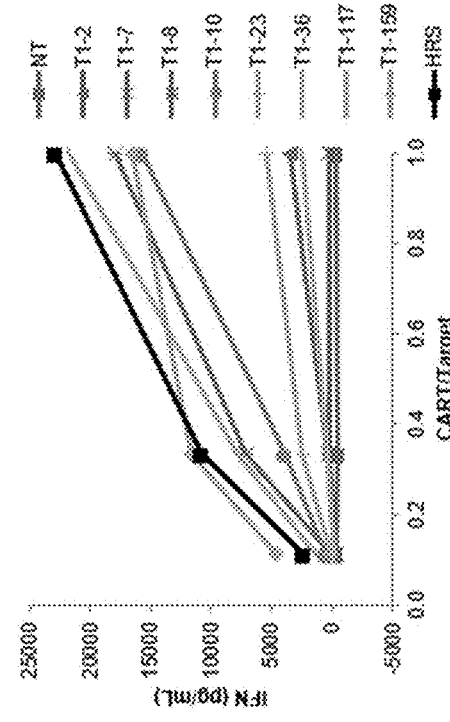

As for IFN release, the IFN secreted to culture media of the CD30-expressing cells and the CD30-CAR-T were quantitated using an ELISA kit (Human IFN-gamma ELISA Set, BD biosciences, 555142) according to the manufacturer's protocol (FIG. 12). As can be seen in FIG. 12, IFN release increased with the increasing of the treated cytotoxic T cell ratio. Consistent with the data of cytotoxicity, IFN release was increased in T1-23, T1-36, and T1-159.

Example 4: Assay for Anti-Tumoral Effect of T1-159-Containing CD30-CAR-T (In Vivo)

Eight NSG mice (8 weeks old) were subcutaneously implanted at the right flank with $1 \times 10^6$ HDLM-2 cells. After 55 days, the tumors had amounted to significant sizes (150-200 $mm^3$). Mice were randomly assigned to two groups of four. One group was injected with 300,000 HRS3-containing CD30-CAR-T cells and the other group was injected with 300,000 T1-159-containing CD30-CAR-T cells. Tumor size was monitored weekly via a digital caliper. Tumor volumes were calculated using Equation 2 below.

$$\text{Tumor volume } (mm^3) = 0.5 \times L \times (W)^2 \qquad \text{Equation 2}$$

wherein, L=length or long axis of tumor (mm); W=width or short axis of tumor (mm).

Figure 13:
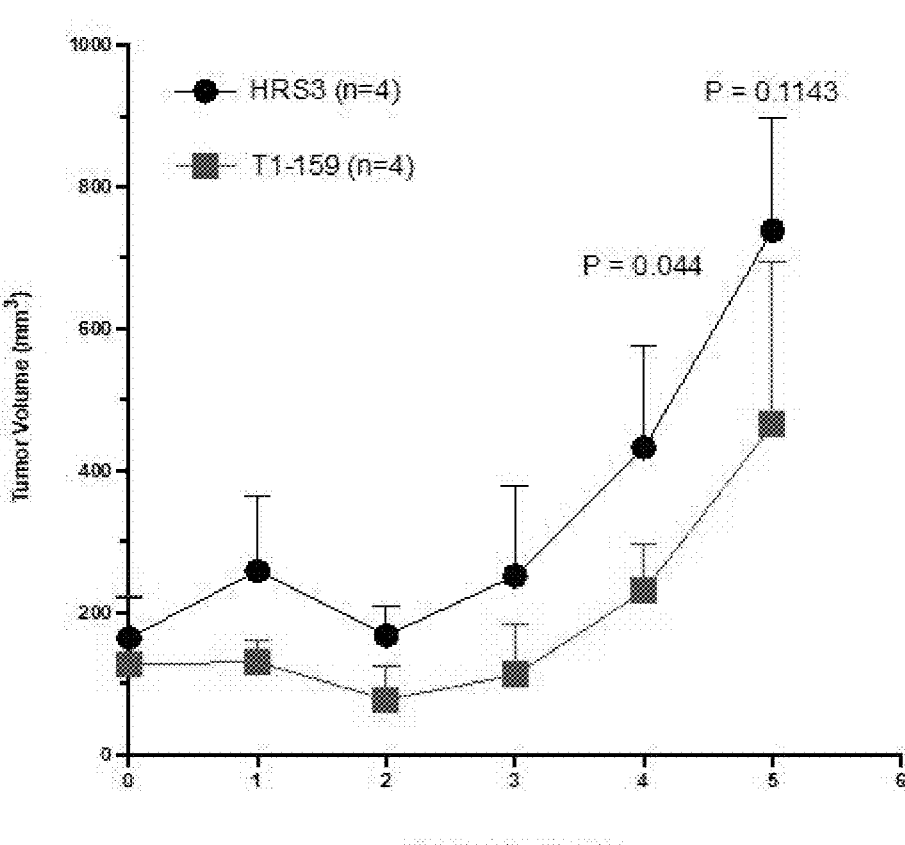
FIG. 13 shows results of an assay for anticancer activity of T1-159 against HDLM-2 cell-implanted NSG mice as measured for tumor volumes.

Results are depicted in FIG. 13. As shown in FIG. 13, CD30-CAR-T containing T1-159 had a significantly lower rate of tumor volume increase over the entire period than CD30-CAR-T containing HRS3. From 1 week after CAR-T treatment, the group treated with the CD30-CAR-T containing HRS3 showed a 50% larger tumor volume than the group treated with the CD30-CAR-T containing T1-159. This data indicates that the CD30-CAR-T containing T1-159 exhibits a very good antitumoral effect.

What is claimed is:

1. An anti-CD30 antibody or an antigen binding fragment thereof, comprising an immunoglobulin heavy-chain variable region domain and an immunoglobulin light-chain variable region domain, wherein:

i) the heavy-chain variable region domain comprises HCDR1, HCDR2, and HCDR3, wherein the HCDR1, HCDR2, and HCDR3 comprise the amino acid sequence of SEQ ID NO: 1, 2, and 3, respectively; and the light-chain variable region domain comprises LCDR1, LCDR2, and LCDR3, wherein the LCDR1, LCDR2, and LCDR3 comprise the amino acid sequence of SEQ ID NO: 4, 5, and 6, respectively;

ii) the heavy-chain variable region domain comprises HCDR1, HCDR2, and HCDR3, wherein the HCDR1, HCDR2, and HCDR3 comprise the amino acid sequence of SEQ ID NO: 21, 22, and 23, respectively; and the light-chain variable region domain comprises LCDR1, LCDR2, and LCDR3, wherein the LCDR1, LCDR2, and LCDR3 comprise the amino acid sequence of SEQ ID NO: 24, 25, and 26, respectively;

iii) the heavy-chain variable region domain comprises HCDR1, HCDR2, and HCDR3, wherein the HCDR1, HCDR2, and HCDR3 comprise the amino acid sequence of SEQ ID NO: 41, 42, and 43, respectively; and the light-chain variable region domain comprises LCDR1, LCDR2, and LCDR3, wherein the LCDR1, LCDR2, and LCDR3 comprise the amino acid sequence of SEQ ID NO: 44, 45, and 46, respectively;

iv) the heavy-chain variable region domain comprises HCDR1, HCDR2, and HCDR3, wherein the HCDR1, HCDR2, and HCDR3 comprise the amino acid sequence of SEQ ID NO: 61, 62, and 63, respectively; and the light-chain variable region domain comprises LCDR1, LCDR2, and LCDR3, wherein the LCDR1, LCDR2, and LCDR3 comprise the amino acid sequence of SEQ ID NO: 64, 65, and 66, respectively;

v) the heavy-chain variable region domain comprises HCDR1, HCDR2, and HCDR3, wherein the HCDR1, HCDR2, and HCDR3 comprise the amino acid sequence of SEQ ID NO: 81, 82, and 83, respectively; and the light-chain variable region domain comprises LCDR1, LCDR2, and LCDR3, wherein the LCDR1, LCDR2, and LCDR3 comprise the amino acid sequence of SEQ ID NO: 84, 85, and 86, respectively;

vi) the heavy-chain variable region domain comprises HCDR1, HCDR2, and HCDR3, wherein the HCDR1, HCDR2, and HCDR3 comprise the amino acid sequence of SEQ ID NO: 101, 102, and 103, respectively; and the light-chain variable region domain comprises LCDR1, LCDR2, and LCDR3, wherein the LCDR1, LCDR2, and LCDR3 comprise the amino acid sequence of SEQ ID NO: 104, 105, and 106, respectively;

vii) the heavy-chain variable region domain comprises HCDR1, HCDR2, and HCDR3, wherein the HCDR1, HCDR2, and HCDR3 comprise the amino acid sequence of SEQ ID NO: 121, 122, and 123, respectively; and the light-chain variable region domain comprises LCDR1, LCDR2, and LCDR3, wherein the LCDR1, LCDR2, and LCDR3 comprise the amino acid sequence of SEQ ID NO: 124, 125, and 126, respectively;

viii) the heavy-chain variable region domain comprises HCDR1, HCDR2, and HCDR3, wherein the HCDR1, HCDR2, and HCDR3 comprise the amino acid sequence of SEQ ID NO: 141, 142, and 143, respectively; and the light-chain variable region domain comprises LCDR1, LCDR2, and LCDR3, wherein the LCDR1, LCDR2, and LCDR3 comprise the amino acid sequence of SEQ ID NO: 144, 145, and 146, respectively;

ix) the heavy-chain variable region domain comprises HCDR1, HCDR2, and HCDR3, wherein the HCDR1, HCDR2, and HCDR3 comprise the amino acid sequence of SEQ ID NO: 161, 162, and 163, respectively; and the light-chain variable region domain comprises LCDR1, LCDR2, and LCDR3, wherein the LCDR1, LCDR2, and LCDR3 comprise the amino acid sequence of SEQ ID NO: 164, 165, and 166, respectively;

x) the heavy-chain variable region domain comprises HCDR1, HCDR2, and HCDR3, wherein the HCDR1, HCDR2, and HCDR3 comprise the amino acid sequence of SEQ ID NO: 181, 182, and 183, respectively; and the light-chain variable region domain comprises LCDR1, LCDR2, and LCDR3, wherein the LCDR1, LCDR2, and LCDR3 comprise the amino acid sequence of SEQ ID NO: 184, 185, and 186, respectively; or xi) the heavy-chain variable region domain comprises HCDR1, HCDR2, and HCDR3, wherein the HCDR1, HCDR2, and HCDR3 comprise the amino acid sequence of SEQ ID NO: 201, 202, and 203, respectively; and the light-chain variable region domain comprises LCDR1, LCDR2, and LCDR3, wherein the LCDR1, LCDR2, and LCDR3 comprise the amino acid sequence of SEQ ID NO: 204, 205, and 206, respectively.

2. The anti-CD30 antibody or the antigen binding fragment thereof according to claim 1, wherein the anti-CD30 antibody or the antigen binding fragment thereof comprises a heavy chain variable region domain and a light chain variable region domain, wherein:

i) the heavy-chain variable region domain comprises the amino acid sequence of SEQ ID NO: 7; and the light-chain variable region domain comprises the amino acid sequence of SEQ ID NO: 8;

ii) the heavy-chain variable region domain comprises the amino acid sequence of SEQ ID NO: 27; and the light-chain variable region domain comprises the amino acid sequence of SEQ ID NO: 28;

iii) the heavy-chain variable region domain comprises the amino acid sequence of SEQ ID NO: 47; and the light-chain variable region domain comprises the amino acid sequence of SEQ ID NO: 48;

iv) the heavy-chain variable region domain comprises the amino acid sequence of SEQ ID NO: 67; and the light-chain variable region domain comprises the amino acid sequence of SEQ ID NO: 68;

v) the heavy-chain variable region domain comprises the amino acid sequence of SEQ ID NO: 87; and the light-chain variable region domain comprises the amino acid sequence of SEQ ID NO: 88;

vi) the heavy-chain variable region domain comprises the amino acid sequence of SEQ ID NO: 107; and the light-chain variable region domain comprises the amino acid sequence of SEQ ID NO: 108;

vii) the heavy-chain variable region domain comprises the amino acid sequence of SEQ ID NO: 127; and the light-chain variable region domain comprises the amino acid sequence of SEQ ID NO: 128;

viii) the heavy-chain variable region domain comprises the amino acid sequence of SEQ ID NO: 147; and the light-chain variable region domain comprises the amino acid sequence of SEQ ID NO: 148;

ix) the heavy-chain variable region domain comprises the amino acid sequence of SEQ ID NO: 167; and the light-chain variable region domain comprises the amino acid sequence of SEQ ID NO: 168;

x) the heavy-chain variable region domain comprises the amino acid sequence of SEQ ID NO: 187; and the light-chain variable region domain comprises the amino acid sequence of SEQ ID NO: 188; or xi) the heavy-chain variable region domain comprises the amino acid sequence of SEQ ID NO: 207; and the light-chain variable region domain comprises the amino acid sequence of SEQ ID NO: 208.

3. The anti-CD30 antibody or the antigen binding fragment thereof according to claim 1, wherein the anti-CD30 antibody or the antigen binding fragment thereof comprises an scFv, wherein the scFv comprises an amino acid sequence selected from the group consisting of the amino acid sequence of SEQ ID NO: 9, the amino acid sequence of SEQ ID NO: 29, the amino acid sequence of SEQ ID NO: 49, the amino acid sequence of SEQ ID NO: 69, the amino acid sequence of SEQ ID NO: 89, the amino acid sequence of SEQ ID NO: 109, the amino acid sequence of SEQ ID NO: 129, the amino acid sequence of SEQ ID NO: 149, the amino acid sequence of SEQ ID NO: 169, the amino acid sequence of SEQ ID NO: 189, and the amino acid sequence of SEQ ID NO: 209.

4. The anti-CD30 antibody or the antigen binding fragment thereof according to claim 1, wherein the antigen binding fragment is a Fab, Fab', F(ab')$_2$, Fv, scFv, or chemically linked F(ab')$_2$.

5. A nucleic acid molecule encoding the anti-CD30 antibody or the antigen binding fragment thereof according to claim 1.

6. The nucleic acid molecule according to claim 5, wherein the nucleic acid molecule comprises nucleotide sequences selected from the group consisting of:

i) the nucleotide sequence of SEQ ID NO: 11, the nucleotide sequence of SEQ ID NO: 12, the nucleotide sequence of SEQ ID NO: 13, the nucleotide sequence of SEQ ID NO: 14, the nucleotide sequence of SEQ ID NO: 15, and the nucleotide sequence of SEQ ID NO: 16, wherein the nucleotide sequence encodes HCDR1, HCDR2, HCDR3, LCDR1, LCDR2, and LCDR3, respectively;

ii) the nucleotide sequence of SEQ ID NO: 31, the nucleotide sequence of SEQ ID NO: 32, the nucleotide sequence of SEQ ID NO: 33, the nucleotide sequence of SEQ ID NO: 34, the nucleotide sequence of SEQ ID NO: 35, and the nucleotide sequence of SEQ ID NO: 36, wherein the nucleotide sequence encodes HCDR1, HCDR2, HCDR3, LCDR1, LCDR2, and LCDR3, respectively;

iii) the nucleotide sequence of SEQ ID NO: 51, the nucleotide sequence of SEQ ID NO: 52, the nucleotide sequence of SEQ ID NO: 53, the nucleotide sequence of SEQ ID NO: 54, the nucleotide sequence of SEQ ID NO: 55, and the nucleotide sequence of SEQ ID NO: 56, wherein the nucleotide sequence encodes HCDR1, HCDR2, HCDR3, LCDR1, LCDR2, and LCDR3, respectively;

iv) the nucleotide sequence of SEQ ID NO: 71, the nucleotide sequence of SEQ ID NO: 72, the nucleotide sequence of SEQ ID NO: 73, the nucleotide sequence of SEQ ID NO: 74, the nucleotide sequence of SEQ ID NO: 75, and the nucleotide sequence of SEQ ID NO: 76, wherein the nucleotide sequence encodes HCDR1, HCDR2, HCDR3, LCDR1, LCDR2, and LCDR3, respectively;

v) the nucleotide sequence of SEQ ID NO: 91, the nucleotide sequence of SEQ ID NO: 92, the nucleotide sequence of SEQ ID NO: 93, the nucleotide sequence of SEQ ID NO: 94, the nucleotide sequence of SEQ ID NO: 95, and the nucleotide sequence of SEQ ID NO: 96, wherein the nucleotide sequence encodes HCDR1, HCDR2, HCDR3, LCDR1, LCDR2, and LCDR3, respectively;

vi) the nucleotide sequence of SEQ ID NO: 111, the nucleotide sequence of SEQ ID NO: 112, the nucleotide sequence of SEQ ID NO: 113, the nucleotide sequence of SEQ ID NO: 114, the nucleotide sequence of SEQ ID NO: 115, and the nucleotide sequence of SEQ ID NO: 116, wherein the nucleotide sequence encodes HCDR1, HCDR2, HCDR3, LCDR1, LCDR2, and LCDR3, respectively;

vii) the nucleotide sequence of SEQ ID NO: 131, the nucleotide sequence of SEQ ID NO: 132, the nucleotide sequence of SEQ ID NO: 133, the nucleotide sequence of SEQ ID NO: 134, the nucleotide sequence of SEQ ID NO: 135, and the nucleotide sequence of SEQ ID NO: 136, wherein the nucleotide sequence encodes HCDR1, HCDR2, HCDR3, LCDR1, LCDR2, and LCDR3, respectively;

viii) the nucleotide sequence of SEQ ID NO: 151, the nucleotide sequence of SEQ ID NO: 152, the nucleotide sequence of SEQ ID NO: 153, the nucleotide sequence of SEQ ID NO: 154, the nucleotide sequence of SEQ ID NO: 155, and the nucleotide sequence of SEQ ID NO: 156, wherein the nucleotide sequence encodes HCDR1, HCDR2, HCDR3, LCDR1, LCDR2, and LCDR3, respectively;

ix) the nucleotide sequence of SEQ ID NO: 171, the nucleotide sequence of SEQ ID NO: 172, the nucleotide sequence of SEQ ID NO: 173, the nucleotide sequence of SEQ ID NO: 174, the nucleotide sequence of SEQ ID NO: 175, and the nucleotide sequence of SEQ ID NO: 176, wherein the nucleotide sequence encodes HCDR1, HCDR2, HCDR3, LCDR1, LCDR2, and LCDR3, respectively;

x) the nucleotide sequence of SEQ ID NO: 191, the nucleotide sequence of SEQ ID NO: 192, the nucleotide sequence of SEQ ID NO: 193, the nucleotide sequence of SEQ ID NO: 194, the nucleotide sequence of SEQ ID NO: 195, and the nucleotide sequence of SEQ ID NO: 196, wherein the nucleotide sequence encodes HCDR1, HCDR2, HCDR3, LCDR1, LCDR2, and LCDR3, respectively; and xi) the nucleotide sequence of SEQ ID NO: 211, the nucleotide sequence of SEQ ID NO: 212, the nucleotide sequence of SEQ ID NO: 213, the nucleotide sequence of SEQ ID NO: 214, the nucleotide sequence of SEQ ID NO: 215, and the nucleotide sequence of SEQ ID NO: 216, wherein the nucleotide sequence encodes HCDR1, HCDR2, HCDR3, LCDR1, LCDR2, and LCDR3, respectively.

7. The nucleic acid molecule according to claim 5, wherein the nucleic acid molecule comprises nucleotide sequences selected from the group consisting of:

i) the nucleotide sequence of SEQ ID NO: 17 and the nucleotide sequence of SEQ ID NO: 18, wherein the nucleotide sequences encode the heavy chain variable domain and the light chain variable domain, respectively;

ii) the nucleotide sequence of SEQ ID NO: 37 and the nucleotide sequence of SEQ ID NO: 38, wherein the nucleotide sequences encode the heavy chain variable domain and the light chain variable domain, respectively;

iii) the nucleotide sequence of SEQ ID NO: 57 and the nucleotide sequence of SEQ ID NO: 58, wherein the nucleotide sequences encode the heavy chain variable domain and the light chain variable domain, respectively;

iv) the nucleotide sequence of SEQ ID NO: 77 and the nucleotide sequence of SEQ ID NO: 78, wherein the nucleotide sequences encode the heavy chain variable domain and the light chain variable domain, respectively;

v) the nucleotide sequence of SEQ ID NO: 97 and the nucleotide sequence of SEQ ID NO: 98, wherein the nucleotide sequences encode the heavy chain variable domain and the light chain variable domain, respectively;

vi) the nucleotide sequence of SEQ ID NO: 117 and the nucleotide sequence of SEQ ID NO: 118, wherein the nucleotide sequences encode the heavy chain variable domain and the light chain variable domain, respectively;

vii) the nucleotide sequence of SEQ ID NO: 137 and the nucleotide sequence of SEQ ID NO: 138, wherein the nucleotide sequences encode the heavy chain variable domain and the light chain variable domain, respectively;

viii) the nucleotide sequence of SEQ ID NO: 157 and the nucleotide sequence of SEQ ID NO: 158, wherein the nucleotide sequences encode the heavy chain variable domain and the light chain variable domain, respectively;

ix) the nucleotide sequence of SEQ ID NO: 177 and the nucleotide sequence of SEQ ID NO: 178, wherein the nucleotide sequences encode the heavy chain variable domain and the light chain variable domain, respectively;

x) the nucleotide sequence of SEQ ID NO: 197 and the nucleotide sequence of SEQ ID NO: 198, wherein the nucleotide sequences encode the heavy chain variable domain and the light chain variable domain, respectively; and xi) the nucleotide sequence of SEQ ID NO: 217 and the nucleotide sequence of SEQ ID NO: 218, wherein the nucleotide sequences encode the heavy chain variable domain and the light chain variable domain, respectively.

8. The nucleic acid molecule according to claim 5, wherein the nucleic acid molecule comprises a nucleotide sequence selected from the group consisting of the nucleotide sequence of SEQ ID NO: 19, the nucleotide sequence of SEQ ID NO: 39, the nucleotide sequence of SEQ ID NO: 59, the nucleotide sequence of SEQ ID NO: 79, the nucleotide sequence of SEQ ID NO: 99, the nucleotide sequence of SEQ ID NO: 119, the nucleotide sequence of SEQ ID NO: 139, the nucleotide sequence of SEQ ID NO: 159, the nucleotide sequence of SEQ ID NO: 179, the nucleotide sequence of SEQ ID NO: 199, and the nucleotide sequence of SEQ ID NO: 219, wherein the nucleotide sequence encodes an scFv.

9. A CD30-specific chimeric antigen receptor, comprising:
an anti-CD30 antibody or an antigen binding fragment thereof;
a transmembrane domain; and
an intracellular signaling domain,
wherein the anti-CD30 antibody or the antigen binding fragment thereof comprises a heavy chain variable region domain and a light chain variable region domain, wherein:
i) the heavy-chain variable region domain comprises HCDR1, HCDR2, and HCDR3, wherein the HCDR1, HCDR2, and HCDR3 comprise the amino acid sequence of SEQ ID NO: 1, 2, and 3, respectively; and the light-chain variable region domain comprises LCDR1, LCDR2, and LCDR3, wherein the LCDR1, LCDR2, and LCDR3 comprise the amino acid sequence of SEQ ID NO: 4, 5, and 6, respectively;
ii) the heavy-chain variable region domain comprises HCDR1, HCDR2, and HCDR3, wherein the HCDR1, HCDR2, and HCDR3 comprise the amino acid sequence of SEQ ID NO: 21, 22, and 23, respectively; and the light-chain variable region domain comprises LCDR1, LCDR2, and LCDR3, wherein the LCDR1, LCDR2, and LCDR3 comprise the amino acid sequence of SEQ ID NO: 24, 25, and 26, respectively;
iii) the heavy-chain variable region domain comprises HCDR1, HCDR2, and HCDR3, wherein the HCDR1, HCDR2, and HCDR3 comprise the amino acid sequence of SEQ ID NO: 41, 42, and 43, respectively; and the light-chain variable region domain comprises LCDR1, LCDR2, and LCDR3, wherein the LCDR1, LCDR2, and LCDR3 comprise the amino acid sequence of SEQ ID NO: 44, 45, and 46, respectively;
iv) the heavy-chain variable region domain comprises HCDR1, HCDR2, and HCDR3, wherein the HCDR1, HCDR2, and HCDR3 comprise the amino acid sequence of SEQ ID NO: 61, 62, and 63, respectively; and the light-chain variable region domain comprises LCDR1, LCDR2, and LCDR3, wherein the LCDR1, LCDR2, and LCDR3 comprise the amino acid sequence of SEQ ID NO: 64, 65, and 66, respectively;
v) the heavy-chain variable region domain comprises HCDR1, HCDR2, and HCDR3, wherein the HCDR1, HCDR2, and HCDR3 comprise the amino acid sequence of SEQ ID NO: 81, 82, and 83, respectively; and the light-chain variable region domain comprises LCDR1, LCDR2, and LCDR3, wherein the LCDR1, LCDR2, and LCDR3 comprise the amino acid sequence of SEQ ID NO: 84, 85, and 86, respectively;
vi) the heavy-chain variable region domain comprises HCDR1, HCDR2, and HCDR3, wherein the HCDR1, HCDR2, and HCDR3 comprise the amino acid sequence of SEQ ID NO: 101, 102, and 103, respectively; and the light-chain variable region domain comprises LCDR1, LCDR2, and LCDR3, wherein the LCDR1, LCDR2, and LCDR3 comprise the amino acid sequence of SEQ ID NO: 104, 105, and 106, respectively;
vii) the heavy-chain variable region domain comprises HCDR1, HCDR2, and HCDR3, wherein the HCDR1, HCDR2, and HCDR3 comprise the amino acid sequence of SEQ ID NO: 121, 122, and 123, respectively; and the light-chain variable region domain comprises LCDR1, LCDR2, and LCDR3, wherein the LCDR1, LCDR2, and LCDR3 comprise the amino acid sequence of SEQ ID NO: 124, 125, and 126, respectively;
viii) the heavy-chain variable region domain comprises HCDR1, HCDR2, and HCDR3, wherein the HCDR1, HCDR2, and HCDR3 comprise the amino acid sequence of SEQ ID NO: 141, 142, and 143, respectively; and the light-chain variable region domain comprises LCDR1, LCDR2, and LCDR3, wherein the LCDR1, LCDR2, and LCDR3 comprise the amino acid sequence of SEQ ID NO: 144, 145, and 146, respectively;
ix) the heavy-chain variable region domain comprises HCDR1, HCDR2, and HCDR3, wherein the HCDR1, HCDR2, and HCDR3 comprise the amino acid sequence of SEQ ID NO: 161, 162, and 163, respectively; and the light-chain variable region domain comprises LCDR1, LCDR2, and LCDR3, wherein the LCDR1, LCDR2, and LCDR3 comprise the amino acid sequence of SEQ ID NO: 164, 165, and 166, respectively;
x) the heavy-chain variable region domain comprises HCDR1, HCDR2, and HCDR3, wherein the HCDR1, HCDR2, and HCDR3 comprise the amino acid sequence of SEQ ID NO: 181, 182, and 183, respectively; and the light-chain variable region domain comprises LCDR1, LCDR2, and LCDR3, wherein the LCDR1, LCDR2, and LCDR3 comprise the amino acid sequence of SEQ ID NO: 184, 185, and 186, respectively; or
xi) the heavy-chain variable region domain comprises HCDR1, HCDR2, and HCDR3, wherein the HCDR1, HCDR2, and HCDR3 comprise the amino acid sequence of SEQ ID NO: 201, 202, and 203, respectively; and the light-chain variable region domain comprises LCDR1, LCDR2, and LCDR3, wherein the LCDR1, LCDR2, and LCDR3 comprise the amino acid sequence of SEQ ID NO: 204, 205, and 206, respectively.

10. The CD30-specific chimeric antigen receptor of claim 9, wherein the anti-CD30 antibody or the antigen binding fragment thereof comprises a heavy chain variable region domain and a light chain variable region domain, wherein:
i) the heavy-chain variable region domain comprises the amino acid sequence of SEQ ID NO: 7; and the light-chain variable region domain comprises the amino acid sequence of SEQ ID NO: 8;
ii) the heavy-chain variable region domain comprises the amino acid sequence of SEQ ID NO: 27; and the light-chain variable region domain comprises the amino acid sequence of SEQ ID NO: 28;

iii) the heavy-chain variable region domain comprises the amino acid sequence of SEQ ID NO: 47; and the light-chain variable region domain comprises the amino acid sequence of SEQ ID NO: 48;

iv) the heavy-chain variable region domain comprises the amino acid sequence of SEQ ID NO: 67; and the light-chain variable region domain comprises the amino acid sequence of SEQ ID NO: 68;

v) the heavy-chain variable region domain comprises the amino acid sequence of SEQ ID NO: 87; and the light-chain variable region domain comprises the amino acid sequence of SEQ ID NO: 88;

vi) the heavy-chain variable region domain comprises the amino acid sequence of SEQ ID NO: 107; and the light-chain variable region domain comprises the amino acid sequence of SEQ ID NO: 108;

vii) the heavy-chain variable region domain comprises the amino acid sequence of SEQ ID NO: 127; and the light-chain variable region domain comprises the amino acid sequence of SEQ ID NO: 128;

viii) the heavy-chain variable region domain comprises the amino acid sequence of SEQ ID NO: 147; and the light-chain variable region domain comprises the amino acid sequence of SEQ ID NO: 148;

ix) the heavy-chain variable region domain comprises the amino acid sequence of SEQ ID NO: 167; and the light-chain variable region domain comprises the amino acid sequence of SEQ ID NO: 168;

x) the heavy-chain variable region domain comprises the amino acid sequence of SEQ ID NO: 187; and the light-chain variable region domain comprises the amino acid sequence of SEQ ID NO: 188; or xi) the heavy-chain variable region domain comprises the amino acid sequence of SEQ ID NO: 207; and the light-chain variable region domain comprises the amino acid sequence of SEQ ID NO: 208.

11. The CD30-specific chimeric antigen receptor of claim 9, wherein the anti-CD30 antibody or the antigen binding fragment thereof comprises an scFv, wherein the scFv comprises an amino acid sequence selected from the group consisting of the amino acid sequence of SEQ ID NO: 9, the amino acid sequence of SEQ ID NO: 29, the amino acid sequence of SEQ ID NO: 49, the amino acid sequence of SEQ ID NO: 69, the amino acid sequence of SEQ ID NO: 89, the amino acid sequence of SEQ ID NO: 109, the amino acid sequence of SEQ ID NO: 129, the amino acid sequence of SEQ ID NO: 149, the amino acid sequence of SEQ ID NO: 169, the amino acid sequence of SEQ ID NO: 189, and the amino acid sequence of SEQ ID NO: 209.

12. The CD30-specific chimeric antigen receptor of claim 9, wherein the CD30-specific chimeric antigen receptor comprises an scFv CAR, wherein the scFv CAR comprises an amino acid sequence selected from the group consisting of the amino acid sequence of SEQ ID NO: 10, the amino acid sequence of SEQ ID NO: 30, the amino acid sequence of SEQ ID NO: 50, the amino acid sequence of SEQ ID NO: 70, the amino acid sequence of SEQ ID NO: 90, the amino acid sequence of SEQ ID NO: 110, the amino acid sequence of SEQ ID NO: 130, the amino acid sequence of SEQ ID NO: 150, the amino acid sequence of SEQ ID NO: 170, the amino acid sequence of SEQ ID NO: 190, and the amino acid sequence of SEQ ID NO: 210.

13. The CD30-specific chimeric antigen receptor of claim 9, wherein the transmembrane domain is the transmembrane domain of a protein selected from the group consisting of a T-cell receptor, CD27, CD28, CD3 epsilon, CD45, CD4, CD5, CD8, CD9, CD16, CD22, CD33, CD37, CD64, CD80, CD86, CD134, CD137, and CD154.

14. The CD30-specific chimeric antigen receptor of claim 9, wherein the signaling domain comprises a functional signaling domain from at least one of 4-1BB, CD28, OX40, and CD3 zeta.

15. A nucleic acid molecule encoding the CD30-specific chimeric antigen receptor of claim 9.

16. An effector cell expressing the CD30-specific chimeric antigen receptor of claim 9.

17. A pharmaceutical composition comprising the anti-CD30 antibody or antigen-binding fragment of claim 1.

18. A method for treating a disease related with a cell over-expressing CD30, the method comprising:
a step of administering the pharmaceutical composition of claim 17 to a subject in need thereof.

* * * * *